US009415049B2

(12) United States Patent
Tester et al.

(10) Patent No.: US 9,415,049 B2
(45) **Date of Patent: *Aug. 16, 2016**

(54) HETEROARYL COMPOUNDS AND USES THEREOF

(71) Applicant: Celgene Avilomics Research, Inc., Bedford, MA (US)

(72) Inventors: Richland Tester, Marlborough, MA (US); Prasoon Chaturvedi, Shrewsbury, MA (US); Zhendong Zhu, Westborough, MA (US); Sekhar S. Surapaneni, Warren, NJ (US); Lisa Beebe, Acton, MA (US)

(73) Assignee: Celgene Avilomics Research, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/137,700

(22) Filed: Dec. 20, 2013

(65) Prior Publication Data

US 2015/0174128 A1 Jun. 25, 2015

(51) Int. Cl.

| | |
|---|---|
| ***A61K 31/535*** | (2006.01) |
| ***A01N 43/54*** | (2006.01) |
| ***A61K 31/505*** | (2006.01) |
| ***A61K 31/506*** | (2006.01) |
| ***A61K 31/4985*** | (2006.01) |
| ***A61K 31/4035*** | (2006.01) |
| ***A61K 31/5377*** | (2006.01) |
| ***A61K 31/454*** | (2006.01) |

(52) U.S. Cl.

CPC ........... *A61K 31/505* (2013.01); *A61K 31/4035* (2013.01); *A61K 31/454* (2013.01); *A61K 31/4985* (2013.01); *A61K 31/506* (2013.01); *A61K 31/5377* (2013.01)

(58) Field of Classification Search

None

See application file for complete search history.

(56) References Cited

U.S. PATENT DOCUMENTS

| | | | |
|---|---|---|---|
| 4,879,303 | A | 11/1989 | Davison et al. |
| 5,958,935 | A | 9/1999 | Davis et al. |
| 6,093,716 | A | 7/2000 | Davis et al. |
| 6,114,333 | A | 9/2000 | Davis et al. |
| 6,127,376 | A | 10/2000 | Davey et al. |
| 6,160,010 | A | 12/2000 | Uckun et al. |
| 6,262,088 | B1 | 7/2001 | Phillips |
| 6,469,168 | B1 | 10/2002 | Ratzne Simonek et al. |
| 6,579,983 | B1 | 6/2003 | Batchelor et al. |
| 6,593,326 | B1 | 7/2003 | Bradbury et al. |
| 6,838,464 | B2 | 1/2005 | Pease et al. |
| 6,939,874 | B2 | 9/2005 | Harmange et al. |
| 7,060,827 | B2 | 6/2006 | Singh et al. |
| 7,122,542 | B2 | 10/2006 | Singh et al. |
| 7,125,879 | B2 | 10/2006 | Guillemont et al. |
| 7,176,212 | B2 | 2/2007 | Breault et al. |
| 7,202,033 | B2 | 4/2007 | Prescott et al. |
| 7,241,769 | B2 | 7/2007 | Stadtmueller et al. |
| 7,282,504 | B2 | 10/2007 | Armistead et al. |
| 7,329,671 | B2 | 2/2008 | Singh et al. |
| 7,329,672 | B2 | 2/2008 | Singh et al. |
| 7,332,484 | B2 | 2/2008 | Singh et al. |
| 7,435,814 | B2 | 10/2008 | Singh et al. |
| 7,452,879 | B2 | 11/2008 | Singh et al. |
| 7,485,724 | B2 | 2/2009 | Singh et al. |
| 7,491,732 | B2 | 2/2009 | Li et al. |
| 7,498,435 | B2 | 3/2009 | Singh et al. |
| 7,504,396 | B2 | 3/2009 | Nunes et al. |
| 7,514,444 | B2 | 4/2009 | Honigberg et al. |
| 7,514,445 | B2 | 4/2009 | Freyne et al. |
| 7,514,446 | B2 | 4/2009 | Davis-Ward et al. |
| 7,528,143 | B2 | 5/2009 | Noronha et al. |
| 7,531,548 | B2 | 5/2009 | Guillemont et al. |
| 7,550,460 | B2 | 6/2009 | Singh et al. |
| 7,557,210 | B2 | 7/2009 | Singh et al. |
| 7,582,648 | B2 | 9/2009 | Singh et al. |
| 7,589,200 | B2 | 9/2009 | Singh et al. |
| 7,642,351 | B2 | 1/2010 | Singh et al. |
| 7,655,797 | B2 | 2/2010 | Singh et al. |
| 7,718,662 | B1 | 5/2010 | Chen et al. |
| 7,741,330 | B1 | 6/2010 | Chen et al. |
| 7,803,939 | B2 | 9/2010 | Singh et al. |
| 7,820,819 | B2 | 10/2010 | Singh et al. |
| 7,858,633 | B2 | 12/2010 | Li et al. |
| 7,884,111 | B2 | 2/2011 | Argade et al. |
| 8,088,781 | B2 | 1/2012 | Honigberg et al. |
| 8,338,439 | B2 | 12/2012 | Singh et al. |
| 8,450,335 | B2 | 5/2013 | Singh et al. |
| 8,501,751 | B2 | 8/2013 | Honigberg et al. |
| 8,563,568 | B2 | 10/2013 | Witowski et al. |
| 8,609,679 | B2 | 12/2013 | Singh et al. |
| 8,710,222 | B2 | 4/2014 | Singh et al. |

(Continued)

FOREIGN PATENT DOCUMENTS

| | | | |
|---|---|---|---|
| CN | 102558149 A | | 7/2012 |
| CN | 103159742 A | | 6/2013 |
| EP | 1 054 004 A1 | | 11/2000 |
| JP | 07041461 A | | 2/1995 |
| WO | WO-96/28427 A1 | | 9/1996 |
| WO | WO-97/19065 A1 | | 5/1997 |

(Continued)

OTHER PUBLICATIONS

International Search Report for PCT/US2013/077275, 3 pages (Apr. 16, 2014).

(Continued)

*Primary Examiner* — Jared D Barsky

(74) *Attorney, Agent, or Firm* — Choate, Hall & Stewart, LLP; Kristen C. Buteau

(57) ABSTRACT

The present invention provides compounds, pharmaceutically acceptable compositions thereof, and methods of using the same.

27 Claims, No Drawings

(56) References Cited

U.S. PATENT DOCUMENTS

| | | | |
|---|---|---|---|
| 8,796,255 | B2 | 8/2014 | Lee et al. |
| 8,822,685 | B2 | 9/2014 | Singh et al. |
| 8,975,249 | B2 | 3/2015 | Lee et al. |
| 9,119,854 | B2 | 9/2015 | Chopra et al. |
| 9,126,950 | B2 | 9/2015 | Tester et al. |
| 9,133,134 | B2 | 9/2015 | Chen et al. |
| 2004/0019067 | A1 | 1/2004 | Armistead et al. |
| 2004/0023957 | A1 | 2/2004 | Wang et al. |
| 2004/0077661 | A1 | 4/2004 | Arbiser |
| 2005/0004125 | A1 | 1/2005 | Freyne et al. |
| 2005/0014753 | A1 | 1/2005 | Ding et al. |
| 2005/0085637 | A1 | 4/2005 | Cheung et al. |
| 2005/0209221 | A1 | 9/2005 | Nunes et al. |
| 2005/0272083 | A1 | 12/2005 | Seshagiri |
| 2006/0030018 | A1 | 2/2006 | Zuccola et al. |
| 2006/0079543 | A1 | 4/2006 | Sum et al. |
| 2006/0084644 | A1 | 4/2006 | Pal et al. |
| 2006/0084645 | A1 | 4/2006 | Pal et al. |
| 2006/0100227 | A1 | 5/2006 | Baenteli et al. |
| 2006/0148800 | A1 | 7/2006 | Stadtmueller et al. |
| 2006/0160803 | A1 | 7/2006 | Adams et al. |
| 2006/0247241 | A1 | 11/2006 | Garcia-Echeverria et al. |
| 2006/0247262 | A1 | 11/2006 | Baenteli et al. |
| 2006/0270694 | A1 | 11/2006 | Wong |
| 2006/0293311 | A1 | 12/2006 | Li et al. |
| 2007/0010668 | A1 | 1/2007 | Davis-Ward et al. |
| 2007/0032493 | A1 | 2/2007 | Foley et al. |
| 2007/0066658 | A1 | 3/2007 | Chappell |
| 2007/0203161 | A1 | 8/2007 | Argade et al. |
| 2007/0203162 | A1 | 8/2007 | Li et al. |
| 2007/0259904 | A1 | 11/2007 | Noronha et al. |
| 2008/0009484 | A1 | 1/2008 | Argade et al. |
| 2008/0009494 | A1 | 1/2008 | Li et al. |
| 2008/0021020 | A1 | 1/2008 | Argade et al. |
| 2008/0027045 | A1 | 1/2008 | Argade et al. |
| 2008/0039622 | A1 | 2/2008 | Singh et al. |
| 2008/0058358 | A1 | 3/2008 | Luecking et al. |
| 2008/0076921 | A1 | 3/2008 | Honigberg et al. |
| 2008/0132504 | A1 | 6/2008 | Garcia-Echeverria et al. |
| 2008/0139582 | A1 | 6/2008 | Honigberg et al. |
| 2008/0182852 | A1 | 7/2008 | Johnson et al. |
| 2008/0194603 | A1 | 8/2008 | Li et al. |
| 2008/0207613 | A1 | 8/2008 | Styles et al. |
| 2008/0214501 | A1 | 9/2008 | Pan et al. |
| 2008/0260754 | A1 | 10/2008 | Li et al. |
| 2008/0279867 | A1 | 11/2008 | Atuegbu et al. |
| 2008/0300268 | A1 | 12/2008 | Singh et al. |
| 2008/0312438 | A1 | 12/2008 | Singh et al. |
| 2009/0131436 | A1 | 5/2009 | Imbach et al. |
| 2009/0137588 | A1 | 5/2009 | Singh et al. |
| 2009/0156622 | A1 | 6/2009 | Singh et al. |
| 2009/0171086 | A1 | 7/2009 | Singh et al. |
| 2009/0181987 | A1 | 7/2009 | Honigberg et al. |
| 2009/0215803 | A1 | 8/2009 | Rice et al. |
| 2009/0286778 | A1 | 11/2009 | Combs et al. |
| 2009/0298830 | A1 | 12/2009 | Mann et al. |
| 2009/0318407 | A1 | 12/2009 | Bauer et al. |
| 2010/0004270 | A1 | 1/2010 | Honigberg et al. |
| 2010/0016296 | A1 | 1/2010 | Singh et al. |
| 2010/0022561 | A1 | 1/2010 | Honigberg et al. |
| 2010/0029610 | A1 | 2/2010 | Singh et al. |
| 2010/0041677 | A1 | 2/2010 | Honigberg et al. |
| 2010/0081679 | A1 | 4/2010 | Greul et al. |
| 2010/0088912 | A1 | 4/2010 | Higgs et al. |
| 2010/0173285 | A1 | 7/2010 | Varmus et al. |
| 2010/0197918 | A1 | 8/2010 | Singh et al. |
| 2010/0249092 | A1* | 9/2010 | Singh et al. .............. 514/210.18 |
| 2010/0254905 | A1 | 10/2010 | Honigberg et al. |
| 2011/0039868 | A1 | 2/2011 | Honigberg et al. |
| 2011/0105472 | A1 | 5/2011 | Greul et al. |
| 2011/0207736 | A1 | 8/2011 | Gray et al. |
| 2011/0224235 | A1 | 9/2011 | Honigberg et al. |
| 2011/0245156 | A1 | 10/2011 | Sielecki-Dzurdz |
| 2011/0245284 | A1 | 10/2011 | Greul et al. |
| 2011/0281322 | A1 | 11/2011 | Honigberg et al. |
| 2012/0040968 | A1 | 2/2012 | Shimada et al. |
| 2012/0065201 | A1 | 3/2012 | Honigberg et al. |
| 2012/0071497 | A1 | 3/2012 | Buggy et al. |
| 2012/0083006 | A1 | 4/2012 | Ramsden et al. |
| 2012/0087915 | A1* | 4/2012 | Buggy et al. ............... 424/133.1 |
| 2012/0088912 | A1 | 4/2012 | Honigberg et al. |
| 2012/0094999 | A1 | 4/2012 | Gray et al. |
| 2012/0101113 | A1 | 4/2012 | Honigberg et al. |
| 2012/0101114 | A1 | 4/2012 | Honigberg et al. |
| 2012/0149687 | A1 | 6/2012 | Lee et al. |
| 2012/0149722 | A1 | 6/2012 | Lee et al. |
| 2012/0157426 | A1 | 6/2012 | Lee et al. |
| 2012/0165328 | A1 | 6/2012 | Honigberg et al. |
| 2012/0165332 | A1 | 6/2012 | Major et al. |
| 2012/0184013 | A1 | 7/2012 | Honigberg et al. |
| 2012/0184567 | A1 | 7/2012 | Honigberg et al. |
| 2012/0202264 | A1 | 8/2012 | Honigberg et al. |
| 2012/0270237 | A9 | 10/2012 | Ramsden et al. |
| 2012/0296089 | A1 | 11/2012 | Honigberg et al. |
| 2012/0316135 | A1 | 12/2012 | Dalgarno et al. |
| 2012/0329130 | A1 | 12/2012 | Honigberg et al. |
| 2013/0065879 | A1 | 3/2013 | Singh et al. |
| 2013/0065899 | A1 | 3/2013 | Singh et al. |
| 2013/0072469 | A1 | 3/2013 | Singh et al. |
| 2013/0137708 | A1 | 5/2013 | Garske et al. |
| 2013/0165462 | A1 | 6/2013 | Singh et al. |
| 2014/0057929 | A1 | 2/2014 | Witowski et al. |
| 2014/0134265 | A1 | 5/2014 | Buggy et al. |
| 2014/0142123 | A1 | 5/2014 | Honigberg et al. |
| 2014/0163046 | A1 | 6/2014 | Honigberg et al. |
| 2014/0187564 | A1 | 7/2014 | Honigberg et al. |
| 2014/0187565 | A1 | 7/2014 | Honigberg et al. |
| 2014/0213574 | A1 | 7/2014 | Singh et al. |
| 2014/0303154 | A1 | 10/2014 | Singh et al. |
| 2014/0314751 | A1 | 10/2014 | Hege et al. |
| 2014/0314752 | A1 | 10/2014 | Lopez-Girona et al. |
| 2014/0314753 | A1 | 10/2014 | Hege et al. |
| 2014/0315848 | A1 | 10/2014 | Raymon |
| 2014/0315884 | A1 | 10/2014 | Goff et al. |
| 2014/0328832 | A1 | 11/2014 | Chopra et al. |
| 2014/0330007 | A1 | 11/2014 | Singh et al. |
| 2015/0005297 | A1 | 1/2015 | Singh et al. |
| 2015/0025055 | A1 | 1/2015 | Lee et al. |
| 2015/0246040 | A1 | 9/2015 | Lee et al. |

FOREIGN PATENT DOCUMENTS

| | | | |
|---|---|---|---|
| WO | WO-00/27825 | A1 | 5/2000 |
| WO | WO-00/46203 | A2 | 8/2000 |
| WO | WO-00/78731 | A1 | 12/2000 |
| WO | WO-01/47897 | A1 | 7/2001 |
| WO | WO-01/60816 | A1 | 8/2001 |
| WO | WO-01/64654 | A1 | 9/2001 |
| WO | WO-01/64655 | A1 | 9/2001 |
| WO | WO-01/85699 | A2 | 11/2001 |
| WO | WO-02/083653 | A1 | 10/2002 |
| WO | WO-03/016306 | A1 | 2/2003 |
| WO | WO-03/030909 | A1 | 4/2003 |
| WO | WO-03/063794 | A2 | 8/2003 |
| WO | WO-03/066601 | A1 | 8/2003 |
| WO | WO-2004/014382 | A1 | 2/2004 |
| WO | WO-2004/031232 | A1 | 4/2004 |
| WO | WO-2004/056786 | A2 | 7/2004 |
| WO | WO-2004/069812 | A1 | 8/2004 |
| WO | WO-2004/074244 | A2 | 9/2004 |
| WO | WO-2004/080980 | A1 | 9/2004 |
| WO | WO-2004/096224 | A2 | 11/2004 |
| WO | WO-2005/013996 | A2 | 2/2005 |
| WO | WO-2005/016893 | A2 | 2/2005 |
| WO | WO-2005/016894 | A1 | 2/2005 |
| WO | WO-2005/026130 | A1 | 3/2005 |
| WO | WO-2005/026158 | A1 | 3/2005 |
| WO | WO-2005/063722 | A1 | 7/2005 |
| WO | WO-2005/070890 | A2 | 8/2005 |
| WO | WO-2006/021544 | A1 | 3/2006 |
| WO | WO-2006/045066 | A2 | 4/2006 |
| WO | WO-2006/053109 | A1 | 5/2006 |
| WO | WO-2006/055561 | A2 | 5/2006 |
| WO | WO-2006/068770 | A1 | 6/2006 |

(56) References Cited

FOREIGN PATENT DOCUMENTS

| | | | |
|---|---|---|---|
| WO | WO-2006/074057 | A2 | 7/2006 |
| WO | WO-2006/078846 | A1 | 7/2006 |
| WO | WO-2006/101977 | A2 | 9/2006 |
| WO | WO-2006/108487 | A1 | 10/2006 |
| WO | WO-2006/124874 | A2 | 11/2006 |
| WO | WO-2006/128129 | A2 | 11/2006 |
| WO | WO-2006/129100 | A1 | 12/2006 |
| WO | WO-2006/133426 | A2 | 12/2006 |
| WO | WO-2007/027238 | A2 | 3/2007 |
| WO | WO-2007/048064 | A2 | 4/2007 |
| WO | WO-2007/053452 | A1 | 5/2007 |
| WO | WO-2007/056151 | A2 | 5/2007 |
| WO | WO-2007/085833 | A2 | 8/2007 |
| WO | WO-2007/089768 | A2 | 8/2007 |
| WO | WO-2007/113254 | A1 | 10/2007 |
| WO | WO-2007/113256 | A1 | 10/2007 |
| WO | WO-2007/120339 | A1 | 10/2007 |
| WO | WO-2007/120980 | A2 | 10/2007 |
| WO | WO-2007/125351 | A1 | 11/2007 |
| WO | WO-2008/005538 | A2 | 1/2008 |
| WO | WO-2008/009458 | A1 | 1/2008 |
| WO | WO-2008/025556 | A1 | 3/2008 |
| WO | WO-2008/049123 | A2 | 4/2008 |
| WO | WO-2008/064274 | A1 | 5/2008 |
| WO | WO-2008/073687 | A2 | 6/2008 |
| WO | WO-2008/074515 | A1 | 6/2008 |
| WO | WO-2008/079719 | A1 | 7/2008 |
| WO | WO-2008/079907 | A1 | 7/2008 |
| WO | WO-2008/080964 | A1 | 7/2008 |
| WO | WO-2008/080965 | A2 | 7/2008 |
| WO | WO-2008/088303 | A1 | 7/2008 |
| WO | WO-2008/092199 | A1 | 8/2008 |
| WO | WO-2008/107096 | A1 | 9/2008 |
| WO | WO-2008/115738 | A1 | 9/2008 |
| WO | WO-2008/115742 | A1 | 9/2008 |
| WO | WO-2008/118822 | A1 | 10/2008 |
| WO | WO-2008/118823 | A2 | 10/2008 |
| WO | WO-2009/012421 | A1 | 1/2009 |
| WO | WO-2009/017838 | A2 | 2/2009 |
| WO | WO-2009/029682 | A1 | 3/2009 |
| WO | WO-2009/032668 | A2 | 3/2009 |
| WO | WO-2009/032694 | A1 | 3/2009 |
| WO | WO-2009/032703 | A1 | 3/2009 |
| WO | WO-2009/080638 | A2 | 7/2009 |
| WO | WO-2009/105675 | A1 | 8/2009 |
| WO | WO-2009/112490 | A1 | 9/2009 |
| WO | WO-2009/115267 | A2 | 9/2009 |
| WO | WO-2009/127642 | A2 | 10/2009 |
| WO | WO-2009/143389 | A1 | 11/2009 |
| WO | WO-2009/158571 | A1 | 12/2009 |
| WO | WO-2010/025833 | A1 | 3/2010 |
| WO | WO-2010/081679 | A2 | 7/2010 |
| WO | WO-2010/129053 | A2 | 11/2010 |
| WO | WO-2011/079231 | A1 | 6/2011 |
| WO | WO-2011/090760 | A1 | 7/2011 |
| WO | WO-2011/140338 | A1 | 11/2011 |
| WO | WO-2011/153514 | A2 | 12/2011 |
| WO | WO-2012/021444 | A1 | 2/2012 |
| WO | WO-2012/061299 | A1 | 5/2012 |
| WO | WO-2012/061303 | A1 | 5/2012 |
| WO | WO-2012/061415 | A1 | 5/2012 |
| WO | WO-2012/064706 | A1 | 5/2012 |
| WO | WO-2012/158843 | A2 | 11/2012 |
| WO | WO-2013/173518 | A1 | 11/2013 |
| WO | WO-2014/100748 | A1 | 6/2014 |
| WO | WO-2014/172429 | A1 | 10/2014 |
| WO | WO-2014/172430 | A1 | 10/2014 |
| WO | WO-2014/172432 | A1 | 10/2014 |
| WO | WO-2014/172436 | A1 | 10/2014 |
| WO | WO-2014/179661 | A1 | 11/2014 |

OTHER PUBLICATIONS

Written Opinion for PCT/US2013/077275, 10 pages (Apr. 16, 2014).
U.S. Appl. No. 13/518,833, filed Jun. 22, 2012, Gray et al.
U.S. Appl. No. 14/636,905, filed Mar. 3, 2015, Lee et al.
Aliagas-Martin, I. et al., A class of 2,4-bisanilinopyrimidine Aurora A inhibitors with unusually high selectivity against Aurora B, J. Med. Chem. 52:3300-3307 (2009).
Andrulis, I. et al., Neu/ErbB-2 amplification identifies a poor-prognosis group of women with node-negative breast cancer, J Clin Oncol 16:1340-9 (1998).
Bamborough, P. et al., N-4-Pyrimidinyl-1H-indazol-4-amine inhibitors of Lck: Indazoles as phenol isosteres with improved pharmacokinetics, Bioorg. & Med. Chem. Lett. 17:4363-4368 (2007).
Calvo, E. et al., Administration of CI-1033, an Irreversible Pan-erbB Tyrosine Kinase Inhibitor, Is Feasible on a 7-Day Off Schedule: A Phase I Pharmacokinetic and Food Effect Study, Clinical Cancer Research, 10: 7112-7120 (2004).
Carter, T. et al, Inhibition of drug-resistant mutants of ABL, KIT, and EGF receptor kinases, Proc. Natl. Acad. Sci. USA 102(31):11011-11016 (2005).
Cohen, M. et al., Structural bioinformatics-based design of selective, irreversible inhibitors, Science 308:1318-1321 (2005).
Curto, M. et al., Contact-dependent inhibition of EGFR signaling by Nf2/Merlin, J Cell Biol 177:893-903 (2007).
Ding, K. et al., Design, Synthesis and Biological Evaluation of Novel Conformationally Constrained Inhibitors Targeting Epidermal Growth Factor Receptor T790M mutant, J. Med. Chem., Just Accepted Manuscript, 1-36 (2012).
Extended European Search Report for EP11816874.9, 5 pages (Dec. 12, 2014).
Extended European Search Report for EP11838624.2, 5 pages (Jun. 6, 2014).
Extended European Search Report for EP11838628.3, 7 pages (Jun. 20, 2014).
Extended European Search Report for EP11839800.7, 8 pages (Jun. 24, 2014).
Fabian, M. et al., A small molecule-kinase interaction map for clinical kinase inhibitors, Nature Biotechnology, 23(3): 329 (2005).
Fallon, K. et al., Constitutive activation of the neuregulin-1/erbB signaling pathway promotes the proliferation of a human peripheral neuroepithelioma cell line, J Neuro Oncol 66:273-84 (2004).
Frank, D., STAT signaling in the pathogenesis and treatment of cancer, Mol. Med. 5 :432-456 (1999).
Fry, D. et al., Specific, irreversible inactivation of the epidermal growth factor receptor and erbB2, by a new class of tyrosine kinase inhibitor, Proc. Natl. Acad. Sci. USA 95:12022-12027 (1998).
Ghoneim, K., Synthesis and evaluation of some 2-, 4-, di-substituted-6-methylpyrimidine derivatives for antimicrobial activity, J. Indian Chem. Soc. 63(10):914-917 (1986).
Ghosh, D., 2-4-bis (arylamino) -5- methylpyrimidines as antimicrobial agents, J. Med. Chem. 10(5):974 (1967).
Ghosh, D., 2-4-bis (arylamino) -6- methylpyrimidines as antimicrobial agents, J. Indian Chem. Soc. 58(5):512-573 (1981).
Gonzales, A. et al, Antitumor activity and pharmacokinetic properties of PF-00299804, a second-generation, irreversible pan-erbB receptor tyrosine kinase inhibitor, Mol. Cancer Ther. 7(7):1880-1889 (2008).
Gura, Trisha et al., Systems for identifying new drugs are often faulty, Science, 278:1041-1042 (1997).
Hacken, E.T. and Burger, J.A., Microenvironment dependency in Chronic Lymphocytic Leukemia: The basis for new targeted therapies, Pharmacology & Therapeutics, http://dx.doi.org/10.1016/j.pharmthera.2014.07.003, (2014).
Hur, W. et al., Clinical stage EGFR inhibitors irreversibly alkylate Bmx kinase, Bioorg. Med. Chem. Lett. 18:5916-5919 (2008).
International Search Report for PCT/US10/31714 dated Aug. 13, 2010.
International Search Report for PCT/US11/46926, 2 pages (Dec. 22, 2011).
International Search Report for PCT/US11/58610, 4 pages (Mar. 27, 2012).
International Search Report for PCT/US11/58616, 3 pages (Mar. 27, 2012).
International Search Report for PCT/US11/59726, 3 pages (Mar. 20, 2012).

(56) References Cited

OTHER PUBLICATIONS

International Search Report for PCT/US2009/048784, 8 pages (Nov. 16, 2009).
International Search Report for PCT/US2010/062432, 4 pages (May 26, 2011).
Johnson, J. et al., Relationships between drug activity in NCI preclinical in vitro and in vivo models and early clinical trials, British Journal of Cancer, 84(10): 1424-1431 (2001).
Kirken, R., Targeting Jak3 for immune suppression and allograft acceptance, Transplant. Proc. 33 :3268-3270 (2001).
Kumar, A., et al, Structure and Clinical Relevance of the Epidermal Growth Factor Receptor in Human Cancer, Journal of Clinical Oncology 26(10):1742-1751 (2008).
Kwak, E. et al., Irreversible inhibitors of the EGF receptor may circumvent acquired resistance to gefitinib, Proc. Natl. Acad. Sci. USA 102:7665-7670 (2005).
Lajeunesse, D. et al., A systematic screen for dominant second-site modifiers of Merlin/NF2 phenotypes reveals an interaction with blistered/DSRF and scribbler, Genetics 158:667-79 (2001).
Li, D. et al., BIBW2992, an irreversible EGFR/HER2 inhibitor highly effective in preclinical lung cancer models, Oncogene 27:4702-4711 (2008).
Lin, N. and Winer, E., New targets for therapy in breast cancer: Small molecule tyrosine kinase inhibitors, Breast Cancer Res 6:204-210 (2004).
Malaviya, R. et al., Targeting Janus Kinase 3 in Mast Cells Prevents Immediate Hypersensitivity Reactions and Anaphylaxis, J. Biol. Chem. 274 :27028-27038 (1999).
McClatchey, A. and Giovannini, M., Membrane organization and tumorigenesis—the NF2 tumor suppressor, Merlin, Genes Dev 19:2265-77 (2005).
Minkovsky, N. and Berezov, A., BIBW-2992, a dual receptor tyrosine kinase inhibitor for the treatment of solid tumors, Curr Opin Invest Drugs 9:1336-1346 (2008).
Pearce, H.L. et al., Failure modes in anticancer drug discovery and development, Cancer Drug Design and Discovery Edited by Stephen Neidle, 18: 424-435 (2008).
Pelton, P. et al., Ruffling membrane, stress fiber, cell spreading and proliferation abnormalities in human Schwann cells, Oncogene 17:2195-2209 (1998).
PubChem CID 44594695. Feb. 1, 2010. [Retrieved from the Internet May 15, 2011: http://pubchem.ncbi.nlm.nih.gov/summary.cgi?cid=44594695&loc=ec_rcs].
Readinger, J. et al., Selective Targeting of ITK Blocks Multiple Steps of HIV Replication, Proc. Natl. Acad. Sci. USA 105: 6684-6689 (2008).
Seidel, H. et al., Pharmaceutical intervention in the JAK/STAT signaling pathway, Oncogene 19: 2645-2656 (2000).
Sequist, L., Second-Generation Epidermal Growth Factor Receptor Tyrosine Kinase Inhibitors in Non-Small Cell Lung Cancer, The Oncologist 12(3):325-330 (2007).
Simone, J.V., Oncology: Introduction, Cecil Textbook of Medicine, 20th Edition, 1: 1004-1010 (1995).
Singh, J. et al, Structure-based design of a potent, selective, and irreversible inhibitor of the catalytic domain of the erbB receptor subfamily of protein tyrosine kinases, J. Med. Chem. 40:1130-1135 (1997).
Stonecypher, M. et al., Activation of the neuregulin-1/ErbB signaling pathway promotes the proliferation of neoplastic Schwann cells in human malignant peripheral nerve sheath tumors, Oncogene 24:5589-5605 (2005).
Sudbeck, E. et al., Structure-based Design of Specific Inhibitors of Janus Kinase 3 as Apoptosis-inducing Antileukemic Agents, Clin. Cancer Res. 5: 1569-1582 (1999).
Supplementary European Search Report for EP10844293.0, 8 pages (Jun. 27, 2013).
Trieu, V. et al., A specific inhibitor of janus kinase-3 increases survival in a transgenic mouse model of amyotrophic lateral sclerosis, Biochem. Biophys. Res. Commun. 267 :22-25 (2000).
Wong, K. et al, A phase I study with neratinib (Hki-272), an irreversible pan Erb B receptor tyrosine kinase inhibitor, in patients with solid tumors, Clin. Cancer Res. 15(7):2552-2558 (2009).
Written Opinion for PCT/US10/31714 dated Aug. 13, 2010.
Written Opinion for PCT/US11/46926, 9 pages (Dec. 22, 2011).
Written Opinion for PCT/US11/58610, 8 pages (Mar. 27, 2012).
Written Opinion for PCT/US11/58616, 9 pages (Mar. 27, 2012).
Written Opinion for PCT/US11/59726, 7 pages (Mar. 20, 2012).
Written Opinion for PCT/US2009/048784, 9 pages (Nov. 16, 2009).
Written Opinion for PCT/US2010/062432, 14 pages (May 26, 2011).
Zhang, J. et al., Targeting Cancer with Small Molecule Kinase Inhibitors, Nature Rev. Cancer 9:28-39 (2009).
Zhang, Y. et al., Antitumor Activity of Epidermal Growth Factor Receptor-Related Protein Is Mediated by Inactivation of ErbB Receptors and Nuclear Factor-kB in Pancreatic Cancer, Cancer Res 66:1025-1032 (2006).
Zhou, W. et al. Novel mutant-selective EGFR kinase inhibitors against EGFR T790M, Nature, 462(7276): 1070-1074 (2009).

* cited by examiner

HETEROARYL COMPOUNDS AND USES THEREOF

FIELD OF THE INVENTION

The present invention provides compounds, and compositions thereof, useful as inhibitors of protein kinases.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of the present invention, and compositions thereof, are useful as inhibitors of one or more protein kinases and exhibit desirable characteristics for the same. Such compounds have general Formula I:

I

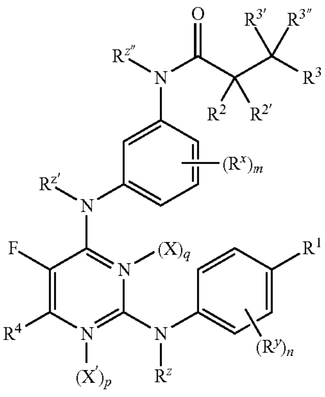

or a pharmaceutically acceptable salt thereof, wherein $R^1$, $R^2$, $R^{2'}$, $R^3$, $R^{3'}$, $R^{3''}$, $R^4$, $R^x$, $R^y$, $R^z$, $R^{z'}$, $R^{z''}$, X, X', m and n are as defined herein.

Compounds of the present invention, and pharmaceutically acceptable compositions thereof, are useful for treating a variety of diseases, disorders or conditions, associated with abnormal cellular responses triggered by protein kinase-mediated events. Such diseases, disorders, or conditions include those described herein.

Compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

1. General Description of Certain Aspects of the Invention

As described above, the present invention provides certain compounds, and compositions thereof, useful as protein kinase inhibitors. In particular, the present invention provides certain 2,4-disubstituted pyrimidine compounds which inhibit activity of one or more protein kinases, including Bruton's tyrosine kinase ("BTK"), a member of TEC-kinases (e.g., TEC, BTK, IL2-inducible T-cell kinase (ITK), receptor-like kinases (RLK) and bone marrow kinase on chromosome X (BMX)). Such compounds have the structure of Formula I:

I

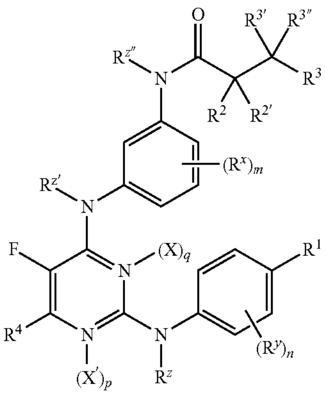

or a pharmaceutically acceptable salt thereof, wherein:

X and X' are each independently O;

p and q are each independently 0 or 1, wherein p and q are not both 1;

$R^1$ is —OR', —$OCH_2CH_2OR'$ or —$OCH_2CO_2H$;

R' is —H, —$CH_3$, —$SO_3H$ or -Glu;

each Glu is a glucuronyl moiety;

$R^2$ and $R^3$ are each independently —H, —OH, —$OSO_3H$, —OGlu, —$SR^5$, or:

$R^2$ and $R^3$ are taken together to form a double bond; or:

$R^2$ and $R^3$ are taken together with their intervening atoms to form an epoxide moiety;

$R^{2'}$ is —H, or:

$R^2$ and $R^{2'}$ are taken together to form =O;

$R^{3'}$ and $R^{3''}$ are each —H, or:

$R^{3'}$ and $R^{3''}$ are taken together to form =O;

$R^4$ is —H, —OH, —$OSO_3H$ or —OGlu;

$R^5$ is selected from:

i

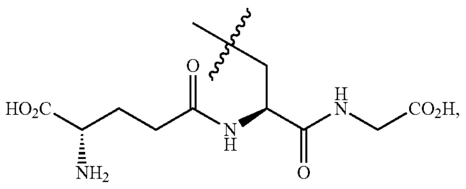

ii

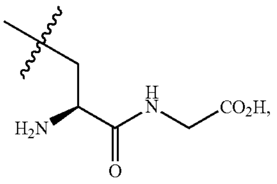

iii

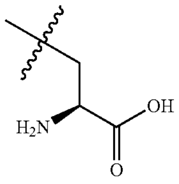

or

-continued iv

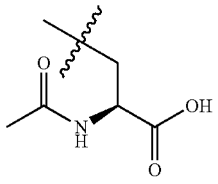

$R^x$ and $R^y$ are each independently —OH, —$OSO_3H$, or —OGlu;

$R^z$, $R^{z'}$ and $R^{z''}$ are each independently —H, —$CH_3$, —OH, —$OSO_3H$, or —OGlu; or $R^{z''}$ and $R^3$ are taken together to form —O—;

m and n are each independently 0, 1, 2, 3 or 4, provided that when $R^2$ and $R^3$ are taken together to form a double bond, at least one of the following is true:

(a) $R^1$ is —OH, —$OSO_3H$, —OGlu, —$OCH_2CH_2OH$, —$OCH_2CO_2H$, —$OCH_2CH_2OSO_3H$ or —$OCH_2CH_2OGlu$;

(b) at least one of $R^4$, $R^x$, $R^y$, $R^z$, $R^{z'}$ and $R^{z''}$ is —OH, —$OSO_3H$ or —OGlu; or (c) one of p or q is 1.

In some embodiments, the present invention provides a compound of Formula I, wherein the compound is a compound other than

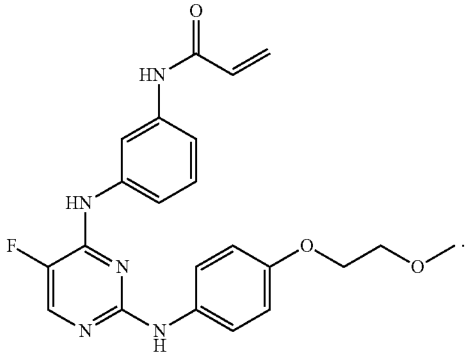 [SMILES: C=CC(=O)Nc1cccc(Nc2nc(Nc3ccc(OCCOC)cc3)ncc2F)c1]

In some embodiments, the present invention provides a compound of Formula I, wherein the compound is a compound other than

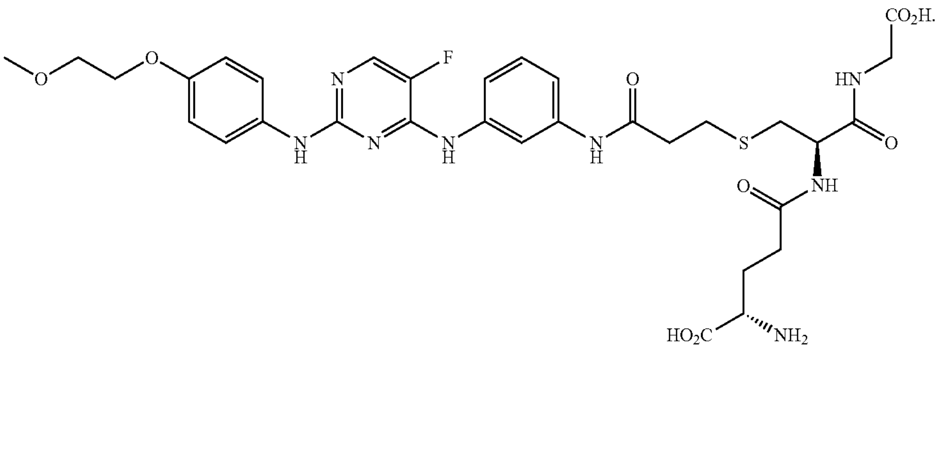 [SMILES: COCCOc1ccc(Nc2ncc(F)c(Nc3cccc(NC(=O)CCSC[C@H](NC(=O)CC[C@H](N)C(=O)O)C(=O)NCC(=O)O)c3)n2)cc1]

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "carbocyclic", "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "carbocyclic" (or "cycloaliphatic" or "carbocycle" or "cycloalkyl") refers to a monocyclic $C_3$-$C_8$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, "aralkyl" refers to a straight or branched aliphatic group in which one of the hydrogen atoms of the aliphatic is replaced by an aryl group, wherein the aliphatic group has from 1 to 10 carbon atoms. Substituted aralkyl groups may be substituted at the aliphatic, the aryl, or both the aliphatic and the aryl portions of the group. Representative aralkyl groups include but are not limited to benzyl and phenethyl groups and fused (cycloalkylaryl)alkyl groups such as 4-ethyl-indanyl.

As used herein, an "amino acid fragment" The term "amino acid fragment" refers to a portion of an amino acid, such as by way of example only, the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), or a dipeptide, tripeptide or other polypeptide comprising a combination of the 20 common amino acids or a non-natural amino acid. In some embodiments, the amino acid fragment is attached to the compound of Formula VII via the side chain of the amino acid. In one embodiment, the amino acid fragment is a cysteine fragment wherein the remaining portion of the compound of Formula VII is bound via a sulfur bond. In another embodiment, the amino acid fragment is a glutathione fragment wherein the remaining portion of a compound of Formula VII is bound via a sulfur bond of the glutathione fragment. In another embodiment, the amino acid fragments are derived from beta-amino acids. In further embodiments, the amino acid fragments are derived from portions of polypeptides or proteins. In yet further embodiments, the amino acid fragment is attached to the compound of Formula VII via the N-terminal or the acyl-terminal of the amino acid.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

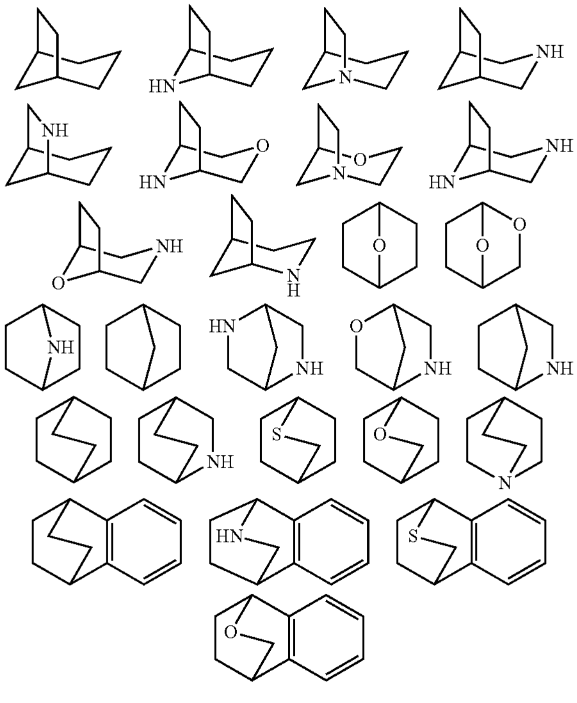

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

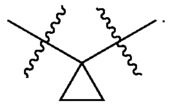 [SMILES: *C1(*)CC1]

The term "cycloalkylalkyl" refers to a bivalent straight or branched aliphatic group that is substituted with a cycloalkyl group, wherein the aliphatic group has from 1 to 10 carbon atoms. Examples of a cycloalkylalkyl group include $-(CH_2)_x$-cyclopentyl, $-(CH_2)_x$-cyclohexyl, $-(CH_2)_x$-cycloheptyl, etc., wherein x is 1-10. In some embodiments, the aliphatic chain of a cycloalkylalkyl group may be straight or branched, for example, $-(CH_2)_yCH(CH_3)(CH_2)_y$-cyclopentyl, $-(CH_2)_yCH(CH_3)(CH_2)_y$-cyclohexyl, $-(CH_2)_yCH(CH_3)(CH_2)_y$-cycloheptyl, etc., wherein y is 0-10. In some embodiments, the cycloalkyl ring of a cycloalkylalkyl group is saturated or partially unsaturated. Substituted cycloalkylalkyl groups may be substituted at the aliphatic, the cycloalkyl, or both the aliphatic and the cycloalkyl portions of the group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, 1,3-dihydro-2H-benzo[d]imidazole-2-one, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 $\pi$ electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted.

The term "heteroaralkyl" refers to an straight or branched aliphatic group substituted by a heteroaryl, wherein the aliphatic group has from 1 to 10 carbon atoms and wherein the aliphatic and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "heterocyclylalkyl" refers to a bivalent straight or branched aliphatic group that is substituted with a heterocyclyl moiety, wherein the aliphatic group has from 1 to 10 carbon atoms. Examples of a heterocyclylalkyl group include, without limitation, $-(CH_2)_x$-piperidinyl, $-(CH_2)_x$-piperazinyl, $-(CH_2)_x$-pyrrolidinyl, $-(CH_2)_x$- morpholinyl, —$(CH_2)_x$-pyrrolidinyl, —$(CH_2)_x$-tetrahydrofuranyl, —$(CH_2)_x$-tetrahydropyranyl, etc., wherein x is 1-10. In some embodiments, the aliphatic chain of a heterocyclylalkyl group may be straight or branched, for example, —$(CH_2)_yCH(CH_3)(CH_2)_y$-piperidinyl, —$(CH_2)_yCH(CH_3)(CH_2)_y$-tetrahydrofuranyl, —$(CH_2)_yCH(CH_3)(CH_2)_y$-tetrahydropyranyl, —$(CH_2)_yCH(CH_3)(CH_2)_y$-morpholinyl, etc., wherein y is 0-10. In some embodiments, the heterocyclyl ring of a heterocyclylalkyl group is saturated or partially unsaturated. Substituted heterocyclylalkyl groups may be substituted at the aliphatic, the heterocyclyl, or both the aliphatic and the heterocyclyl portions of the group.

An "alkoxy" group is —O-(aliphatic), wherein aliphatic is defined above.

An "alkoxyalkyl" group is -(aliphatic)-O-(aliphatic), wherein aliphatic is defined above.

An "amino" group is a radical of the formula —$NH_2$.

An "alkylamino" group is a radical of the formula: —NH-aliphatic or —N(aliphatic)$_2$, wherein each aliphatic is independently as defined above.

A "carboxy" group is a radical of the formula —C(O)OH.

An "aminocarbonyl" group is a radical of the formula —C(O)N$(R^{\#})_2$, —C(O)NH$(R^{\#})$ or —C(O)$NH_2$, wherein each $R^{\#}$ is independently a substituted or unsubstituted aliphatic, cycloalkyl, aryl, aralkyl, heterocyclyl, heterocyclylalkyl, heteroaryl or heteroaralkyl group as defined herein.

An "acylamino" group is a radical of the formula: —NHC(O)$(R^{\#})$ or —N(alkyl)C(O)$(R^{\#})$, wherein each alkyl and $R^{\#}$ are independently as defined above.

An "alkylsulfonylamino" group is a radical of the formula: —$NHSO_2(R^{\#})$ or —N(alkyl)$SO_2(R^{\#})$, wherein each aliphatic and $R^{\#}$ are defined above.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —$O(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH═CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR^\circ$, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —($C_{1-4}$ straight or branched alkylene)O—$N(R^\circ)_2$; or —($C_{1-4}$ straight or branched)alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^{\bullet}$, —(halo$R^{\bullet}$), —$(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR^{\bullet}$, —($C_{1-4}$ straight or branched alkylene)C(O)$OR^{\bullet}$, or —$SSR^{\bullet}$ wherein each $R^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include ═O and ═S.

Suitable divalent substituents on a saturated carbon atom of an "optionally substituted" group include the following: ═O ("oxo"), ═S, ═$NNR^*_2$, ═$NNHC(O)R^*$, ═$NNHC(O)OR^*$, ═$NNHS(O)_2R^*$, ═$NR^*$, ═$NOR^*$, —$O(C(R^*_2))_{2-3}O$—, or —$S(C(R^*_2))_{2-3}S$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^{\bullet}$, -(halo$R^{\bullet}$), —OH, —$OR^{\bullet}$, —O(halo$R^{\bullet}$), —CN, —C(O)OH, —C(O)$OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —$C(O)R^\dagger$, —$C(O)OR^\dagger$, —$C(O)C(O)R^\dagger$, —$C(O)CH_2C(O)R^\dagger$, —$S(O)_2R^\dagger$, —$S(O)_2NR^\dagger_2$, —$C(S)NR^\dagger_2$, —$C(NH)NR^\dagger_2$, or —$N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —$R^\bullet$, -(halo$R^\bullet$), —OH, —$OR^\bullet$, —O(halo$R^\bullet$), —CN, —C(O)OH, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms.

As used herein, the term "irreversible" or "irreversible inhibitor" refers to an inhibitor (i.e. a compound) that is able to be covalently bonded to a target protein kinase in a substantially non-reversible manner. That is, whereas a reversible inhibitor is able to bind to (but is generally unable to form a covalent bond) the target protein kinase, and therefore can become dissociated from the target protein kinase, an irreversible inhibitor will remain substantially bound to the target protein kinase once covalent bond formation has occurred. Irreversible inhibitors usually display time dependency, whereby the degree of inhibition increases with the time with which the inhibitor is in contact with the enzyme. Methods for identifying if a compound is acting as an irreversible inhibitor are known to one of ordinary skill in the art. Such methods include, but are not limited to, enzyme kinetic analysis of the inhibition profile of the compound with the protein kinase target, the use of mass spectrometry of the protein drug target modified in the presence of the inhibitor compound, discontinuous exposure, also known as "washout," experiments, and the use of labeling, such as radiolabelled inhibitor, to show covalent modification of the enzyme, as well as other methods known to one of skill in the art.

As used herein, the term "inhibitor" is defined as a compound that binds to and/or inhibits the target protein kinase with measurable affinity. In certain embodiments, an inhibitor has an $IC_{50}$ and/or binding constant of less about 50 μM, less than about 1 μM, less than about 500 nM, less than about 100 nM, or less than about 10 nM.

The terms "measurable affinity" and "measurably inhibit," as used herein, means a measurable change in at least one of ErbB1, ErbB2, ErbB3, ErbB4, a TEC-kinase (e.g., TEC, BTK, ITK, RLK or BMX), and/or JAK3 activity between a sample comprising a compound of the present invention, or composition thereof, and at least one of ErbB1, ErbB2, ErbB3, ErbB4, a TEC-kinase (e.g., TEC, BTK, ITK, RLK or BMX), and/or JAK3, and an equivalent sample comprising at least one of ErbB1, ErbB2, ErbB3, ErbB4, a TEC-kinase (e.g., TEC, BTK, ITK, RLK or BMX), and/or JAK3, in the absence of said compound, or composition thereof.

3. Description of Exemplary Compounds

According to one aspect, the present invention provides a compound of Formula I:

I

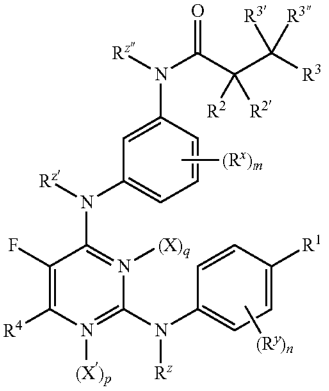

or a pharmaceutically acceptable salt thereof, wherein:

X and X' are each independently O;

p and q are each independently 0 or 1, wherein p and q are not both 1;

$R^1$ is —OR', $—OCH_2CH_2OR'$ or $—OCH_2CO_2H$;

R' is —H, $—CH_3$, $—SO_3H$ or -Glu;

each Glu is a glucuronyl moiety;

$R^2$ and $R^3$ are each independently —H, —OH, $—OSO_3H$, —OGlu, $—SR^5$, or:

$R^2$ and $R^3$ are taken together to form a double bond; or:

$R^2$ and $R^3$ are taken together with their intervening atoms to form an epoxide moiety;

$R^{2'}$ is —H, or:

$R^2$ and $R^{2'}$ are taken together to form ═O;

$R^{3'}$ and $R^{3''}$ are each —H, or:

$R^{3'}$ and $R^{3''}$ are taken together to form ═O;

$R^4$ is —H, —OH, $—OSO_3H$ or —OGlu;

$R^5$ is selected from:

i

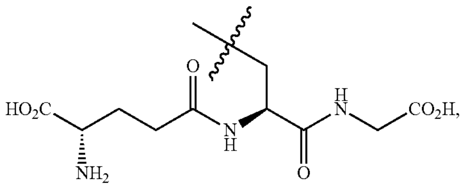

-continued ii

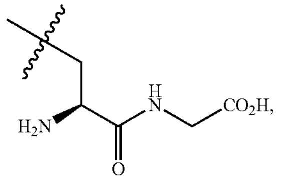

iii

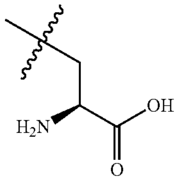

or iv

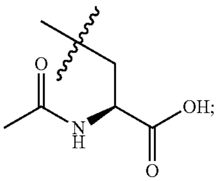

$R^x$ and $R^y$ are each independently —OH, $—OSO_3H$, or —OGlu;

$R^z$, $R^{z'}$ and $R^{z''}$ are each independently —H, $—CH_3$, —OH, $—OSO_3H$, or —OGlu; or $R^{z''}$ and $R^3$ are taken together to form —O—;

m and n are each independently 0, 1, 2, 3 or 4, provided that when $R^2$ and $R^3$ are taken together to form a double bond, at least one of the following is true:

(a) $R^1$ is —OH, $—OSO_3H$, —OGlu, $—OCH_2CH_2OH$, $—OCH_2CO_2H$, $—OCH_2CH_2OSO_3H$ or $—OCH_2CH_2OGlu$;

(b) at least one of $R^4$, $R^x$, $R^y$, $R^z$, $R^{z'}$ and $R^{z''}$ is —OH, $—OSO_3H$ or —OGlu; or (c) one of p or q is 1;

wherein the compound is a compound other than

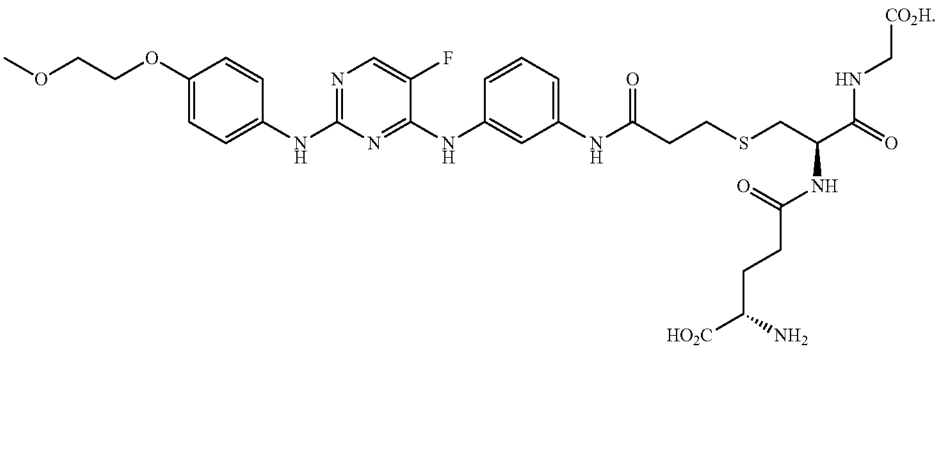 [SMILES: COCCOc1ccc(Nc2ncc(F)c(Nc3cccc(NC(=O)CCSC[C@H](NC(=O)CC[C@H](N)C(=O)O)C(=O)NCC(=O)O)c3)n2)cc1]

In some embodiments, the present invention provides a compound of Formula I':

I'

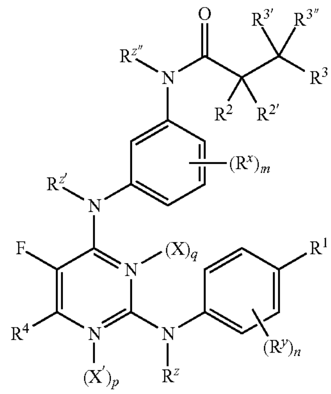

or a pharmaceutically acceptable salt thereof, wherein:

X and X' are each independently O;

p and q are each independently 0 or 1, wherein p and q are not both 1;

$R^1$ is —OR', —$OCH_2CH_2OR'$ or —$OCH_2CO_2H$;

R' is —H, —$CH_3$, —$SO_3H$ or -Glu;

each Glu is a glucuronyl moiety;

$R^2$ and $R^3$ are each independently —H, —OH, —$OSO_3H$ or —OGlu, or:

$R^2$ and $R^3$ are taken together to form a double bond; or:

$R^2$ and $R^3$ are taken together with their intervening atoms to form an epoxide moiety;

$R^{2'}$ is —H, or:

$R^2$ and $R^{2'}$ are taken together to form ═O;

$R^{3'}$ and $R^{3''}$ are each —H, or:

$R^{3'}$ and $R^{3''}$ are taken together to form ═O;

$R^4$ is —H, —OH, —$OSO_3H$ or —OGlu;

$R^x$ and $R^y$ are each independently —OH, —$OSO_3H$, or —OGlu;

$R^z$, $R^{z'}$ and $R^{z''}$ are each independently —H, —$CH_3$, —OH, —$OSO_3H$, or —OGlu; or $R^{z''}$ and $R^3$ are taken together to form —O—;

m and n are each independently 0, 1, 2, 3 or 4, provided that when $R^2$ and $R^3$ are taken together to form a double bond, at least one of the following is true:

(a) $R^1$ is —OH, —$OSO_3H$, —OGlu, —$OCH_2CH_2OH$, —$OCH_2CO_2H$, —$OCH_2CH_2OSO_3H$ or —$OCH_2CH_2OGlu$;

(b) at least one of $R^4$, $R^x$, $R^y$, $R^z$, $R^{z'}$ and $R^{z''}$ is —OH, —$OSO_3H$ or —OGlu; or (c) one of p or q is 1.

In some embodiments, the present invention provides a compound of Formula I'':

I''

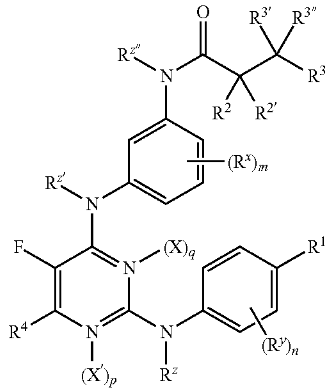

or a pharmaceutically acceptable salt thereof, wherein:

X and X' are each independently O;

p and q are each independently 0 or 1, wherein p and q are not both 1;

$R^1$ is —OR', —$OCH_2CH_2OR'$ or —$OCH_2CO_2H$;

R' is —H, —$CH_3$, —$SO_3H$ or -Glu;

each Glu is a glucuronyl moiety;

$R^2$ is —H, —OH, —$OSO_3H$ or —OGlu;

$R^3$ is —$SR^5$;

$R^{2'}$ is —H, or:

$R^2$ and $R^{2'}$ are taken together to form ═O;

$R^{3'}$ and $R^{3''}$ are each —H, or:

$R^{3'}$ and $R^{3''}$ are taken together to form ═O;

$R^4$ is —H, —OH, —$OSO_3H$ or —OGlu;

$R^5$ is selected from:

i

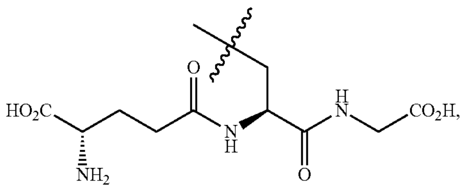

ii

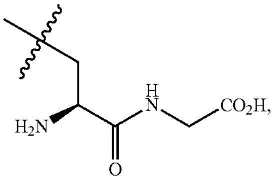

iii

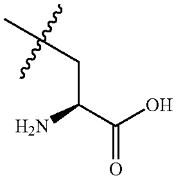

or

-continued iv

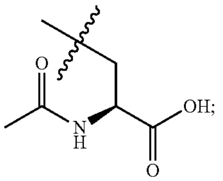

$R^x$ and $R^y$ are each independently —OH, —$OSO_3H$, or —OGlu;

$R^z$, $R^{z\prime}$ and $R^{z\prime\prime}$ are each independently —H, —$CH_3$, —OH, —$OSO_3H$, or —OGlu; or $R^{z\prime\prime}$ and $R^3$ are taken together to form —O—;

m and n are each independently 0, 1, 2, 3 or 4;

wherein the compound is a compound other than

—$OSO_3H$, —OGlu, —$OCH_2CH_2OH$, —$OCH_2CH_2OCH_3$, —$OCH_2CH_2OSO_3H$, —$OCH_2CH_2OGlu$ and —$OCH_2CO_2H$.

In some embodiments, $R^1$ is —OH. In some embodiments, $R^1$ is —$OCH_3$. In some embodiments, $R^1$ is —$OSO_3H$. In some embodiments, $R^1$ is —OGlu. In some embodiments, $R^1$ is —$OCH_2CH_2OH$. In some embodiments, $R^1$ is —$OCH_2CH_2OCH_3$. In some embodiments, $R^1$ is —$OCH_2CH_2OSO_3H$. In some embodiments, $R^1$ is —$OCH_2CH_2OGlu$.

As defined generally above, $R^2$ is selected from —H, —OH, —$OSO_3H$ and —OGlu. In some embodiments, $R^2$ is —H. In some embodiments, $R^2$ is selected from —OH, —$OSO_3H$ and —OGlu. In some embodiments, $R^2$ is —OH. In some embodiments, $R^2$ is —$OSO_3H$. In some embodiments, $R^2$ is —OGlu.

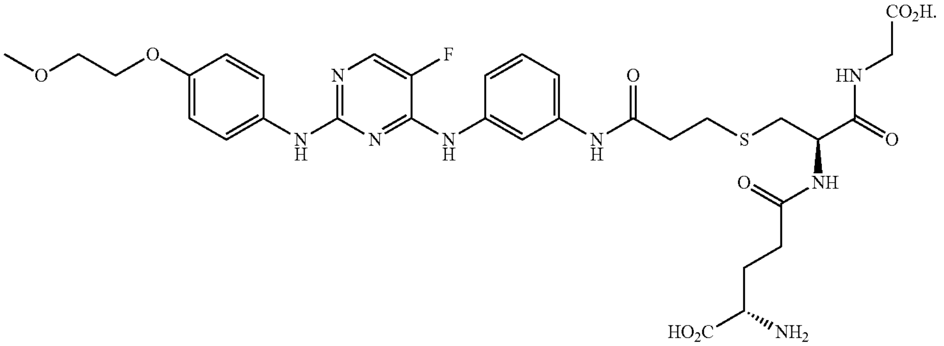

As used herein, the term “glucuronyl moiety” refers to a group having the structure:

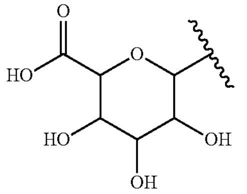 [SMILES: *C1OC(C(=O)O)C(O)C(O)C1O]

wherein the wavy line depicted designates the point of attachment to a compound of Formula I.

In some embodiments, an —OH group on a compound of Formula I is glucuronidated to a —OGlu group. In some embodiments, an —OH group of Formula I is sulfated to a —$OSO_3H$ group.

As defined generally above, $R^1$ is —OR', —$OCH_2CH_2OR'$ or —$OCH_2CO_2H$. In some embodiments, $R^1$ is —OR'. In some embodiments, $R^1$ is —$OCH_2CO_2H$. In certain embodiments, $R^1$ is —$OCH_2CH_2OR'$.

As defined generally above, R' is —H, —$CH_3$, —$SO_3H$ or -Glu. In some embodiments, R' is —H. In some embodiments, R' is selected from —$CH_3$, —$SO_3H$ and -Glu. In some embodiments, R' is —$CH_3$. In some embodiments, R' is —$SO_3H$. In some embodiments, R' is -Glu. Accordingly, in some embodiments, $R^1$ is selected from —OH, —$OCH_3$, As defined generally above, $R^3$ is selected from —H, —OH, —$OSO_3H$, —OGlu and —$SR^5$. In some embodiments, $R^3$ is —H. In some embodiments, $R^3$ is selected from —OH, —$OSO_3H$ and —OGlu. In some embodiments, $R^3$ is —OH. In some embodiments, $R^3$ is —$OSO_3H$. In some embodiments, $R^3$ is —OGlu.

In some embodiments, $R^3$ is —$SR^5$. In some such embodiments, $R^5$ is

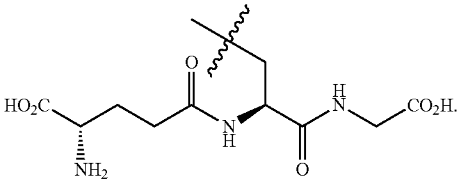 [SMILES: *C[C@H](NC(=O)CC[C@H](N)C(=O)O)C(=O)NCC(=O)O]

Such moiety is generally referred to as a glutathione fragment.

In some embodiments, $R^3$ is —$SR^5$, wherein $R^5$ is

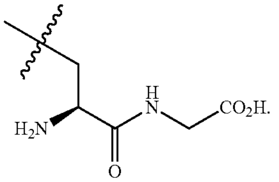 [SMILES: *C[C@H](N)C(=O)NCC(=O)O]

Such moiety is generally referred to as a cysteine-glycine fragment.

In some embodiments, $R^3$ is —$SR^5$, wherein $R^5$ is

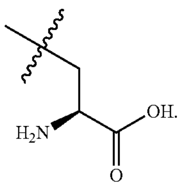 [SMILES: *C[C@H](N)C(=O)O]

Such moiety is generally referred to as a cysteine fragment.

In some embodiments, $R^3$ is —$SR^5$, wherein $R^5$ is

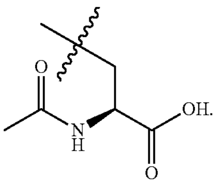 [SMILES: *C[C@H](NC(C)=O)C(=O)O]

Such moiety is generally referred to as an N-acetyl cysteine fragment.

In some embodiments, $R^2$ is H and $R^3$ is —$SR^5$. In some such embodiments, $R^5$ is

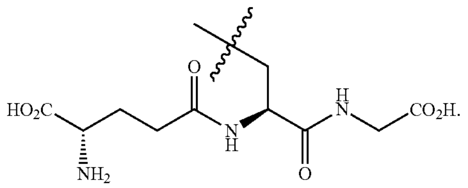 [SMILES: *C[C@H](NC(=O)CC[C@H](N)C(=O)O)C(=O)NCC(=O)O]

In some embodiments, $R^2$ is H and $R^3$ is —$SR^5$, wherein $R^5$ is

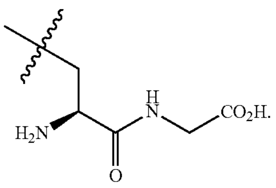 [SMILES: *C[C@H](N)C(=O)NCC(=O)O]

In some embodiments, $R^2$ is H and $R^3$ is —$SR^5$, wherein $R^5$ is

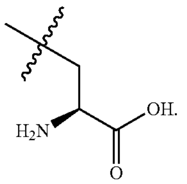 [SMILES: *C[C@H](N)C(=O)O]

In some embodiments, $R^2$ is H and $R^3$ is —$SR^5$, wherein $R^5$ is

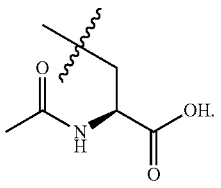 [SMILES: *C[C@H](NC(C)=O)C(=O)O]

In some embodiments, $R^2$ is H, $R^3$ is —$SR^5$ and $R^1$ is —OH. In some such embodiments, $R^5$ is

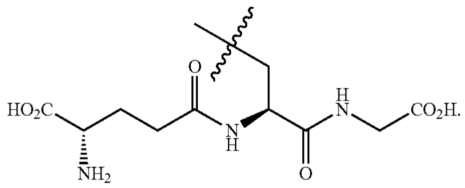 [SMILES: *C[C@H](NC(=O)CC[C@H](N)C(=O)O)C(=O)NCC(=O)O]

In some embodiments, $R^2$ is H, $R^3$ is —$SR^5$ and $R^1$ is —OH, wherein $R^5$ is

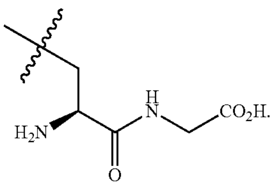 [SMILES: *C[C@H](N)C(=O)NCC(=O)O]

In some embodiments, $R^2$ is H, $R^3$ is —$SR^5$ and $R^1$ is —OH, wherein $R^5$ is

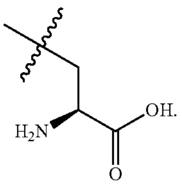 [SMILES: *C[C@H](N)C(=O)O]

In some embodiments, $R^2$ is H, $R^3$ is —$SR^5$ and $R^1$ is —OH, wherein $R^5$ is

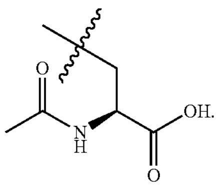 [SMILES: *C[C@H](NC(C)=O)C(=O)O]

In some embodiments, $R^2$ is H, $R^3$ is —$SR^5$ and $R^1$ is —$OCH_2CH_2OH$. In some such embodiments, $R^5$ is

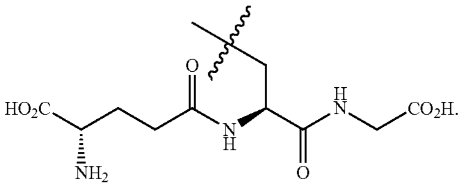 [SMILES: *C[C@H](NC(=O)CC[C@H](N)C(=O)O)C(=O)NCC(=O)O]

In some embodiments, $R^2$ is H, $R^3$ is —$SR^5$ and $R^1$ is —$OCH_2CH_2OH$, wherein $R^5$ is

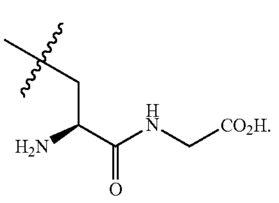 [SMILES: *C[C@H](N)C(=O)NCC(=O)O]

In some embodiments, $R^2$ is H, $R^3$ is —$SR^5$ and $R^1$ is —$OCH_2CH_2OH$, wherein $R^5$ is

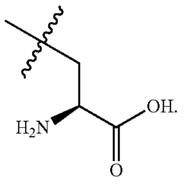 [SMILES: *C[C@H](N)C(=O)O]

In some embodiments, $R^2$ is H, $R^3$ is —$SR^5$ and $R^1$ is —$OCH_2CH_2OH$, wherein $R^5$ is

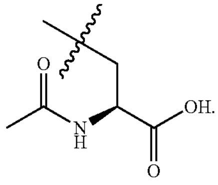 [SMILES: *C[C@H](NC(C)=O)C(=O)O]

In some embodiments, $R^2$ is H, $R^3$ is —$SR^5$ and $R^1$ is —$OCH_2CH_2OCH_3$. In some such embodiments, $R^5$ is

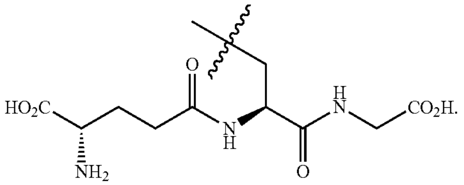 [SMILES: *C[C@H](NC(=O)CC[C@H](N)C(=O)O)C(=O)NCC(=O)O]

In some embodiments, $R^2$ is H, $R^3$ is —$SR^5$ and $R^1$ is —$OCH_2CH_2OCH_3$, wherein $R^5$ is

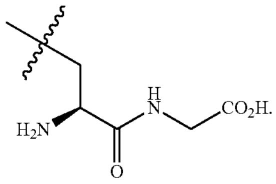 [SMILES: *C[C@H](N)C(=O)NCC(=O)O]

In some embodiments, $R^2$ is H, $R^3$ is —$SR^5$ and $R^1$ is —$OCH_2CH_2OCH_3$, wherein $R^5$ is

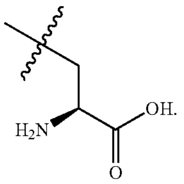 [SMILES: *C[C@H](N)C(=O)O]

In some embodiments, $R^2$ is H, $R^3$ is —$SR^5$ and $R^1$ is —$OCH_2CH_2OCH_3$, wherein $R^5$ is

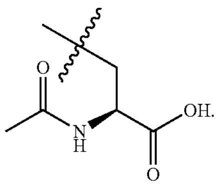 [SMILES: *C[C@H](NC(C)=O)C(=O)O]

In some embodiments, $R^2$ and $R^3$ are the same. In some embodiments, $R^2$ and $R^3$ are each —OH. In some embodiments, $R^2$ and $R^3$ are each —$SO_3H$. In some embodiments, $R^2$ and $R^3$ are each —OGlu.

In some embodiments, $R^2$ and $R^3$ are different. In some embodiments, one of $R^2$ and $R^3$ is —H and the other is —OH. In some embodiments, one of $R^2$ and $R^3$ is —H and the other is —$OSO_3H$. In some embodiments, one of $R^2$ and $R^3$ is —H and the other is —OGlu. In some embodiments, one of $R^2$ and $R^3$ is —OH and the other is —OGlu. In some embodiments, one of $R^2$ and $R^3$ is —OH and the other is —$OSO_3H$.

In some embodiments, $R^2$ is —OH and $R^3$ is —OGlu. In some embodiments, $R^2$ is —OGlu and $R^3$ is —OH. In some embodiments, $R^2$ is —OH and $R^3$ is —$OSO_3H$. In some embodiments, $R^2$ is —$OSO_3H$ and $R^3$ is —OH. In some embodiments, each of $R^2$ and $R^3$ is —$OSO_3H$. In some embodiments, each of $R^2$ and $R^3$ is —OGlu.

In some embodiments, $R^2$ and $R^3$ are taken together to form a double bond.

In some embodiments, $R^2$ and $R^3$ are taken together with their intervening atoms to form an epoxide moiety. In some embodiments, $R^2$ and $R^3$ are taken together with their intervening atoms to form an epoxide moiety and $R^1$ is —$OCH_2CH_2OH$. In some embodiments, $R^2$ and $R^3$ are taken together with their intervening atoms to form an epoxide moiety and $R^1$ is —$OCH_2CH_2OCH_3$.

In some embodiments, $R^{2'}$ is —H. In some embodiments, $R^2$ and $R^{2'}$ are each —H. In some embodiments, $R^2$ is —OH and $R^{2'}$ is —H. In some embodiments, $R^2$ is —$OSO_3H$ and $R^{2'}$ is —H. In some embodiments, $R^2$ is —OGlu and $R^{2'}$ is —H.

In some embodiments, $R^{3'}$ and $R^{3''}$ are each —H. In some embodiments, $R^3$ is —OH and $R^{3'}$ and $R^{3''}$ are each —H. In some embodiments, $R^3$ is —$OSO_3H$ and $R^{3'}$ and $R^{3''}$ are each —H. In some embodiments, $R^3$ is —OGlu and $R^{3'}$ and $R^{3''}$ are each —H. In some embodiments, $R^3$, $R^{3'}$ and $R^{3''}$ are each —H.

In some embodiments, $R^2$ and $R^{2'}$ are taken together to form =O. In some embodiments, $R^2$ and $R^{2'}$ are taken together to form =O and $R^3$, $R^{3'}$ and $R^{3''}$ are each hydrogen. In some embodiments, $R^2$ and $R^{2'}$ are taken together to form =O and $R^3$ is —OH.

In some embodiments, $R^{3'}$ and $R^{3''}$ are taken together to form =O. In some embodiments, $R^{3'}$ and $R^{3''}$ are taken together to form =O and $R^3$ is —H. In some embodiments, $R^{3'}$ and $R^{3''}$ are taken together to form =O and $R^3$ is —OH.

As defined generally above, $R^4$ is selected from —H, —OH, —$OSO_3H$ and —OGlu. In some embodiments, $R^4$ is —H. In some embodiments, $R^4$ is selected from —OH, —$OSO_3H$ and —OGlu. In some embodiments, $R^4$ is selected from —OH, —$OSO_3H$ and OGlu. In some embodiments, $R^4$ is —OH. In some embodiments, $R^4$ is —$OSO_3H$. In some embodiments, $R^4$ is —OGlu.

As defined generally above, p and q are each independently selected from 0 and 1. In some embodiments, one of p and q is 1. In some embodiments, p is 1. In some embodiments, p is 0. In some embodiments, q is 1. In some embodiments, q is 0. In some embodiments, both p and q are 0.

As defined generally above, m and n are independently selected from 0, 1, 2, 3 and 4. In some embodiments, m is 0, 1, 2, 3 or 4. In some embodiments, m is 1, 2, 3 or 4. In some embodiments, n is 0, 1, 2, 3 or 4. In some embodiments, n is 1, 2, 3 or 4. In some embodiments, m is 0. In some embodiments, m is 1. In some embodiments, m is 2. In some embodiments, m is 3. In some embodiments, m is 4. In some embodiments, n is 0. In some embodiments, n is 1. In some embodiments, n is 2. In some embodiments, n is 3. In some embodiments, n is 4.

As defined generally above, $R^x$ is selected from —H, —OH, —$OSO_3H$ and —OGlu. In some embodiments, $R^x$ is —H. In some embodiments, $R^x$ is selected from —OH, —$OSO_3H$ and —OGlu. In some embodiments, $R^x$ is selected from —OH, —$OSO_3H$ and —OGlu. In some embodiments, $R^x$ is —OH. In some embodiments, $R^x$ is —$OSO_3H$. In some embodiments, $R^x$ is —OGlu.

As defined generally above, $R^y$ is selected from —H, —OH, —$OSO_3H$ and —OGlu. In some embodiments, $R^y$ is —H. In some embodiments, $R^y$ is selected from —OH, —$OSO_3H$ and —OGlu. In some embodiments, $R^y$ is selected from —OH, —$OSO_3H$ and —OGlu. In some embodiments, $R^y$ is —OH. In some embodiments, $R^y$ is —$OSO_3H$. In some embodiments, $R^y$ is —OGlu.

As defined generally above, $R^z$, $R^{z'}$ and $R^{z''}$ are each independently selected from —H, —$CH_3$, —OH, —$OSO_3H$ and —OGlu. In some embodiments, $R^z$, $R^{z'}$ and $R^{z''}$ are each independently selected from —$CH_3$, —OH, —$OSO_3H$ and —OGlu. In some embodiments, at least one of $R^z$, $R^{z'}$ and $R^{z''}$ is —OH. In some embodiments, one of $R^z$, $R^{z'}$ and $R^{z''}$ is —OH. In some embodiments, one of $R^z$, $R^{z'}$ and $R^{z''}$ is —$CH_3$. In some embodiments, $R^z$ is —H. In some embodiments, $R^z$ is selected from —$CH_3$, —OH, —$OSO_3H$ and —OGlu. In some embodiments, $R^z$ is —OH. In some embodiments, $R^z$ is —$CH_3$. In some embodiments, $R^z$ is —$OSO_3H$. In some embodiments, $R^z$ is —OGlu. In some embodiments, $R^{z'}$ is —H. In some embodiments, $R^{z'}$ is selected from —$CH_3$, —OH, —$OSO_3H$ and —OGlu. In some embodiments, $R^{z'}$ is —OH. In some embodiments, $R^{z'}$ is —$CH_3$. In some embodiments, $R^{z'}$ is —$OSO_3H$. In some embodiments, $R^{z'}$ is —OGlu. In some embodiments, $R^{z''}$ is —H. In some embodiments, $R^{z''}$ is selected from —$CH_3$, —OH, —$OSO_3H$ and —OGlu. In some embodiments, $R^{z''}$ is —OH. In some embodiments, $R^{z''}$ is —$CH_3$. In some embodiments, $R^{z''}$ is —$OSO_3H$. In some embodiments, $R^{z''}$ is —OGlu.

In some embodiments, $R^{z''}$ and $R^3$ are taken together to form —O—. In some such embodiments, $R^1$ is —$OCH_2CH_2OCH_3$.

In some embodiments of Formula I, I' or I", one of $R^z$, $R^{z'}$ and $R^{z''}$ is —$CH_3$ and $R^1$ is —$OCH_2CH_2OR'$. In some such embodiments, R' is —H. In some embodiments of Formula I, I' or I", $R^z$ is —$CH_3$ and $R^1$ is —$OCH_2CH_2OH$. In some embodiments of Formula I, I' or I", $R^{z'}$ is —$CH_3$ and $R^1$ is —$OCH_2CH_2OH$. In some embodiments of Formula I, I' or I", $R^{z''}$ is —$CH_3$ and $R^1$ is —$OCH_2CH_2OH$.

In some embodiments, the present invention provides a compound of Formula I:

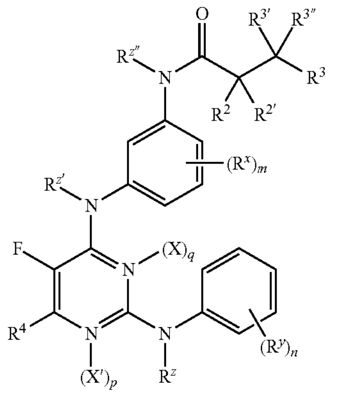

I or a pharmaceutically acceptable salt thereof, wherein:

X and X' are each independently O;

p and q are each independently 0 or 1, wherein p and q are not both 1;

$R^1$ is —OR', —$OCH_2CH_2OR'$ or —$OCH_2CO_2H$;

R' is —H or —$CH_3$;

$R^2$ and $R^3$ are each independently —H or —OH, or:

$R^2$ and $R^3$ are taken together to form a double bond; or:

$R^2$ and $R^3$ are taken together with their intervening atoms to form an epoxide moiety;

$R^{2'}$ is —H, or:

$R^2$ and $R^{2'}$ are taken together to form =O;

$R^{3'}$ and $R^{3''}$ are each —H, or:

$R^{3'}$ and $R^{3''}$ are taken together to form =O;

$R^4$ is —H or —OH;

$R^x$ and $R^y$ are each independently —OH;

$R^z$, $R^{z'}$ and $R^{z''}$ are each independently —H, —$CH_3$ or —OH; or $R^{z''}$ and $R^3$ are taken together to form —O—;

m and n are each independently 0, 1, 2, 3 or 4, provided that when $R^2$ and $R^3$ are taken together to form a double bond, at least one of the following is true:

(a) $R^1$ is —OH, —$OCH_2CH_2OH$ or —$OCH_2CO_2H$;

(b) at least one of $R^4$, $R^z$, $R^{z'}$ and $R^{z''}$ is —OH;

(c) at least one of m and n is 1, 2, 3, or 4; or (d) one of p or q is 1.

As described above, in some embodiments, $R^2$ and $R^3$ are taken together to form a double bond. Accordingly, in some embodiments, the present invention provides a compound of Formula I-a:

I-a

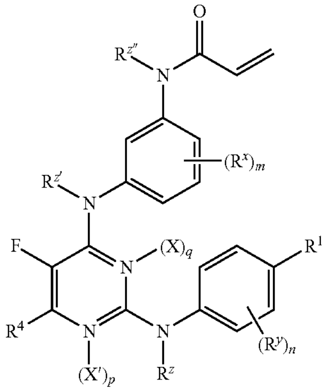

wherein each of $R^1$, $R^4$, $R^z$, $R^{z'}$, $R^{z''}$, $R^x$, $R^y$, X, X', m, n, p and q is as defined above and described herein.

In some embodiments of Formula I-a, $R^1$ is $—OCH_2CH_2OCH_3$ and $R^z$ is —OH.

In some embodiments of Formula I-a, $R^1$ is $—OCH_2CH_2OCH_3$ and $R^{z'}$ is —OH. In some embodiments of Formula I-a, $R^1$ is $—OCH_2CH_2OCH_3$ and $R^{z''}$ is —OH.

In some embodiments of Formula I-a, $R^1$ is $—OCH_2CH_2OCH_3$ and $R^z$ is $—CH_3$. In some embodiments of Formula I-a, $R^1$ is $—OCH_2CH_2OCH_3$ and $R^{z'}$ is $—CH_3$. In some embodiments of Formula I-a, $R^1$ is $—OCH_2CH_2OCH_3$ and $R^{z''}$ is $—CH_3$.

In some embodiments of Formula I-a, $R^1$ is $—OCH_2CH_2OH$ and $R^z$ is $—CH_3$. In some embodiments of Formula I-a, $R^1$ is $—OCH_2CH_2OH$ and $R^{z'}$ is $—CH_3$. In some embodiments of Formula I-a, $R^1$ is $—OCH_2CH_2OH$ and $R^{z''}$ is $—CH_3$.

In some embodiments of Formula I-a, $R^1$ is $—OCH_2CH_2OCH_3$ and p is 1. In some embodiments of Formula I-a, $R^1$ is $—OCH_2CH_2OCH_3$ and q is 1. As described above, in some embodiments, p and q are both 0. Accordingly, in some embodiments, the present invention provides a compound of Formula II:

II

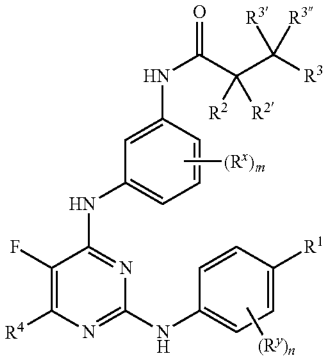

or a pharmaceutically acceptable salt thereof, wherein each of $R^1$, $R^2$, $R^{2'}$, $R^3$, $R^{3'}$, $R^{3''}$, $R^4$, $R^x$, $R^y$, m and n is as defined above and described herein.

In some embodiments of Formula II, $R^2$ and $R^{2'}$ are taken together to form ═O. In some embodiments of Formula II, $R^2$ and $R^{2'}$ are taken together to form ═O and each of $R^3$, $R^{3'}$ and $R^{3''}$ is H. In some such embodiments, $R^1$ is $—OCH_2CH_2OCH_3$.

In some embodiments of Formula II, $R^2$ and $R^{2'}$ are each —H, $R^{3'}$ and $R^{3''}$ are taken together to form ═O. In some embodiments of Formula II, $R^2$ and $R^{2'}$ are each —H, $R^{3'}$ and $R^{3''}$ are taken together to form ═O and $R^2$ and $R^{2'}$ are each —H. In some embodiments of Formula II, $R^2$ and $R^{2'}$ are each —H, $R^{3'}$ and $R^{3''}$ are taken together to form ═O and $R^3$ is —OH. In some such embodiments, $R^1$ is $—OCH_2CH_2OCH_3$.

In some embodiments of Formula II, $R^2$ and $R^{2'}$ are taken together with their intervening atoms to form an epoxide moiety. In some such embodiments, $R^1$ is $—OCH_2CH_2OR'$. In some embodiments of Formula II, $R^2$ and $R^{2'}$ are taken together with their intervening atoms to form an epoxide moiety and $R^1$ is $—OCH_2CH_2OH$. In some embodiments of Formula II, $R^2$ and $R^{2'}$ are taken together with their intervening atoms to form an epoxide moiety and $R^1$ is $—OCH_2CH_2OCH_3$.

In some embodiments of Formula II, $R^2$, $R^{2'}$, $R^{3'}$ and $R^{3''}$ are each —H and $R^3$ is —OH. In some such embodiments, $R^1$ is $—OCH_2CH_2OCH_3$.

In some embodiments, the present invention provides a compound of Formula II:

II

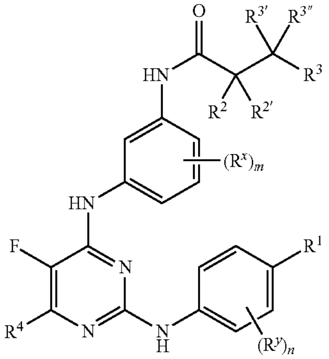

or a pharmaceutically acceptable salt thereof, wherein:

$R^1$ is —OR', $—OCH_2CH_2OR'$ or $—OCH_2CO_2H$;

R' is —H or $—CH_3$;

$R^2$ and $R^3$ are each independently —H or —OH or:

$R^2$ and $R^3$ are taken together to form a double bond; or:

$R^2$ and $R^3$ are taken together with their intervening atoms to form an epoxide moiety;

$R^{2'}$ is —H, or:

$R^2$ and $R^{2'}$ are taken together to form a ═O;

$R^{3'}$ and $R^{3''}$ are each —H, or:

$R^{3'}$ and $R^{3''}$ are taken together to form a ═O;

$R^4$ is —H or —OH;

$R^x$ and $R^y$ are each independently —OH; and m and n are each independently 0, 1, 2, 3 or 4;

provided that when $R^2$ and $R^3$ are taken together to form a double bond, at least one of the following is true:

(a) $R^1$ is —OH, $—OCH_2CH_2OH$ or $—OCH_2CO_2H$; or (b) $R^4$ is —OH;

(c) at least one of m and n is 1, 2, 3 or 4.

In some embodiments, the present invention provides a compound of Formula III:

III

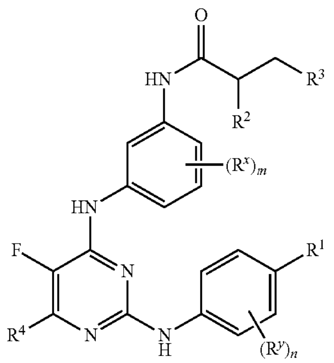

or a pharmaceutically acceptable salt thereof, wherein each of $R^1$, $R^2$, $R^3$, $R^4$, $R^x$, $R^y$, m and n is as defined above and described herein.

In some embodiments of Formula III, $R^2$ is —H and $R^3$ is —OH. In some such embodiments of Formula III, $R^1$ is —$OCH_2CH_2OCH_3$.

In some embodiments of Formula III, $R^2$ and $R^3$ are each —OH.

In some embodiments of Formula III, $R^2$ and $R^3$ are each —OH and $R^1$ is —OH.

In some embodiments of Formula III, $R^2$ and $R^3$ are each —OH and $R^1$ is —$OCH_2CH_2OR'$.

In some embodiments of Formula III, $R^2$ and $R^3$ are each —OH and $R^1$ is —$OCH_2CH_2OH$.

In some embodiments of Formula III, $R^2$ and $R^3$ are each —OH and $R^1$ is —$OCH_2CH_2OCH_3$.

In some embodiments of Formula III, $R^2$ is H and $R^3$ is —$OCH_2CO_2H$. In some such embodiments, $R^1$ is —$OCH_2CH_2OCH_3$.

In some embodiments of Formula III, $R^2$ and $R^3$ are taken together to form an epoxide moiety and $R^1$ is —$OCH_2CH_2OCH_3$. In some embodiments of Formula III, $R^2$ and $R^3$ are taken together to form an epoxide moiety and $R^1$ is —$OCH_2CH_2OH$.

In some embodiments the present invention provides a compound of Formula III:

III

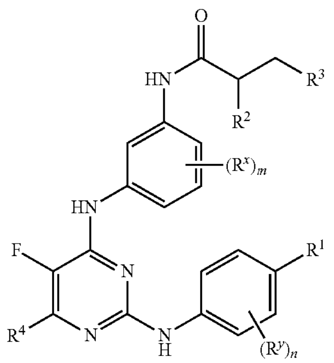

or a pharmaceutically acceptable salt thereof, wherein:

$R^1$ is —OR', —$OCH_2CH_2OR'$ or —$OCH_2CO_2H$;

R' is —H or —$CH_3$;

$R^2$ and $R^3$ are each independently —H or —OH; or:

$R^2$ and $R^3$ are taken together to form a double bond;

$R^4$ is —H or —OH;

$R^x$ and $R^y$ are each independently —OH; and m and n are each independently 0, 1, 2, 3 or 4;

provided that when $R^2$ and $R^3$ are taken together to form a double bond, at least one of the following is true:

(a) $R^1$ is —OH, —$OCH_2CH_2OH$ or —$OCH_2CO_2H$;

(b) $R^4$ is —OH; or (c) at least one of m and n is 1, 2, 3 or 4.

As described above, in some embodiments, $R^2$ and $R^3$ are taken together to form a double bond. Accordingly, in some embodiments, the present invention provides a compound of Formula IV:

IV

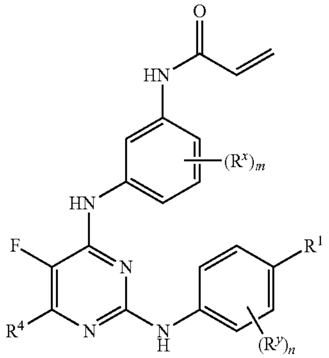

or a pharmaceutically acceptable salt thereof, wherein each of $R^1$, $R^4$, $R^x$, $R^y$, m and n is as defined above and described herein.

In some embodiments of Formula IV, $R^1$ is —$OCH_2CH_2OR'$. In some embodiments of Formula IV, $R^1$ is —$OCH_2CH_2OR'$, wherein R' is —H. Accordingly, in some embodiments for Formula IV, $R^1$ is —$OCH_2CH_2OH$.

In some embodiments of Formula IV, $R^1$ is —$OCH_2CH_2OCH_3$ and $R^4$ is —OH.

In some embodiments of Formula IV, $R^1$ is —OH.

In some embodiments of Formula IV, $R^1$ is —$OCH_2CO_2H$.

In some embodiments of Formula IV, $R^4$ is —OH. In some such embodiments, $R^1$ is —$OCH_2CH_2OCH_3$.

In some embodiments of Formula IV, m is 1. In some embodiments of Formula IV, m is 1 and $R^x$ is —OH. In some embodiments of Formula IV, $R^1$ is —$OCH_2CH_2OCH_3$, m is 1 and $R^x$ is —OH.

In some embodiments of Formula IV, n is 1. In some embodiments of Formula IV, n is 1 and $R^y$ is —OH. In some embodiments of Formula IV, $R^1$ is —$OCH_2CH_2OCH_3$, n is 1 and $R^y$ is —OH.

In some embodiments of Formula IV, the present invention provides a compound selected from the group consisting of:

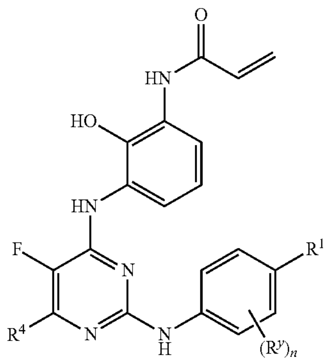

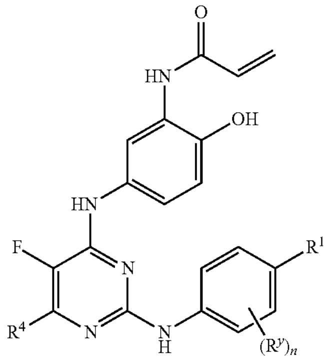

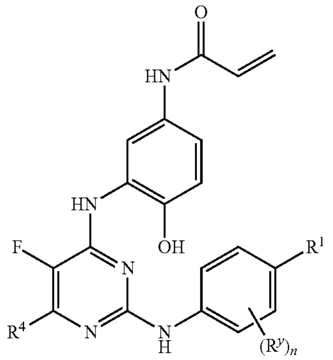

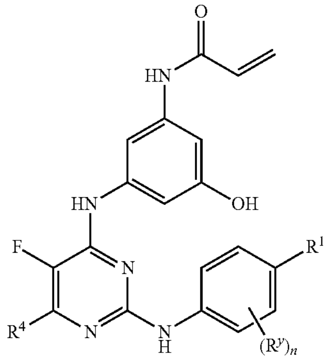

In some embodiments of Formula IV, the present invention provides a compound selected from the group consisting of:

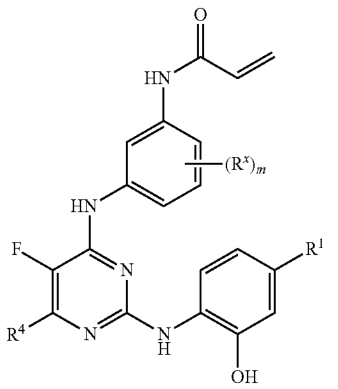

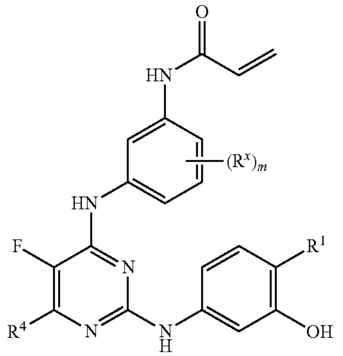

In some embodiments, the present invention provides a compound of Formula IV:

IV

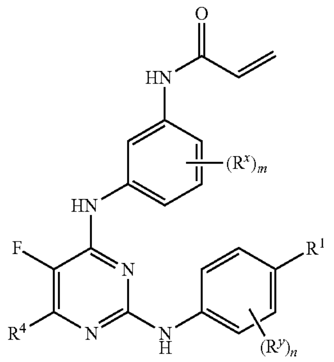

or a pharmaceutically acceptable salt thereof, wherein $R^1$ is —OH, —$OCH_2CH_2OR'$ or —$OCH_2CO_2H$;

R' is —H or —$CH_3$;

$R^4$ is —H or —OH;

$R^x$ and $R^y$ are each independently —OH; and m and n are each independently 0, 1, 2, 3 or 4;

provided that at least one of the following is true:

(a) $R^1$ is —OH, —$OCH_2CH_2OH$ or —$OCH_2CO_2H$; or (b) $R^4$ is —OH; or (c) at least one of m and n is 1, 2, 3 or 4.

In some embodiments, the present invention provides a compound of Formula V:

V

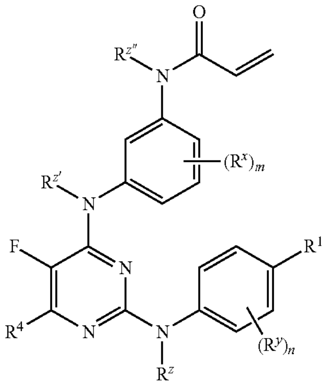

In some embodiments of Formula V, $R^{z''}$ is $—CH_3$ and $R^1$ is $—OCH_2CH_2OH$.

In some embodiments of Formula V, $R^{z'}$ is $—CH_3$ and $R^1$ is $—OCH_2CH_2OH$.

In some embodiments of Formula V, $R^z$ is $—CH_3$ and $R^1$ is $—OCH_2CH_2OH$.

In some embodiments of Formula V, $R^{z''}$ is —OH and $R^1$ is $—OCH_2CH_2OCH_3$.

In some embodiments of Formula V, $R^{z'}$ is —OH and $R^1$ is $—OCH_2CH_2OCH_3$.

In some embodiments of Formula V, $R^z$ is —OH and $R^1$ is $—OCH_2CH_2OCH_3$.

In some embodiments, the present invention provides a compound of Formula VII:

VII

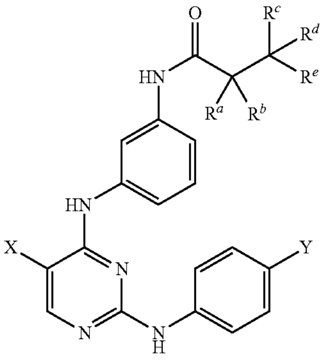

or a pharmaceutically acceptable salt or solvate thereof, wherein each of $R^a$, $R^b$, $R^c$, $R^d$ and $R^e$ are independently selected from H, F, Cl, Br, I, —CN, $—SR^2$, $—OR^3$, $—N(R^3)_2$, and $CO_2R^3$; or one of $R^a$ and $R^b$ together with one of $R^c$, $R^d$ and $R^e$ and the carbon atoms to which they are attached form an epoxide;

X is F, Cl, Br, I or $—CF_3$;

Y is F, Cl, Br or I; $—OC_1$-$C_2$aliphatic optionally substituted with halogen or $—OC_1$-$C_2$aliphatic; an optionally substituted 5-6-membered heteroaryl ring having 1-4 heteroatoms selected from nitrogen, oxygen and sulfur; or an optionally substituted 3-10-membered saturated or partially unsaturated heterocyclic ring having 1-4 heteroatoms selected from nitrogen, oxygen or sulfur;

$R^2$ is selected from H, $C_1$-$C_4$aliphatic, a cysteine amino acid fragment, and a glutathione fragment;

each $R^3$ is independently selected from H, $C_1$-$C_4$aliphatic, phenyl and benzyl;

wherein $R^a$, $R^b$, $R^c$, $R^d$ and $R^e$ cannot all be H.

In some embodiments of Formula VII, one of $R^a$ and $R^b$ is $—OR^3$ and one of $R^c$, $R^d$ and $R^e$ is $—OR^3$. In some such embodiments, $R^3$ is H. In some embodiments of Formula VII, one of $R^a$ and $R^b$ is $—OR^3$, one of $R^c$, $R^d$ and $R^e$ is $—OR^3$, wherein $R^3$ is $C_1$-$C_4$aliphatic. In some embodiments of Formula VII, one of $R^a$ and $R^b$ is $—OR^3$, one of $R^c$, $R^d$ and $R^e$ is $—OR^3$, wherein $R^3$ is phenyl. In some embodiments of Formula VII, one of $R^a$ and $R^b$ is $—OR^3$, one of $R^c$, $R^d$ and $R^e$ is $—OR^3$, wherein $R^3$ is benzyl.

In some embodiments of Formula VII, $R^a$ is H.

In some embodiments of Formula VII, each of $R^a$ and $R^b$ is H.

In some such embodiments, $R^b$ is $—OR^3$. In some such embodiments, $R^3$ is H.

In some embodiments of Formula VII, $R^3$ is H.

In some embodiments of Formula VII, $R^a$ is H, $R^b$ is $—OR^3$ and $R^3$ is H.

In some embodiments of Formula VII, at least two of $R^c$, $R^d$ and $R^e$ are H. In some such embodiments, $R^c$ and $R^d$ are both H.

In some embodiments of Formula VII, $R^e$ is $—OR^3$. In some such embodiments, $R^3$ is H.

In some embodiments of Formula VII, $R^c$ and $R^d$ are both H and $R^e$ is $—OR^3$.

In some embodiments of Formula VII, $R^c$ and $R^d$ are both H, $R^e$ is $—OR^3$ and $R^3$ is H.

In some embodiments of Formula VII, each of $R^a$, $R^b$, $R^c$ and $R^d$ is H, $R^e$ is $—OR^3$ and $R^3$ is H.

In some embodiments of Formula VII, each of $R^a$, $R^c$ and $R^d$ is H and $R^e$ is $—OR^3$.

In some embodiments of Formula VII, each of $R^a$, $R^c$ and $R^d$ is H, $R^e$ is $—OR^3$ and $R^3$ is H.

In some embodiments of Formula VII, each of $R^a$, $R^c$ and $R^d$ is H, each of $R^b$ and $R^e$ is $—OR^3$ and $R^3$ is H.

In some embodiments of Formula VII, each of $R^c$, $R^d$ and $R^e$ are H.

In some embodiments of Formula VII, $R^a$ is H and $R^b$ is $—OR^3$. In some such embodiments, $R^3$ is H.

In some embodiments of formula VII, each of $R^a$, $R^c$, $R^d$ and $R^e$ is H and $R^b$ is —OH.

In some embodiments of formula VII, each of $R^a$, $R^b$, $R^c$ and $R^d$ is H and $R^e$ is —OH.

In some embodiments of Formula VII, $R^a$ is H, $R^b$ is $—OR^3$ and $R^3$ is H.

In some embodiments of formula VII, each of $R^a$, $R^b$, $R^c$ and $R^d$ is H and $R^e$ is $—SR^2$.

In some embodiments of formula VII, each of $R^a$, $R^b$, $R^c$ and $R^d$ is H, $R^e$ is $—SR^2$ and $R^2$ is a cysteine amino acid fragment.

In some embodiments of formula VII, each of $R^a$, $R^b$, $R^c$ and $R^d$ is H, $R^e$ is $—SR^2$ and $R^2$ is a glutathione fragment.

In some embodiments of Formula VII, one of $R^a$ and $R^b$ together with one of $R^c$, $R^d$ and $R^e$ and the carbon atoms to which they are attached form an epoxide.

In some embodiments of Formula VII, one of $R^c$, $R^d$ and $R^e$ is Cl, Br or I. In some embodiments of Formula VII, one of $R^c$, $R^d$ and $R^e$ is Cl.

In some embodiments of Formula VII, X is F.

In some embodiments of Formula VII, X is Cl. In some embodiments of Formula VII, X is Br. In some embodiments of Formula VII, X is I. In some embodiments of Formula VII, X is $CF_3$.

In some embodiments of Formula VII, Y is F. In some embodiments of Formula VII, Y is Cl. In some embodiments of Formula VII, Y is Br. In some embodiments of Formula VII, Y is I.

In embodiments of Formula VII, Y is —$OC_1$-$C_2$ aliphatic optionally substituted with halogen.

In embodiments of Formula VII, Y is —$OC_1$-$C_2$aliphatic optionally substituted with —$OC_1$-$C_2$aliphatic. In some such embodiments, Y is —$OCH_2CH_2OCH_3$.

In some embodiments of Formula VII, Y is —$OCH_3$.

In some embodiments of Formula VII, Y is —$OCH_2CH_3$.

In some embodiments of Formula VII, Y is an optionally substituted 5-6-membered heteroaryl ring having 1-4 heteroatoms selected from nitrogen, oxygen and sulfur. In some embodiments, Y is an optionally substituted 3-10-membered saturated or partially unsaturated heterocyclic ring having 1-4 heteroatoms selected from nitrogen, oxygen or sulfur.

In some embodiments of Formula VII, X is F and Y is —$OCH_3$.

In some embodiments of Formula VII, X is F and Y is —$OCH_2CH_3$.

In some embodiments of Formula VII, X is F and Y is —$OCH_2CH_2OCH_3$.

In some embodiments of Formula VII, X is Cl and Y is —$OCH_3$.

In some embodiments of Formula VII, X is Cl and Y is —$OCH_2CH_3$.

In some embodiments of Formula VII, X is Cl and Y is —$OCH_2CH_2OCH_3$.

In some embodiments, the present invention provides a compound of Formula VII-i:

VII-i

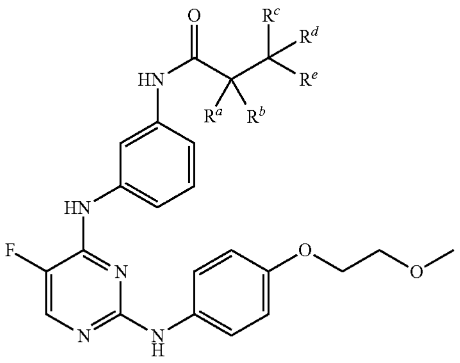

or a pharmaceutically acceptable salt or solvate thereof, wherein each of $R^a$, $R^b$, $R^c$, $R^d$ and $R^e$ is as defined above and described herein.

In some embodiments of formula VII-i, $R^a$ is H.

In some embodiments of formula VII-i, $R^b$ is —$OR^3$. In some such embodiments, $R^b$ is —$OR^3$ wherein $R^3$ is H.

In some embodiments of formula VII-i, at least two of $R^c$, $R^d$ and $R^e$ are H. In some embodiments of formula VII-i, each of $R^c$ and $R^d$ is H.

In some embodiments of formula VII-i, $R^e$ is —$OR^3$. In some such embodiments, $R^e$ is —$OR^3$ wherein $R^3$ is H.

In some embodiments of formula VII-i, each of $R^a$ and $R^b$ is H.

In some embodiments of formula VII-i, each of $R^a$, $R^b$, $R^c$ and $R^d$ is H and $R^e$ is —$SR^2$.

In some embodiments of formula VII-i, each of $R^a$, $R^b$, $R^c$ and $R^d$ is H, $R^e$ is —$SR^2$ and $R^2$ is a cysteine amino acid fragment.

In some embodiments of formula VII-i, each of $R^a$, $R^b$, $R^c$ and $R^d$ is H, $R^e$ is —$SR^2$ and $R^2$ is a glutathione fragment.

In some embodiments of formula VII-i, $R^a$ is H and $R^b$ is —$OR^3$. In some embodiments of formula VII-i, $R^a$ is H, $R^b$ is —$OR^3$ and $R^3$ is H.

In some embodiments of formula VII-i, each of $R^a$, $R^c$, $R^d$ and $R^e$ is H and $R^b$ is —OH.

In some embodiments of formula VII-i, each of $R^a$, $R^b$, $R^c$ and $R^d$ is H and $R^e$ is —OH.

In some embodiments of formula VII-i, each of $R^a$, $R^c$ and $R^d$ is H and each of $R^b$ and $R^e$ is —OH.

In some embodiments of formula VII-i, each of $R^c$, $R^d$ and $R^e$ are H.

In some embodiments of formula VII-i, one of $R^a$ and $R^b$ together with one of $R^c$, $R^d$ and $R^e$ and the carbon atoms to which they are attached form an epoxide.

Compounds where $R^2$ and $R^3$ together form a double bond possess an acrylamide or α,β-unsaturated carbonyl moiety. Such acrylamide moieties are capable of and particularly suitable for covalently binding to a key cysteine residue in the binding domain of certain protein kinases. Protein kinases having a cysteine residue in the binding domain are known to one of ordinary skill in the art and include ErbB1, ErbB2, and ErbB4, or a mutant thereof. In certain embodiments, compounds of the present invention having an acrylamide group target one or more of the following cysteine residues:

ERBB1 ITQLMPFGCLLDYVREH

ERBB2 VTQLMPYGCLLDHVREN

ERBB4 VTQLMPHGCLLEYVHEH

Thus, in some embodiments, compounds of the present invention having an acrylamide group are capable of covalently binding to a cysteine residue thereby irreversibly inhibiting the enzyme. In certain embodiments, the cysteine residue is Cys797 of ErbB1, Cys805 of ErbB2 and Cys803 of ErbB4, or a mutant thereof, where the provided residue numbering is in accordance with Uniprot (code POO533 for ErbB1; code PO4626 for ErbB2, and Q15303 for ErbB4). It will be understood that the Cys of ErbB1 (EGFR) is variably called 773 or 797 depending on whether the parent sequence contains the signal peptide or not. Thus, in accordance with the present invention, the relevant cysteine residue of ErbB1 may be described as Cys 773 or Cys 797 and these terms are used interchangeably.

In certain embodiments, compounds of the present invention having an acrylamide group are capable of covalently binding to a cysteine residue of TEC, thereby irreversibly inhibiting the enzyme. In some embodiments, the cysteine residue is Cys 449.

In certain embodiments, compounds of the present invention having an acrylamide group are capable of covalently binding to a cysteine residue of BTK, thereby irreversibly inhibiting the enzyme. In some embodiments, the cysteine residue is Cys 481.

In certain embodiments, compounds of the present invention having an acrylamide group are capable of covalently binding to a cysteine residue of ITK, thereby irreversibly inhibiting the enzyme. In some embodiments, the cysteine residue is Cys 442.

In certain embodiments, compounds of the present invention having an acrylamide group are capable of covalently binding to a cysteine residue of BMX, thereby irreversibly inhibiting the enzyme. In some embodiments, the cysteine residue is Cys 496.

In certain embodiments, compounds of the present invention having an acrylamide group are capable of covalently binding to a cysteine residue of JAK3, thereby irreversibly inhibiting the enzyme. In some embodiments, the cysteine residue is Cys 909.

In certain embodiments, compounds of the present invention having an acrylamide group are capable of covalently binding to a cysteine residue of TXK, thereby irreversibly inhibiting the enzyme. In some embodiments, the cysteine residue is Cys 350.

Exemplary compounds of the present invention are set forth in Table 1 below.

TABLE 1

| Exemplary Compounds |
|---|
| 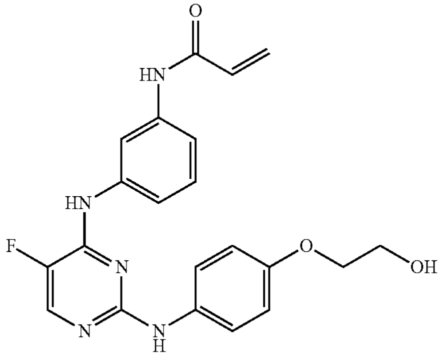 [SMILES: C=CC(=O)Nc1cccc(Nc2nc(Nc3ccc(OCCO)cc3)ncc2F)c1] I-1 |
| 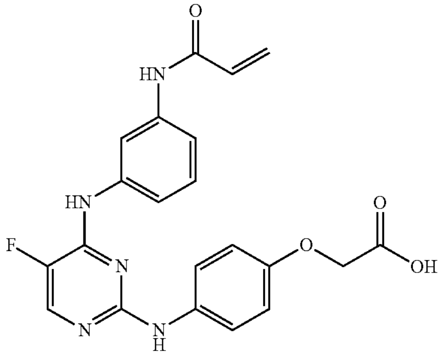 [SMILES: C=CC(=O)Nc1cccc(Nc2nc(Nc3ccc(OCC(=O)O)cc3)ncc2F)c1] I-2 |
| 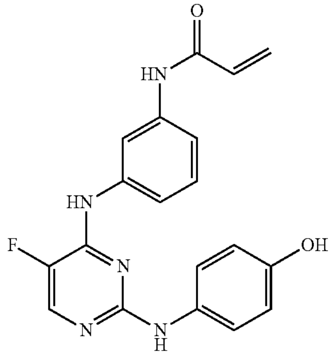 [SMILES: C=CC(=O)Nc1cccc(Nc2nc(Nc3ccc(O)cc3)ncc2F)c1] I-3 |

TABLE 1-continued

| Exemplary Compounds |
|---|
| 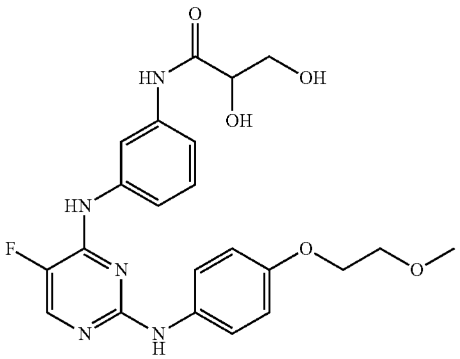 [SMILES: COCCOc1ccc(Nc2ncc(F)c(Nc3cccc(NC(=O)C(O)CO)c3)n2)cc1] I-4 |
| 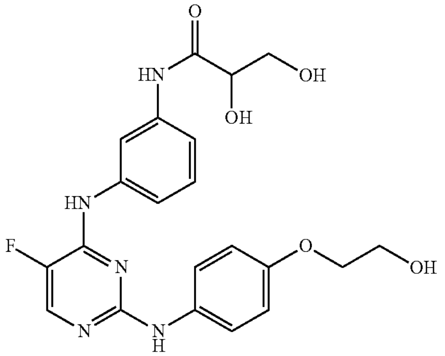 [SMILES: O=C(Nc1cccc(Nc2nc(Nc3ccc(OCCO)cc3)ncc2F)c1)C(O)CO] I-5 |
| 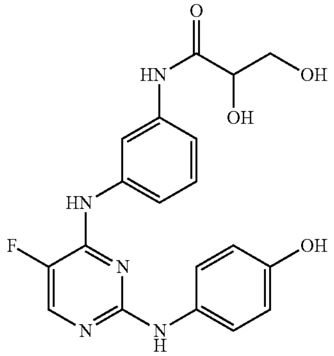 [SMILES: O=C(Nc1cccc(Nc2nc(Nc3ccc(O)cc3)ncc2F)c1)C(O)CO] I-6 |
| 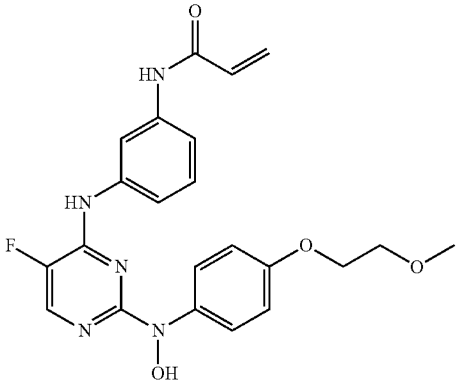 [SMILES: C=CC(=O)Nc1cccc(Nc2nc(N(O)c3ccc(OCCOC)cc3)ncc2F)c1] I-7 |

TABLE 1-continued
| Exemplary Compounds |
|---|
I-8
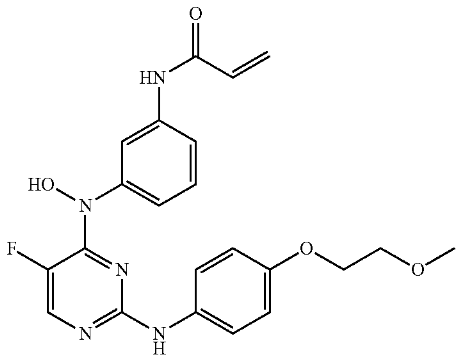 [SMILES: C=CC(=O)Nc1cccc(N(O)c2nc(Nc3ccc(OCCOC)cc3)ncc2F)c1]
I-9
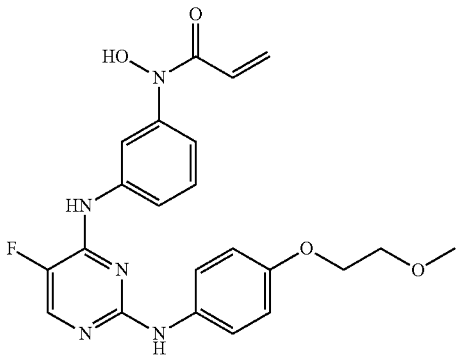 [SMILES: C=CC(=O)N(O)c1cccc(Nc2nc(Nc3ccc(OCCOC)cc3)ncc2F)c1]
I-10
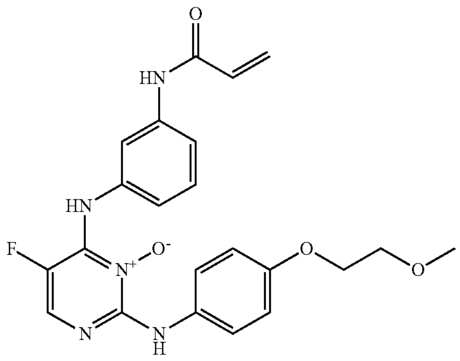 [SMILES: C=CC(=O)Nc1cccc(Nc2c(F)cnc(Nc3ccc(OCCOC)cc3)[n+]2[O-])c1]
I-11
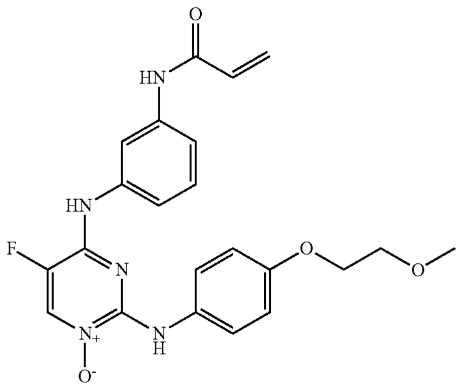 [SMILES: C=CC(=O)Nc1cccc(Nc2nc(Nc3ccc(OCCOC)cc3)[n+]([O-])cc2F)c1]
TABLE 1-continued
| Exemplary Compounds |
|---|
I-12
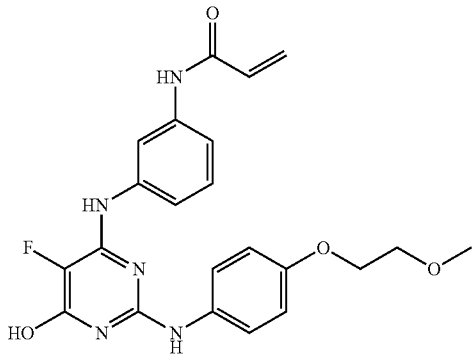 [SMILES: C=CC(=O)Nc1cccc(Nc2nc(Nc3ccc(OCCOC)cc3)nc(O)c2F)c1]
I-13
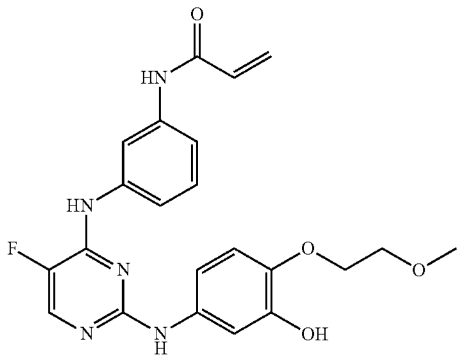 [SMILES: C=CC(=O)Nc1cccc(Nc2nc(Nc3ccc(OCCOC)c(O)c3)ncc2F)c1]
I-14
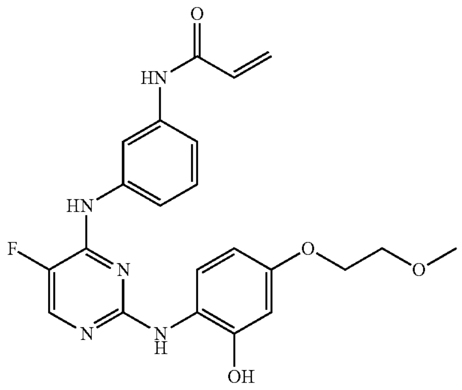 [SMILES: C=CC(=O)Nc1cccc(Nc2nc(Nc3ccc(OCCOC)cc3O)ncc2F)c1]
I-15
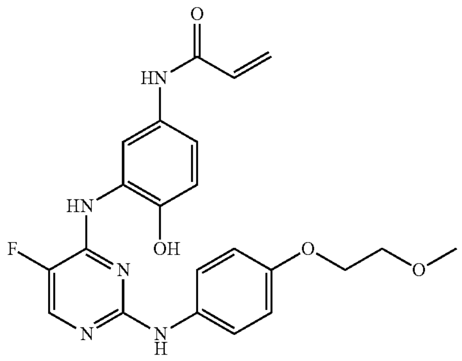 [SMILES: C=CC(=O)Nc1ccc(O)c(Nc2nc(Nc3ccc(OCCOC)cc3)ncc2F)c1]

TABLE 1-continued
| Exemplary Compounds |
|---|
I-16
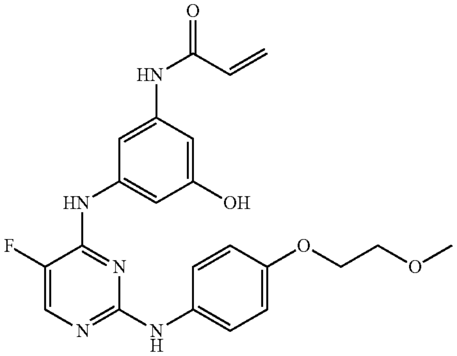 [SMILES: C=CC(=O)Nc1cc(O)cc(Nc2nc(Nc3ccc(OCCOC)cc3)ncc2F)c1]
I-17
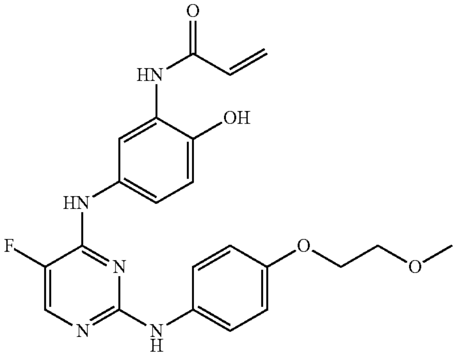 [SMILES: C=CC(=O)Nc1cc(Nc2nc(Nc3ccc(OCCOC)cc3)ncc2F)ccc1O]
I-18
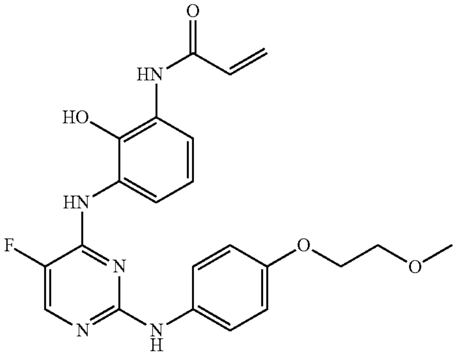 [SMILES: C=CC(=O)Nc1cccc(Nc2nc(Nc3ccc(OCCOC)cc3)ncc2F)c1O]
I-19
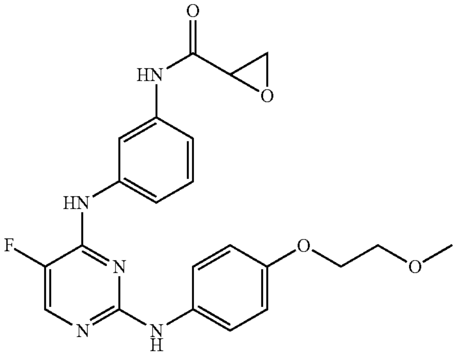 [SMILES: COCCOc1ccc(Nc2ncc(F)c(Nc3cccc(NC(=O)C4CO4)c3)n2)cc1]
TABLE 1-continued
| Exemplary Compounds |
|---|
I-20
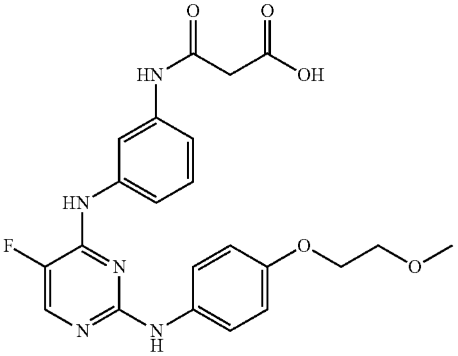 [SMILES: COCCOc1ccc(Nc2ncc(F)c(Nc3cccc(NC(=O)CC(=O)O)c3)n2)cc1]
I-21
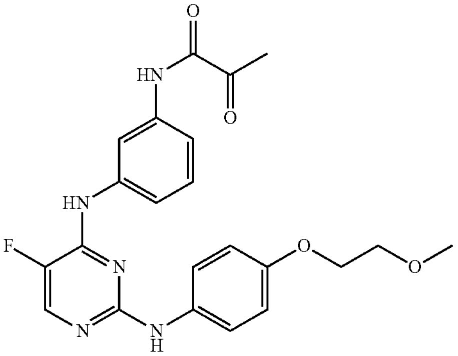 [SMILES: COCCOc1ccc(Nc2ncc(F)c(Nc3cccc(NC(=O)C(C)=O)c3)n2)cc1]
I-22
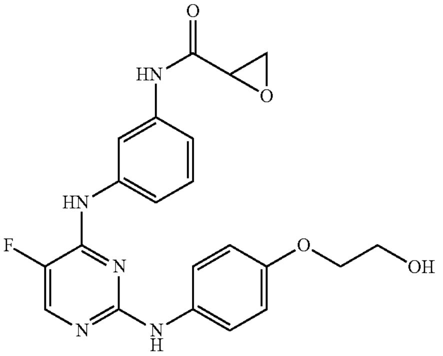 [SMILES: O=C(Nc1cccc(Nc2nc(Nc3ccc(OCCO)cc3)ncc2F)c1)C1CO1]
I-23
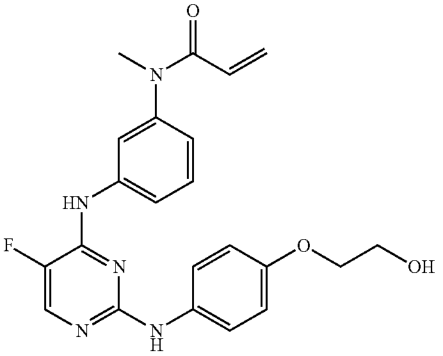 [SMILES: C=CC(=O)N(C)c1cccc(Nc2nc(Nc3ccc(OCCO)cc3)ncc2F)c1]

TABLE 1-continued

Exemplary Compounds

I-24

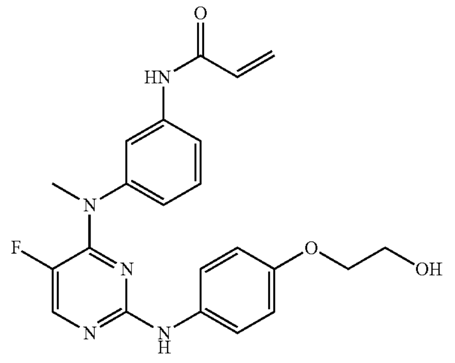 [SMILES: C=CC(=O)Nc1cccc(N(C)c2nc(Nc3ccc(OCCO)cc3)ncc2F)c1]

I-25

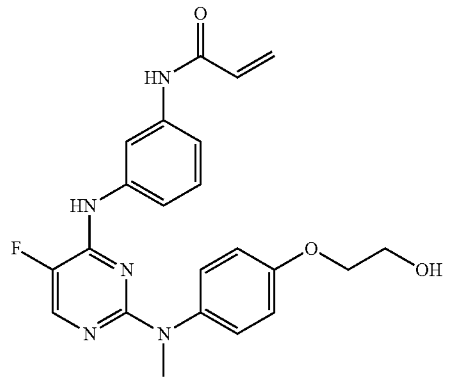 [SMILES: C=CC(=O)Nc1cccc(Nc2nc(N(C)c3ccc(OCCO)cc3)ncc2F)c1]

I-26

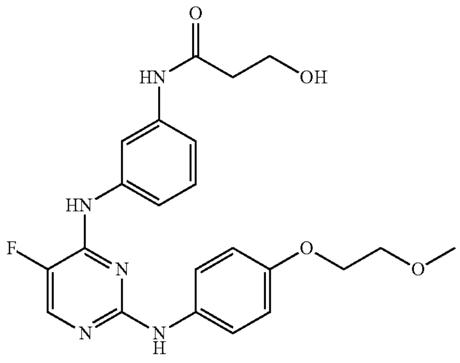 [SMILES: COCCOc1ccc(Nc2ncc(F)c(Nc3cccc(NC(=O)CCO)c3)n2)cc1]

I-27

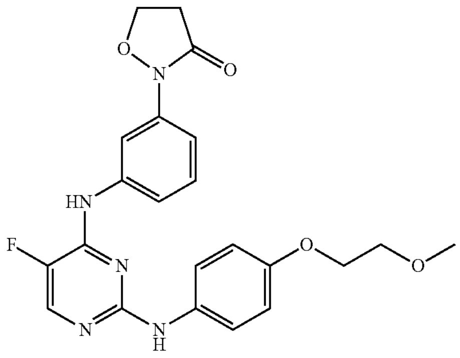 [SMILES: COCCOc1ccc(Nc2ncc(F)c(Nc3cccc(N4OCCC4=O)c3)n2)cc1]

I-28

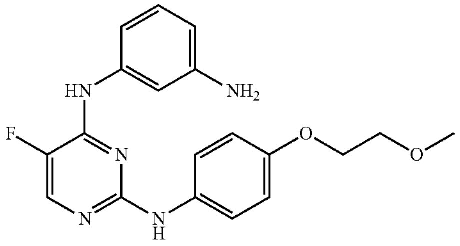 [SMILES: COCCOc1ccc(Nc2ncc(F)c(Nc3cccc(N)c3)n2)cc1]

or a pharmaceutically acceptable salt or solvate thereof.

In certain embodiments, the present invention provides any compound depicted in Table 1, above, or a pharmaceutically acceptable salt thereof.

In some embodiments, the present invention provides any compound described herein in isolated form.

In certain embodiments, the present invention provides a compound selected from:

I-1

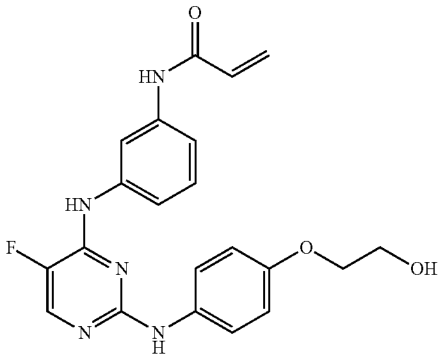

I-2

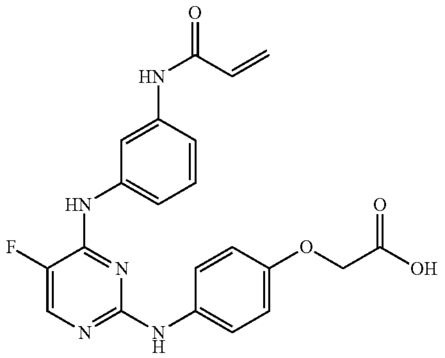

-continued

I-3

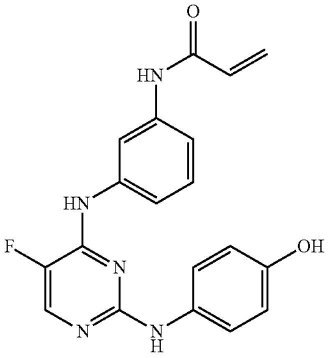

I-4

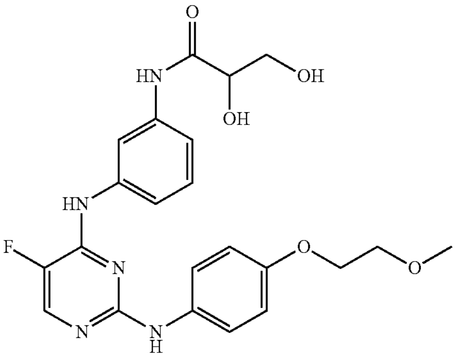

I-5

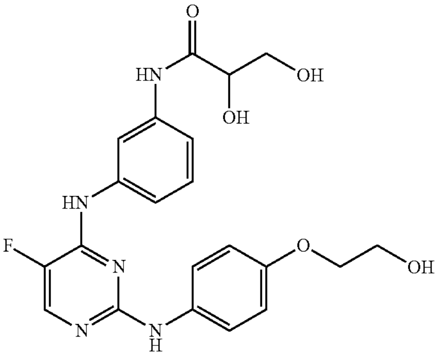

I-6

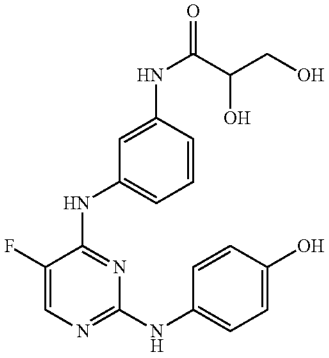

or a pharmaceutically acceptable salt thereof.

In certain embodiments, the present invention provides a compound selected from:

I-1

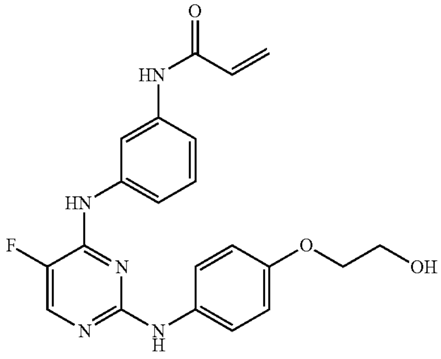

I-2

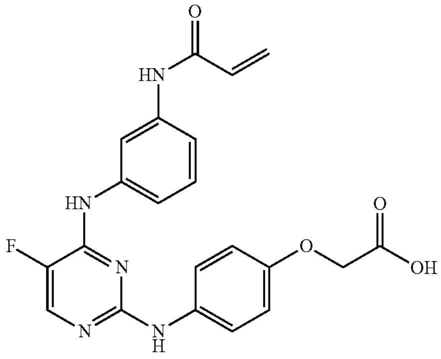

I-3

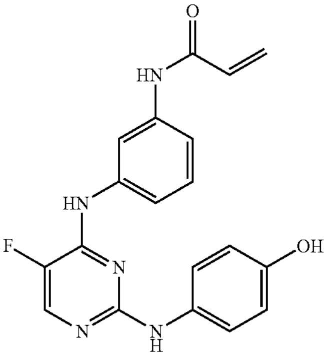

or a pharmaceutically acceptable salt thereof.

As described herein, certain compounds of the present invention are irreversible inhibitors of at least one of ErbB1, ErbB2, ErbB3 and ErbB4, or a mutant thereof. In some embodiments, provided compounds are irreversible inhibitors of a TEC-kinase (e.g., TEC, BTK, ITK, RLK or BMX) and JAK3. One of ordinary skill in the art will recognize that certain compounds of the present invention are reversible inhibitors. In certain embodiments, such compounds are useful as assay comparator compounds. In other embodiments, such reversible compounds are useful as inhibitors of ErbB1, ErbB2, ErbB3, ErbB4, a TEC-kinase (e.g., TEC, BTK, ITK, RLK or BMX), and/or JAK3, or a mutant thereof, and therefore useful for treating one or disorders as described herein.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit a protein kinase, particularly at least one of ErbB1, ErbB2, ErbB3, ErbB4, a TEC-kinase (e.g., TEC, BTK, ITK, RLK or BMX), and/or JAK3, or a mutant thereof, in a biological sample or in a patient. In certain embodiments, the amount of compound in compositions of this invention is such that is effective to measurably inhibit at least one of ErbB1, ErbB2, ErbB3, ErbB4, a TEC-kinase (e.g., TEC, BTK, ITK, RLK or BMX), and/or JAK3, or a mutant thereof, in a biological sample or in a patient. In certain embodiments, a composition of this invention is formulated for administration to a patient in need of such composition. In some embodiments, a composition of this invention is formulated for oral administration to a patient.

In some embodiments, the present invention provides a composition comprising a compound of Formula VI:

VI

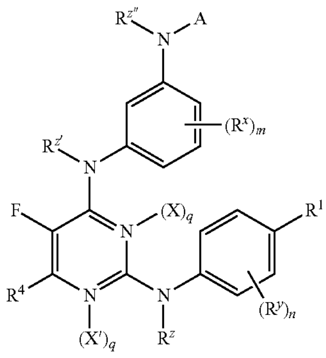

or a pharmaceutically acceptable salt thereof, wherein:

X and X' are each independently O;

p and q are each independently 0 or 1, wherein p and q are not both 1;

$R^1$ is —OR', —$OCH_2CH_2OR'$ or —$OCH_2CO_2H$;

R' is —H, —$CH_3$, —$SO_3H$ or -Glu;

each Glu is a glucuronyl moiety;

A is selected from —H or

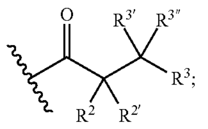

$R^2$ and $R^3$ are each independently —H, —OH, —$OSO_3H$, —OGlu, or:

$R^2$ and $R^3$ are taken together to form a double bond; or:

$R^2$ and $R^3$ are taken together with their intervening atoms to form an epoxide moiety;

$R^{2'}$ is —H, or:

$R^2$ and $R^{2'}$ are taken together to form =O;

$R^{3'}$ and $R^{3''}$ are each —H, or:

$R^{3'}$ and $R^{3''}$ are taken together to form =O;

$R^4$ is —H, —OH, —$OSO_3H$ or —OGlu;

$R^x$ and $R^y$ are each independently —OH, —$OSO_3H$, or —OGlu;

$R^z$, $R^{z'}$ and $R^{z''}$ are each independently —H, —$CH_3$, —OH, —$OSO_3H$, or —OGlu; or $R^{z''}$ and $R^3$ are taken together to form —O—;

m and n are each independently 0, 1, 2, 3 or 4, provided that when $R^2$ and $R^3$ are taken together to form a double bond, at least one of the following is true:

(a) $R^1$ is —OH, —$OSO_3H$, —OGlu, —$OCH_2CH_2OH$, —$OCH_2CO_2H$, —$OCH_2CH_2OSO_3H$ or —$OCH_2CH_2OGlu$;

(b) at least one of $R^4$, $R^z$, $R^{z'}$ and $R^{z''}$ is —OH, —$OSO_3H$ or —OGlu;

(c) at least one of m and n is 1, 2, 3 or 4; or (d) one of p or q is 1.

In some embodiments, the present invention provides a pharmaceutical composition comprising a compound of any of Formulae I, I', I'', I-a, II, III, IV or V, or a pharmaceutically acceptable salt thereof, and one or more pharmaceutically acceptable excipients. In some embodiments, the present invention provides a pharmaceutical composition comprising a compound of Formula VI, or a pharmaceutically acceptable salt thereof, and one or more pharmaceutically acceptable excipients. In some embodiments, the present invention provides a pharmaceutical composition comprising a compound of Formula VII, or a pharmaceutically acceptable salt thereof, and one or more pharmaceutically acceptable excipients.

In some embodiments, the compound of Formula VI is

I-28

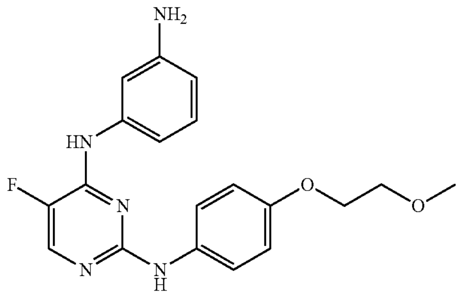

The term "patient", as used herein, means an animal, preferably a mammal, and most preferably a human.

The term "pharmaceutically acceptable carrier, adjuvant, vehicle or excipient" refers to a non-toxic carrier, adjuvant, vehicle or excipient that does not destroy the pharmacological activity of the compound with which it is formulated. Pharmaceutically acceptable carriers, adjuvants, vehicles or excipients that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of at least one of ErbB1, ErbB2, ErbB3, ErbB4, a TEC-kinase (e.g., TEC, BTK, ITK, RLK or BMX), BLK and/or JAK3, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of protein kinase activity of one or more enzymes.

Drug resistance is emerging as a significant challenge for targeted therapies. For example, drug resistance has been reported for Gleevec® and Iressa®, as well as several other kinase inhibitors in development. In addition, drug resistance has been reported for the cKit and PDGFR receptors. It has been reported that irreversible inhibitors may be effective against drug resistant forms of protein kinases (Kwak, E. L., R. Sordella, et al. (2005). "Irreversible inhibitors of the EGF receptor may circumvent acquired resistance to gefitinib." *PNAS* 102(21): 7665-7670.) Without wishing to be bound by any particular theory, it is believed that compounds of the present invention may be effective inhibitors of drug resistant forms of protein kinases.

As used herein, the term "clinical drug resistance" refers to the loss of susceptibility of a drug target to drug treatment as a consequence of mutations in the drug target.

As used herein, the term "resistance" refers to changes in the wild-type nucleic acid sequence coding a target protein, and/or the protein sequence of the target, which changes decrease or abolish the inhibitory effect of the inhibitor on the target protein.

Examples of kinases that are inhibited by the compounds and compositions described herein and against which the methods described herein are useful include ErbB1, ErbB2, ErbB3, ErbB4, a TEC-kinase (including TEC, BTK, ITK, RLK or BMX), BLK and/or JAK3, or a mutant thereof.

The activity of a compound utilized in this invention as an inhibitor of ErbB1, ErbB2, ErbB3, ErbB4, a TEC-kinase (e.g., TEC, BTK, ITK, RLK or BMX), BLK and/or JAK3, or a mutant thereof, may be assayed in vitro, in vivo or in a cell line. In vitro assays include assays that determine inhibition of either the phosphorylation activity and/or the subsequent functional consequences, or ATPase activity of activated ErbB1, ErbB2, ErbB3, ErbB4, a TEC-kinase (e.g., TEC, BTK, ITK, RLK or BMX), BLK and/or JAK3, or a mutant thereof. Alternate in vitro assays quantitate the ability of the inhibitor to bind to ErbB1, ErbB2, ErbB3, ErbB4, a TEC-kinase (e.g., TEC, BTK, ITK, RLK or BMX), BLK and/or JAK3. Inhibitor binding may be measured by radiolabeling the inhibitor prior to binding, isolating the inhibitor/ErbB1, inhibitor/ErbB2, inhibitor/ErbB3, inhibitor/ErbB4, inhibitor/TEC-kinase (e.g., TEC, BTK, ITK, RLK or BMX), inhibitor/BLK or inhibitor/JAK3 complex and determining the amount of radiolabel bound. Alternatively, inhibitor binding may be determined by running a competition experiment where new inhibitors are incubated with ErbB1, ErbB2, ErbB3, ErbB4, a TEC-kinase (e.g., TEC, BTK, ITK, RLK or BMX), BLK and/or JAK3 bound to known radioligands. Detailed conditions for assaying a compound utilized in this invention as an inhibitor of ErbB1, ErbB2, ErbB3, ErbB4, a TEC-kinase (e.g., TEC, BTK, ITK, RLK or BMX), BLK and/or JAK3, or a mutant thereof, are set forth in the Examples below.

Protein tyrosine kinases are a class of enzymes that catalyze the transfer of a phosphate group from ATP or GTP to a tyrosine residue located on a protein substrate. Receptor tyrosine kinases act to transmit signals from the outside of a cell to the inside by activating secondary messaging effectors via a phosphorylation event. A variety of cellular processes are promoted by these signals, including proliferation, carbohydrate utilization, protein synthesis, angiogenesis, cell growth, and cell survival.

(a) ErbB Family

ErbB receptors, a major family of receptor tyrosine kinases, are composed of an extracellular ligand binding domain, a single transmembrane domain, and an intracellular domain with tyrosine kinase activity. The ErbB family comprises ErbB1 (commonly known as EGFR), ErbB2 (commonly known as HER2 or neu), ErbB3 (commonly known as HER3), and ErbB4 (commonly known as HER4). More than 10 ligands (including EGF, TGFα, AR, BTC, EPR, HB-EGF, NRG-1, NRG-2, NRG-3, NRG-4) have been identified for the various receptor family members. Upon ligand binding the extracellular domain undergoes conformational change, allowing the formation of homodimers or heterodimers with other members of the ErbB family. Dimerization induces tyrosine phosphorylation of specific residues in the intracellular domain that serve as docking sites for adaptor proteins and downstream effectors. In some contexts, activation of phosphatidyl-inositol 3-kinase (PI3K) and mitogen-activated protein kinase pathways occur, leading to cell proliferation and survival (Lin, N. U.; Winer, E. P., Breast Cancer Res 6: 204-210, 2004).

Interaction between family members is necessitated by deficiencies in ErbB2, which has no known ligand, and ErbB3, which is kinase dead. EGFR, ErbB3, and ErbB4 bind ligand to induce ErbB receptor homodimerization or heterodimerization, whereas ErbB2 functions as the preferred dimerization partner. The composition of the pairwise combinations is important for signal diversification, as dimer identity determines which downstream pathways are activated. Representative downstream gene products in the ErbB signal transduction pathway include Shc, Grb2, SOS1, Ras, Raf1, Mek, ERK1, ERK2, ERα, Akt, mTOR, FKHR, p27, Cyclin D1, FasL, GSK-3, Bad, and STAT3.

There is strong precedent for involvement of the EGFR and other members of the ErbB family in human cancer because over 60% of all solid tumors overexpress at least one of these proteins or their ligands. Constitutively active, tumorigenic EGFR vIII, a mutant possessing a truncated extracellular domain, has been reported to be present in up to 78% of breast carcinomas and has also been found in glioblastomas. Overexpression of EGFR is commonly found in breast, lung, head and neck, bladder tumors, while ErbB2 expression is frequently elevated in human tumors of epithelial origin. Activating mutations in the tyrosine kinase domain have been identified in patients with non-small cell lung cancer (Lin, N. U.; Winer, E. P., Breast Cancer Res 6: 204-210, 2004). ErbB1 and/or ErbB2 amplification has also been implicated in squamous cell carcinomas, salivary gland carcinomas, ovarian carcinomas, and pancreatic cancers (Cooper, G. C. Oncogenes. $2^{nd}$ ed. Sudbury: Jones and Barlett, 1995; Zhang, Y., et al., Cancer Res 66: 1025-32, 2006). Overexpression of ErbB2 has potent transforming activity, likely due to its ability to cooperate with other ErbB receptors (Sherman, L., et al., Oncogene 18: 6692-99, 1999). In fact, some human cancers that overexpress both EGFR and ErbB2 have a poorer prognosis than cancers that overexpress either receptor alone.

The ErbB signaling network is often a key component in the pathogenesis of breast cancer. Amplification of ErbB2 is associated with an aggressive tumor phenotype that is characterized by relatively rapid tumor growth, metastatic spread to visceral sites, and drug resistance. ErbB2 has been shown to be amplified in 20% of axillary node-negative ("ANN") breast cancer cases, and this amplification has been identified as an independent prognostic factor for risk of recurrence in ANN breast cancer. (Andrulis, I. L., et al., J Clin Oncol 16: 1340-9, 1998).

Targeted blockade of ErbB signaling with trastuzumab (Herceptin), a monoclonal antibody directed at ErbB2, has been shown to improve survival in women with ErbB2-positive, advanced breast cancer. Other monoclonal antibodies directed against ErbB receptors include cetuximab (Erbitux) and panitumumab (Vectibix).

Several small molecule tyrosine kinase inhibitors (TKIs) have been found to act selectively upon ErbB family members. Notable examples include gefitinib (Iressa) and erlotinib (Tarceva), both of which target the EGFR. These small molecules compete with ATP for binding to the kinase domain of the receptor. Compared to monoclonal antibodies, TKIs have several advantages in that they are orally bioavailable, well-tolerated, and appear to be active against truncated forms of ErbB2 and EGFR receptors (e.g., EGFR vIII) in vitro. In addition, the small size of small molecule TKIs may allow them to penetrate sanctuary sites such as the central nervous system. Finally, the homology between kinase domains of ErbB receptors allows for development of TKIs that target more than one member of the ErbB family simultaneously, the advantages of which are described herein.

Although certain malignancies have been linked to the overexpression of individual receptors, efficient signal transduction relies on the coexpression of ErbB receptor family members. This cooperation of ErbB receptor family members in signal transduction and malignant transformation may limit the success of agents that target individual receptors in the treatment of cancer; a potential mechanism of resistance to agents targeting a single ErbB receptor is upregulation of other members of the receptor family (Britten, C. D., Mol Cancer Ther 3: 1335-42, 2004).

Agents that target two or more ErbB receptors are called pan-ErbB regulators. ERRP is a pan-ErbB negative regulator that is expressed in most benign pancreatic ductal epithelium and islet cells. Tumors have been found to experience a progressive loss in ERRP expression. That Erbitux and Herceptin show success in a limited patient base (tumors having increased expression of EGFR or ErbB2) could be partly due to coexpression of multiple ErbB family members.

In both in vitro and in vivo models, strategies that employ a dual ErbB approach seem to have greater antitumor activity than agents targeting a single ErbB receptor. Thus, agents that target multiple members of ErbB family are likely to provide therapeutic benefit to a broader patient population (Zhang, Y., et al., Cancer Res 66: 1025-32, 2006). In certain embodiments, provided compounds inhibit one or more of ErbB1, ErbB2, ErbB3, and ErbB4. In some embodiments, provided compounds inhibit two or more of ErbB1, ErbB2, ErbB3, and ErbB4, or a mutant thereof, and are therefore pan-ErbB inhibitors.

Clearly, there is growing evidence to support the concurrent inhibition of two or more ErbB (e.g., pan-ErbB) receptors in cancer therapy. Possible pan-ErbB approaches with small molecules include using combinations of agents that target individual ErbB receptors, using single agents that target multiple ErbB receptors, or using agents that interfere with ErbB receptor interactions (e.g., dimerization). Additional strategies include therapies utilizing a small molecule in combination with antibodies, or chemoprevention therapies (Lin, N. U.; Winer, E. P., Breast Cancer Res 6: 204-210, 2004).

An example of small molecule pan-ErbB inhibition is CI-1033, an irreversible pan-ErbB inhibitor that covalently binds to the ATP binding site of the intracellular kinase domain. Another irreversible pan-ErbB receptor tyrosine kinase inhibitor is HKI-272, which inhibits the growth of tumor cells that express ErbB-1 (EGFR) and ErbB-2 (HER-2) in culture and xenografts, and has antitumor activity in HER-2-positive breast cancer (Andrulis, I. L., et al., J Clin Oncol 16: 1340-9, 1998). Irreversible inhibitors have demonstrated superior antitumor activity in comparison with reversible inhibitors.

Neurofibromatosis type I (NF1) is a dominantly inherited human disease affecting one in 2500-3500 individuals. Several organ systems are affected, including bones, skin, iris, and the central nervous system, as manifested in learning disabilities and gliomas. A hallmark of NF1 is the development of benign tumors of the peripheral nervous system (neurofibromas), which vary greatly in both number and size among patients. Neurofibromas are heterogeneous tumors composed of Schwann cells, neurons, fibroblasts and other cells, w/Schwann cells being the major (60-80%) cell type.

Abberant expression of the EGFR is associated with tumor development in NF1 and in animal models of NF1, suggesting a role in pathogenesis and representing a novel potential therapeutic target. EGFR expression affects the growth of tumor cell lines derived from NF1 patients under conditions where EGF is not the primary factor driving growth of the cells. These data suggest that EGFR may play an important role in NF1 tumorigenesis and Schwann cell transformation (DeClue, J. E., et al., J Clin Invest 105: 1233-41, 2000).

Patients with NF1 develop aggressive Schwann cell neoplasmas known as malignant peripheral nerve sheath tumors (MPNSTs). Schwann cells are the major supportive cell population in the peripheral nervous system. Neoplastic Schwann cells within these neoplasms variably express the ErbB tyrosine kinases mediating NRG-1 responses (ErbB2, ErbB3, ErbB4). Neuregulin-1 (NRG-1) proteins promote the differentiation, survival, and/or proliferation of many cell types in the developing nervous system, and overexpression of NRG-1 in myelinating Schwann cells induces the formation of malignant peripheral nerve sheath tumors (MPNSTs) (Fallon, K. B., et al., J Neuro Oncol 66: 273-84, 2004).

Deregulation of Schwann cell growth is a primary defect driving the development of both benign neurofibromas and MPNST in neurofibromatosis type I (NF1) patients. Growth of MPNSTs and transformed mouse Schwann cells in vitro is highly EGF-dependent and can be blocked by EGFR inhibitors under conditions where EGF is the primary growth factor. Some human MPNST cell lines have been found to demonstrate constitutive ErbB phosphorylation. While treatment with ErbB inhibitors abolishes ErbB phosphorylation and reduces DNA synthesis in these lines, effective chemotherapeutic regimens for MPNST remain elusive (Stonecypher, M. S., et al., Oncogene 24: 5589-5605, 2005).

Schwannomas are peripheral nerve tumors comprised almost entirely of Schwann-like cells, and typically have mutations in the neurofibromatosis type II (NF2) tumor suppressor gene. Ninety percent of NF2 patients develop bilateral vestibular schwannomas and/or spinal schwannomas. Enlarging schwannomas can compress adjacent structures, resulting in deafness and other neurologic problems. Surgical removal of these tumors is difficult, often resulting in increased patient morbidity.

Both normal human Schwann cells and schwannoma cells express neuregulin receptors (e.g., ErbB receptors), and schwannoma cells proliferate in response to neuregulin. It is possible that aberrant neuregulin production or response contributes to aberrant schwannoma cell proliferation (Pelton, P. D., et al., Oncogene 17: 2195-2209, 1998).

The NF2 tumor suppressor, Merlin, is a membrane/cytoskeleton-associated protein implicated in the regulation of tyrosine kinase activity. Genetic interactions between a Merlin mutation and EGFR pathway mutations have been documented in *Drosophila* (LaJeunesse, D. R., et al., Genetics 158: 667-79, 2001). Other evidence suggests Merlin can inhibit EGFR internalization and signaling upon cell-cell contact by restraining the EGFR into a membrane compartment from which it can neither signal nor be internalized (McClatchey, A. I., et al., Genes and Development 19: 2265-77, 2005; Curto, M. C., et al., J Cell Biol 177: 893-903, 2007).

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of one or more of ErbB1, ErbB2, ErbB3, and ErbB4 and are therefore useful for treating one or more disorders associated with activity of one of more of ErbB1, ErbB2, ErbB3, and ErbB4. Thus, in certain embodiments, the present invention provides a method for treating an ErbB1-mediated, an ErbB2-mediated, an ErbB3-mediated, and/or ErbB4-mediated disorder comprising the step of administering to a patient in need thereof a compound of the present invention, or pharmaceutically acceptable composition thereof.

As used herein, the terms "ErbB1-mediated", "ErbB2-mediated," "ErbB3-mediated," and/or "ErbB4-mediated" disorders or conditions as used herein means any disease or other deleterious condition in which one or more of ErbB1, ErbB2, ErbB3, and/or ErbB4, or a mutant thereof, are known or suspected to play a role. Accordingly, another embodiment of the present invention relates to treating or lessening the severity of one or more diseases in which one or more of ErbB1, ErbB2, ErbB3, and/or ErbB4, or a mutant thereof, are known or suspected to play a role. Specifically, the present invention relates to a method of treating or lessening the severity of a disease or condition selected from a proliferative disorder, wherein said method comprises administering to a patient in need thereof a compound or composition according to the present invention.

In some embodiments, the present invention provides a method for treating or lessening the severity of one or more disorders selected from a cancer. In some embodiments, the cancer is associated with a solid tumor. In certain embodiments, the cancer is breast cancer, glioblastoma, lung cancer, cancer of the head and neck, colorectal cancer, bladder cancer, or non-small cell lung cancer. In some embodiments, the present invention provides a method for treating or lessening the severity of one or more disorders selected from squamous cell carcinoma, salivary gland carcinoma, ovarian carcinoma, or pancreatic cancer.

In certain embodiments, the present invention provides a method for treating or lessening the severity of neurofibromatosis type I (NF1), neurofibromatosis type II (NF2) Schwann cell neoplasms (e.g. MPNST's), or Schwannomas.

(b) TEC Family

The TEC family of non-receptor tyrosine kinases, referred to herein as "TEC-kinases," plays a central role in signaling through antigen-receptors such as the TCR, BCR and Fc receptors (reviewed in Miller A, et al. Current Opinion in Immunology 14; 331-340 (2002). TEC-kinases are essential for T cell activation. Three members of the family, Itk, Rlk and Btk, are activated downstream of antigen receptor engagement in T cells and transmit signals to downstream effectors, including PLC-γ. Combined deletion of Itk and Rlk in mice leads to a profound inhibition of TCR responses including proliferation, cytokine production and immune responses to an intracellular parasite (*Toxoplasma gondii*) (Schaeffer et al., Science 284; 638-641 (1999)). Intracellular signalling following TCR engagement is effected in ITK/RLK deficient T cells; inositol triphosphate production, calcium mobilization and MAP kinase activation are all reduced. Tec-kinases are also essential for B cell development and activation.

TEC-kinases include five family members, which are expressed primarily in hematopoietic cells: TEC, BTK, ITK (also known as TSK and EMT), RLK (also known as TXK), and BMX (also known as ETK). Additional related TEC-kinases have been found in *Drosophila melanogaster*, zebrafish (*Danio rerió*), skate (*Raja eglanteria*), and sea urchin (*Anthocidaris crassispina*).

Provided compounds are inhibitors of one of more TEC-kinases (e.g., TEC, BTK, ITK, RLK or BMX) and are therefore useful for treating one or more disorders associated with activity of one or more TEC-kinases (e.g., TEC, BTK, ITK, RLK or BMX). Thus, in certain embodiments, the present invention provides a method for treating a TEC-mediated disorder comprising the step of administering to a patient in need thereof a compound of the present invention, or pharmaceutically acceptable composition thereof.

The term "TEC-mediated condition", as used herein means any disease or other deleterious condition in which TEC-kinases (e.g., TEC, BTK, ITK, RLK or BMX) are known or suspected to play a role. Such conditions include those described herein and in Melcher, M et al., "The Role of TEC Family Kinases in Inflammatory Processes", *Anti-Inflammatory & Anti-Allergy Agents in Medicinal Chemistry*, Vol. 6, No. 1, pp. 61-69 (February 2007). Accordingly, another embodiment of the present invention relates to treating or lessening the severity of one or more diseases in which TEC-kinases (e.g., TEC, BTK, ITK, RLK or BMX) are known or suspected to play a role. Specifically, the present invention relates to a method of treating or lessening the severity of a disease or condition selected from autoimmune, inflammatory, proliferative, and hyperproliferative diseases and immunologically-mediated diseases including rejection of transplanted organs or tissues and Acquired Immunodeficiency Syndrome (AIDS) (also known as HIV), wherein said method comprises administering to a patient in need thereof a composition of the present invention.

In some embodiments, the present invention provides a method for treating or lessening the severity of one or more diseases and conditions associated with TEC-kinases (e.g., TEC, BTK, ITK, RLK or BMX) including diseases of the respiratory tract including, without limitation, reversible obstructive airways diseases including asthma, such as bronchial, allergic, intrinsic, extrinsic and dust asthma, particularly chronic or inveterate asthma (e.g., late asthma airways hyper-responsiveness) and bronchitis. In some embodiments, the present invention provides a method for treating or lessening the severity of one or more diseases and conditions associated with TEC-kinases (e.g., TEC, BTK, ITK, RLK or BMX) including those conditions characterized by inflammation of the nasal mucus membrane, including acute rhinitis, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung, and idiopathic interstitial pneumonia.

In some embodiments, the present invention provides a method for treating or lessening the severity of one or more diseases and conditions associated with TEC-kinases (e.g., TEC, BTK, ITK, RLK or BMX) including diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, and bone metastasis.

In some embodiments, the present invention provides a method for treating or lessening the severity of one or more diseases and conditions associated with TEC-kinases (i.e., TEC, BTK, ITK, RLK or BMX) including diseases and disorders of the skin, including, without limitation, psoriasis, systemic sclerosis, atopical dermatitis, contact dermatitis and other eczematous dermatitis, seborrhoetic dermatitis, Lichen planus, pemphigus, bullous pemphigus, epidermolysis bullosa, urticaria, angiodermas, vasculitides, erythemas, cutaneous eosinophilias, uveitis, alopecia, areata and vernal conjunctivitis.

In some embodiments, the present invention provides a method for treating or lessening the severity of one or more diseases and conditions associated with TEC-kinases (e.g., TEC, BTK, ITK, RLK or BMX) including diseases and disorders of the gastrointestinal tract, including, without limitation, celiac disease, proctitis, eosinophilic gastro-enteritis, mastocytosis (e.g., diseases characterized by hyperactive mast cells), pancreatitis, Crohn's disease, ulcerative colitis, food-related allergies which have effects remote from the gut, e. g. migraine, rhinitis and eczema.

In some embodiments, the present invention provides a method for treating or lessening the severity of one or more diseases and conditions associated with TEC-kinases (e.g., TEC, BTK, ITK, RLK or BMX) including those diseases and disorders of other tissues and systemic disease, including, without limitation, multiple sclerosis, artherosclerosis, lupus erythematosus, systemic lupus erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia purpura, restenosis following angioplasty, tumours (for example leukemia, lymphomas, and prostate cancers), and artherosclerosis.

In some embodiments, the present invention provides a method for treating or lessening the severity of one or more diseases and conditions associated with TEC-kinases (e.g., TEC, BTK, ITK, RLK or BMX) including allograft rejection including, without limitation, acute and chronic allograft rejection following for example transplantation of kidney, heart, liver, lung, bone marrow, skin and cornea; and chronic graft versus host disease. In some such embodiments, the allograft rejection is antibody mediated rejection (AMR) of transplant allografts (i.e., humoral rejection).

In some embodiments, the present invention relates to a method of treating or lessening the severity of one or more of the diseases or conditions associated with TEC-kinases (e.g., TEC, BTK, ITK, RLK or BMX), as recited above, wherein said method comprises administering to a patient in need thereof a compound or composition according to the present invention.

(c) Bruton's Tyrosine Kinase (BTK)

Bruton's tyrosine kinase ("BTK"), a member of the TEC-kinases (e.g., TEC, BTK, ITK, RLK or BMX), is a key signaling enzyme expressed in all hematopoietic cell types except T lymphocytes and natural killer cells. BTK plays an essential role in the B-cell signaling pathway linking cell surface B-cell receptor (BCR) stimulation to downstream intracellular responses.

BTK is a key regulator of B-cell development, activation, signaling, and survival (Kurosaki, Curr Op Imm, 2000, 276-281; Schaeffer and Schwartzberg, Curr Op Imm 2000, 282-288). In addition, BTK plays a role in a number of other hematopoietic cell signaling pathways, e.g., Toll like receptor (TLR) and cytokine receptor-mediated TNF-$\alpha$ production in macrophages, IgE receptor (Fc_epsilon_RI) signaling in mast cells, inhibition of Fas/APO-1 apoptotic signaling in B-lineage lymphoid cells, and collagen-stimulated platelet aggregation. See, e.g., C. A. Jeffries, et al., (2003), Journal of Biological Chemistry 278:26258-26264; N. J. Horwood, et al., (2003), The Journal of Experimental Medicine 197: 1603-1611; Iwaki et al. (2005), Journal of Biological Chemistry 280(48):40261-40270; Vassilev et al. (1999), Journal of Biological Chemistry 274(3): 1646-1656, and Quek et al. (1998), Current Biology 8(20): 1137-1140.

Patients with mutations in BTK have a profound block in B cell development, resulting in the almost complete absence of mature B lymphocytes and plasma cells, severely reduced Ig levels and a profound inhibition of humoral response to recall antigens (reviewed in Vihinen et al Frontiers in Bioscience 5: d917-928). Mice deficient in BTK also have a reduced number of peripheral B cells and greatly decreased serum levels of IgM and IgG3. BTK deletion in mice has a profound effect on B cell proliferation induced by anti-IgM, and inhibits immune responses to thymus-independent type II antigens (Ellmeier et al, J Exp Med 192: 1611-1623 (2000)). BTK also plays a crucial role in mast cell activation through the high-affinity IgE receptor (Fc_epsilon_RI). BTK deficient murine mast cells have reduced degranulation and decreased production of proinflammatory cytokines following Fc_epsilon_RI cross-linking (Kawakami et al. Journal of Leukocyte Biology 65: 286-290).

Provided compounds are inhibitors of BTK and are therefore useful for treating one or more disorders associated with activity of BTK. Thus, in some embodiments, the present invention provides a method for treating a BTK-mediated disorder comprising the step of administering to a patient in need thereof a compound of the present invention, or pharmaceutically acceptable composition thereof.

As used herein, the term "BTK-mediated" disorders or conditions as used herein means any disease or other deleterious condition in which BTK, or a mutant thereof, is known or suspected to play a role. Accordingly, another embodiment of the present invention relates to treating or lessening the severity of one or more diseases in which BTK, or a mutant thereof, is known or suspected to play a role. Specifically, the present invention relates to a method of treating or lessening the severity of a disease or condition selected from a proliferative disorder or an autoimmune disorder, wherein said method comprises administering to a patient in need thereof a compound or composition according to the present invention.

In some embodiments, the present invention provides a method for treating or lessening the severity of one or more diseases and conditions associated with BTK. In some embodiments, the disease or condition is an autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, multiple sclerosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia. In some embodiments, the disease or condition is a hyperproliferative disease or immunologically-mediated diseases including rejection of transplanted organs or tissues and Acquired Immunodeficiency Syndrome (AIDS, also known as HIV).

In some embodiments, the present invention provides a method for treating or lessening the severity of one or more diseases and conditions associated with BTK, wherein the disease or condition is selected from heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, the present invention provides a method for treating or lessening the severity of one or more diseases and conditions associated with BTK, wherein the disease or condition is selected from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In some embodiments, the present invention provides a method for treating or lessening the severity of one or more diseases and conditions associated with BTK, wherein the disease or condition is selected from a cancer. In one embodiment, the cancer is a B-cell proliferative disorder, e.g., diffuse large B cell lymphoma, follicular lymphoma, chronic lymphocytic lymphoma, chronic lymphocytic leukemia, small lymphocytic lymphoma, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis. In some embodiments, the cancer is breast cancer, prostate cancer, or cancer of the mast cells (e.g., mastocytoma, mast cell leukemia, mast cell sarcoma, systemic mastocytosis). In one embodiment, the cancer is bone cancer. In another embodiment, the cancer is of other primary origin and metastasizes to the bone.

In some embodiments, the present invention provides a method for treating or lessening the severity of a proliferative disease selected from B-cell proliferative disorder, e.g., diffuse large B cell lymphoma (DLBCL), follicular lymphoma, chronic lymphocytic lymphoma, chronic lymphocytic leukemia, small lymphocytic leukemia, small lymphocytic lymphoma, B-cell prolymphocytic leukemia, lymphoplasmacytic lymphoma/Waldenstrom macroglobulinemia, splenic marginal zone lymphoma, plasma cell myeloma, plasmacytoma, extranodal marginal zone B cell lymphoma, extranodal marginal zone B cell lymphoma of mucosa-associated lymphoid tissue (MALT), nodal marginal zone B cell lymphoma, mantle cell lymphoma, mediastinal (thymic) large B cell lymphoma, intravascular large B cell lymphoma, primary effusion lymphoma, burkitt lymphoma/leukemia, hairy cell leukemia, heavy chain diseases (e.g., alpha heavy chain disease, gamma heavy chain disease, mu heavy chain disease), primary cutaneous B cell lymphoma, ALK+ large cell lymphoma, Castleman's disease, lymphomatoid granulomatosis, breast cancer, prostate cancer, cancer of the mast cells (e.g., mastocytoma, mast cell leukemia, mast cell sarcoma, systemic mastocytosis), multiple myeloma, colorectal cancer, pancreatic cancer, B-cell prolymphocytic leukemia, solitary plasmacytoma of bone, extraosseous plasmacytoma, primary cutaneous follicle center lymphoma, primary mediastinal (thymic) large B-cell lymphoma, intravascular large B-cell lymphoma, primary cutaneous DLBCL and plasmablastic lymphoma.

In some embodiments, the present invention provides a method for treating or lessening the severity of one or more diseases or conditions associated with BTK including diseases of the bone and joints including, without limitation, rheumatoid arthritis, seronegative spondyloarthropathies (including ankylosing spondylitis, psoriatic arthritis and Reiter's disease), bone resorption disorders (including Paget's disease of bone, bone changes secondary to cancer, such as occur in myeloma and metastases from breast cancer, etc.), Behcet's disease, Sjogren's syndrome, systemic sclerosis, osteoporosis, bone cancer, and bone metastasis.

In some embodiments, the present invention provides a method for treating or lessening the severity of one or more diseases and conditions associated with BTK, wherein the disease or condition is selected from a thromboembolic disorder, e.g., myocardial infarct, angina pectoris (including unstable angina), reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In some embodiments, the present invention provides a method for treating or lessening the severity of one or more diseases and conditions associated with BTK, including infectious and noninfectious inflammatory events and autoimmune and other inflammatory diseases. These autoimmune and inflammatory diseases, disorders, and syndromes include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In some embodiments, the present invention provides a method for treating or lessening the severity of an autoimmune disease selected from inflammatory bowel disease (IBD), Crohn's disease, ulcerative colitis, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome (including anterior scleritis), multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, antineutrophil cytoplasmic Ab (ANCA)-associated vasculitis (including Churg-Strauss syndrome, microscopic polyangiitis, mixed cryoglobulinemia and Wegener's granulomatosis), psoriasis, alopecia universalis, Behcet's disease, chronic fatigue, dysautonomia, endometriosis, interstitial cystitis, neuromyotonia, scleroderma, or vulvodynia, systemic lupus erythematosus (SLE) (including lupus nephritis, neuropsychiatric and childhood-onset SLE), vasculitis, idiopathic thrombocytopenic purpura (ITP), autoimmune thyroiditis, systemic sclerosis, Lyme neuroborreliosis, autoimmune gastritis, pernicious anemia, celiac disease, Goodpasture's syndrome, idiopathic thrombocytopenic purpura, membranous glomerulonephropathy, pemphigus vulgaris, bullous pemphigoid, rejection of transplanted organs or tissues and Acquired Immunodeficiency Syndrome (AIDS, also known as HIV), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholecystitus, agammaglobulinemia, psoriasis, allergy, Crohn's disease, irritable bowel syndrome, ulcerative colitis, Sjogren's disease, tissue graft rejection, hyperacute rejection of transplanted organs, chronic obstructive pulmonary disease (COPD), autoimmune polyglandular disease (also known as autoimmune polyglandular syndrome), autoimmune alopecia, pernicious anemia, glomerulonephritis, IgA nephropathy, dermatomyositis (including juvenile dermatomyositis), autoimmune hemolytic and thrombocytopenic states, atherosclerosis, Addison's disease, Parkinson's disease, Alzheimer's disease, diabetes (e.g., type I diabetes), septic shock, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, mycosis fungoides, acute inflammatory responses (such as acute respiratory distress syndrome and ischemia/reperfusion injury) and antiphospholipid syndrome.

In some embodiments, the present invention provides a method for treating or lessening the severity of a heteroimmune disease selected from graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic eczema.

In some embodiments, the present invention provides a method for treating or lessening the severity of one or more diseases and conditions associated with BTK, selected from rheumatoid arthritis, multiple sclerosis, B-cell chronic lymphocytic leukemia, acute lymphocytic leukemia, hairy cell leukemia, non-Hodgkin's lymphoma, Hodgkin's lymphoma, multiple myeloma, bone cancer, bone metastasis, osteoporosis, irritable bowel syndrome, Crohn's disease, lupus and renal transplant.

In some embodiments, the present invention provides a method for treating or lessening the severity of an inflammatory disease selected from asthma, inflammatory bowel disease (including Crohn's disease and ulcerative colitis), appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis, dermatitis, contact dermatitis, eczema, urticaria, rosacea, scarring, atopic dermatitis, allergy, chronic graft rejection, Henoch-Schonlein purpura, immunoglobulin A nephropathy, interstitial lung disease, polymyositis, ulcerative colitis and cryoglobulinemia, myocardial infarction and thrombosis.

In some embodiments, the present invention provides a method for treating or lessening the severity of a skin disorder selected from bullous skin diseases (e.g., pemphigus vulgaris including childhood/juvenile pemphigus vulgaris, pemphigus foliaceus, paraneoplastic pemphigus, bullous pemphigoid, mucous membrane pemphigoid and epidermolysis bullosa aquisita).

In some embodiments, the present invention provides a method for treating or lessening the severity of a platelet disorder, for example, abberant platelet aggregation. See, for example, Liu et al., *Blood* 2006, 108: 2596-2603, incorporated by reference in its entirety.

In some embodiments, the present invention provides a method for treating or lessening the severity of fibrosis. Fibrosis is the formation of excess fibrous connective tissue in an organ or tissue in a reparative or reactive process. Fibrosis can be a reactive, benign, or pathological state. Fibrosis in response to injury is often referred to as scarring. Fibrosis arising from a single cell line is called a fibroma. Physiologically, fibrosis acts to deposit connective tissue, which can obliterate the architecture and function of the underlying organ or tissue. Fibrosis can be used to describe the pathological state of excess deposition of fibrous tissue, as well as the process of connective tissue deposition in healing.

Idiopathic pulmonary fibrosis (IPF), (also called cryptogenic fibrosing alveolitis) is a fibrotic condition seen most commonly in patients between 40 and 60 years of age. Patients with IPF typically present with progressive shortness of breath and a dry cough. Pulmonary function tests show a restrictive pattern with reduced lung volumes and impairment in gas exchange. Idiopathic pulmonary fibrosis has a poor prognosis, with a mean survival of 4 years from the onset of symptoms.

Pathologically, the large majority of patients with IPF show typical histological findings of usual interstitial pneumonia and/or desquamative interstitial pneumonia. The earliest histological abnormality in IPF is alveolitis with increased cellularity of the alveolar walls. This inflammatory process can lead to progressive fibrosis. Alveolar wall inflammation and intra-alveolar macrophages in IPF indicate disease activity and are potentially reversible. Fibrosis and honeycombing are irreversible.

In certain embodiments, the present invention provides a method for the treatment of a disease or disorder selected from an accumulation of excess extracellular matrix; a fibrotic condition (which can be induced by drug or radiation)

(e.g., systemic sclerosis/scleroderma, lupus nephritis, connective tissue disease, wound healing, surgical scarring, spinal cord injury, CNS scarring, acute lung injury, pulmonary fibrosis (such as idiopathic pulmonary fibrosis and cystic fibrosis), chronic obstructive pulmonary disease, adult respiratory distress syndrome, acute lung injury, drug-induced lung injury, glomerulonephritis, chronic kidney disease (including diabetic nephropathy), hypertension-induced nephropathy, alimentary track or gastrointestinal fibrosis, renal fibrosis, hepatic or biliary fibrosis, liver fibrosis (nonalcoholic steatohepatitis, Hepatitis C/hepatocellular carcinoma, etc.), cirrhosis (such as primary biliary cirrhosis and cirrhosis due to fatty liver disease (alcoholic and nonalcoholic steatosis)), radiation-induced fibrosis (such as head and neck, gastrointestinal and pulmonary), primary sclerosing cholangitis, restenosis, cardiac fibrosis (such as endomyocardial fibrosis and atrial fibrosis), opthalmic scarring, fibrosclerosis, fibrotic cancers, fibroids, fibroma, fibroadenomas, fibrosarcomas, transplant arteriopathy, and keloid), mediastinal fibrosis, myelofibrosis, retroperitoneal fibrosis, progressive massive fibrosis, nephrogenic systemic fibrosis, Crohn's disease, arthrofibrosis, adhesive capsulitis and other conditions such as Dupuytren's Disease, colorectal cancer, tumor metastasis, Myc-mediated solid tumors (such as colon cancer, prostate cancer, myeloma, lymphoma), metabolic disease (such as Type 2 diabetes), metabolic myopathies (such as glycogen and lipid storage disorders), cachexia, hypertension, ankylosing spondylitis, demyelination in multiple sclerosis, cerebral angiopathy and Alzheimer's disease, wherein said method comprises administering to a patient in need thereof a compound of the present invention, or pharmaceutically acceptable composition thereof.

In some embodiments, the disease or disorder is a fibrotic condition selected from systemic sclerosis/scleroderma, lupus nephritis, connective tissue disease, wound healing, surgical scarring, spinal cord injury, CNS scarring, acute lung injury, pulmonary fibrosis, chronic obstructive pulmonary disease, adult respiratory distress syndrome, acute lung injury, drug-induced lung injury, glomerulonephritis, chronic kidney disease, hypertension-induced nephropathy, alimentary track or gastrointestinal fibrosis, renal fibrosis, hepatic or biliary fibrosis, liver fibrosis, cirrhosis, radiation-induced fibrosis, primary sclerosing cholangitis, restenosis, cardiac fibrosis, opthalmic scarring, fibrosclerosis, fibrotic cancers, fibroids, fibroma, fibroadenomas, fibrosarcomas, transplant arteriopathy and keloid.

In some embodiments, pulmonary fibrosis is selected from idiopathic pulmonary fibrosis and cystic fibrosis.

In some embodiments, chronic kidney disease is diabetic nephropathy.

In some embodiments, liver fibrosis is selected from nonalcoholic steatohepatitis, Hepatitis C/hepatocellular carcinoma.

In some embodiments, cirrhosis is selected from primary biliary cirrhosis and cirrhosis due to fatty liver disease (alcoholic and nonalcoholic steatosis).

In some embodiments, radiation-induced fibrosis is selected from head and neck, gastrointestinal and pulmonary.

In some embodiments, cardiac fibrosis is selected from endomyocardial fibrosis and atrial fibrosis.

In some embodiments, Myc-mediated solid tumors selected from colon cancer, prostate cancer, myeloma, lymphoma.

In some embodiments, the metabolic disease is Type 2 diabetes.

In some embodiments, the metabolic myopathy is selected from glycogen and lipid storage disorders.

(d) ITK

Interleukin-2 inducible T-cell kinase ("ITK") is expressed in T cells, mast cells and natural killer cells. It is activated in T cells upon stimulation of the T cell receptor (TCR), and in mast cells upon activation of the high affinity IgE receptor. Following receptor stimulation in T cells, Lck, a Src tyrosine kinase family member, phosphorylates Y511 in the kinase domain activation loop of ITK (S. D. Heyeck et al., 1997, J. Biol. Chem, 272, 25401-25408). Activated ITK, together with Zap-70 is required for phosphorylation and activation of PLC-gamma (S. C. Bunnell et al., 2000, J. Biol. Chem., 275, 2219-2230). PLC-gamma catalyzes the formation of inositol 1,4,5-triphosphate and diacylglycerol, leading to calcium mobilization and PKC activation, respectively. These events activate numerous downstream pathways and lead ultimately to degranulation (mast cells) and cytokine gene expression (T cells) (Y. Kawakami et al., 1999, J. Leukocyte Biol., 65, 286-290).

The role of ITK in T cell activation has been confirmed in ITK knockout mice. $CD4^+$ T cells from ITK knockout mice have a diminished proliferative response in a mixed lymphocyte reaction or upon Con A or anti-CD3 stimulation. (X. C. Liao and D. R. Littman, 1995, Immunity, 3, 757-769). Also, T cells from ITK knockout mice produced little IL-2 upon TCR stimulation resulting in reduced proliferation of these cells. In another study, ITK deficient $CD4^+$ T cells produced reduced levels of cytokines including IL-4, IL-5 and IL-13 upon stimulation of the TCR, even after priming with inducing conditions (D. J. Fowell, 1999, Immunity, 11, 399-409).

The role of ITK in PLC-gamma activation and in calcium mobilization was also confirmed in the T cells of these knockout mice, which had severely impaired $IP_3$ generation and no extracellular calcium influx upon TCR stimulation (K. Liu et al., 1998, J. Exp. Med. 187, 1721-1727). Such studies support a key role for ITK in activation of T cells and mast cells. Thus an inhibitor of ITK would be of therapeutic benefit in diseases mediated by inappropriate activation of these cells.

It has been well established that T cells play an important role in regulating the immune response (Powrie and Coffman, 1993, Immunology Today, 14, 270-274). Indeed, activation of T cells is often the initiating event in immunological disorders. Following activation of the TCR, there is an influx of calcium that is required for T cell activation. Upon activation, T cells produce cytokines, including IL-2, 4, 5, 9, 10, and 13 leading to T cell proliferation, differentiation, and effector function. Clinical studies with inhibitors of IL-2 have shown that interference with T cell activation and proliferation effectively suppresses immune response in vivo (Waldmann, 1993, Immunology Today, 14, 264-270). Accordingly, agents that inhibit T lymphocyte activation and subsequent cytokine production, are therapeutically useful for selectively suppressing the immune response in a patient in need of such immunosuppression.

Mast cells play a critical roll in asthma and allergic disorders by releasing proinflammatory mediators and cytokines Antigen-mediated aggregation of Fc.epsilon.RI, the high-affinity receptor for IgE, results in activation of mast cells (D. B. Corry et al., 1999, Nature, 402, B18-23). This triggers a series of signaling events resulting in the release of mediators, including histamine, proteases, leukotrienes and cytokines (J. R. Gordon et al., 1990, Immunology Today, 11, 458-464.) These mediators cause increased vascular permeability, mucus production, bronchoconstriction, tissue degradation and inflammation thus playing key roles in the etiology and symptoms of asthma and allergic disorders.

Published data using ITK knockout mice suggests that in the absence of ITK function, increased numbers of memory T cells are generated (A. T. Miller et al., 2002 The Journal of Immunology, 168, 2163-2172). One strategy to improve vaccination methods is to increase the number of memory T cells generated (S. M. Kaech et al., Nature Reviews Immunology, 2, 251-262). In addition, deletion of ITK in mice results in reduced T cell receptor (TCR)-induced proliferation and secretion of the cytokines IL-2, IL-4, IL-5, IL-10 and IFN-y (Schaeffer et al, Science 284; 638-641 (1999)), Fowell et al, Immunity 11, 399-409 (1999), Schaeffer et al, Nature Immunology 2 (12): 1183-1188 (2001))). The immunological symptoms of allergic asthma are attenuated in ITK−/−mice. Lung inflammation, eosinophil infiltration and mucus production are drastically reduced in ITK−/−mice in response to challenge with the allergen OVA (Mueller et al, Journal of Immunology 170: 5056-5063 (2003)). ITK has also been implicated in atopic dermatitis. This gene has been reported to be more highly expressed in peripheral blood T cells from patients with moderate and/or severe atopic dermatitis than in controls or patients with mild atopic dermatitis (Matsumoto et al, International Archives of Allergy and Immunology 129: 327-340 (2002)).

Splenocytes from RLK−/−mice secrete half the IL-2 produced by wild type animals in response to TCR engagement (Schaeffer et al, Science 284: 638-641 (1999)), while combined deletion of ITK and RLK in mice leads to a profound inhibition of TCR-induced responses including proliferation and production of the cytokines IL-2, IL-4, IL-5 and IFN-y (Schaeffer et al, Nature Immunology 2 (12): 1183-1188 (2001), Schaeffer et al, Science 284: 638-641 (1999)). Intracellular signalling following TCR engagement is effected in ITK/RLK deficient T cells; inositol triphosphate production, calcium mobilization, MAP kinase activation, and activation of the transcription factors NFAT and AP-1 are all reduced (Schaeffer et al, Science 284: 638-641 (1999), Schaeffer et al, Nature Immunology 2 (12): 1183-1188 (2001)).

Provided compounds are inhibitors of ITK and are therefore useful for treating one or more disorders associated with activity of ITK. Thus, in some embodiments, the present invention provides a method for treating an ITK-mediated disorder comprising the step of administering to a patient in need thereof a compound of the present invention, or pharmaceutically acceptable composition thereof.

As used herein, the term "ITK-mediated" disorders or conditions as used herein means any disease or other deleterious condition in which ITK, or a mutant thereof, is known or suspected to play a role. Accordingly, another embodiment of the present invention relates to treating or lessening the severity of one or more diseases in which ITK, or a mutant thereof, is known or suspected to play a role. Specifically, the present invention relates to a method of treating or lessening the severity of a disease or condition selected from a mast cell-mediated condition, a basophil-mediated disorder, an immune or allergic disorder, wherein said method comprises administering to a patient in need thereof a compound or composition according to the present invention.

In some embodiments, the present invention provides a method for treating or lessening the severity of one or more diseases and conditions associated with ITK, wherein the disease or condition is an immune disorder, including inflammatory diseases, autoimmune diseases, organ and bone marrow transplant rejection and other disorders associated with T cell-mediated immune response or mast cell-mediated immune response.

In certain embodiments, the present invention provides a method for treating or lessening the severity of one or more diseases and conditions associated with ITK, wherein the disease or condition is acute or chronic inflammation, an allergy, contact dermatitis, psoriasis, rheumatoid arthritis, multiple sclerosis, type 1 diabetes, inflammatory bowel disease, Guillain-Barre syndrome, Crohn's disease, ulcerative colitis, cancer, graft versus host disease (and other forms of organ or bone marrow transplant rejection) or lupus erythematosus.

In certain embodiments, the present invention provides a method for treating or lessening the severity of one or more diseases and conditions associated with ITK, wherein the disease or condition is a mast cell driven conditions, a basophil-mediated disorder, reversible obstructive airway disease, asthma, rhinitis, chronic obstructive pulmonary disease (COPD), peripheral T-cell lymphomas or HIV [also known as Acquired Immunodeficiency Syndrome (AIDS)]. Such conditions include those described in Readinger, et al., PNAS 105: 6684-6689 (2008).

(e) JAK Family

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed [Frank, Mol. Med. 5: 432-456 (1999) & Seidel, et al, Oncogene 19: 2645-2656 (2000)].

JAK1, JAK2, and TYK2 are ubiquitously expressed, while JAK3 is predominantly expressed in hematopoietic cells. JAK3 binds exclusively to the common cytokine receptor gamma chain (yc) and is activated by IL-2, IL-4, IL-7, IL-9, and IL-15.

The proliferation and survival of murine mast cells induced by IL-4 and IL-9 have, in fact, been shown to be dependent on JAK3- and yc-signaling [Suzuki et al, Blood 96: 2172-2180 (2000)].

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions [Gordon et al, Nature 346: 274-276 (1990) & Galli, N. Engl. J. Med., 328: 257-265 (1993)]. A crucial role for JAK3 in IgE receptor-mediated mast cell responses in vitro and in vivo has been established [Malaviya, et al, Biochem. Biophys. Res. Commun. 257: 807-813 (1999)]. In addition, the prevention of type I hypersensitivity reactions, including anaphylaxis, mediated by mast cell-activation through inhibition of JAK3 has also been reported [Malaviya et al, J. Biol. Chem. 274: 27028-27038 (1999)]. Targeting mast cells with JAK3 inhibitors modulated mast cell degranulation in vitro and prevented IgE receptor/antigen-mediated anaphylactic reactions in vivo.

A recent study described the successful targeting of JAK3 for immune suppression and allograft acceptance. The study demonstrated a dose-dependent survival of buffalo heart allograft in Wistar Furth recipients upon administration of inhibitors of JAK3 indicating the possibility of regulating unwanted immune responses in graft versus host disease [Kirken, Transpl. Proc. 33: 3268-3270 (2001)].

IL-4-mediated STAT-phosphorylation has been implicated as the mechanism involved in early and late stages of rheumatoid arthritis (RA). Up-regulation of proinflammatory cytokines in RA synovium and synovial fluid is a characteristic of the disease. It has been demonstrated that IL-4-mediated activation of IL-4/STAT pathway is mediated through the Janus kinases (JAK 1 & 3) and that IL-4-associated JAK kinases are expressed in the RA synovium [Muller-Ladner, et al, J. Immunol. 164: 3894-3901 (2000)].

Familial amyotrophic lateral sclerosis (FALS) is a fatal neurodegenerative disorder affecting about 10% of ALS patients. The survival rates of FALS mice were increased upon treatment with a JAK3 specific inhibitor. This confirmed that JAK3 plays a role in FALS [Trieu, et al, Biochem. Biophys. Res. Commun. 267: 22-25 (2000)].

Signal transducer and activator of transcription (STAT) proteins are activated by, among others, the JAK family kinases. Results form a recent study suggested the possibility of intervention in the JAK/STAT signaling pathway by targeting JAK family kinases with specific inhibitors for the treatment of leukemia [Sudbeck, et al., Clin. Cancer Res. 5: 1569-1582 (1999)]. JAK3 specific compounds were shown to inhibit the clonogenic growth of JAK3-expressing cell lines DAUDI, RAMOS, LC1; 19, NALM-6, MOLT-3 and HL-60. Inhibition of JAK3 and TYK 2 abrogated tyrosine phosphorylation of STAT3, and inhibited cell growth of mycosis fungoides, a form of cutaneous T cell lymphoma.

According to another embodiment, the invention provides a method for treating or lessening the severity of a JAK3-mediated disease or condition in a patient comprising the step of administering to said patient a composition according to the present invention.

The term "JAK3-mediated disease", as used herein means any disease or other deleterious condition in which a JAK3 kinase is known or suspected to play a role. Accordingly, another embodiment of the present invention relates to treating or lessening the severity of one or more diseases in which JAK3 is known or suspected to play a role. Specifically, the present invention relates to a method of treating or lessening the severity of a disease or condition selected from immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as familial amyotrophic lateral sclerosis (FALS), as well as in solid and hematologic malignancies such as leukemias and lymphomas, wherein said method comprises administering to a patient in need thereof a composition according to the present invention.

The compounds and compositions, according to the method of the present invention, may be administered using any amount and any route of administration effective for treating or lessening the severity of cancer, an autoimmune disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting ErbB1, ErbB2, ErbB3, ErbB4, a TEC-kinase (e.g., TEC, BTK, ITK, RLK or BMX), and/or JAK3, or a mutant thereof, activity in a biological sample comprising the step of contacting said biological sample with a compound of this invention, or a composition comprising said compound. In certain embodiments, the invention relates to a method of irreversibly inhibiting ErbB1, ErbB2, ErbB3, ErbB4, a TEC-kinase (e.g., TEC, BTK, ITK, RLK or BMX), and/or JAK3, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of protein kinase, or a protein kinase selected from ErbB1, ErbB2, ErbB3, ErbB4, a TEC-kinase (i.e TEC, BTK, ITK, RLK or BMX), and/or JAK3, or a mutant thereof, activity in a biological sample is useful for a variety of purposes that are known to one of skill in the art. Examples of such purposes include, but are not limited to, blood transfusion, organ transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting one or more of ErbB1, ErbB2, ErbB3, ErbB4, a TEC-kinase (e.g., TEC, BTK, ITK, RLK or BMX), and/or JAK3, or a mutant thereof, activity in a patient comprising the step of administering to said patient a compound of the present invention, or a composition comprising said compound. According to certain embodiments, the invention relates to a method of irreversibly inhibiting one or more of ErbB1, ErbB2, ErbB3, ErbB4, a TEC-kinase (e.g., TEC, BTK, ITK, RLK or BMX), and/or JAK3, or a mutant thereof, activity in a patient comprising the step of administering to said patient a compound of the present invention, or a composition comprising said compound. In other embodiments, the present invention provides a method for treating a disorder mediated by one or more of ErbB1, ErbB2, ErbB3, ErbB4, a TEC-kinase (e.g., TEC, BTK, ITK, RLK or BMX), and/or JAK3, or a mutant thereof, in a patient in need thereof, comprising the step of administering to said patient a compound according to the present invention or pharmaceutically acceptable composition thereof. Such disorders are described in detail herein.

Combinations

Depending upon the particular condition, or disease, to be treated, additional therapeutic agents, which are normally administered to treat that condition, may also be present in the compositions of this invention. As used herein, additional therapeutic agents that are normally administered to treat a particular disease, or condition, are known as "appropriate for the disease, or condition, being treated."

For example, compounds of the present invention, or a pharmaceutically acceptable composition thereof, are administered in combination with chemotherapeutic agents to treat proliferative diseases and cancer. Chemotherapeutic or anti-proliferative agents include proapoptotic agents, microtubule stabilizing agents, inhibitors of mitogen-activated protein kinase signaling agents, mTOR inhibitors, TOR inhibitors, interferon agonists, matrix metalloproteinase inhibitors, proteasome inhibitors, protein A-based immune modulators, protein kinase C inhibitors, protein tyrosine phosphatase inhibitors, purine nucleoside phosphorylase inhibitors, raf antagonists, ras farnesyl protein transferase inhibitors, ras inhibitors, ribozymes, ras-GAP inhibitors, Syk inhibitors, ALL-TK antagonists, angiogenesis inhibitors, apoptosis gene modulators, apoptosis regulators, BCR/ABL antagonists, bFGF inhibitors, casein kinase inhibitors, cartilage derived inhibitors, multiple drug resistance gene inhibitors, insulin-like growth factor-1 receptor inhibitors, matrilysin inhibitors, MIF inhibitors, glutathione inhibitors, phosphatase inhibitors, plasminogen activator inhibitors, telomerase inhibitors, translation inhibitors, tyrosine kinase inhibitors, urokinase receptor antagonists, UBC inhibitors, biological response modifiers (e.g., interferon alpha, etc.), adrenocortical suppressants (e.g., mitotane, aminoglutethimide), thymopoietin receptor agonists, stromelysin inhibitors, stem cell inhibitors, stem-cell division inhibitors, Sdi 1 mimetics, signal transduction inhibitors and signal transduction modulators.

Examples of known chemotherapeutic or anti-proliferative agents include, but are not limited to, Adriamycin, dexamethasone, vincristine, cyclophosphamide, fluorouracil, topotecan, taxol, interferons (e.g., interferon alfa-2a; interferon alfa-2b; interferon alfa-n1; interferon alfa-n3; interferon beta-1a; interferon gamma-1b, etc.), interleukins (e.g., interleukin 2, including recombinant interleukin 2, also known as rIL2), platinum derivatives (e.g., lipophilic platinum agents, platinum compounds, platinum coordination complexes (e.g., cisplatin, carboblatin, etc.), platinum-triamine complexes, etc.), anti-CD20 antibodies (e.g., rituximab (Rituxan®), ocreluzimab, ofatumumab (Arzerra®), obinutuzumab (Gazyva®), Ha20 (IMMU-106, etc.)), anti-CD22 antibodies (e.g., belimumab (Benlysta®), epratuzumab, etc.), taxane (e.g., paclitaxel), *vinca* alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, campthothecin, cisplatin, metronidazole, and Gleevec™, purpurins, beta lactam derivatives, camptothecin derivatives, clomifene analogues, combretastatin analogues, monoclonal antibodies, oligonucleotides, lytic peptides, linear polyamine analogues, lipophilic disaccharide peptides, mismatched double stranded RNA, N-substituted benzamides, cryptophycin A derivatives, cyclopentanthraquinones, estrogen agonists, estrogen antagonists, estramustine analogues, multiple tumor suppressor 1-based therapys, imidazoacridones, immunostimulant peptides, mitomycin analogues, antisense oligonucleotides, superactive vasoactive intestinal peptide antagonists, synthetic glycosaminoglycans, thyroid stimulating hormones, alkylating agents (e.g., nitrogen mustards (e.g., mechlorethamine, cyclophosphamide, chlorambucil, melphalan, etc.), alkyl sulfonates (e.g., busulfan, etc.), nitrosoureas (e.g., carmustine, lomustine, semustine, streptozocin, etc.), erythrocyte gene therapies, antimetabolites (e.g., folic acid analogs such as methotrexate, etc.), pyrimidine analogs (e.g., fluorouracil, floxuridine, cytarabine, etc.), purine analogs (e.g., mercaptopurine, thioguanine, pentostatin, etc.), natural products (e.g., vinca alkaloids such as vinblastin, vincristine, etc.), epipodophyllotoxins (e.g., etoposide, etc.), antibiotics (e.g., daunorubicin, doxorubicin, bleomycin), enzymes (e.g., L-asparaginase, etc.), hormones (adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide)), anthracenediones (e.g., mitoxantrone, etc.), substituted ureas (e.g., hydroxyureas, etc.), methyl hydrazine derivatives (e.g., procarbazine, etc.), triazenes (decarbazine, etc.), ethylenimine and methylmelamines (e.g., hexamethylmelamine, thiotepa, etc.), thrombopoietin mimetics, baccatin III derivatives, and anti-thromboembolic agents (such as thrombolytic agents (e.g., altepase anistreplase, streptokinase, urokinase or tissue plasminogen activator, etc.), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, YM150, etc.), factor VIIa inhibitors, ticlopidine, clopidogrel, CS-747 (prasugrel, LY640315), ximelagatran, BIBR1048, etc.), among others. In other embodiments, a compound of the present invention is administered in combination with a biologic agent, such as Avastin or VECTIBIX.

In certain embodiments, compounds of the present invention, or a pharmaceutically acceptable composition thereof, are administered in combination with an antiproliferative or chemotherapeutic agent selected from any one or more of abarelix, acivicin, aclarubicin, acodazole hydrochloride, acronine, adozelesin, aldesleukin, alemtuzumab, alitretinoin, allopurinol, altretamine, ambomycin, ametantrone acetate, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene hydrochloride, bisnafide dimesylate, bizelesin, BCG Live, bevacuzimab, fluorouracil, bexarotene, bleomycin, bleomycin sulfate, bortezomib, brequinar sodium, bropirimine, bryostatin, busulfan, cactinomycin, calusterone, capecitabine, camptothecin, caracemide, carbetimer, carboplatin, carmustine, carubicin hydrochloride, carzelesin, cedefingol, celecoxib, cetuximab, chlorambucil, chlorofusin, cirolemycin, cisplatin, cladribine, clofarabine, crisnatol mesylate, cyclophosphamide, cytarabine, cytarabine ocfosfate, dactinomycin, darbepoetin alfa, dacarbazine, daunorubicin, daunorubicin hydrochloride, decitabine, denileukin, dexormaplatin, dexrazoxane, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin, epirubicin hydrochloride, epoetin alfa, erbulozole, esorubicin hydrochloride, erlotinib, estramustine, estramustine phosphate sodium, etanidazole, etoposide phosphate, etoposide, etoprine, exemestane, fadrozole hydrochloride, fazarabine, fenretinide, filgrastim, floxuridine, fludarabine, fludarabine phosphate, flavopiridol, floxuridine, fluorocitabine, fosquidone, fostriecin sodium, geldanamycin, gemcitabine, gemcitabine hydrochloride, genasense; gossyphol, fulvestrant, gefitinib, gemcitabine, gemtuzumab, goserelin acetate, histrelin acetate, hydroxyurea, ibritumomab, idarubicin, idarubicin hydrochloride, ifosfamide, ilmofosine, imatinib (Gleevec™), imatinib mesylate, interferon alfa-2a, interferon alfa-2b, interferon alfa-n1, interferon alfa-n3, interferon beta-1a, interferon gamma-1b, iproplatin, irinotecan, irinotecan hydrochloride, lanreotide acetate, lenalidomide, letrozole, leucovorin, leuprolide acetate, levamisole, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, 6-MP, mesna, methotrexate, methotrexate sodium, methoxsalen, metoprine, meturedepa, mitindomide, mitocarcin, mitocromin, mitogillin, mitomalcin, mitomycin, mitomycin C, mitosper, mitotane, mitoxantrone, mitoxantrone hydrochloride, mycophenolic acid, nandrolone, nelarabine, nocodazole, nofetumomab, nogalamycin, oblimersen sodium, ormaplatin, oprelvekin, oxaliplatin, oxisuran, paclitaxel (Taxol™) and analogs thereof, such as Taxotere™, palifermin, pamidronate, pegademase, pegaspargase, pegfilgrastim, peliomycin, pemetrexed disodium, pentamustine, pentostatin, peplomycin sulfate, perfosfamide, pipobroman, piposulfan, piroxantrone hydrochloride, plicamycin, plomestane, pomalidomide, porfimer sodium, porfiromycin, prednimustine, procarbazine, procarbazine hydrochloride, puromycin, puromycin hydrochloride, pyrazofurin, quinacrine, rasburicase, rituximab, riboprine, rogletimide; safingol; safingol hydrochloride; sargramostim, semustine; simtrazene; sorafenib, sparfosate sodium; sparsomycin; spirogermanium hydrochloride; spiromustine; spiroplatin; streptonigrin, streptozocin, sulofenur, sunitinib maleate, talc, talisomycin, tamoxifen, tamoxifen methiodide, tecogalan sodium, tegafur, teloxantrone hydrochloride, temoporfin, temozolomide, teniposide, teroxirone, VM-26, testolactone, thiamiprine, thioguanine, 6-TG, thiotepa, tiazofurin, tirapazamine, topotecan, toremifene, toremifene citrate, tositumomab, trastuzumab, trestolone acetate, tretinoin, triciribine phosphate, trimetrexate, trimetrexate glucuronate, triptorelin, tubulozole hydrochloride, ATRA, uracil mustard, uredepa, valrubicin, vapreotide, verteporfin, vinblastine, vinblastine sulfate, vincristine, vincristine sulfate, vindesine, vindesine sulfate, vinepidine sulfate, vinglycinate sulfate, vinleurosine sulfate, vinorelbine, vinorelbine tartrate, vinrosidine sulfate, vinzolidine, vinzolidine sulfate, vorozole, zeniplatin; zinostatin zoledronate, zoledronic acid, zorubicin and zorubicin hydrochloride.

In some embodiments, compounds of the present invention, or a pharmaceutically acceptable composition thereof, are administered in combination with an antiproliferative or chemotherapeutic agent selected from any one or more of polyphenol E, all trans-retinoic acid (ATRA), tumor necrosis factor-related apoptosis-inducing ligand (TRAIL), 5-aza-2'-deoxycytidine, all trans retinoic acid, 17-N-Allylamino-17-Demethoxygeldanamycin (17-AAG), LY294002, BAY 11-7082, PKC412, PD184352, 20-epi-1,25 dihydroxyvitamin D3, 5-ethynyluracil, abiraterone, aclarubicin, acylfulvene, adecypenol, adozelesin, ambamustine, amidox, amifostine, aminolevulinic acid, amrubicin, amsacrine, anagrelide, andrographolide, antagonist D, antagonist G, antarelix, anti-dorsalizing morphogenetic protein-1, antiandrogen, prostatic carcinoma, antiestrogen, antineoplaston, aphidicolin glycinate, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, balanol, batimastat, benzochlorins, benzoylstaurosporine, beta-alethine, betaclamycin B, betulinic acid, bicalutamide, bisantrene, bisaziridinylspermine, bisnafide, bistratene A, bizelesin, breflate, bropirimine, budotitane, buthionine sulfoximine, calcipotriol, calphostin C, canarypox IL-2, carboxamide-amino-triazole, carboxyamidotriazole, CaRest M3, CARN 700, carzelesin, castanospermine, cecropin B, cetrorelix, chlorins, chloroquinoxaline sulfonamide, cicaprost, cis-porphyrin, clotrimazole, collismycin A, collismycin B, combretastatin A4, conagenin, crambescidin 816, crisnatol, cryptophycin 8, curacin A, cycloplatam, cypemycin, cytolytic factor, cytostatin, dacliximab, decitabine, dehydrodidemnin B, deslorelin, dexifosfamide, dexverapamil, diaziquone, didemnin B, didox, diethylnorspermine, dihydro-5-azacytidine, 9-dioxamycin, diphenyl spiromustine, docosanol, dolasetron, doxifluridine, droloxifene, dronabinol, duocarmycin SA, ebselen, ecomustine, edelfosine, edrecolomab, eflornithine, elemene, emitefur, epirubicin, epristeride, etanidazole, etoposide phosphate, fadrozole, fazarabine, fenretinide, finasteride, flavopiridol, flezelastine, fluasterone, fluorodaunorunicin hydrochloride, forfenimex, formestane, fostriecin, fotemustine, gadolinium texaphyrin, gallium nitrate, galocitabine, ganirelix, gelatinase inhibitors, hepsulfam, heregulin, hexamethylene bisacetamide, hypericin, ibandronic acid, idarubicin, idoxifene, idramantone, ilomastat, imiquimod, iobenguane, iododoxorubicin, 4-ipomeanol, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide+estrogen+progesterone, leuprorelin, liarozole, lissoclinamide 7, lobaplatin, lombricine, lometrexol, lonidamine, losoxantrone, lovastatin, loxoribine, lurtotecan, lutetium texaphyrin, lysofylline, maitansine, mannostatin A, marimastat, masoprocol, maspin, menogaril, merbarone, meterelin, methioninase, metoclopramide, mifepristone, miltefosine, mirimostim, mitoguazone, mitolactol, mitonafide, mitotoxin fibroblast growth factor-saporin, mofarotene, molgramostim, human chorionic gonadotrophin, monophosphoryl lipid A+*mycobacterium* cell wall sk, mopidamol, mycaperoxide B, mycobacterial cell wall extract, myriaporone, N-acetyldinaline, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, onapristone, ondansetron, ondansetron, oracin, oral cytokine inducer, ormaplatin, osaterone, oxaunomycin, palauamine, palmitoylrhizoxin, pamidronic acid, panaxytriol, panomifene, parabactin, pazelliptine, peldesine, pentosan polysulfate sodium, pentrozole, perflubron, perfosfamide, perillyl alcohol, phenazinomycin, phenylacetate, picibanil, pilocarpine hydrochloride, pirarubicin, piritrexim, placetin A, placetin B, porfimer sodium, porfiromycin, prednisone, propyl bis-acridone, prostaglandin J2, microalgal, pyrazoloacridine, pyridoxylated hemoglobin polyoxyethylerie conjugate, raltitrexed, ramosetron, retelliptine demethylated, rhenium Re 186 etidronate, rhizoxin, RII retinamide, rogletimide, rohitukine, romurtide, roquinimex, rubiginone B1, ruboxyl, safingol, saintopin, SarCNU, sarcophytol A, semustine, senescence derived inhibitor 1, sense oligonucleotides, single chain antigen-binding protein, sizofiran, sobuzoxane, sodium borocaptate, sodium phenylacetate, solverol, somatomedin binding protein, sonermin, sparfosic acid, spicamycin D, spiromustine, splenopentin, spongistatin 1, squalamine, stipiamide, sulfinosine, suradista, suramin, swainsonine, tallimustine, tauromustine, tazarotene, tecogalan sodium, tegafur, tellurapyrylium, temoporfin, tetrachlorodecaoxide, tetrazomine, thaliblastine, thiocoraline, thrombopoietin, thymalfasin, thymotrinan, tin ethyl etiopurpurin, tirapazamine, titanocene bichloride, topsentin, toremifene, totipotent stem cell factor, triacetyluridine, triciribine, trimetrexate, triptorelin, tropisetron, turosteride, tyrphostins, ubenimex, urogenital sinus-derived growth inhibitory factor, vapreotide, variolin B, vector system, velaresol, veramine, verdins, verteporfin, vinxaltine, vitaxin, vorozole, zanoterone, zeniplatin, zilascorb and zinostatin stimalamer.

In some embodiments, compounds of the present invention, or a pharmaceutically acceptable composition thereof, are administered in combination with an antiproliferative or chemotherapeutic agent selected from any one or more of Erbulozole (also known as R-55104), Dolastatin 10 (also known as DLS-10 and NSC-376128), Mivobulin isethionate (also known as CI-980), NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armaad), AM-138 (Armad/Kyowa Hakko), IDN-5005 (Indena), Cryptophycin 52 (also known as LY-355703), AC-7739 (Ajinomoto, also known as AVE-8063A and CS-39.HCI), AC-7700 (Ajinomoto, also known as AVE-8062, AVE-8062A, CS-39-L-Ser.HCI, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, lnanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B. D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbot), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Inhibitors of mitogen-activated protein kinase signalling include, without limitation, U0126, PD98059, PD184352, PD0325901, ARRY-142886, SB239063, SP600125, BAY 43-9006, wortmannin, or LY294002.

In some embodiments, compounds of the present invention, or a pharmaceutically acceptable composition thereof, are administered in combination with an anti-inflammatory agent. In some embodiments, compounds of the present invention, or a pharmaceutically acceptable composition thereof, are administered in combination with an immunomodulator. In some embodiments, anti-inflammatory agents or immunomodulators are selected from one or more of immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-acylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, allergy vaccines, antihistamines, antileukotrienes, beta-agonists, theophylline, and anticholinergics.

Other examples of agents the inhibitors of this invention may also be combined with include, without limitation: treatments for Alzheimer's Disease such as donepezil hydrochloride) (Aricept® and rivastigmine)(Exelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif), glatiramer acetate)(Copaxone®, and mitoxantrone; treatments for asthma such as albuterol and montelukast (Singulair®); agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

In certain embodiments, compounds of the present invention, or a pharmaceutically acceptable composition thereof, are administered in combination with a monoclonal antibody or an siRNA therapeutic.

In some embodiments, compounds of the present invention are administered in combination with a TOR kinase inhibitor of formula A:

A

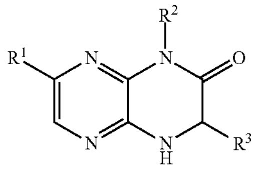

or a pharmaceutically acceptable salt thereof, wherein:

$R^1$ is an optionally substituted group selected from straight or branched $C_{1-8}$ aliphatic, aryl, cycloalkyl, heteroaryl, heterocyclyl, heteroaralkyl, or heterocyclylalkyl;

$R^2$ is hydrogen or an optionally substituted group selected from straight or branched $C_{1-8}$ aliphatic, cycloalkyl, heteroaryl, heterocyclyl, heteroaralkyl, heterocyclylalkyl, aralkyl, or cycloalkylalkyl;

$R^3$ is hydrogen or an optionally substituted straight or branched $C_{1-8}$ aliphatic group;

wherein when an aliphatic group is substituted with one or more substituents, such substituents are independently selected from halogen; aliphatic; hydroxyl; alkoxy; alkoxyaliphatic; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; oxo (=O); $B(OH)_2$, or —O(aliphatic)aminocarbonyl.

In some embodiments, a compound of formula A is not 7-(4-hydroxyphenyl)-1-(3-methoxybenzyl)-3,4-dihydropyrazino[2,3-b]pyrazin-2(1H)-one:

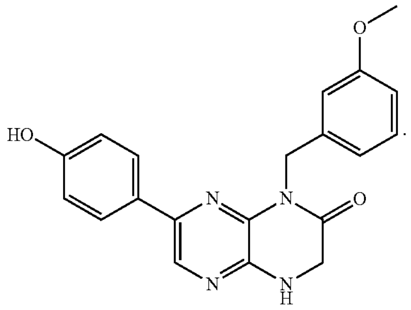 [SMILES: COc1cccc(CN2C(=O)CNc3ncc(-c4ccc(O)cc4)nc32)c1 ; "."]

As described generally above for formula A, $R^1$ is an optionally substituted group selected from straight or branched $C_{1-8}$ aliphatic, aryl, cycloalkyl, heteroaryl, heterocyclyl, heteroaralkyl or heterocyclylalkyl.

In some embodiments of formula A, $R^1$ is an optionally substituted aryl or heteroaryl. In some such embodiments, $R^1$ is selected from an optionally substituted group selected from phenyl, pyridyl, pyrimidyl, benzimidazolyl, 1H-pyrrolo[2,3-b]pyridyl, indazolyl, indolyl, 1H-imidazo[4,5-b]pyridyl, 1H-imidazo[4,5-b]pyridin-2(3H)-onyl, 3H-imidazo[4,5-b]pyridyl, or pyrazolyl.

In some embodiments of formula A, $R^1$ is phenyl substituted with one or more substituents independently selected from the group consisting of optionally substituted straight or branched $C_{1-8}$ aliphatic, optionally substituted heterocyclyl, optionally substituted heteroaryl, aminocarbonyl, halogen, cyano, hydroxyalkyl and hydroxy.

In some embodiments of formula A, $R^1$ is phenyl substituted with an optionally substituted straight or branched $C_{1-8}$ aliphatic group. In some such embodiments, $R^1$ is phenyl substituted with an optionally substituted methyl group.

In some embodiments of formula A, $R^1$ is phenyl substituted with an optionally substituted heterocyclyl group. In some embodiments of formula A, $R^1$ is phenyl substituted with an optionally substituted heteroaryl group. In some such embodiments, $R^1$ is phenyl substituted with an optionally substituted triazolyl or pyrazolyl group.

In some embodiments of formula A, $R^1$ is phenyl substituted with aminocarbonyl. In some embodiments of formula A, $R^1$ is phenyl substituted with halogen. In some such embodiments, $R^1$ is phenyl substituted with fluorine.

In some embodiments of formula A, $R^1$ is phenyl substituted with cyano. In some embodiments of formula A, $R^1$ is phenyl substituted with hydroxyalkyl. In some embodiments of formula A, $R^1$ is phenyl substituted with hydroxy.

In other embodiments of formula A, $R^1$ is pyridyl substituted with one or more substituents independently selected from the group consisting of optionally substituted straight or branched $C_{1-8}$ aliphatic, optionally substituted heterocyclyl, optionally substituted heteroaryl, halogen, aminocarbonyl, cyano, hydroxyalkyl, —OR, and —$NR_2$, wherein each R is independently H, or a substituted or unsubstituted straight or branched $C_{1-4}$ aliphatic.

In some embodiments of formula A, $R^1$ is pyridyl substituted with an optionally substituted straight or branched $C_{1-8}$ aliphatic group. In some such embodiments, $R^1$ is pyridyl substituted with optionally substituted methyl.

In some embodiments of formula A, $R^1$ is pyridyl substituted with an optionally substituted heterocyclyl. In some embodiments of formula A, $R^1$ is pyridyl substituted with an optionally substituted heteroaryl. In some such embodiments, $R^1$ is pyridyl substituted with optionally substituted triazolyl.

In some embodiments of formula A, $R^1$ is pyridyl substituted with halogen.

In some embodiments of formula A, $R^1$ is pyridyl substituted with aminocarbonyl.

In some embodiments of formula A, $R^1$ is pyridyl substituted with cyano.

In some embodiments of formula A, $R^1$ is pyridyl substituted with hydroxyalkyl. In some such embodiments, $R^1$ is pyridyl substituted with hydroxypropyl.

In some embodiments of formula A, $R^1$ is pyridyl substituted with —OR, wherein R is independently hydrogen or an optionally substituted straight or branched $C_{1-4}$ aliphatic.

In some embodiments of formula A, $R^1$ is pyridyl substituted with —$NR_2$, wherein R is independently hydrogen or an optionally substituted straight or branched $C_{1-4}$ aliphatic.

In some embodiments of formula A, $R^1$ is 1H-pyrrolo[2,3-b]pyridyl or benzimidazolyl, optionally substituted with one or more substituents independently selected from the group consisting of optionally substituted straight or branched $C_{1-8}$ aliphatic, and —$NR_2$, wherein R is independently hydrogen or an optionally substituted straight or branched $C_{1-4}$ aliphatic.

In some embodiments of formula A, $R^1$ is selected from

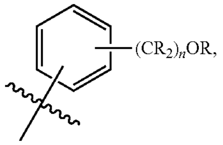 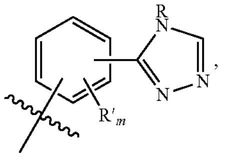

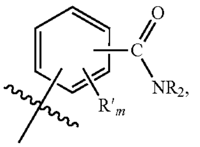 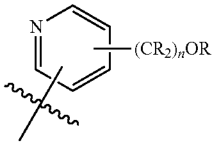 ,

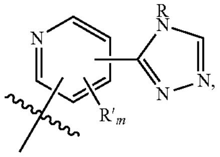 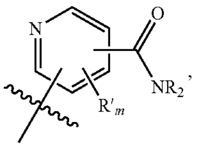

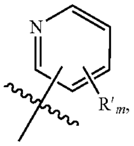 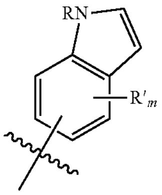 , 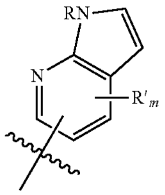 ,

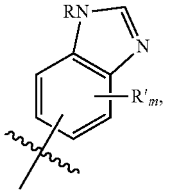 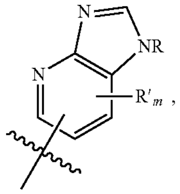

-continued

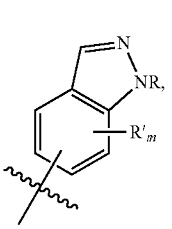 or 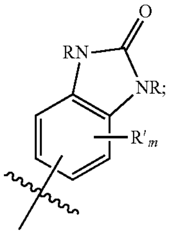

wherein:

R is at each occurrence independently hydrogen, or an optionally substituted straight or branched $C_{1-4}$ aliphatic group;

R' is at each occurrence independently an optionally substituted straight or branched $C_{1-4}$ aliphatic, halogen, cyano, —OR, or —$NR_2$;

m is 0-3; and n is 0-3;

wherein when an aliphatic group is substituted with one or more substituents, such substituents are independently selected from halogen; aliphatic; hydroxyl; alkoxy; alkoxyaliphatic; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxo (=O); $B(OH)_2$, or —O(aliphatic)aminocarbonyl.

It will be understood by those skilled in the art that any of the substituents R' may be attached to any suitable atom of any of the rings in the fused ring systems.

In some embodiments of formula A, R is an optionally substituted straight or branched $C_{1-4}$ aliphatic group. In some embodiments of formula A, R is an optionally substituted straight or branched $C_{1-2}$ aliphatic group. In some such embodiments, R is an optionally substituted methyl group.

In some embodiments of formula A, R' is an optionally substituted straight or branched $C_{1-4}$ aliphatic group. In some such embodiments, R' is an optionally substituted methyl group.

In some embodiments of formula A, R' is halogen. In some such embodiments, R' is fluoro.

In some embodiments of formula A, R' is cyano. In some embodiments of formula A, R' is —OR. In some embodiments of formula A, R' is —$NR_2$.

In some embodiments of formula A, $R^1$ is selected from

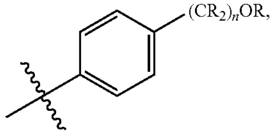 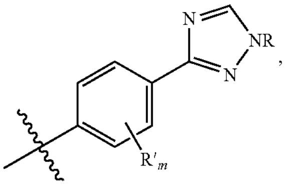

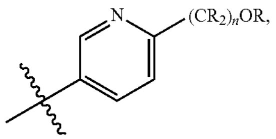 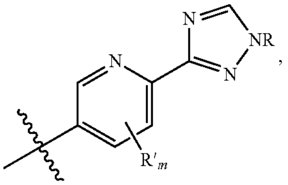

-continued

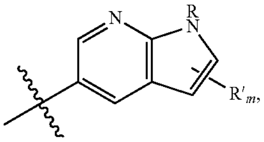 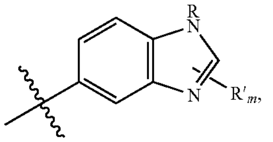

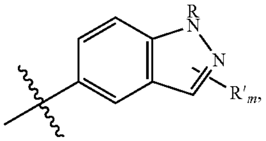 or

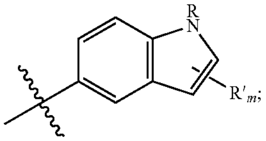

wherein each of R and R' is as defined above.

As described generally above for formula A, $R^2$ is hydrogen or an optionally substituted group selected from $C_{1-8}$ aliphatic, cycloalkyl, heteroaryl, heterocyclyl, heteroaralkyl, heterocyclylalkyl, aralkyl, or cycloalkylalkyl.

In some embodiments of formula A, $R^2$ is hydrogen.

In some embodiments of formula A, $R^2$ is an optionally substituted straight or branched $C_{1-8}$ aliphatic group. In some such embodiments, $R^2$ is an optionally substituted group selected from methyl, ethyl, n-propyl, isopropyl, n-butyl, sec-butyl, isobutyl, tert-butyl, n-pentyl and isopentyl.

In some embodiments of formula A, $R^2$ is an optionally substituted cycloalkyl group.

In some embodiments of formula A, $R^2$ is an optionally substituted heterocyclyl group.

In some embodiments of formula A, $R^2$ is an optionally substituted heteroaryl group.

In some embodiments of formula A, $R^2$ is an optionally substituted heterocyclylalkyl group. In some such embodiments, $R^2$ is —($C_{1-4}$ aliphatic)-heterocyclyl.

In some embodiments of formula A, $R^2$ is an optionally substituted heteroaralkyl group. In some such embodiments, $R^2$ is —($C_{1-4}$ aliphatic)-heteroaryl.

In some embodiments of formula A, $R^2$ is an optionally substituted aralkyl. In some such embodiments, $R^2$ is —($C_{1-4}$ aliphatic)-aryl.

In some embodiments of formula A, $R^2$ is an optionally substituted cycloalkylalkyl. In some such embodiments, $R^2$ is —($C_{1-4}$ aliphatic)-cycloalkyl.

In some embodiments of formula A, $R^2$ is cyclopentyl, cyclohexyl, tetrahydrofuranyl, tetrahydropyranyl, —($C_{1-4}$ aliphatic)-phenyl, —($C_{1-4}$ aliphatic)-cyclopropyl, —($C_{1-4}$ aliphatic)-cyclobutyl, —($C_{1-4}$ aliphatic)-cyclopentyl, —($C_{1-4}$ aliphatic)-cyclohexyl, —($C_{1-4}$ aliphatic)-pyrrolidyl, —($C_{1-4}$ aliphatic)-piperidyl, —($C_{1-4}$ aliphatic)-piperazinyl, —($C_{1-4}$ aliphatic)-morpholinyl, —($C_{1-4}$ aliphatic)-tetrahydrofuranyl, or —($C_{1-4}$ aliphatic)-tetrahydropyranyl.

In some embodiments of formula A, $R^2$ is selected from hydrogen, straight or branched $C_{1-4}$ aliphatic, —($C_{1-4}$ aliphatic)(OR), or a group selected from:

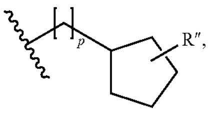 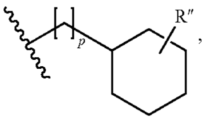

-continued

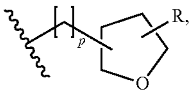 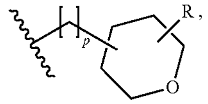

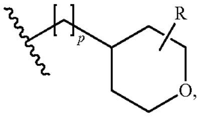 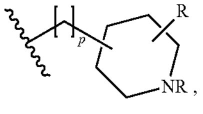

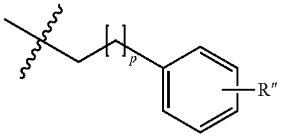 or 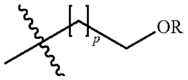 ;

wherein R is as defined above;

R" is at each occurrence independently hydrogen, —OR, cyano, or an optionally substituted straight or branched $C_{1-4}$ aliphatic; and p is 0-3;

wherein when an aliphatic group is substituted with one or more substituents, such substituents are independently selected from halogen; hydroxyl; alkoxy; alkoxyaliphatic; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; $B(OH)_2$, or —O(aliphatic)aminocarbonyl.

In some embodiments of formula A, R is an optionally substituted straight or branched $C_{1-2}$ aliphatic group.

In some embodiments of formula A, R" is hydrogen.

In some embodiments of formula A, R" is —OR.

In some embodiments of formula A, R" is cyano.

In some embodiments of formula A, R" is an optionally substituted straight or branched $C_{1-4}$ aliphatic group. In some embodiments of formula A, R" is an optionally substituted straight or branched $C_{1-2}$ aliphatic group. In some such embodiments, R" is an optionally substituted methyl group.

In some embodiments of formula A, p is 0 or 1.

As described generally above for formula A, $R^3$ is hydrogen, or an optionally substituted straight or branched $C_{1-8}$ aliphatic group.

In some embodiments of formula A, $R^3$ is hydrogen.

In some embodiments of formula A, $R^3$ is an optionally substituted straight or branched $C_{1-8}$ aliphatic group. In some embodiments of formula A, $R^3$ is an optionally substituted straight or branched $C_{1-6}$ aliphatic group. In some embodiments of formula A, $R^3$ is an optionally substituted straight or branched $C_{1-4}$ aliphatic group. In some embodiments of formula A, $R^3$ is an optionally substituted straight or branched $C_{1-2}$ aliphatic group. In some such embodiments, $R^3$ is methyl or ethyl.

In some embodiments, a TOR kinase inhibitor, or a pharmaceutically salt thereof, is selected from those set forth in Table 2.

TABLE 2

Exemplary TOR Kinase Inhibitors.

| Compound # | Name |
|---|---|
| A-1 | 7-(5-fluoro-2-methyl-4-(1H-1,2,4-triazol-3-yl)phenyl)-1-((trans-4-methoxycyclohexyl)methyl)-3,4-dihydropyrazino[2,3-b]pyrazin-2(1H)-one |
| A-2 | 7-(6-( 1H-1,2,4-triazol-3-yl)pyridin-3-yl)-1-(cis-4-methoxycyclohexyl)-3,4-dihydropyrazino[2,3-b]pyrazin-2(1H)-one |
| A-3 | 7-(1H-pyrrolo[2,3-b]pyrazin-3-yl)-1-(2-(tetrahydro-2H-pyran-4-yl)ethyl)-3,4-dihydropyrazino[2,3-b]pyrazin-2(1H)-one |
| A-4 | 7-(5-fluoro-2-methyl-4-(1H-1,2,4-triazol-3-yl)phenyl)-1-((cis-4-methoxycyclohexyl)methyl)-3,4-dihydropyrazino[2,3-b]pyrazin-2(1H)-one |
| A-5 | 1-ethyl-7-(1H-pyrrolo-[3,2-b]pyridin-5-yl)-3,4-dihydropyrazino[2,3-b]pyrazin-2(1H)-one |
| A-6 | 7-(6-( 1H-1,2,4-triazol-3-yl)pyridin-3-yl)-1-((cis-4-methoxycyclohexyl)methyl)-3,4-dihydropyrazino[2,3-b]pyrazin-2(1H)-one |
| A-7 | 7-(1H-benzo[d]imidazol-4-yl)-1-(2-(tetrahydro-2H-pyran-4-yl)ethyl)-3,4-dihydropyrazino[2,3-b]pyrazin-2(1H)-one |
| A-8 | 7-(1H-pyrrolo[2,3-b]pyrazin-4-yl)-1-(2-(tetrahydro-2H-pyran-4-yl)ethyl)-3,4-dihydropyrazino[2,3-b]pyrazin-2(1H)-one |
| A-9 | 7-(6-(1H-1,2,4-triazol-3-yl)pyridin-3-yl)-1-((trans-4-methoxycyclohexyl)methyl)-3,4-dihydropyrazino[2,3-b]pyrazin-2(1H)-one |
| A-10 | 7-(6-(1H-1,2,4-triazol-3-yl)pyridin-3-yl)-1-((trans-4-hydroxycyclohexyl)methyl)-3,4-dihydropyrazino[2,3-b]pyrazin-2(1H)-one |
| A-11 | 7-(6-(1H-1,2,4-triazol-3-yl)pyridin-3-yl)-1-(cis-4-hydroxycyclohexyl)-3,4-dihydropyrazino[2,3-b]pyrazin-2(1H)-one |
| A-12 | 7-(5-fluoro-2-methyl-4-(1H-1,2,4-triazol-3-yl)phenyl)-1-(cis-4-hydroxycyclohexyl)-3,4-dihydropyrazino[2,3-b]pyrazin-2(1H)-one |
| A-13 | 7-(6-(1H-1,2,4-triazol-3-yl)pyridin-3-yl)-1-(tetrahydro-2H-pyran-4-yl)-3,4-dihydropyrazino[2,3-b]pyrazin-2(1H)-one |
| A-14 | 7-(6-(1H-1,2,4-triazol-3-yl)pyridin-3-yl)-1-(2-methoxyethyl)-3,4-dihydropyrazino[2,3-b]pyrazin-2(1H)-one |
| A-15 | 7-(6-(1H-1,2,4-triazol-3-yl)pyridin-3-yl)-1-ethyl-3,4-dihydropyrazino [2,3-b]pyrazin-2(1H)-one |
| A-16 | 7-(5-fluoro-2-methyl-4-(1H-1,2,4-triazol-3-yl)phenyl)-1-((cis-4-hydroxycyclohexyl)methyl)-3,4-dihydropyrazino[2,3-b]pyrazin-2(1H)-one |
| A-17 | 7-(5-fluoro-2-methyl-4-(1H-1,2,4-triazol-3-yl)phenyl)-1-(tetrahydro-2H-pyran-4-yl)-3,4-dihydropyrazino[2,3-b]pyrazin-2(1H)-one |
| A-18 | 7-(1H-indol-4-yl)-1-(2-(tetrahydro-2H-pyran-4-yl)ethyl)-3,4-dihydropyrazino[2,3-b]pyrazin-2(1H)-one |
| A-19 | 7-(5-fluoro-2-methyl-4-(1H-1,2,4-triazol-3-yl)phenyl)-1-((trans-4-hydroxycyclohexyl)methyl)-3,4-dihydropyrazino[2,3-b]pyrazin-2(1H)-one |
| A-20 | 7-(6-(1H-1,2,4-triazol-3-yl)pyridin-3-yl)-1-((cis-4-hydroxycyclohexyl)methyl)-3,4-dihydropyrazino[2,3-b]pyrazin-2(1H)-one |
| A-21 | 7-(6-(1H-1,2,4-triazol-3-yl)pyridin-3-yl)-1-(trans-4-hydroxycyclohexyl)-3,4-dihydropyrazino[2,3-b]pyrazin-2(1H)-one |
| A-22 | 7-(6-(1H-1,2,4-triazol-3-yl)pyridin-3-yl)-1-(trans-4-methoxycyclohexyl)-3,4-dihydropyrazino[2,3-b]pyrazin-2(1H)-one |
| A-23 | 7-(6-(1H-1,2,4-triazol-3-yl)pyridin-3-yl)-1-isopropyl-3,4-dihydropyrazino [2,3-b]pyrazin-2(1H)-one |
| A-24 | 7-(5-fluoro-2-methyl-4-(1H-1,2,4-triazol-3-yl)phenyl)-1-(trans-4-methoxycyclohexyl)-3,4-dihydropyrazino[2,3-b]pyrazin-2(1H)-one |
| A-25 | 7-(5-fluoro-2-methyl-4-(1H-1,2,4-triazol-3-yl)phenyl)-1-(trans-4-hydroxycyclohexyl)-3,4-dihydropyrazino[2,3-b]pyrazin-2(1H)-one |
| A-26 | 7-(5-fluoro-2-methyl-4-(1H-1,2,4-triazol-3-yl)phenyl)-1-(2-methoxyethyl)-3,4-dihydropyrazino[2,3-b]pyrazin-2(1H)-one |
| A-27 | 7-(5-fluoro-2-methyl-4-(1H-1,2,4-triazol-3-yl)phenyl)-1-isopropyl-3,4-dihydropyrazino[2,3-b]pyrazin-2(1H)-one |
| A-28 | 1-ethyl-7-(5-fluoro-2-methyl-4-(1H-1,2,4-triazol-3-yl)phenyl)-3,4-dihydropyrazino[2,3-b]pyrazin-2(1H)-one |
| A-29 | 7-(2-hydroxypyridin-4-yl)-1-(2-(tetrahydro-2H-pyran-4-yl)ethyl)-3,4-dihydropyrazino[2,3-b]pyrazin-2(1H)-one |
| A-30 | 1-isopropyl-7-(4-methyl-6-(1H-1,2,4-triazol-3-yl)pyridin-3-yl)-3,4-dihydropyrazino[2,3-b]pyrazin-2(1H)-one |
| A-31 | 5-(8-isopropyl-7-oxo-5,6,7,8-tetrahydropyrazino[2,3-b]pyrazin-2-yl)-4-methylpicolinamide |
| A-32 | 7-(1H-indazol-4-yl)-1-(2-(tetrahydro-2H-pyran-4-yl)ethyl)-3,4-dihydropyrazino[2,3-b]pyrazin-2(1H)-one |
| A-33 | 7-(2-aminopyrimidin-5-yl)-1-(2-(tetrahydro-2H-pyran-4-yl)ethyl)-3,4-dihydropyrazino[2,3-b]pyrazin-2(1H)-one |
| A-34 | 7-(2-aminopyridin-4-yl)-1-(2-(tetrahydro-2H-pyran-4-yl)ethyl)-3,4-dihydropyrazino[2,3-b]pyrazin-2(1H)-one |
| A-35 | 7-(6-(methylamino)pyridin-3-yl)-1-(2-(tetrahydro-2H-pyran-4-yl)ethyl)-3,4-dihydropyrazino[2,3-b]pyrazin-2(1H)-one |
| A-36 | 7-(6-hydroxypyridin-3-yl)-1-(2-(tetrahydro-2H-pyran-4-yl)ethyl)-3,4-dihydropyrazino[2,3-b]pyrazin-2(1H)-one |
| A-37 | 7-(4-(1H-pyrazol-3-yl)phenyl)-1-(2-methoxyethyl)-3,4-dihydropyrazino [2,3-b]pyrazin-2(1H)-one |
| A-38 | 7-(pyridin-3-yl)-1-(2-(tetrahydro-2H-pyran-4-yl)ethyl)-3,4-dihydropyrazino [2,3-b]pyrazin-2(1H)-one |

TABLE 2-continued

| Exemplary TOR Kinase Inhibitors. | |
|---|---|
| Compound # | Name |
| A-39 | 7-(1H-indazol-4-yl)-1-(2-methoxyethyl)-3,4-dihydropyrazino [2,3-b]pyrazin-2(1H)-one |
| A-40 | 7-(1H-indazol-6-yl)-1-(2-methoxyethyl)-3,4-dihydropyrazino [2,3-b]pyrazin-2(1H)-one |
| A-41 | 7-(pyrimidin-5-yl)-1-(2-(tetrahydro-2H-pyran-4-yl)ethyl)-3,4 dihydropyrazino[2,3-b]pyrazin-2(1H)-one |
| A-42 | 7-(6-methoxypyridin-3-yl)-1-(2-(tetrahydro-2H-pyran-4-yl)ethyl)-3,4-dihydropyrazino[2,3-b]pyrazin-2(1H)-one |
| A-43 | 1-(2-methoxyethyl)-7-(1H-pyrrolo[2,3-b]pyrazin-5-yl)-3,4-dihydropyrazino [2,3-b]pyrazin-2(1H)-one |
| A-44 | 1-ethyl-7-(1H-pyrrolo[2,3-b]pyridin-5-yl)-3,4-dihydropyrazino[2,3-b]pyrazin-2(1H)-one |
| A-45 | 1-ethyl-7-(1H-indazol-4-yl)-3,4-dihydropyrazino[2,3-b]pyrazin-2(1H)-one |
| A-46 | 7-(pyridin-4-yl)-1-(2-(tetrahydro-2H-pyran-4-yl)ethyl)-3,4-dihydropyrazino [2,3-b]pyrazin-2(1H)-one |
| A-47 | 7-(6-aminopyridin-3-yl)-1-(2-(tetrahydro-2H-pyran-4-yl)ethyl)-3,4-dihydropyrazino[2,3-b]pyrazin-2(1H)-one |
| A-48 | 1-methyl-7-(2-methyl-6-(4H-1,2,4-triazol-3-yl)pyridin-3-yl)-3,4-dihydropyrazino[2,3-b]pyrazin-2(1H)-one |
| A-49 | 2-(2-hydroxypropan-2-yl)-5-(8-(trans-4-methoxycyclohexyl)-7-oxo-5,6,7,8-tetrahydropyrazino[2,3-b]pyrazin-2-yl)pyridine 1-oxide |
| A-50 | 4-methyl-5-(7-oxo-8-((tetrahydro-2H-pyran-4-yl)methyl)-5,6,7,8-tetrahydropyrazino[2,3-b]pyrazin-2-yl)picolinamide |
| A-51 | 5-(8-((cis-4-methoxycyclohexyl)methyl)-7-oxo-5,6,7,8-tetrahydropyrazino[2,3-b]pyrazin-2-yl)-4-methylpicolinamide |
| A-52 | 7-(1H-pyrazol-4-yl)-1-(2-(tetrahydro-2H-pyran-4-yl)ethyl)-3,4-dihydropyrazino[2,3-b]pyrazin-2(1H)-one |
| A-53 | 1-(trans-4-methoxycyclohexyl)-7-(4-methyl-6-(1H-1,2,4-triazol-3-yl)pyridin-3-yl)-3,4-dihydropyrazino[2,3-b]pyrazin-2(1H)-one |
| A-54 | 3-((7-(2-methyl-6-(4H-1,2,4-triazol-3-yl)pyridin-3-yl)-2-oxo-3,4-dihydropyrazino[2,3-b]pyrazin-1(2H)-yl)methyl)benzonitrile |
| A-55 | 1-((trans-4-methoxycyclohexyl)methyl)-7-(4-methyl-6-(1H-1,2,4-triazol-3-yl)pyridin-3-yl)-3,4-dihydropyrazino[2,3-b]pyrazin-2(1H)-one |
| A-56 | 3-(7-oxo-8-(2-(tetrahydro-2H-pyran-4-yl)ethyl)-5,6,7,8-tetrahydropyrazino[2,3-b]pyrazin-2-yl)benzamide |
| A-57 | 5-(8-((trans-4-methoxycyclohexyl)methyl)-7-oxo-5,6,7,8-tetrahydropyrazino[2,3-b]pyrazin-2-yl)-4-methylpicolinamide |
| A-58 | 3-((7-(6-(2-hydroxypropan-2-yl)pyridin-3-yl)-2-oxo-3,4-dihydropyrazino[2,3-b]pyrazin-1(2H)-yl)methyl)benzonitrile |
| A-59 | 7-(6-(2-hydroxypropan-2-yl)pyridin-3-yl)-1-((1R,3R)-3-methoxycyclopentyl)-3,4-dihydropyrazino[2,3-b]pyrazin-2(1H)-one |
| A-60 | 7-(6-(2-hydroxypropan-2-yl)pyridin-3-yl)-1-((1S,3R)-3-methoxycyclopentyl)-3,4-dihydropyrazino[2,3-b]pyrazin-2(1H)-one |
| A-61 | 7-(6-(2-hydroxypropan-2-yl)pyridin-3-yl)-1-((1S,3S)-3-methoxycyclopentyl)-3,4-dihydropyrazino[2,3-b]pyrazin-2(1H)-one |
| A-62 | 7-(6-(2-hydroxypropan-2-yl)pyridin-3-yl)-1-((1R,3S)-3-methoxycyclopentyl)-3,4-dihydropyrazino[2,3-b]pyrazin-2(1H)-one |
| A-63 | 7-(1H-indazol-6-yl)-1-(2-(tetrahydro-2H-pyran-4-yl)ethyl)-3,4-dihydropyrazino[2,3-b]pyrazin-2(1H)-one |
| A-64 | 7-(2-methyl-6-(4H-1,2,4-triazol-3-yl)pyridin-3-yl)-1-(2-morpholinoethyl)-3,4-dihydropyrazino[2,3-b]pyrazin-2(1H)-one |
| A-65 | 1-(trans-4-hydroxycyclohexyl)-7-(2-methyl-6-(4H-1,2,4-triazol-3-yl)pyridin-3-yl)-3,4-dihydropyrazino[2,3-b]pyrazin-2(1H)-one |
| A-66 | 1-(cis-4-hydroxycyclohexyl)-7-(2-methyl-6-(4H-1,2,4-triazol-3-yl)pyridin-3-yl)-3,4-dihydropyrazino[2,3-b]pyrazin-2(1H)-one |
| A-67 | 7-(6-(2-hydroxypropan-2-yl)pyridin-3-yl)-1-(2-morpholinoethyl)-3,4-dihydropyrazino[2,3-b]pyrazin-2(1H)-one |
| A-68 | 1-isopropyl-7-(2-methyl-6-(4H-1,2,4-triazol-3-yl)pyridin-3-yl)-3,4-dihydropyrazino[2,3-b]pyrazin-2(1H)-one |
| A-69 | 7-(1H-imidazo[4,5-b]pyridin-6-yl)-1-(2-(tetrahydro-2H-pyran-4-yl)ethyl)-3,4-dihydropyrazino[2,3-b]pyrazin-2(1H)-one |
| A-70 | 1-((cis-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one |
| A-71 | 1-(trans-4-hydroxycyclohexyl)-7-(6-(2-hydroxypropan-2-yl)pyridin-3-yl)-3,4-dihydropyrazino[2,3-b]pyrazin-2(1H)-one |
| A-72 | 1-(cis-4-hydroxycyclohexyl)-7-(6-(2-hydroxypropan-2-yl)pyridin-3-yl)-3,4-dihydropyrazino[2,3-b]pyrazin-2(1H)-one |
| A-73 | 4-(7-oxo-8-(2-(tetrahydro-2H-pyran-4-yl)ethyl)-5,6,7,8-tetrahydropyrazino [2,3-b]pyrazin-2-yl)benzamide |
| A-74 | 7-(1H-indazol-5-yl)-1-(2-(tetrahydro-2H-pyran-4-yl)ethyl)-3,4-dihydropyrazino[2,3-b]pyrazin-2(1H)-one |
| A-75 | 7-(1H-pyrrolo[2,3-b]pyridin-5-yl)-1-(2-(tetrahydro-2H-pyran-4-yl)ethyl)-3,4-dihydropyrazino[2,3-b]pyrazin-2(1H)-one |
| A-76 | 7-(2-methyl-6-(4H-1,2,4-triazol-3-yl)pyridin-3-yl)-1-(tetrahydro-2H-pyran-4-yl)-3,4-dihydropyrazino[2,3-b]pyrazin-2(1H)-one |

TABLE 2-continued

| Exemplary TOR Kinase Inhibitors. | |
|---|---|
| Compound # | Name |
| A-77 | 1-((1S,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one |
| A-78 | 1-((1R,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one |
| A-79 | 1-((1R,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one |
| A-80 | 1-((1S,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one |
| A-81 | 7-(1H-indol-5-yl)-1-(2-(tetrahydro-2H-pyran-4-yl)ethyl)-3,4-dihydropyrazino[2,3-b]pyrazin-2(1H)-one |
| A-82 | 1-ethyl-7-(2-methyl-6-(1H-1,2,4-triazol-3-yl)pyridin-3-yl)-3,4-dihydropyrazino[2,3-b]pyrazin-2(1H)-one |
| A-83 | 7-(1H-indol-6-yl)-1-(2-(tetrahydro-2H-pyran-4-yl)ethyl)-3,4-dihydropyrazino[2,3-b]pyrazin-2(1H)-one |
| A-84 | 7-(4-(2-hydroxypropan-2-yl)phenyl)-1-(trans-4-methoxycyclohexyl)-3,4-dihydropyrazino[2,3-b]pyrazin-2(1H)-one |
| A-85 | 7-(6-(2-hydroxypropan-2-yl)pyridin-3-yl)-1-(tetrahydro-2H-pyran-4-yl)-3,4-dihydropyrazino[2,3-b]pyrazin-2(1H)-one |
| A-86 | 1-((trans-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one |
| A-87 | 7-(6-(2-hydroxypropan-2-yl)pyridin-3-yl)-1-((cis-4-methoxycyclohexyl)methyl)-3,4-dihydropyrazino[2,3-b]pyrazin-2(1H)-one |
| A-88 | 1-(2-methoxyethyl)-7-(4-methyl-2-(methylamino)-1H-benzo[d]imidazol-6-yl)-3,4-dihydropyrazino[2,3-b]pyrazin-2(1H)-one |
| A-89 | 7-(7-methyl-2-oxo-2,3-dihydro-1H-benzo[d]imidazol-5-yl)-1-((tetrahydro-2H-pyran-4-yl)methyl)-3,4-dihydropyrazino[2,3-b]pyrazin-2(1H)-one |
| A-90 | 7-(2-methyl-4-(4H-1,2,4-triazol-3-yl)phenyl)-3,4-dihydropyrazino [2,3-b]pyrazin-2(1H)-one |
| A-91 | 1-(2-methoxyethyl)-7-(4-methyl-6-(1H-1,2,4-triazol-3-yl)pyridin-3-yl)-3,4-dihydropyrazino[2,3-b]pyrazin-2(1H)-one |
| A-92 | 1-benzyl-7-(2-methyl-4-(4H-1,2,4-triazol-3-yl)phenyl)-3,4-dihydropyrazino [2,3-b]pyrazin-2(1H)-one |
| A-93 | 7-(3-fluoro-4-(4H-1,2,4-triazol-3-yl)phenyl)-1-(2-methoxyethyl)-3,4-dihydropyrazino[2,3-b]pyrazin-2(1H)-one |
| A-94 | 7-(3-fluoro-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one |
| A-95 | 7-(3-fluoro-2-methyl-4-(1H-1,2,4-triazol-3-yl)phenyl)-1-(2-methoxyethyl)-3,4-dihydropyrazino[2,3-b]pyrazin-2(1H)-one |
| A-96 | 1-(trans-4-methoxycyclohexyl)-7-(2-methyl-6-(4H-1,2,4-triazol-3-yl)pyridin-3-yl)-3,4-dihydropyrazino[2,3-b]pyrazin-2(1H)-one |
| A-97 | 7-(6-(2-hydroxypropan-2-yl)pyridin-3-yl)-1-(trans-4-methoxycyclohexyl)-3,4-dihydropyrazino[2,3-b]pyrazin-2(1H)-one |
| A-98 | 7-(5-fluoro-2-methyl-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one |
| A-99 | 7-(3-fluoro-2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one |
| A-100 | 1-(2-methoxyethyl)-7-(2-methyl-6-(4H-1,2,4-triazol-3-yl)pyridin-3-yl)-3,4-dihydropyrazino[2,3-b]pyrazin-2(1H)-one |
| A-101 | 7-(6-(2-hydroxypropan-2-yl)pyridin-3-yl)-1-((trans-4-methoxycyclohexyl)methyl)-3,4-dihydropyrazino[2,3-b]pyrazin-2(1H)-one |
| A-102 | 1-(cyclopentylmethyl)-7-(6-(2-hydroxypropan-2-yl)pyridin-3-yl)-3,4-dihydropyrazino[2,3-b]pyrazin-2(1H)-one |
| A-103 | 7-(4-(2-hydroxypropan-2-yl)phenyl)-1-(2-methoxyethyl)-3,4-dihydropyrazino[2,3-b]pyrazin-2(1H)-one |
| A-104 | (S)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one |
| A-105 | (R)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one |
| A-106 | 7-(2-methyl-6-(4H-1,2,4-triazol-3-yl)pyridin-3-yl)-1-((tetrahydro-2H-pyran-4-yl)methyl)-3,4-dihydropyrazino[2,3-b]pyrazin-2(1H)-one |
| A-107 | 7-(4-(2-hydroxypropan-2-yl)phenyl)-1-(2-(tetrahydro-2H-pyran-4-yl)ethyl)-3,4-dihydropyrazino[2,3-b]pyrazin-2(1H)-one |
| A-108 | 7-(6-(2-hydroxypropan-2-yl)pyridin-3-yl)-1-(4-(trifluoromethyl)benzyl)-3,4-dihydropyrazino[2,3-b]pyrazin-2(1H)-one |
| A-109 | 7-(6-(2-hydroxypropan-2-yl)pyridin-3-yl)-1-(3-(trifluoromethyl)benzyl)-3,4-dihydropyrazino[2,3-b]pyrazin-2(1H)-one |
| A-110 | 7-(6-(2-hydroxypropan-2-yl)pyridin-3-yl)-1-(3-methoxypropyl)-3,4-dihydropyrazino[2,3-b]pyrazin-2(1H)-one |
| A-111 | 7-(4-methyl-6-(1H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one |
| A-112 | 7-(6-(2-hydroxypropan-2-yl)pyridin-3-yl)-1-(2-methoxyethyl)-3,4-dihydropyrazino[2,3-b]pyrazin-2(1H)-one |
| A-113 | 7-(6-(2-hydroxypropan-2-yl)pyridin-3-yl)-1-((tetrahydro-2H-pyran-4-yl)methyl)-3,4-dihydropyrazino[2,3-b]pyrazin-2(1H)-one |
| A-114 | 7-(4-methyl-2-(methylamino)-1H-benzo[d]imidazol-6-yl)-1-((tetrahydro-2H-pyran-4-yl)methyl)-3,4-dihydropyrazino[2,3-b]pyrazin-2(1H)-one |

TABLE 2-continued

| Exemplary TOR Kinase Inhibitors. | |
|---|---|
| Compound # | Name |
| A-115 | 7-(2-amino-4-methyl-1H-benzo[d]imidazol-6-yl)-1-((tetrahydro-2H-pyran-4-yl)methyl)-3,4-dihydropyrazino[2,3-b]pyrazin-2(1H)-one |
| A-116 | 7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one |
| A-117 | (R)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one |
| A-118 | (S)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one |
| A-119 | 7-(6-(2-hydroxypropan-2-yl)pyridin-3-yl)-3,3-dimethyl-1-(2-(tetrahydro-2H-pyran-4-yl)ethyl)-3,4-dihydropyrazino[2,3-b]pyrazin-2(1H)-one |
| A-120 | 7-(2-amino-4-methyl-1H-benzo[d]imidazol-6-yl)-1-(2-(tetrahydro-2H-pyran-4-yl)ethyl)-3,4-dihydropyrazino[2,3-b]pyrazin-2(1H)-one |
| A-121 | 7-(6-(2-hydroxypropan-2-yl)pyridin-3-yl)-1-(2-(tetrahydro-2H-pyran-4-yl)ethyl)-3,4-dihydropyrazino[2,3-b]pyrazin-2(1H)-one |
| A-122 | 7-(2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one |
| A-123 | 7-(4-(1H-1,2,4-triazol-5-yl)phenyl)-1-(2-(tetrahydro-2H-pyran-4-yl)ethyl)-3,4-dihydropyrazino[2,3-b]pyrazin-2(1H)-one |
| A-124 | 1-(1-hydroxypropan-2-yl)-7-(2-methyl-6-(1H-1,2,4-triazol-3-yl)pyridin-3-yl)-3,4-dihydropyrazino[2,3-b]pyrazin-2(1H)-one |
| A-125 | 1-(2-hydroxyethyl)-7-(2-methyl-6-(1H-1,2,4-triazol-3-yl)pyridin-3-yl)-3,4-dihydropyrazino[2,3-b]pyrazin-2(1H)-one |

In some embodiments, the TOR kinase inhibitor is a compound as described herein. In some embodiments, the TOR kinase inhibitor is a compound of formula A. In some embodiments, the TOR kinase inhibitor is a compound from Table 2. In some embodiments, the TOR kinase inhibitor is a compound having a molecular formula of $C_{21}H_{27}N_5O_3$. In some embodiments, the TOR kinase inhibitor is a compound having a molecular formula of $C_{16}H_{16}N_8O$. In some embodiments, the TOR kinase inhibitor is a compound having a molecular formula of $C_{21}H_{24}N_8O_2$. In some embodiments, the TOR kinase inhibitor is a compound having a molecular formula of $C_{20}H_{25}N_5O_3$. In some embodiments, the TOR kinase inhibitor is 7-(6-(2-hydroxypropan-2-yl)pyridin-3-yl)-1-((trans)-4-methoxycyclohexyl)-3,4-dihydropyrazino-[2,3-b]pyrazin-2(1H)-one. In some embodiments, the TOR kinase inhibitor is 1-ethyl-7-(2-methyl-6-(1H-1,2,4-triazol-3-yl)pyridin-3-yl)-3,4-dihydropyrazino[2,3-b]pyrazin-2(1H)-one. In some embodiments, the TOR kinase inhibitor is 7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one. In some embodiments, the TOR kinase inhibitor is 1-((1r,4r)-4-hydroxycyclohexyl)-7-(6-(2-hydroxypropan-2-yl)pyridin-3-yl)-3,4-dihydropyrazino[2,3-b]pyrazin-2(1H)-one.

In some embodiments, the present invention provides a method of treating or lessening the severity of BTK-mediated disease or disorder comprising administering a compound of any of formulae I, I', I'', I-a, II, III, IV, V, VI or VII in combination with a compound of formula A. In some embodiments, the present invention provides a method of treating or lessening the severity of BTK-mediated disease or disorder comprising administering a compound of any of formulae I, I', I'', I-a, II, III, IV, V, VI or VII in combination with an antibody and a compound of formula A.

In some embodiments, compounds of the present invention are administered in combination with compound B:

B

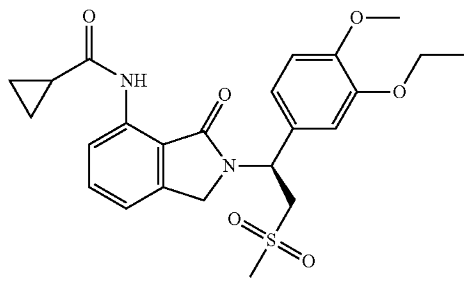

or a pharmaceutically acceptable salt thereof.

Compound B is known by the chemical names cyclopropyl {2-[(1S)-1-(3-ethoxy-4-methoxyphenyl)-2-(methylsulfonyl)ethyl]-3-oxoisoindolin-4-yl}carboxamide and/or N-[2-[(1S)-1-(3-ethoxy-4-methoxyphenyl)-2-(methylsulfonyl)ethyl]-2,3-dihydro-3-oxo-1H-isoindol-4-yl]-cyclopropanecarboxamide.

Compound B can be prepared according to a number of methods. For example, compound B can be prepared according to the preparation procedure for Example 57 of U.S. Pat. No. 6,667,316, titled "Pharmaceutically Active Isoindoline Derivatives," issued Dec. 23, 2003, which is incorporated herein by reference in its entirety. Alternatively or additionally, compound B can be isolated from the corresponding racemic mixture, the preparation of which can be found at, for example, Example 55 of U.S. Pat. No. 6,667,316.

In some embodiments, the present invention provides a method of treating or lessening the severity of BTK-mediated disease or disorder comprising administering a compound of any of formulae I, I', I'', I-a, II, III, IV, V, VI or VII in combination with compound B. In some embodiments, the present invention provides a method of treating or lessening the severity of BTK-mediated disease or disorder comprising administering a compound of any of formulae I, I', I", I-a, II, III, IV, V, VI or VII in combination with an antibody and compound B.

In some embodiments, compounds of the present invention are administered in combination with a compound of formula C:

C

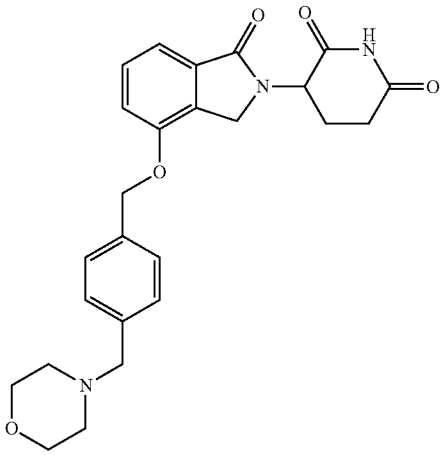

or a pharmaceutically acceptable salt thereof.

The compound of formula C is also known as 3-[4-(4-morpholin-4-ylmethyl-benzyloxy)-1-oxo-1,3-dihydro-isoindol-2-yl]-piperidine-2,6-dione. In some embodiments, a compound of formula C is a hydrochloride salt. In some such embodiments, a compound of formula C is 3-[4-(4-morpholin-4-ylmethyl-benzyloxy)-1-oxo-1,3-dihydro-isoindol-2-yl]-piperidine-2,6-dione hydrochloride.

In some embodiments, a compound of formula C is (S)-3-[4-(4-morpholin-4-ylmethyl-benzyloxy)-1-oxo-1,3-dihydro-isoindol-2-yl]-piperidine-2,6-dione:

C-i

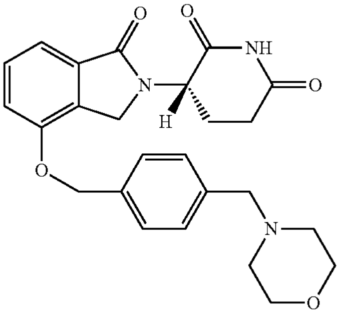

or a pharmaceutically acceptable salt thereof.

In some embodiments, the compound of formula C-i is a hydrochloride salt. In some such embodiments, the compound of formula C-i is (S)-3-[4-(4-morpholin-4-ylmethyl-benzyloxy)-1-oxo-1,3-dihydro-isoindol-2-yl]-piperidine-2,6-dione hydrochloride.

In some embodiments, a compound of formula C is (R)-3-[4-(4-morpholin-4-ylmethyl-benzyloxy)-1-oxo-1,3-dihydro-isoindol-2-yl]-piperidine-2,6-dione:

C-ii

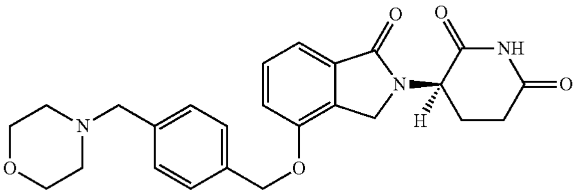

or a pharmaceutically acceptable salt thereof.

In some embodiments, the compound of formula C-ii is a hydrochloride salt. In some such embodiments, the compound of formula C-ii is (R)-3-[4-(4-morphlin-4-ylmethyl-benzyloxy)-1-oxo-1,3-dihydro-isoindo-2-yl]piperidine-2,6-dione hydrochloride.

Compounds of formulae C, C-i and C-ii, or pharmaceutically acceptable salts, solvates, hydrates, stereoisomers, tautomers or racemic mixtures thereof, can be prepared for example, according to the procedures described in U.S. Publication No. 2011/0196150, published Aug. 11, 2011, the entirety of which is hereby incorporated by reference.

In some embodiments, the present invention provides a method of treating or lessening the severity of BTK-mediated disease or disorder comprising administering a compound of any of formulae I, I', I", I-a, II, III, IV, V, VI or VII in combination with a compound of formulae C, C-i or C-ii. In some embodiments, the present invention provides a method of treating or lessening the severity of BTK-mediated disease or disorder comprising administering a compound of any of formulae I, I', I", I-a, II, III, IV, V, VI or VII in combination with an antibody and a compound of formulae C, C-i or C-ii.

In some embodiments, compounds of the present invention are administered in combination with a compound of formula D:

D

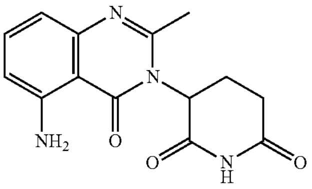

or a pharmaceutically acceptable salt thereof.

The compound of formula D, also known as 3-(5-amino-2-methyl-4-oxo-4H-quinazolin-3-yl)-piperidine-2,6-dione, can be prepared according to the methods described in the Examples in U.S. Pat. No. 7,635,700, the disclosure of which is incorporated herein by reference in its entirety.

In some embodiments, the compound of formula D is a hydrochloride salt. In some such embodiments, the compound of formula D is 3-(5-amino-2-methyl-4-oxo-4H-quinazolin-3-yl)-piperidine-2,6-dione hydrochloride.

The compound of formula D markedly inhibits TNF-α, IL-1β, and other inflammatory cytokines in LPS-stimulated hPBMC and human whole blood. TNF-α, an inflammatory cytokine produced by macrophages and monocytes during acute inflammation, is responsible for a diverse range of signaling events within cells. TNF-α may play a pathological role in cancer. The compound of formula D is an immunomodulatory agent. Without wishing to be bound by theory, it is believed that the compound of formula D inhibits or reduces the synthesis of TNF-α. The compound of formula D also enhances the degradation of TNF-α mRNA and potently inhibits IL-1β and stimulates IL-10.

In some embodiments, the compound of formula D exhibits both anti-angiogenic and immune modulating effects. Accordingly, in some embodiments, the compound of formula D is useful in treating diseases or disorders which are characterized by aberrant angiogenesis. In some embodiments, the present invention provides a method of treating or lessening the severity of an autoimmune disease or disorder comprising administering a compound of any of formulae I, I', I'', I-a, II, III, IV, V, VI or VII in combination with the compound of formula D.

In some embodiments, compounds of the present invention are administered in combination with compound E:

E

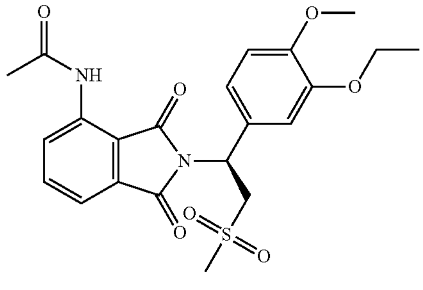

or a pharmaceutically acceptable salt thereof.

Compound E is also known as (S)-2-[1-(3-ethoxy-4-methoxyphenyl)-2-methylsulfonylethyl]-4-acetylaminoisoindoline-1,3-dione. Racemate 2-[1-(3-ethoxy-4-methoxyphenyl)-2-methylsulfonylethyl]-4-acetylaminoisoindoline-1,3-dione is readily prepared using the methods in U.S. Pat. No. 6,020,358, which is hereby incorporated by reference in its entirety.

Compound E can be isolated from the racemic compound by techniques known in the art. Compound E can also be synthesized in its enantiomerically pure form, for example, from 3-acetamidophthalic anhydride and a chiral amino acid salt of (S)-2-(3-ethoxy-4-methoxyphenyl)-1-(methylsulphonyl)-eth-2-ylamine. Chiral amino acid salts of (S)-2-(3-ethoxy-4-methoxyphenyl)-1-(methylsulphonyl)-eth-2-ylamine include, but not limited to salts formed with the L isomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, 4-aminobutyric acid, 2 amino isobutyric acid, 3 amino propionic acid, ornithine, norleucine, norvaline, hydroxyproline, sarcosine, citrulline, cysteic acid, t-butylglycine, t-butylalanine, phenylglycine, cyclohexylalanine, and N-acetyl-leucine. In some embodiments, the chiral amino acid salt is (S)-2-(3-ethoxy-4-methoxyphenyl)-1-(methylsulphonyl)-eth-2-ylamine N-acetyl-L-leucine salt, which is resolved from 2-(3-ethoxy-4-methoxyphenyl)-1-(methylsulphonyl)-eth-2-ylamine and N-acetyl-L-leucine in methanol.

Compound E is an inhibitor of phosphodiesterase 4 (PDE4). Accordingly, in some embodiments, compound E is useful in treating inflammatory diseases or disorders. In some embodiments, compound E is useful for moderating and/or mediating the production of proinflammatory and anti-inflammatory mediators. Accordingly, in some embodiments, the present invention provides a method of treating or lessening the severity of an inflammatory disease or disorder comprising administering a compound of any of formulae I, I', I'', I-a, II, III, IV, V, VI or VII in combination with compound E.

In some embodiments, compounds of the present invention are administered in combination with a compound of formulae F or G:

F

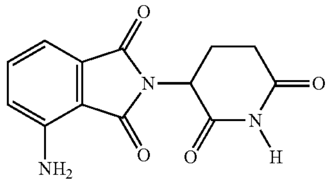

G

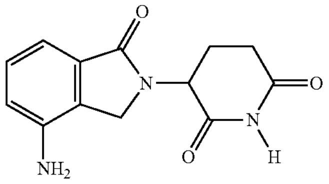

or a pharmaceutically acceptable salt thereof.

The compound of formula F is also referred to as 4-(amino)-2-(2,6-dioxo(3-piperidyl))-isoindoline-1,3-dione.

The compound of formula G is also referred to as 3-(4-amino-1-oxo-1,3-dihydro-isoindol-2-yl)-piperidine-2,6-dione.

Compounds F and G are prepared by methods such as those described in U.S. Pat. No. 5,635,517, which is hereby incorporated by reference.

It will be appreciated that compounds of formula F and G can exist as either the racemates (i.e., compounds of formula F and G, respectively) or as single enantiomers. Accordingly, in some embodiments, a compound F is (S)-4-(amino)-2-(2,6-dioxo(3-piperidyl))-isoindoline-1,3-dione:

F-i

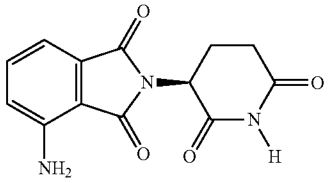

or a pharmaceutically acceptable salt thereof.

In some embodiments, compound F is (R)-4-(amino)-2-(2,6-dioxo(3-piperidyl))-isoindoline-1,3-dione:

F-ii

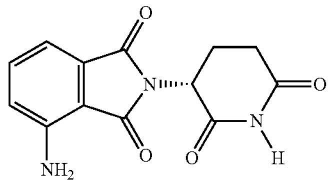

or a pharmaceutically acceptable salt thereof.

Compounds of formula F, F-i and F-ii are useful in treating or lessening the severity of proliferative disorders such as cancer. Compounds of formula F, F-i and F-ii are also useful in treating or lessening the severity of inflammatory and/or autoimmune diseases or disorders. Accordingly, the present invention provides methods of treating or lessening the severity of a disease or disorder selected from a proliferative disorder or an inflammatory or autoimmune disease or disorder comprising administering a compound of any of formulae I, I', I", I-a, II, III, IV, V, VI or VII in combination with the a compound of formula F, F-i or F-ii.

In some embodiments, the present invention provides a method of treating or lessening the severity of BTK-mediated disease or disorder comprising administering a compound of any of formulae I, I', I", I-a, II, III, IV, V, VI or VII in combination with an antibody and a compound of formula F, F-i or F-ii.

In some embodiments, a compound of formula G is (S)-3-(4-amino-1-oxo-1,3-dihydro-isoindol-2-yl)-piperidine-2,6-dione:

G-i

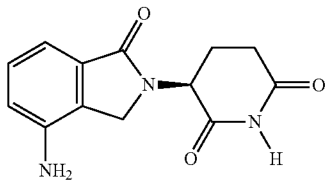

or a pharmaceutically acceptable salt thereof.

In some embodiments, a compound of formula G is (R)-3-(4-amino-1-oxo-1,3-dihydro-isoindol-2-yl)-piperidine-2,6-dione:

G-ii

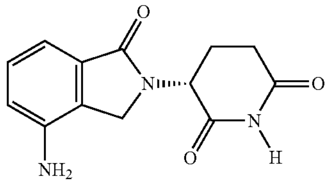

or a pharmaceutically acceptable salt thereof.

Compounds of formula G, G-i and G-ii are useful in treating or lessening the severity of proliferative disorders such as cancer. Compounds of formula G, G-i and G-ii are also useful in treating or lessening the severity of inflammatory and/or autoimmune diseases or disorders. Accordingly, the present invention provides methods of treating or lessening the severity of a disease or disorder selected from a proliferative disorder or an inflammatory or autoimmune disease or disorder comprising administering a compound of any of formulae I, I', I", I-a, II, III, IV, V, VI or VII in combination with a compound of formula G, G-i or G-ii.

In some embodiments, the present invention provides a method of treating or lessening the severity of BTK-mediated disease or disorder comprising administering a compound of any of formulae I, I', I", I-a, II, III, IV, V, VI or VII in combination with an antibody and a compound of formula G, G-i or G-ii.

In some embodiments, the present invention provides a method of treating or lessening the severity of BTK-mediated disease or disorder comprising administering a compound of any of formulae I, I', I", I-a, II, III, IV, V, VI or VII in combination with a compound selected from a compound of formulae A, C, D, F or G or a compound selected from B and E. In some embodiments, the present invention provides a method of treating or lessening the severity of BTK-mediated disease or disorder comprising administering a compound of any of formulae I, I', I", I-a, II, III, IV, V, VI or VII in combination with (i) a compound selected from a compound of formulae A, C, D, F or G or a compound selected from B and E, and (ii) an additional therapeutic agent. In some such embodiments, the additional therapeutic agent is selected from among those described herein. In some embodiments, the additional therapeutic agent is an anti-proliferative agent as described above. In some embodiments, the additional therapeutic agent is an anti-inflammatory agent as described above. In some embodiments, the additional therapeutic agent is an immunomodulator as described above.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. In some embodiments, provided combinations refer to contemporaneously administering to a subject separate dosage forms of each agent, wherein one agent is administered before, during or after administration of the second agent. In some embodiments, simultaneous or contemporaneous exposure of each agent is effected via different dosage regimens appropriate for each therapeutic agent. Accordingly, the present invention provides a single unit dosage form comprising a provided compound, an additional therapeutic agent, and a pharmaceutically acceptable carrier, adjuvant, or vehicle.

The amount of both, an inventive compound and additional therapeutic agent (in those compositions which comprise an additional therapeutic agent as described above)) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Compound numbers utilized in the Examples below correspond to compound numbers set forth in Table 1, supra.

Example 1

N-(3-((5-fluoro-2-((4-hydroxyphenyl)amino)pyrimidin-4-yl)amino)phenyl)acrylamide (I-3)

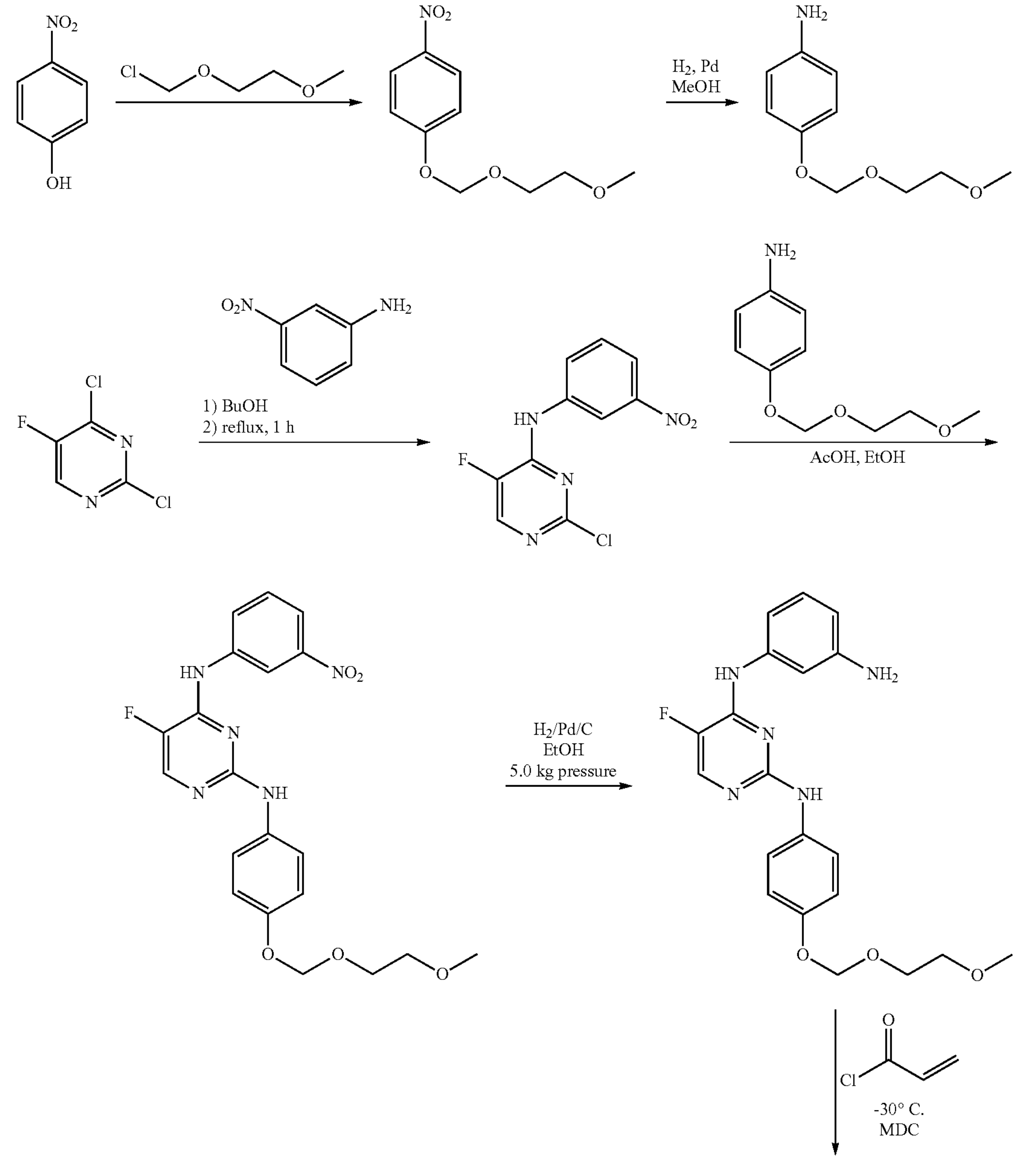

-continued

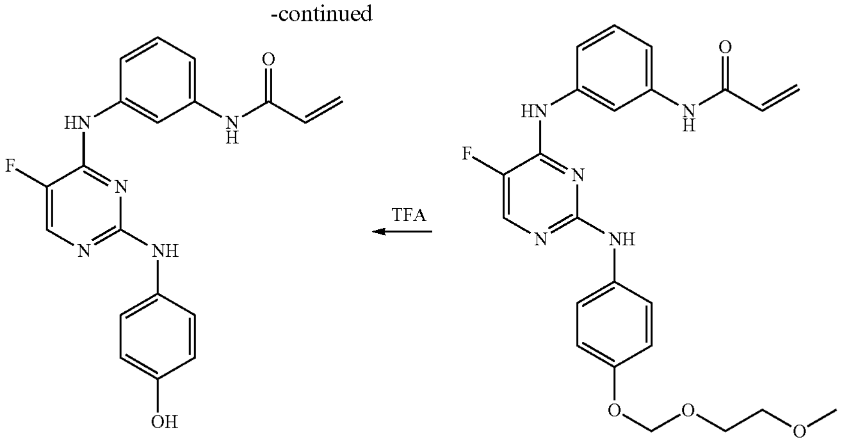

I-3

Synthesis of 1-[(2-methoxyethoxy)methoxy]-4-nitrobenzene

In a 50 mL, 3-neck RBF equipped with a magnetic stirrer, reflux condenser, calcium chloride guard tube and thermometer pocket were sequentially charged 4-nitrophenol (1.50 g), DIPEA (2.90 mL) and DCM (25 mL). MEM-Cl (2.016 g) was added drop wise to the reaction at 0° C. The reaction mixture was stirred at 0° C. for 30 minutes and then allowed to stir at room temperature for 4 hours. The reaction was monitored on TLC using hexane:ethyl acetate (8:2) as mobile phase. After completion, the reaction was poured into water and the product was extracted in ethyl acetate and washed with brine. The organic layer was dried over sodium sulfate and the solvent was removed under reduced pressure to give 2.35 g of 1-[(2-methoxyethoxy)methoxy]-4-nitrobenzene as a solid, which was used in the next step without further purification.

Synthesis of 4-[(2-methoxyethoxy)methoxy]aniline

To a suspension of Pd/C (0.5 g) in methanol (25 mL), 1-[(2-methoxyethoxy)methoxy]-4-nitrobenzene (2.35 g) was added to a 50 mL 3-neck RBF at room temperature under nitrogen atmosphere. Hydrogen gas was bubbled through the reaction mixture for 1-2 hr at room temperature and the reaction was monitored on TLC using chloroform:methanol (9.8:0.2) as mobile phase. After completion, the reaction mixture was filtered using Celite and washed with methanol. The combined filtrate was concentrated under reduced pressure at 40° C. to give 2.0 g of 4-[(2-methoxyethoxy)methoxy]aniline as a dark brown liquid.

Synthesis of 2-chloro-5-fluoro-N-(3-nitrophenyl)pyrimidin-4-amine

In a 50 mL 3-neck RBF equipped with $N_2$ bubbler and reflux condenser 2,4-dichloro-5-fluoropyrimidine (1.79 g) in 1-butanol (20 mL), 4-nitroaniline (1.0 g) and DIPEA (2.6 mL) were charge at room temperature. The reaction mixture was heated to 120° C. for 2 hr. The reaction was monitored on TLC using hexane:ethyl acetate (8:2) as mobile phase. After completion, the reaction mixture was cooled to room temperature. Solid precipitate was filtrated and washed with cold hexanes and dried to give 1.26 g of 2-chloro-5-fluoro-N-(3-nitrophenyl)pyrimidin-4-amine.

Synthesis of 5-fluoro-N2-(4-((2-methoxyethoxy)methoxy)phenyl)-N4-(3-nitrophenyl)pyrimidine-2,4-diamine To a solution of 2-chloro-5-fluoro-N-(3-nitrophenyl)pyrimidin-4-amine (0.400 g) and 4-[(2-methoxyethoxy)methoxy]aniline (0.458 g), in ethanol (20 mL), was added acetic acid (4.65 mg). The reaction mixture was heated to reflux for 24 hr. Completion of reaction was monitored by TLC using hexane:ethyl acetate (8:2) as mobile phase. After completion of the reaction, ethanol was removed under reduced pressure at 40° C. To the residue water (25 mL) was added and mixture was extracted with ethyl acetate. The organic layer was dried over sodium sulfate and distilled under reduced pressure to give 0.4 g of 5-fluoro-N2-(4-((2-methoxyethoxy)methoxy)phenyl)-N4-(3-nitrophenyl)pyrimidine-2,4-diamine as a solid.

Synthesis of N4-(3-aminophenyl)-5-fluoro-N2-(4-((2-methoxyethoxy)methoxy)phenyl)pyrimidine-2,4-diamine To a suspension of Pd/C (0.2 g) in methanol (20 mL), 5-fluoro-N2-(4-((2-methoxyethoxy)methoxy)phenyl)-N4-(3-nitrophenyl)pyrimidine-2,4-diamine (0.40 g) was added under nitrogen atmosphere into the autoclave at room temperature. Hydrogen pressure (70 psi) was applied and the reaction mixture was stirred overnight at room temperature. The reaction was monitored on TLC using hexane:ethyl acetate (4:6) as mobile phase. After completion, the reaction mixture was filtered using Celite and the filter cake was washed with methanol. The combined filtrate was concentrated under reduced pressure at 40° C. to give 0.3 g of N4-(3-aminophenyl)-5-fluoro-N2-(4-((2-methoxyethoxy)methoxy)phenyl)pyrimidine-2,4-diamine as a solid.

Synthesis of N-(3-((5-fluoro-2-((4-((2-methoxyethoxy)methoxy)phenyl)amino)pyrimidin-4-yl)amino)phenyl)acrylamide In a 50 mL, 3-neck RBF equipped with a magnetic stirrer, calcium chloride guard tube and thermo pocket was charged N4-(3-aminophenyl)-5-fluoro-N2-(4-((2-methoxyethoxy)methoxy)phenyl)pyrimidine-2,4-diamine (0.380 g) in DCM (10 mL) and was cooled to −30° C. To the reaction mixture was slowly added acryloyl chloride solution in DCM (0.090 g in 5.0 mL DCM) and the reaction mixture was stirred at −30° C. for approx. 40 minutes. The reaction was monitored on TLC using chloroform:methanol (9.6:0.4) as mobile phase. The reaction mixture was poured into water (100 mL) and basified using sodium bicarbonate. The reaction mixture was extracted with DCM (25 mL×2) and the combined organic layers were washed with 50 mL brine solution. The organic layer was dried over sodium sulfate and concentrated completely under reduce pressure at 40° C. The crude product was purified by column chromatography eluting in 35% of ethyl acetate in hexane to give 0.36 g of N-(3-((5-fluoro-2-((4-((2-methoxyethoxy)methoxy)phenyl)amino)pyrimidin-4-yl)amino)phenyl)acrylamide.

Synthesis of N-(3-((5-fluoro-2-((4-hydroxyphenyl)amino)pyrimidin-4-yl)amino)phenyl)acrylamide (I-3)

In a 25 mL 3-neck RBF equipped with a rubber septum, N-(3-((5-fluoro-2-((4-((2-methoxyethoxy)methoxy)phenyl)amino)pyrimidin-4-yl)amino)phenyl)acrylamide (0.180 g) was taken and TFA (1.0 mL) was added drop wise at room temperature under stirring. The reaction mixture was further stirred for 30 min. Completion of reaction was monitored by TLC using $CHCl_3$:MeOH (9.5:0.5). After completion, the reaction mixture was quenched in water. The aqueous solution was basified with saturated sodium bicarbonate solution. The product was extracted into DCM, washed with water and dried over sodium sulfate. The solvent was evaporated under reduced pressure. The crude product was treated with DBU and 75 mg of product was collected. This was further purified by preparative TLC using $CHCl_3$:MeOH (9.5:0.5) as a mobile phase to give 10 mg of N-(3-((5-fluoro-2-((4-hydroxyphenyl)amino)pyrimidin-4-yl)amino)phenyl)acrylamide.

M+1=365.9 $^1$H NMR: DMSO-$d_6$ (400 MHz) 5.73-5.76 (dd, 1H, J=2, 8), 6.23-6.28 (dd, 1H, J=2, 18.8), 6.48-6.55 (m, 1H), 6.59. 6.61 (d, 2H, J=8.8), 7.22-7.261 (t, 1H, J=8.16), 7.40-7.51 (m, 4H), 8.03-8.04 (d, 2H, J=3.6), 8.426 (s, 1H), 8.902 (s, 1H), 9.331 (s, 1H), 10.26 (s, 1H).

Example 2

N-(3-((5-fluoro-2-((4-(2-hydroxyethoxy)phenyl)amino)pyrimidin-4-yl)amino)phenyl)acrylamide (I-1)

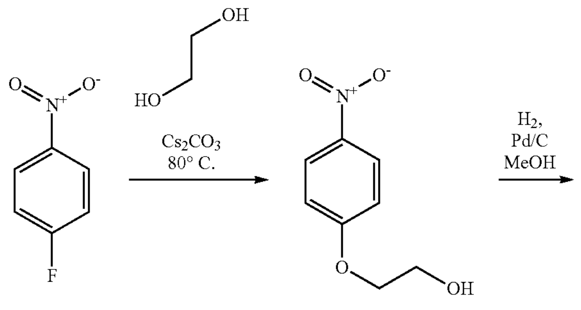

-continued

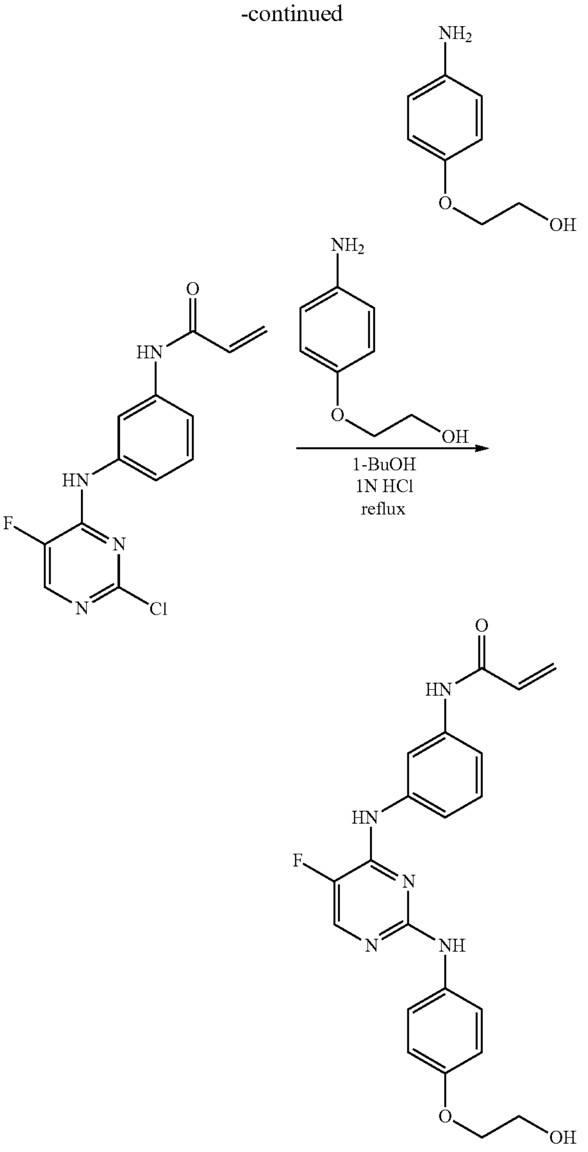

I-1

Synthesis of 2-(4-nitrophenoxy)ethanol

In a 50 mL, 3-neck RBF equipped with a magnetic stirrer, reflux condenser, and thermo pocket were sequentially charged 4-fluoro nitrobenzene (2.00 g), $Cs_2CO_3$ (9.21 g) and ethylene glycol (20 mL). The reaction mixture was heated to 80° C. for 30 minutes. The reaction was monitored on TLC using Hexane: Ethyl acetate (7:3) as mobile phase. After completion of the reaction, the reaction mixture was cooled to room temperature and poured into cold water. Solid precipitate was filtered and washed with water. Solid was dried under reduced pressure at 45° C. for 1 hr. 2.70 g of 2-(4-nitrophenoxy)ethanol was obtained as a solid and was taken for the next step without further purification.

Synthesis of 2-(4-aminophenoxy)ethanol

To a suspension of Pd/C (0.27 g) in methanol (27 mL), 2-(4-nitrophenoxy)ethanol (2.70 g) was added under nitrogen atmosphere into the 50 mL 3-neck RBF at room temperature. Hydrogen gas was bubbled for 1-2 hr at room temperature. The reaction was monitored on TLC using chloroform: methanol (9.8:0.2) as mobile phase. After completion, the reaction mixture was filtered using Celite and washed with methanol. The filtrate was concentrated under reduced pressure at 40° C. to give 1.8 g of 2-(4-aminophenoxy)ethanol as a dark brown liquid.

Synthesis of N-{3-[(5-fluoro-2-{[4-(2-hydroxyethoxy)phenyl]amino}pyrimidin-4-yl)amino]phenyl}prop-2-enamide (I-1)

To a solution of N-{3-[(2-chloro-5-fluoropyrimidin-4-yl)amino]phenyl}prop-2-enamide (0.05 g) and 2-(4-aminophenoxy)ethanol (0.031 g) in 1-butanol (2 mL), was added HCl (0.3 mg). The reaction mixture was heated to reflux for 5 hr. Completion of reaction was monitored by TLC using chloroform:methanol (9:1) as mobile phase. After completion, the reaction mixture was allowed to cool at room temperature. The reaction mixture was quenched in water and neutralized with sodium bicarbonate. The mixture was extracted in ethyl acetate, organic layer washed with brine, dried over sodium sulfate and concentrated completely under reduce pressure at 50° C. The obtained semisolid was purified by preparative HPLC to give 13 mg of N-{3-[(5-fluoro-2-{[4-(2-hydroxyethoxy)phenyl]amino}pyrimidin-4-yl)amino]phenyl}prop-2-enamide. M+1=410.1 $^1$H NMR (DMSO-$d_6$, 400 MHz) 3.671-3.694 (t, 2H, J=4.4), 3.880-3.906 (t, 2H, J=5.2), 4.83 (br, 1H), 5.741-5.771 (dd, 1H, J=2.8, 8.4), 6.237-6.284 (dd, 1H, J=2, 15.2), 6.460-6.527 (dd, 1H, J=10, 6.8), 6.749-6.771 (d, 2H, J=8.8), 7.253-7.293 (t, 1H, J=8), 7.426-7.447 (d, 1H, J=8.4), 7.473-7.492 (d, 1H, J=7.6), 7.527-7.550 (d, 2H, J=9.2), 7.998 (s, 1H), 8.062-8.071 (d, 1H, J=3.6), 9.071 (s, 1H), 9.381 (s, 1H), 10.206 (s, 1H).

Example 3

N-(3-((5-fluoro-2-((4-(2-methoxyethoxy)phenyl)amino)pyrimidin-4-yl)amino)phenyl)-2,3-dihydroxypropanamide (I-4)

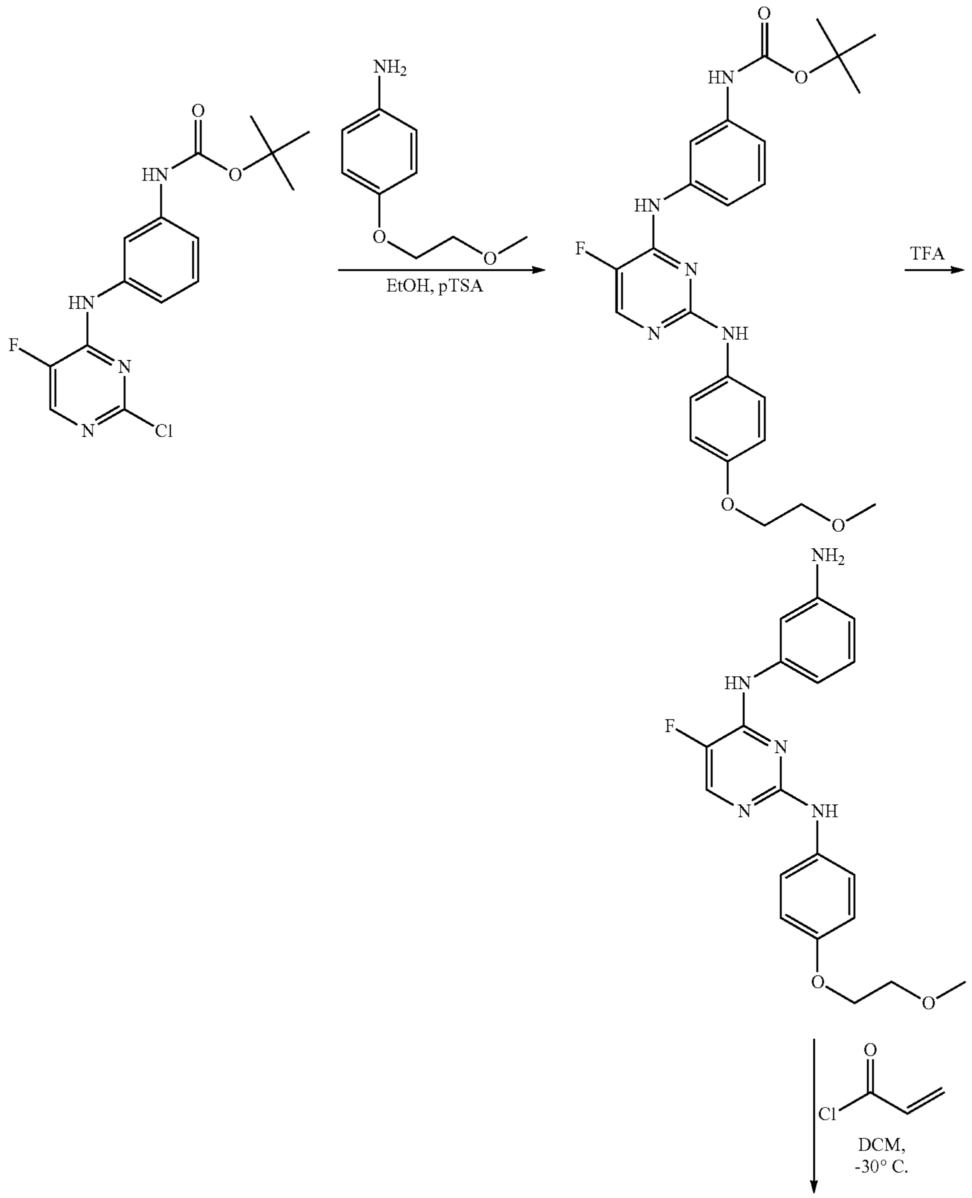

-continued

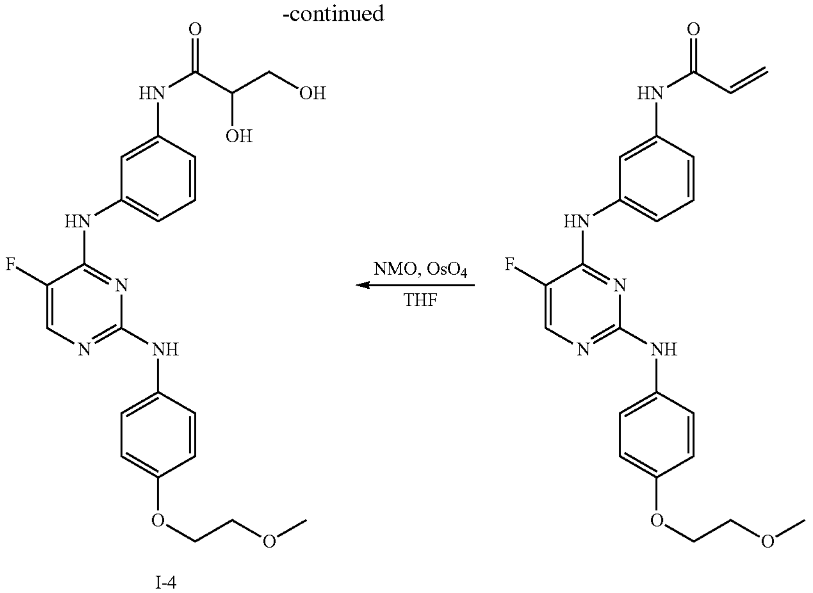

I-4

Synthesis of tert-butyl (3-((5-fluoro-2-((4-(2-methoxyethoxy)phenyl)amino)pyrimidin-4-yl)amino)phenyl)carbamate To a solution of 4-(2-methoxyethoxy)aniline (1.5 g) and tert-butyl (3-((2-chloro-5-fluoropyrimidin-4-yl)amino)phenyl) (1.48 g) in ethanol (15 mL) was added para-toluenesulfonic acid (84.4 mg). The reaction mixture was heated to reflux for 24 hr. Completion of reaction was monitored by TLC using hexane:ethyl acetate (5:5) as mobile phase. After completion, the reaction mixture was allowed to cool to room temperature and ethanol was distilled out under reduced pressure. Water was added and stirred for 30 minutes at room temperature. Solid precipitate was filtered, washed with water and dried to give 1.2 g of tert-butyl (3-((5-fluoro-2-((4-(2-methoxyethoxy)phenyl)amino)pyrimidin-4-yl)amino)phenyl)carbamate.

Synthesis of N4-(3-aminophenyl)-5-fluoro-N2-(4-(2-methoxyethoxy)phenyl)pyrimidine-2,4-diamine In a 25 mL, 3-neck RBF equipped with a magnetic stirrer, and thermo pocket was sequentially charged with tert-butyl (3-((5-fluoro-2-((4-(2-methoxyethoxy)phenyl)amino)pyrimidin-4-yl)amino)phenyl)carbamate (1.2 g) in DCM (10 mL). Trifluoroacetic acid (6.0 mL) was added drop wise into the reaction mixture at 0° C. The reaction mixture was stirred at 0° C. for 45 minutes. The reaction was monitored by TLC using ethyl acetate:hexane (7:3) as mobile phase. After completion, the reaction mixture was quenched in water and neutralized with sodium bicarbonate. The mixture was extracted into DCM. The organic layer was washed with brine, dried over sodium sulfate and concentrated completely under reduce pressure at 40° C. to give 0.94 g of N4-(3-aminophenyl)-5-fluoro-N2-(4-(2-methoxyethoxy)phenyl)pyrimidine-2,4-diamine which was used without further purification.

Synthesis of N-(3-((5-fluoro-2-((4-(2-methoxyethoxy)phenyl)amino)pyrimidin-4-yl)amino)phenyl)acrylamide In a 50 mL 3-neck RBF equipped with a magnetic stirrer, calcium chloride guard tube and thermo pocket was charged N4-(3-aminophenyl)-5-fluoro-N2-(4-(2-methoxyethoxy)phenyl)pyrimidine-2,4-diamine (0.40 g) in dry DCM (10 mL) and was cooled to −30° C. An acryloyl chloride solution in DCM (0.107 g in 5.0 mL DCM) was added slowly and the reaction mixture was stirred at −30° C. for approx. 40 minutes. The reaction was monitored on TLC using chloroform:methanol (9.6:0.4) as mobile phase. The reaction mixture was poured into water (100 mL) and basified using sodium bicarbonate. The reaction mixture was extracted with MDC (2×25 mL) and the combined organic layer was washed with 50 mL brine solution. The organic layer was dried over sodium sulfate and concentrated completely under reduce pressure at 40° C. Obtained solid was purified by triturating with diethyl ether (2×mL) and dried under vacuum to give 0.28 g N-(3-((5-fluoro-2-((4-(2-methoxyethoxy)phenyl)amino)pyrimidin-4-yl)amino)phenyl)acrylamide.

Synthesis of N-(3-((5-fluoro-2-((4-(2-methoxyethoxy)phenyl)amino)pyrimidin-4-yl)amino)phenyl)-2,3-dihydroxypropanamide (I-4)

In a 25 mL 3-neck RBF equipped with a calcium chloride guard tube N-(3-((5-fluoro-2-((4-(2-methoxyethoxy)phenyl)amino)pyrimidin-4-yl)amino)phenyl)acrylamide (0.275 g) in THF (8 mL), NMO (0.07 g) and $OsO_4$ (4% in water) solution were charged at room temperature. The reaction mixture was stirred at room temperature for 3 to 4 h. The reaction was monitored on TLC using ethyl acetate (100%) as mobile phase. After completion, the reaction mixture was poured into water and extracted into ethyl acetate. The organic layer was washed with water, dried over sodium sulfate and concentrated under reduced pressure at 40° C. Crude material was purified by Combiflash chromatography. Product was eluted with 90% ethyl acetate in hexane to give 0.08 g of N-(3-((5-fluoro-2-((4-(2-methoxyethoxy)phenyl)amino)pyrimidin-4-yl)amino)phenyl)-2,3-dihydroxypropanamide. M+H=457.8 $^1$H NMR: DMSO-$d_6$ (400 MHz): 3.28 (s, 3H), 3.60 (m, 4H), 4.04 (m, 3H), 4.82 (t, 1H, J=5.6), 5.78 (d, 1H, J=5.6), 6.79 (d, 2H, J=8.8), 7.26 (d, 1H, J=8), 7.43 (d, 1H, J=8), 7.52 (d, 3H, J=9.2), 7.97 (s, 1H), 8.05 (d, 1H, J=3.6), 8.98 (s, 1H), 9.34 (s, 1H), 9.55 (s, 1H).

Example 4

N-(3-((5-fluoro-2-((4-(2-methoxyethoxy)phenyl) amino)pyrimidin-4-yl)amino)phenyl)oxirane-2-carboxamide (I-19)

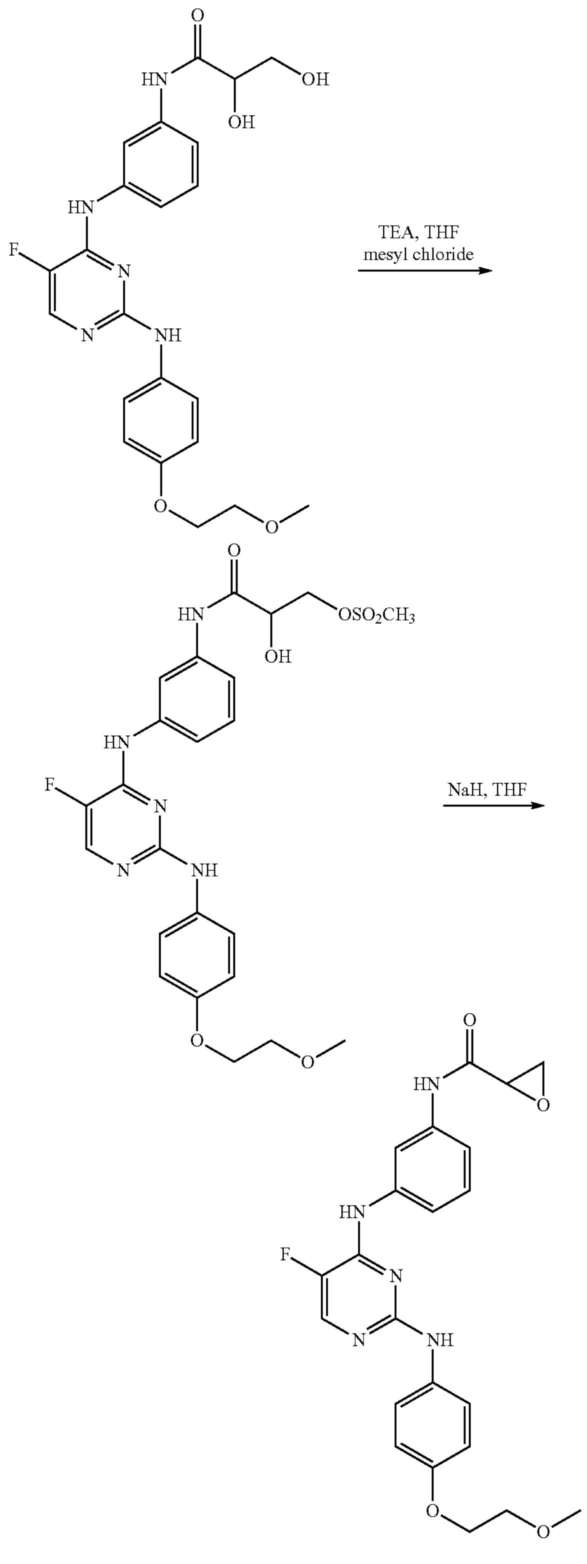

I-19

Synthesis of 3-((3-((5-fluoro-2-((4-(2-methoxyethoxy)phenyl)amino)pyrimidin-4-yl)amino)phenyl) amino)-2-hydroxy-3-oxopropyl methanesulfonate In a 25 mL 3-neck RBF equipped with $N_2$-bubbler and thermo-pocket, N-(3-((5-fluoro-2-((4-(2-methoxyethoxy) phenyl)amino)pyrimidin-4-yl)amino)phenyl)-2,3-dihydroxypropanamide (I-4) (0.08 g) was dissolved in THF (5 mL), TEA (0.0212 g) was added at room temperature. The reaction mixture was cooled to 0° C. Methane sulphonyl chloride (0.021 g) was slowly added at 0° C. The reaction mixture was stirred at room temperature for 1 h. The reaction was monitored on TLC by using ethyl acetate (100%) as mobile phase. (Only 50% of the reaction was complete on TLC). The reaction was diluted with ethyl acetate (20 mL), washed with saturated $NaHCO_3$ (25 mL). The organic layer was separated and dried over sodium sulfate. Ethyl acetate was removed under reduced pressure at 40° C. Crude material was purified by Combiflash chromatography eluted with 7% ethyl acetate in hexane. The solvent was removed under vacuum to give 0.03 g of 3-((3-((5-fluoro-2-((4-(2-methoxyethoxy)phenyl) amino)pyrimidin-4-yl)amino)phenyl)amino)-2-hydroxy-3-oxopropyl methanesulfonate.

Synthesis of N-(3-((5-fluoro-2-((4-(2-methoxyethoxy)phenyl)amino)pyrimidin-4-yl)amino)phenyl) oxirane-2-carboxamide (I-19)

Into a 25 mL 3-neck RBF equipped with $N_2$-bubbler and thermo pocket was charged 3-((3-((5-fluoro-2-((4-(2-methoxyethoxy)phenyl)amino)pyrimidin-4-yl)amino)phenyl) amino)-2-hydroxy-3-oxopropyl methanesulfonate (0.03 g) and THF (2.0 mL). The reaction mixture was cooled to 0° C. and NaH (2.2 mg) was added. The reaction mixture was warmed to room temperature and stirred for 45 min. Completion of reaction was monitored on TLC using hexane:ethyl acetate (2:8) as mobile phase. After completion of reaction, the mixture was diluted with ethyl acetate (20 mL) and water was added. The organic layer was dried over sodium sulfate and solvent was removed under reduced pressure. Crude product purified by tituration with diethyl ether to give 0.011 g of N-(3-((5-fluoro-2-((4-(2-methoxyethoxy)phenyl) amino)pyrimidin-4-yl)amino)phenyl)oxirane-2-carboxamide. $^1H$ NMR: DMSO-$d_6$ (400 MHz): 2.881 (d, 1H, J=4.4), 2.98 (t, 1H), 3.30 (s, 3H), 3.63 (m, 3H), 4.01 (t, 2H, J=4.0), 6.77 (d, 2H, J=9.2), 7.27 (t, 1H, J=8), 7.35 (d, 1H, J=8.4), 7.52 (d, 3H, J=8.8), 7.93 (s, 1H), 8.07 (d, 1H, J=3.2), 8.99 (s, 1H), 9.37 (d, 1H, J=18), 10.19 (s, 1H).

Example 5

N-(3-((5-fluoro-2-((4-(2-hydroxyethoxy)phenyl) amino)pyrimidin-4-yl)amino)phenyl)-2,3-dihydroxypropanamide (I-5)

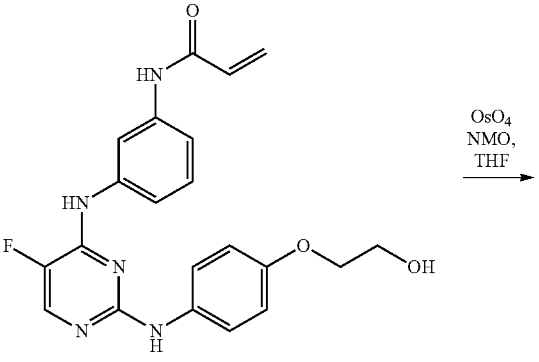

-continued

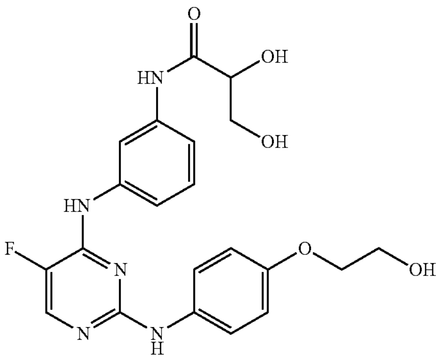

I-5

-continued

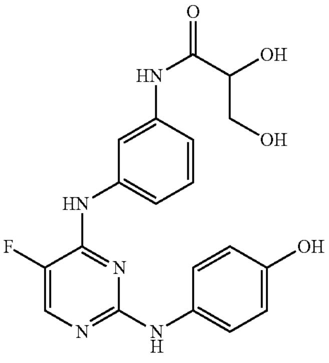

I-6

Into a 25 mL 3-neck RBF equipped with a calcium chloride guard tube, N-{3-[(5-fluoro-2-{[4-(2-hydroxyethoxy)phenyl]amino}pyrimidin-4-yl)amino]phenyl}prop-2-enamide (I-1) (0.120 g), in THF (2 mL), NMO (0.030 g) and $OSO_4$ (0.175 mL 4% in water) solution were charged at room temperature. The reaction mixture was stirred at room temperature for 3 to 4 h. The reaction was monitored on TLC using DCM:methanol (9:1). After completion of the reaction, the reaction mixture was poured in water and extracted into ethyl acetate. The organic layer was washed with sat. bicarbonate, dried over sodium sulfate and concentrated under reduced pressure at 40° C. The compound was purified by reverse phase Combiflash chromatography to give 25 mg of N-(3-((5-fluoro-2-((4-(2-hydroxyethoxy)phenyl)amino)pyrimidin-4-yl)amino)phenyl)-2,3-dihydroxypropanamide. M+1=443.9. $^1$H NMR (DMSO-$d_6$, 400 MHz): 3.603 (s, 2H), 3.660 (s, 2H), 3.906-3.930 (t, 2H, J=4.8), 4.062 (s, 1H), 4.846 (s, 2H), 5.791 (s, 1H), 6.782-6.804 (d, 2H, J=8.8), 7.233-7.274 (t, 1H, J=8.4), 7.425-7.445 (d, 1H, J=8), 7.537-7.515 (d, 3H, J=8.8), 7.972 (s, 1H), 8.053-8.062 (d, 1H, J=3.6), 8.983 (s, 1H), 9.345 (s, 1H), 9.557 (s, 1H).

Example 6

N-(3-((5-fluoro-2-((4-hydroxyphenyl)amino)pyrimidin-4-yl)amino)phenyl)-2,3-dihydroxypropanamide (I-6)

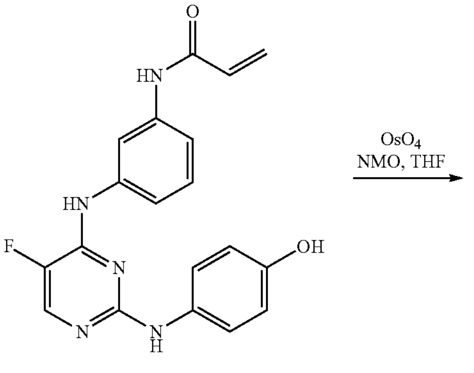

Into a 25 mL 3-neck RBF equipped with a calcium chloride guard tube, N-(3-((5-fluoro-2-((4-hydroxyphenyl)amino)pyrimidin-4-yl)amino)phenyl)acrylamide (I-3) (0.100 g), in THF (4 mL), NMO (0.032 g) and $OSO_4$(4% in water) solution were charged at room temperature The reaction mixture was stirred at room temperature for approx. 4 h. The reaction was monitored on TLC using ethyl acetate (100%) as mobile phase. After completion, the reaction mixture was poured in water and extracted into ethyl acetate. Organic layer was washed with water, dried over sodium sulfate and concentrated under reduced pressure at 40° C. Crude material was purified by preparative HPLC using 0.1% TFA in ACN and 0.1% TFA in water as mobile phase to give 10 mg of N-(3-((5-fluoro-2-((4-hydroxyphenyl)amino)pyrimidin-4-yl)amino)phenyl)-2,3-dihydroxypropanamide. $^1$H NMR: DMSO-$d_6$ (400 MHz) 3.58-3.61 (m, 2H), 4.045-4.059 (t, 1H, J=4), 4.836-4.851 (d, 1H, J=6), 5.771-5.785 (d, 1H, J=5.6), 6.605-6.627 (d, 2H, J=8.8), 7.201-7.242 (t, 1H, J=8), 7.377-7.442 (m, 3H), 7.541-7.561 (d, 1H, J=8), 7.953 (s, 1H), 8.020-8.029 (d, 1H, J=3.6), 8.827 (s, 1H), 8.931 (s, 1H), 9.300 (s, 1H), 9.520 (s, 1H).

Example 7

N-(3-((5-fluoro-2-((3-hydroxy-4-(2-methoxyethoxy)phenyl)amino)pyrimidin-4-yl)amino)phenyl)acrylamide (I-13)

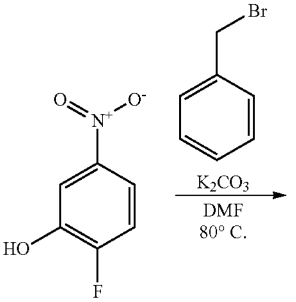

-continued
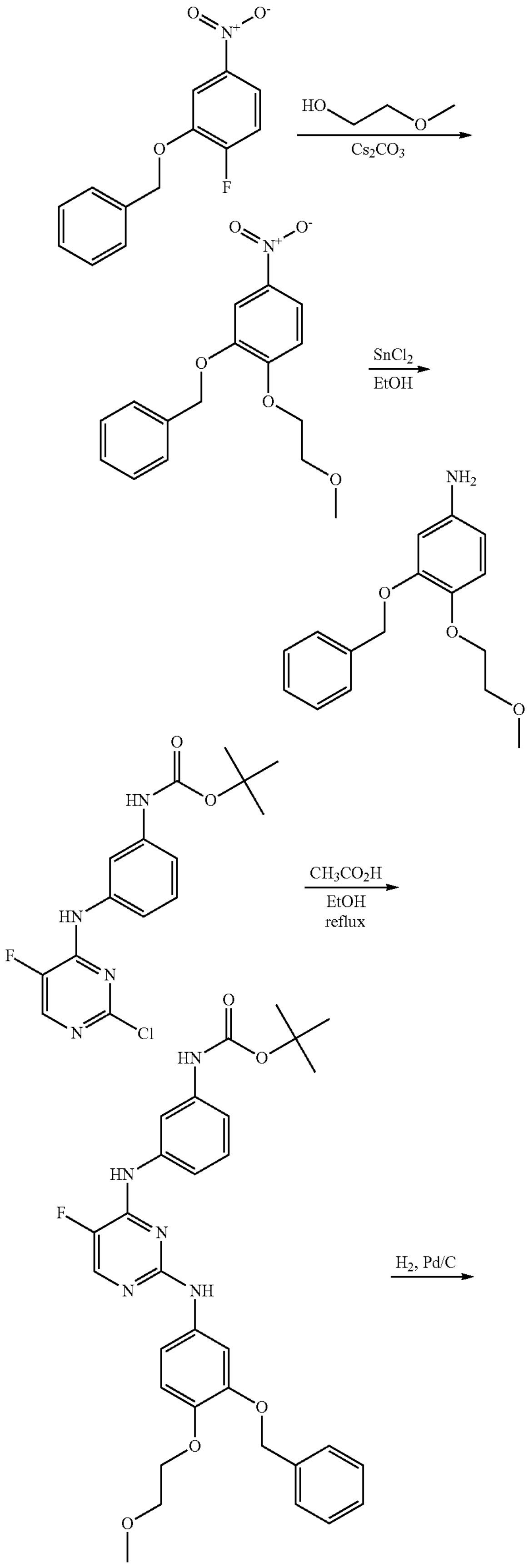
-continued
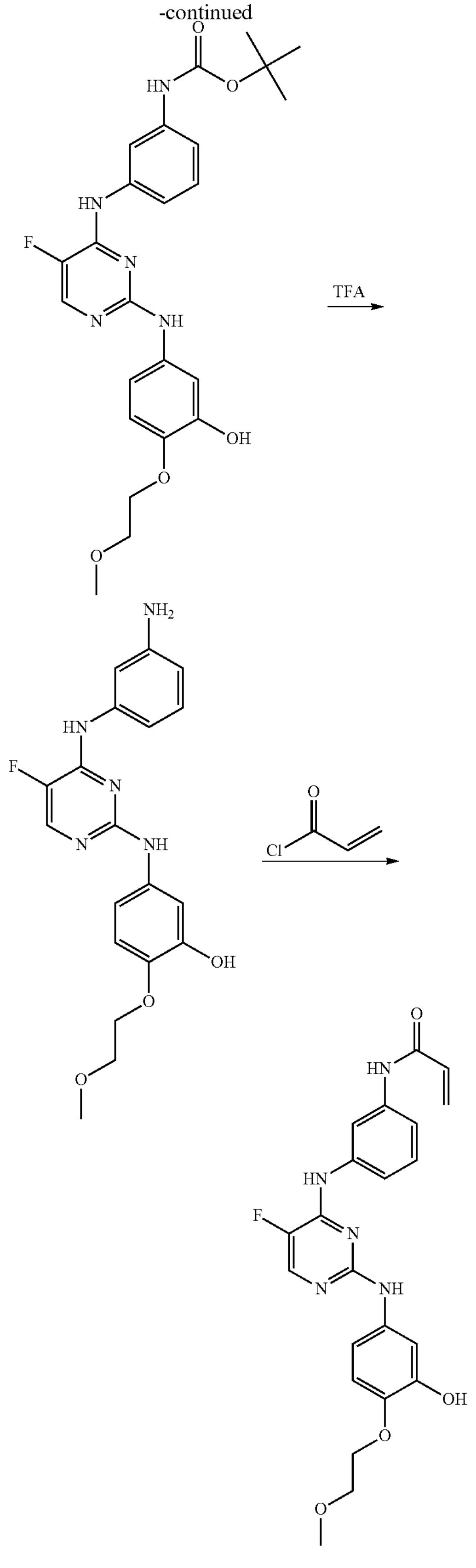
I-13

Synthesis of 2-(benzyloxy)-1-fluoro-4-nitrobenzene

In a 50 mL 3-neck RBF equipped with reflux condenser, magnetic stirrer and thermo pocket were charged 2-fluoro-5-nitrophenol (2.4 g), $K_2CO_3$ (3.16 g) and dry DMF (20 mL). The reaction mixture was heated at 50° C. for 30 min. followed by addition of benzyl bromide (2.87 g) in DMF and the reaction mixture was heated to 80° C. for 18 hr. The reaction was monitored on TLC using hexane:ethyl acetate (5:5) as mobile phase. The reaction was complete after 30 minutes. After completion, the reaction mixture was poured into cold water. The solid precipitate was filtered and washed with water and dried under reduced pressure at 45° C. to give 3.20 g of 2-(benzyloxy)-1-fluoro-4-nitrobenzene. $^1H$ NMR: DMSO-$d_6$ (400 MHz): 5.35 (s, 2H), 7.358-7.397 (m, 1H), 7.415-7.454 (m, 2H), 7.448-7.530 (m, 2H), 7.553-7.579 (m, 1H), 7.900-7.939 (m, 1H), 8.091-8.116 (dd, 1H, J=2.8, 4.4).

Synthesis of 2-(benzyloxy)-1-(2-methoxyethoxy)-4-nitrobenzene

Into a 25 mL 3-neck RBF equipped with reflux condenser and thermo pocket were charged 2-(benzyloxy)-1-fluoro-4-nitrobenzene (3.3 g), 2-methoxy ethanol (16.0 mL) and $Cs_2CO_3$ (8.67 g). The reaction mixture was heated at 80° C. for 2 hr. The reaction was monitored on TLC using hexane: ethyl acetate (5:5) as mobile phase. The reaction was complete after 2 hr. After completion, the reaction mixture was cooled to room temperature and poured into cold water. Solid precipitate was filtered and washed with water. Solid was dried under reduced pressure. The obtained 3.90 g of solid 2-(benzyloxy)-1-(2-methoxyethoxy)-4-nitrobenzene was taken onto the next step without further purification. $^1H$ NMR: DMSO-$d_6$ (400 MHz): 3.34 (s, 3H), 3.722-3.700 (t, 2H, J=4.4), 4.269-4.291 (t, 2H, J=4.4), 5.256 (s, 2H), 7.216-7.239 (d, 1H, J=9.2), 7.328-7.364 (m, 1H), 7.393-7.430 (m, 2H), 7.471 (s, 1H), 7.489 (s, 1H), 7.849-7.855 (d, 1H, J=2.4), 7.889-7.971 (dd, 1H, J=2.4, 6.4).

Synthesis of 3-(benzyloxy)-4-(2-methoxyethoxy)aniline

In a 50 mL 3-neck RBF equipped with a magnetic stirrer, reflux condenser, and thermo pocket were charged 2-(benzyloxy)-1-(2-methoxyethoxy)-4-nitrobenzene (2.00 g), ethanol (15 mL) and $SnCl_2$ (4.49 g). The reaction mixture was heated to 80° C. for 3 hr. The reaction was monitored by TLC using hexane:ethyl acetate (5:5) as mobile phase. After completion, the reaction mixture was allowed to cool at room temperature. The reaction mixture was poured in water and basified by using saturated sodium bicarbonate solution. Product was extracted with ethyl acetate (50 mL×3) and the organic layer was washed with 50 mL brine solution. Organic layer was dried over sodium sulfate and concentrated under reduced pressure. Crude material was purified by using Combiflash chromatography. Product was eluted with 30% ethyl acetate in hexane to give 0.600 g of 3-(benzyloxy)-4-(2-methoxyethoxy)aniline. $^1H$ NMR: DMSO-$d_6$ (400 MHz): 3.348 (s, 3H), 3.556-3.580 (t, 2H, J=4.8), 3.928-3.951 (t, 2H, J=4.4), 4.702 (s, 2H), 5.006 (s, 2H), 6.004-6.031 (dd, 1H, J=2.4, 6), 6.334-6.340 (d, 1H, J=2.4), 6.676-6.697 (d, 1H, J=8.4), 7.303-7.339 (m, 1H), 7.373-7.410 (m, 2H), 7.438-7.747 (m, 2H).

Synthesis of tert-butyl (3-((2-((3-(benzyloxy)-4-(2-methoxyethoxy)phenyl)amino)-5-fluoropyrimidin-4-yl)amino)phenyl)carbamate To a solution of 3-(benzyloxy)-4-(2-methoxyethoxy) aniline (0.500 g) and tert-butyl (3-((2-chloro-5-fluoropyrimidin-4-yl)amino)phenyl)carbamate (0.556 g) in ethanol (10 mL), was added $CH_3COOH$ (54 mg). The reaction mixture was heated to reflux for 24 hr. Completion of reaction was monitored by TLC using hexane:ethyl acetate (5:5) as mobile phase. After completion, reaction mixture was allowed to cool at room temperature and poured into cold water. Product was extracted with ethyl acetate (50 mL×3). Ethyl acetate layer washed with 50 mL brine solution. Ethyl acetate layer was dried over sodium sulfate and concentrated under reduced pressure. Crude material was purified by using Combiflash chromatography. Desired spot eluted with 18% ethyl acetate in hexane to give 0.35 g of tert-butyl (3-((2-((3-(benzyloxy)-4-(2-methoxyethoxy)phenyl)amino)-5-fluoropyrimidin-4-yl)amino)phenyl)carbamate. $^1H$ NMR: DMSO-$d_6$ (400 MHz): 1.467 (s, 9H), 3.357 (s, 3H), 3.614-3.636 (t, 2H, J=4.4), 4.024-4.046 (t, 2H, J=4.0), 4.921 (s, 2H), 6.811-6.833 (d, 1H, J=8.8), 7.120-7.197 (m, 3H), 7.311-7.448 (m, 7H), 7.827 (s, 1H), 8.05-8.068 (d, 1H, J=3.6), 8.935 (s, 1H), 9.306 (s, 1H), 9.353 (s, 1H).

Synthesis of tert-butyl (3-((5-fluoro-2-((3-hydroxy-4-(2-methoxyethoxy)phenyl)amino)pyrimidin-4-yl)amino)phenyl)carbamate In a 100 mL Autoclave, Pd—C (0.035 g) and ethanol were charged. tert-butyl (3-((2-((3-(benzyloxy)-4-(2-methoxyethoxy)phenyl)amino)-5-fluoropyrimidin-4-yl)amino)phenyl)carbamate (0.35 g) was added to the above reaction mixture, and the autoclave was flushed with nitrogen. Hydrogen pressure (140 psi) was applied and reaction mixture was stirred at room temperature for 50 hr. After completion, the reaction mixture was filtered using Celite and the filter cake was washed with ethanol. The filtrate was concentrated under reduced pressure at 40° C. to give 0.240 g of tert-butyl (3-((5-fluoro-2-((3-hydroxy-4-(2-methoxyethoxy)phenyl)amino) pyrimidin-4-yl)amino)phenyl)carbamate. $^1H$ NMR: DMSO-$d_6$ (400 MHz): 1.475 (s, 9H), 3.316 (s, 3H), 3.618-3.641 (t, 2H, J=4.4), 4.028-4.050 (t, 2H, J=4.4), 6.732-6.753 (d, 1H, J=8.4), 7.075-7.097 (m, 2H), 7.141-7.208 (m, 2H), 7.476-7.495 (d, 1H, J=7.6), 7.851 (s, 1H), 8.036-8.045 (d, 1H, J=3.6), 8.784-8.796 (d, 2H, J=4.8), 9.260-9.301 (d, 2H, J=16.4).

Synthesis of 5-((4-((3-aminophenyl)amino)-5-fluoropyrimidin-2-yl)amino)-2-(2-methoxyethoxy)phenol To a solution of tert-butyl (3-((5-fluoro-2-((3-hydroxy-4-(2-methoxyethoxy)phenyl)amino)pyrimidin-4-yl)amino) phenyl)carbamate (0.240 g) in DCM (5.0 mL) TFA (2.0 mL) was added at 0° C. The reaction mixture was stirred at 0° C. for 15 minutes followed by stirring at room temperature for 30 minutes. The reaction was monitored by TLC using ethyl acetate:hexane (7:3) as mobile phase. After completion of the reaction, the mixture was quenched in water and basified with saturated sodium bicarbonate solution. Product was extracted into DCM. The organic layer was washed with brine and dried over sodium sulfate and concentrated completely under reduce pressure at 40° C. The obtained solid was purified by trituration with ether to give 0.175 g of 5-((4-((3-aminophenyl)amino)-5-fluoropyrimidin-2-yl)amino)-2-(2-methoxyethoxy)phenol. $^1H$ NMR: DMSO-$d_6$ (400 MHz): 3.282 (s, 3H), 3.617-3.640 (t, 2H, J=4.4), 4.004-4.040 (t, 2H, J=4.4), 4.992 (s, 2H), 6.306-6.316 (d, 1H, J=3.2), 6.772-6.793 (d, 1H, J=8.4), 6.952-7.042 (m, 3H), 7.095 (s, 1H), 7.187 (s, 1H), 8.004-8.013 (d, 1H, J=3.6), 8.811 (s, 1H), 8.861 (s, 1H), 9.001 (s, 1H).

Synthesis of N-(3-((5-fluoro-2-((3-hydroxy-4-(2-methoxyethoxy)phenyl)amino)pyrimidin-4-yl)amino)phenyl)acrylamide (I-13)

In a 50 mL 3-neck RBF equipped with a magnetic stirrer, calcium chloride guard tube and thermo pocket was charged 5-((4-((3-aminophenyl)amino)-5-fluoropyrimidin-2-yl)amino)-2-(2-methoxyethoxy)phenol (0.17 g in 5 mL DCM) and cooled to −30° C. To the reaction mixture was slowly added acryloyl chloride solution in DCM (0.043 g in 5.0 mL DCM) and reaction mixture was stirred at −30° C. for 30 to 40 minutes. The reaction was monitored on TLC using benzene: acetone (8.5:1.5) as mobile phase. The reaction mixture was poured in water (100 mL) and basified using sodium bicarbonate. The solution was extracted with DCM (25 mL×2) and the combined organic layer was washed with 25 mL brine solution. The organic layer was dried over sodium sulfate and concentrated completely under reduce pressure at 40° C. Crude material was purified by preparative HPLC using 0.1% TFA in ACN and 0.1% TFA in water as mobile phase to give 23 mg of N-(3-((5-fluoro-2-((3-hydroxy-4-(2-methoxyethoxy)phenyl)amino)pyrimidin-4-yl)amino)phenyl)acrylamide. M+1=439.3. $^1$H NMR: DMSO-$d_6$ (400 MHz): 3.294 (s, 3H), 3.871-3.902 (t, 2H, J=6.0), 3.970-3.993 (t, 2H, J=4.4), 5.774-5.749 (d, 1H, J=10), 6.246-6.288 (d, 1H, J=16.8), 6.436-6.503 (m, 1H), 6.724-7.753 (d, 1H, J=11.6), 7.099 (s, 2H), 7.252-7.333 (m, 1H), 7.404-7.423 (d, 1H, J=7.6), 7.612-7.592 (d, 1H, J=8), 7.934 (s, 1H), 8.057-8.065 (d, 1H, J=3.2), 8.788 (s, 1H), 8.861 (s, 1H), 9.366 (s, 1H), 10.110 (s, 1H).

Example 8

N-(3-((5-fluoro-2-((2-hydroxy-4-(2-methoxyethoxy)phenyl)amino)pyrimidin-4-yl)amino)phenyl)acrylamide (I-14)

I-14

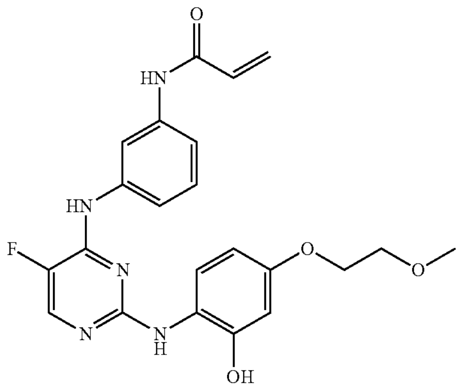

The synthesis of N-(3-((5-fluoro-2-((3-hydroxy-4-(2-methoxyethoxy)phenyl)amino)pyrimidin-4-yl)amino)phenyl)acrylamide was achieved as described above for N-(3-((5-fluoro-2-((3-hydroxy-4-(2-methoxyethoxy)phenyl)amino)pyrimidin-4-yl)amino)phenyl)acrylamide (I-13) in Example 7 using 5-fluoro-2-nitrophenol in place of 2-fluoro-5-nitrophenol in the first step.

Example 9

N-(3-((5-fluoro-2-((4-(2-methoxyethoxy)phenyl)amino)pyrimidin-4-yl)amino)-4-hydroxyphenyl)acrylamide (I-15)

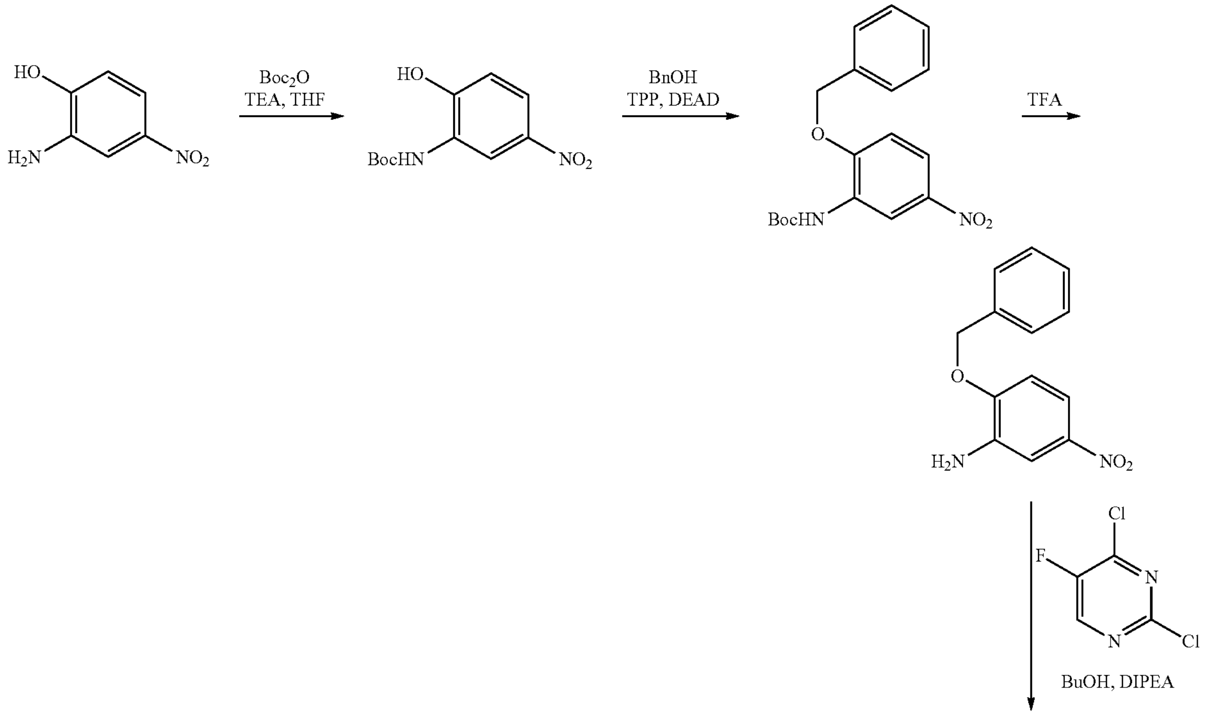

-continued

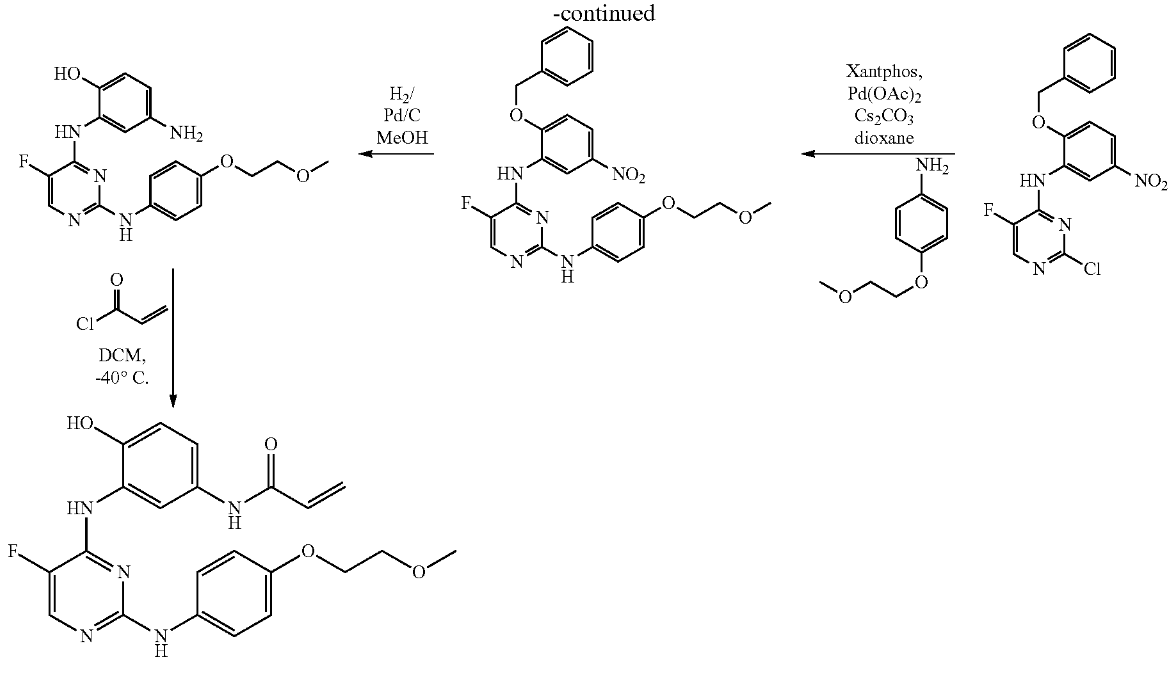

I-15

Synthesis of tert-butyl (2-hydroxy-5-nitrophenyl)carbamate

In a 50 mL 3-neck RBF, 2-amino-4-nitrophenol (3.0 g) in THF (20 mL), di-tert-butyl dicarbonate (4.25 g) and TEA (3.94 g) were charged. The reaction mixture was stirred at room temperature for 1.5 h. The reaction was monitored by TLC using hexane:ethyl acetate (6:4) as mobile phase. After completion of the reaction, THF was removed under reduced pressure at 50° C. to give light brown color oil. Purification was carried out by column chromatography. Desired product eluted with 10% Ethyl acetate in hexane to give, after concentration, 3.2 g of tert-butyl (2-hydroxy-5-nitrophenyl)carbamate. $^1$H NMR: DMSO-$d_6$ (400 MHz) 1.485 (s, 9H), 6.98 (d, 1H, J=8.8), 7.86 (dd, 1H, J=2.8, 8.8), 8.21 (s, 1H), 8.64 (d, 1H, J=2.4), 11.57 (s, 1H).

Synthesis of tert-butyl (2-(benzyloxy)-5-nitrophenyl)carbamate

In a 50 mL 3-neck RBF equipped with $N_2$-bubbler and thermo pocket, tert-butyl (2-hydroxy-5-nitrophenyl)carbamate (2.0 g), benzyl alcohol (1.02 g) and triphenyl phosphine (2.48 g) were taken in 10 mL DCM. The reaction mixture was cooled to 0° C. Diethyl azodicarboxylate (1.65 g) was dissolved in 10 mL DCM was added dropwise in the reaction. The reaction mixture was stirred at room temperature for 24 h. The reaction mixture was monitored on TLC using hexane: ethyl acetate (6:4) as mobile phase. After completion, the reaction was poured into water and extracted with DCM (3×50 mL). The DCM layer was washed with brine solution, dried over sodium sulfate and concentrated under reduced pressure at 40° C. Purification was carried out by column chromatography. Desired product eluted with 5% ethyl acetate in hexane to give, after concentration, 1.03 g of tert-butyl (2-(benzyloxy)-5-nitrophenyl)carbamate. $^1$H NMR: DMSO-$d_6$ (400 MHz) 1.48 (s, 9H), 5.34 (s, 2H), 7.26 (d, 1H, J=9.2), 7.35 (m, 1H), 7.41 (m, 2H), 7.54 (d, 2H, J=6.8), 7.95 (dd, 1H, J=2.8, 9.2), 8.51 (s, 1H), 8.64 (d, 1H, J=2.8).

Synthesis of 2-(benzyloxy)-5-nitroaniline

To a solution of tert-butyl (2-(benzyloxy)-5-nitrophenyl) carbamate (1.0 g) in DCM (10 mL), cooled to 0° C., was added trifluoroacetic acid (5.0 mL). The reaction mixture was stirred at 0° C. for 15 minutes and then at room temperature for 30 minutes. The reaction was monitored by TLC using hexane:ethyl acetate (3:7) as mobile phase. After completion, the reaction mixture was quenched in water and neutralized with sodium bicarbonate. Product was extracted into DCM. The organic layer was washed with brine, dried over sodium sulfate and concentrated completely under reduce pressure at 40° C. Crude material was purified by trituration with diethyl ether to give 0.7 g of 2-(benzyloxy)-5-nitroaniline. $^1$H NMR: DMSO-$d_6$ (400 MHz): 5.26 (s, 2H), 5.44 (s, 2H), 7.04 (d, 1H, J=8.8), 7.34 (m, 1H), 7.45 (m, 3H), 7.50 (s, 1H), 7.520 (d, 2H, J=2.8).

Synthesis of N-(2-(benzyloxy)-5-nitrophenyl)-2-chloro-5-fluoropyrimidin-4-amine

In a pressure tube 2-(benzyloxy)-5-nitroaniline (0.65 g), 2,4-dichloro-5-fluoropyrimidine (0.66 g) and DIPEA (0.69 g) were taken in n-butanol (10 mL). The reaction mixture was heated at 120° C. for 24 hr. The reaction was monitored on TLC using DCM:hexane:ethyl acetate (3:5:2) as mobile phase. The reaction was complete after 24 h. After completion, reaction mixture was allowed to cool at room temperature. The reaction was poured into water and extracted with ethyl acetate (3×25 mL). The ethyl acetate layer washed with brine solution, dried over sodium sulfate and concentrated under reduced pressure at 40° C. Crude material was purified by triturating with diethyl ether to give 0.25 g of N-(2-(benzyloxy)-5-nitrophenyl)-2-chloro-5-fluoropyrimidin-4-amine. M+1=374.8.

Synthesis of N4-(2-(benzyloxy)-5-nitrophenyl)-5-fluoro-N2-(4-(2-methoxyethoxy)phenyl)pyrimidine-2,4-diamine In a 100 mL 3-neck RBF, N-(2-(benzyloxy)-5-nitrophenyl)-2-chloro-5-fluoropyrimidin-4-amine (0.205 g), 4-(2-methoxyethoxy)aniline (0.137 g), $Cs_2CO_3$ (0.266 g) and Xantphos (0.032 g) were taken in degassed 1,4-dioxane (8.0 mL) and reaction mixture was degassed under argon for 30 minutes. Palladium acetate (0.013 g) was added to reaction mixture and again it was degassed for 30 minutes. The reaction mixture was heated to 80° C. and stirred for 3.5 h. The reaction was monitored on TLC using hexane:ethyl acetate: (5:5) as mobile phase. After completion, the reaction mixture was allowed to cool at room temperature. The reaction mixture was poured into water and product was extracted with ethyl acetate (3×25 mL). The ethyl acetate layer washed with brine solution, dried over sodium sulfate and concentrated under reduced pressure. Crude material was purified by triturating with diethyl ether to give 0.1 g of N4-(2-(benzyloxy)-5-nitrophenyl)-5-fluoro-N2-(4-(2-methoxyethoxy)phenyl)pyrimidine-2,4-diamine. $^1$H NMR: $CDCl_3$ (400 MHz): 3.47 (d, 3H, J=11.6), 3.77 (dd, 2H, J=4.8, 8.8), 4.15 (t, 2H, J=4.8), 5.28 (s, 2H), 6.96 (d, 1H, J=8.8), 7.03 (d, 1H, J=8.8), 7.08 (d, 1H, J=9.2), 7.45 (m, 7H), 7.83 (s, 1H), 7.9 (d, 2H, J=2.8), 8.02 (dd, 1H, J=2.1, 6.8), 9.18 (s, 1H).

Synthesis of 4-amino-2-((5-fluoro-2-((4-(2-methoxyethoxy)phenyl)amino)pyrimidin-4-yl)amino)phenol Into a 50 mL autoclave was charged Pd—C (0.025 g). MeOH was added under nitrogen. A solution of N4-(2-(benzyloxy)-5-nitrophenyl)-5-fluoro-N2-(4-(2-methoxyethoxy)phenyl)pyrimidine-2,4-diamine (0.10 g) in methanol and THF was added to the suspension. The autoclave was flushed with nitrogen and 8 kg/cm$^2$ Hydrogen pressure was applied. The reaction mixture was stirred at room temperature for 18 h at same pressure. After completion, the reaction mixture was filtered using Celite and the filter cake was washed with methanol. The filtrate was concentrated under reduced pressure at 40° C. to give 0.08 g of 4-amino-2-((5-fluoro-2-((4-(2-methoxyethoxy)phenyl)amino)pyrimidin-4-yl)amino)phenol. Crude material was taken in next step without further purification.

Synthesis of N-(3-((5-fluoro-2-((4-(2-methoxyethoxy)phenyl)amino)pyrimidin-4-yl)amino)-4-hydroxyphenyl)acrylamide (I-15)

To a 25 mL 3-neck RBF previously equipped with a magnetic stirrer and $CaCl_2$ guard tube was added 4-amino-2-((5-fluoro-2-((4-(2-methoxyethoxy)phenyl)amino)pyrimidin-4-yl)amino)phenol (0.075 g in 5 mL DCM) and it was cooled to −40° C. and acryloyl chloride (0.019 g in 3 mL DCM) was slowly added. The reaction was warmed to room temperature and stirred for 30 min. The reaction was monitored on TLC using hexane:ethyl acetate (7:3) as mobile phase. The reaction was complete after 30 min. The reaction mixture was poured in water (100 mL) and basified using sodium bicarbonate. The mixture was extracted with DCM (2×25 mL) and the combined organic layer was washed with brine solution, dried over sodium sulfate and concentrated completely under reduced pressure at 40° C. Crude material was purified by preparative-HPLC to give 2.7 mg of N-(3-((5-fluoro-2-((4-(2-methoxyethoxy)phenyl)amino)pyrimidin-4-yl)amino)-4-hydroxyphenyl)acrylamide. $^1$H NMR: DMSO-$d_6$ (400 MHz) 3.25 (s, 3H), 3.58 (s, 2H), 3.91 (s, 2H), 5.70 (d, 1H, J=10), 6.20 (d, 1H, J=16.8), 6.39 (dd, 1H, J=10.4, 17.2), 6.65 (d, 2H, J=8.8), 6.87 (d, 1H, J=8.8), 7.45 (m, 3H), 7.78 (s, 1H), 8.01 (s, 1H), 8.21 (s, 1H), 8.48 (s, 1H), 8.92 (s, 1H), 9.98 (s, 1H).

Example 10

N-(5-((5-fluoro-2-((4-(2-methoxyethoxy)phenyl)amino)pyrimidin-4-yl)amino)-2-hydroxyphenyl)acrylamide (I-17)

I-17

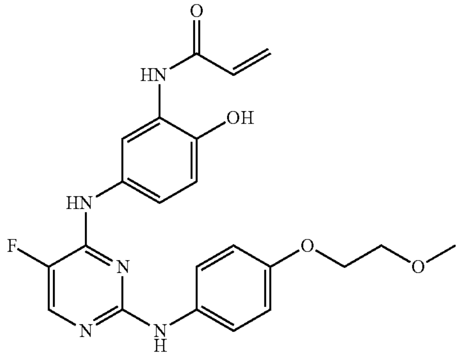

The synthesis of N-(5-((5-fluoro-2-((4-(2-methoxyethoxy)phenyl)amino)pyrimidin-4-yl)amino)-2-hydroxyphenyl)acrylamide was achieved as described above in Example 9 using 4-(benzyloxy)-3-nitroaniline in place of 2-(benzyloxy)-5-nitroaniline. $^1$H NMR: DMSO-$d_6$ (400 MHz): 3.30 (s, 3H), 3.617-3.640 (t, 2H), 3.982-4.005 (t, 2H, J=4.4), 5.713-5.718 (d, 1H, J=2) 6.223-6.255 (dd, 1H, J=2, 15.2), 6.683-6.872 (m, 4H), 7.281-7.300 (d, 1H, J=7.6), 7.481-7.504 (d, 1H, J=9.2), 7.989-7.998 (d, 1H, J=3.6), 8.086-8.091 (d, 2H, J=2), 8.933 (s, 1H), 9.196 (s, 1H), 9.622 (s, 1H), 9.777 (s, 1H).

Example 11

N-(3-((5-fluoro-2-((4-(2-methoxyethoxy)phenyl)amino)pyrimidin-4-yl)amino)-2-hydroxyphenyl)acrylamide (I-18)

I-18

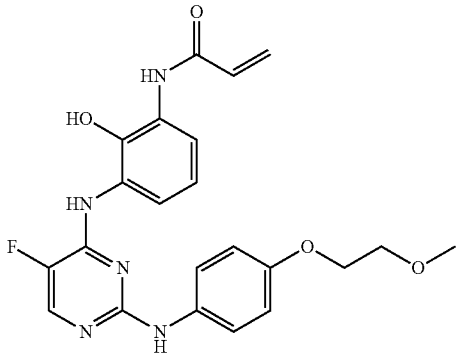

The synthesis of N-(3-((5-fluoro-2-((4-(2-methoxyethoxy)phenyl)amino)pyrimidin-4-yl)amino)-2-hydroxyphenyl)acrylamide was achieved as described above in Example 9 using 2-(benzyloxy)-3-nitroaniline in place of 2-(benzyloxy)-5-nitroaniline. $^1$H NMR: DMSO-$d_6$ (400 MHz): 3.30 (s, 3H), 3.619 (s, 2H), 3.987 (s, 2H), 5.793-5.818 (d, 1H, J=10), 6.285-6.327 (d, 1H, J=16.8), 6.657-6.735 (m, 3H), 6.852-6.891 (t, 1H, J=8), 7.448-7.469 (d, 2H, J=8.4), 7.519-7.536 (d, 2H, J=6.8), 8.032-8.038 (d, 1H, J=2.4), 8.534 (s, 1H), 8.980 (s, 1H), 10.002 (s, 1H).

Example 12

Synthesis of N-(3-((5-fluoro-2-((4-(2-methoxyethoxy)phenyl)amino)pyrimidin-4-yl)amino)phenyl)-3-hydroxypropanamide (I-26)

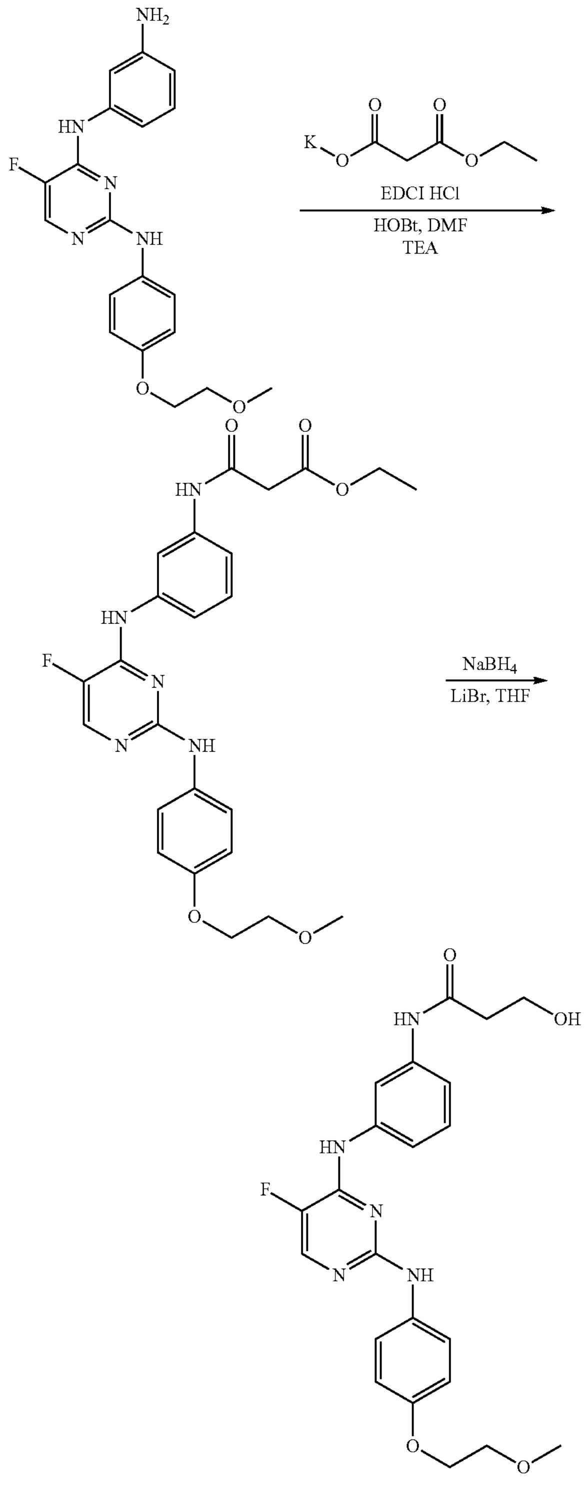

I-26

Synthesis of ethyl 3-((3-((5-fluoro-2-((4-(2-methoxyethoxy)phenyl)amino)pyrimidin-4-yl)amino)phenyl)amino)-3-oxopropanoate Into a 25 ml, three neck flask under nitrogen atmosphere, a solution of N4-(3-aminophenyl)-5-fluoro-N2-(4-(2-methoxyethoxy)phenyl)pyrimidine-2,4-diamine (0.15 g) in DMF (5 mL) was charged potassium 3-ethoxy-3-oxopropanoate (0.089 g), EDCI.HCl (0.117 g), HOBt (0.093 g) and TEA (0.164 g). The reaction mixture was stirred for 8 hr at room temperature. Completion of the reaction was monitored by TLC using hexane:ethyl acetate (5:5) as the mobile phase. After completion, the reaction mixture was poured into water. The product was extracted with ethyl acetate and the organic layer was washed with brine. The solvent was removed under reduced pressure at 40° C. The obtained solid was purified by triturating with diethyl ether (2×10 mL) to give 0.19 g of ethyl 3-((3-((5-fluoro-2-((4-(2-methoxyethoxy)phenyl)amino)pyrimidin-4-yl)amino)phenyl)amino)-3-oxopropanoate. $^1$H NMR: DMSO-$d_6$ (400 MHz): 1.182-1.234 (q, 3H, J=6.8), 3.306 (s, 3H), 3.461 (s, 2H), 3.623-3.646 (t, 2H, J=4.8), 4.010-4.033 (t, 2H, J=4.4), 4.090-4.144 (t, 2H, J=7.2), 6.775-6.797 (d, 2H, J=8.8), 7.267-7.283 (d, 2H, J=6.4), 7.511-7.533 (d, 1H, J=8), 7.575-7.591 (d, 1H, J=6.4), 7.817 (s, 1H), 8.058-8.066 (d, 1H, J=3.2), 8.963 (s, 1H), 9.375 (s, 1H), 10.162 (s, 1H).

Synthesis of N-(3-((5-fluoro-2-((4-(2-methoxyethoxy)phenyl)amino)pyrimidin-4-yl)amino)phenyl)-3-hydroxypropanamide (I-26)

To a solution of ethyl 3-((3-((5-fluoro-2-((4-(2-methoxyethoxy)phenyl)amino)pyrimidin-4-yl)amino)phenyl)amino)-3-oxopropanoate (0.17 g) in THF (5 mL), in a 25 mL 3-necked RBF equipped with $N_2$ bubbler, were added LiBr (0.182 g) and $NaBH_4$ (0.081 g). The reaction mixture was stirred at reflux temperature for 3 hr. The reaction was monitored on TLC using ethyl acetate:hexane (8:2) as mobile phase. After completion, the reaction mixture was poured into water. The product was extracted with ethyl acetate and the organic layer was washed with brine and concentrated completely under reduce pressure at 40° C. The obtained solid was purified by column chromatography. Product was eluted with 100% ethyl acetate to give, after concentration, 10.2 mg of N-(3-((5-fluoro-2-((4-(2-methoxyethoxy)phenyl)amino)pyrimidin-4-yl)amino)phenyl)-3-hydroxypropanamide. $^1$H NMR: DMSO-$d_6$ (400 MHz): 2.50 (s, 2H), 3.30 (s, 3H), 3.63 (t, 2H, J=4.4), 3.70 (t, 2H, J=5.2), 4.01 (t, 2H, J=4), 4.67 (t, 1H, J=5.2), 6.79 (m, 2H), 7.24 (t, 1H, J=8), 7.33 (d, 1H, J=7.6), 7.51 (m, 3H), 7.85 (s, 1H), 8.05 (d, 1H, J=3.6), 8.94 (s, 1H), 9.34 (s, 1H), 9.87 (s, 1H).

Example 13
N-(3-((5-fluoro-2-((4-(2-hydroxyethoxy)phenyl) amino)pyrimidin-4-yl)amino)phenyl)oxirane-2-carboxamide (I-22)
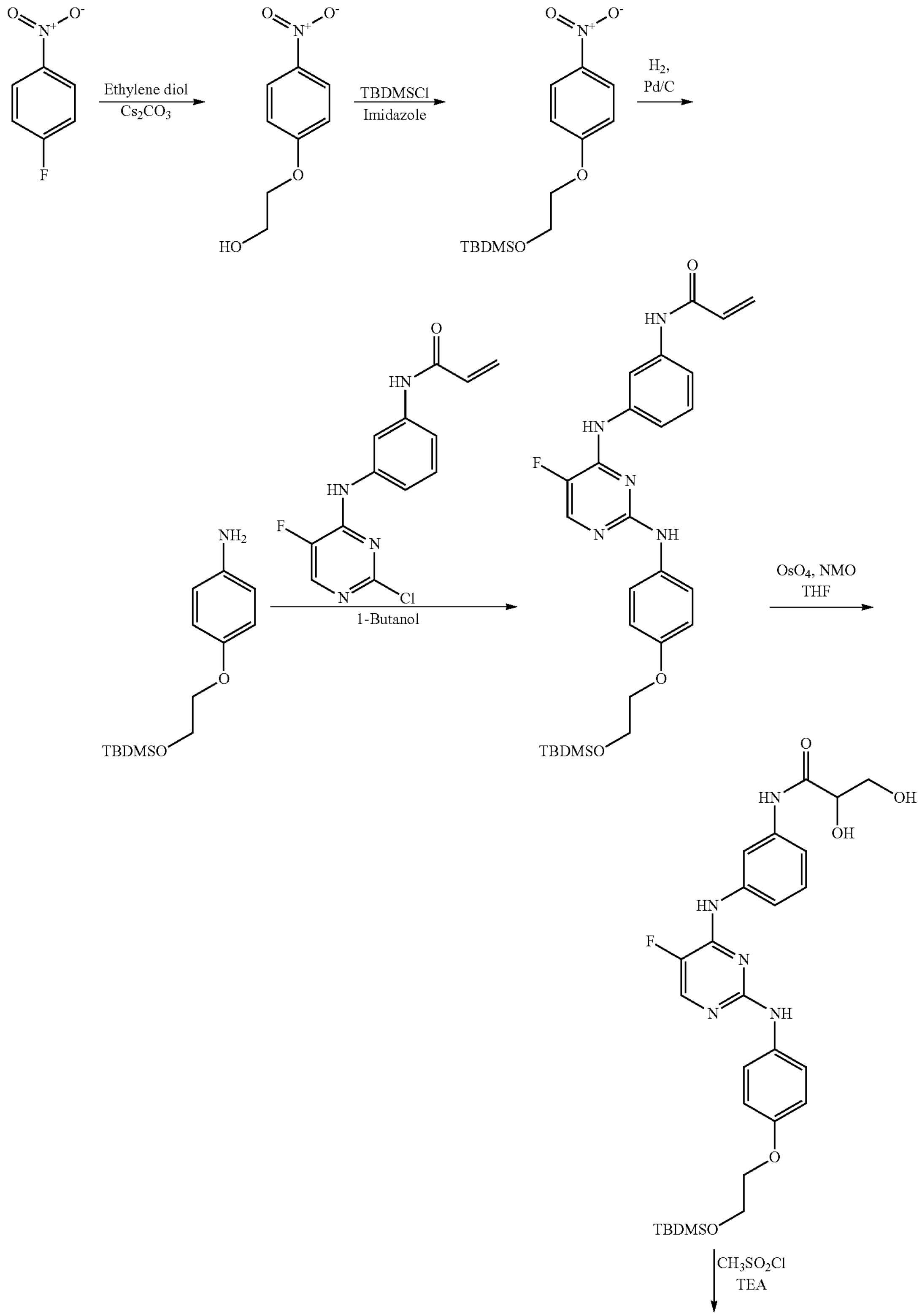

-continued

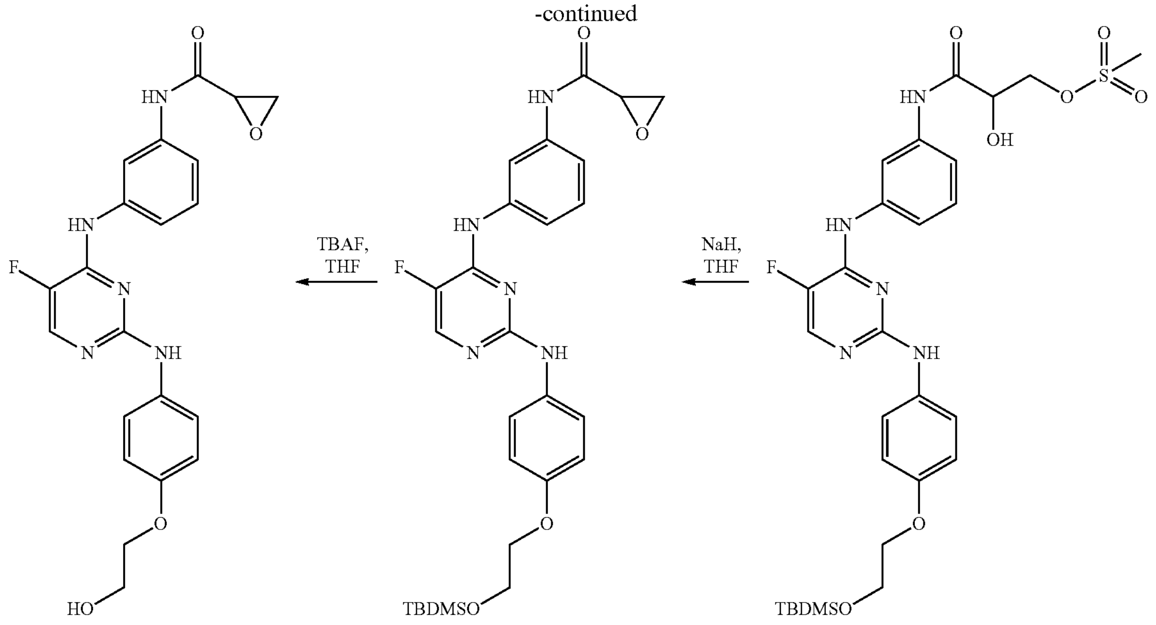

I-22

Synthesis of 2-(4-nitrophenoxy)ethanol

Into a 100 mL 3-neck RBF equipped with a magnetic stirrer, reflux condenser, and thermo pocket were added 4-fluoro nitrobenzene (5.00 g), $Cs_2CO_3$ (23.0 g) and ethylene glycol (50 mL). The reaction mixture was heated to 80° C. for 30 minutes. The reaction was monitored on TLC using hexane:ethyl acetate (7:3) as mobile phase. After completion, the reaction mixture was cooled to room temperature and poured into cold water. Solid precipitate was filtered and washed with water. Solid material was dried under reduced pressure at 45° C. for 1 hr to give 6.43 g of 2-(4-nitrophenoxy)ethanol. The obtained solid was taken for the next step without further purification.

Synthesis of tert-butyldimethyl(2-(4-nitrophenoxy)ethoxy)silane

To a solution of 2-(4-nitrophenoxy)ethanol (6.40 g) in DMF were added imidazole (4.75 g) and TBDMSCl (6.84 g) and reaction mixture was stirred at room temperature for 1 hr. The reaction was monitored on TLC using hexane:ethyl acetate (7:3) as mobile phase. After completion of the reaction, water was added and the mixture was extracted with ethyl acetate. The organic layer was dried over sodium sulfate and the solvent removed under reduced pressure. The crude material was purified by column chromatography eluted with 6% ethyl acetate in hexane to give, after concentration, 10 g of tert-butyldimethyl(2-(4-nitrophenoxy)ethoxy)silane.

Synthesis of 4-(2-((tert-butyldimethylsilyl)oxy)ethoxy)aniline

To a suspension of Pd/C (2.5 g) in methanol (30 mL), in a 100 mL 3-neck RBF, was added tert-butyldimethyl(2-(4-nitrophenoxy)ethoxy)silane (5.0 g) under a nitrogen atmosphere at room temperature. Hydrogen gas was bubbled through the reaction for 3 hr at room temperature. The reaction was monitored on TLC using ethyl acetate:hexane (3:7) as mobile phase. After completion, the reaction mixture was filtered using Celite and the filter cake was washed with methanol. The filtrate was concentrated under reduced pressure at 40° C. to give 4.12 g of 4-(2-((tert-butyldimethylsilyl)oxy)ethoxy)aniline as a brown liquid. M+1=309.2.

Synthesis of N-(3-((2-((4-(2-((tert-butyldimethylsilyl)oxy)ethoxy)phenyl)amino)-5-fluoropyrimidin-4-yl)amino)phenyl)acrylamide A solution of 4-(2-((tert-butyldimethylsilyl)oxy)ethoxy)aniline (4.02 g) and N-(3-((2-chloro-5-fluoropyrimidin-4-yl)amino)phenyl)acrylamide (4.0 g) in 1-butanol (10 mL) was heated to 135° C. for 3 hr. The reaction was monitored on TLC using $CHCl_3$:methanol (9.5:0.5) as mobile phase. After completion of the reaction, butanol was removed under reduced pressure and water was added. The mixture was extracted with ethyl acetate. Organic layer was dried over sodium sulfate and solvent was removed under reduced pressure. Crude material was purified by Combiflash chromatography eluting with 2.5% methanol in $CHCl_3$ to give 0.828 g of N-(3-((2-((4-(2-((tert-butyldimethylsilyl)oxy)ethoxy)phenyl)amino)-5-fluoropyrimidin-4-yl)amino)phenyl)acrylamide. $^1H$ NMR: DMSO-$d_6$ (400 MHz) 0.036 (s, 6H), 0.844 (s, 9H), 3.859-3.895 (d, 4H), 5.737-5.767 (dd, 1H, J=1.6, 8.4), 6.245-6.292 (dd, 1H, J=2, 15.2), 6.437-6.505 (m, 1H), 6.737-6.760 (d, 2H, J=9.2), 7.252-7.293 (t, 1H, J=8), 7.415-7.542 (m, 4H), 7.944-7.956 (d, 1H, J=4.8), 8.065-8.074 (d, 1H, J=3.6), 8.896 (s, 1H), 8.896 (s, 1H), 9.379 (s, 1H), 10.1190 (s, 1H).

Synthesis of N-(3-((2-((4-(2-((tert-butyldimethylsilyl)oxy)ethoxy)phenyl)amino)-5-fluoropyrimidin-4-yl)amino)phenyl)-2,3-dihydroxypropanamide Into a 25 mL 3-neck RBF equipped with a calcium chloride guard tube, N-(3-((2-((4-(2-((tert-butyldimethylsilyl)oxy)ethoxy)phenyl)amino)-5-fluoropyrimidin-4-yl)amino)phenyl)acrylamide (2.0 g), in THF (15 mL), NMO (0.671 g) and $OSO_4$ (4.85 mL 4% in water) solution were charged at room temperature. The reaction mixture was stirred at room temperature for 2 hr. The reaction was monitored on TLC using $CHCl_3$:methanol (9:1). After completion, the reaction mixture was poured in water and extracted into ethyl acetate. The organic layer was washed with water, dried over sodium sulfate and concentrated under reduced pressure at 40° C. Crude material was purified by Combiflash chromatography eluted with 1.9% methanol in $CHCl_3$ to give 2.0 g of N-(3-((2-((4-(2-((tert-butyldimethylsilyl)oxy)ethoxy)phenyl)amino)-5-fluoropyrimidin-4-yl)amino)phenyl)-2,3-dihydroxypropanamide.

Synthesis of 3-((3-((2-((4-(2-((tert-butyldimethylsilyl)oxy)ethoxy)phenyl)amino)-5-fluoropyrimidin-4-yl)amino)phenyl)amino)-2-hydroxy-3-oxopropyl methanesulfonate In a 25 mL 3-neck RBF equipped with a calcium chloride guard tube, N-(3-((2-((4-(2-((tert-butyldimethylsilyl)oxy)ethoxy)phenyl)amino)-5-fluoropyrimidin-4-yl)amino)phenyl)-2,3-dihydroxypropanamide (2.0 g), in THF (25 mL), was added TEA (0.724 g). The reaction mixture was cooled to 0° C. and a solution of $CH_3SO_2Cl$ (0.491 g) in THF was added dropwise. The reaction mixture was stirred at room temperature for 3 hr. The reaction was monitored on TLC using $CHCl_3$:methanol (9:1) as mobile phase. After completion of reaction, water and saturated $NaHCO_3$ solution were added. The mixture was extracted into ethyl acetate. The organic layer was washed dried over sodium sulfate and concentrated under reduced pressure at 40° C. The crude material was purified by Combiflash eluted with 2.2% methanol in $CHCl_3$ to give 0.24 g of 3-((3-((2-((4-(2-((tert-butyldimethylsilyl)oxy)ethoxy)phenyl)amino)-5-fluoropyrimidin-4-yl)amino)phenyl)amino)-2-hydroxy-3-oxopropyl methanesulfonate.

Synthesis of N-(3-((2-((4-(2-((tert-butyldimethylsilyl)oxy)ethoxy)phenyl)amino)-5-fluoropyrimidin-4-yl)amino)phenyl)oxirane-2-carboxamide To a solution of 3-((3-((2-((4-(2-((tert-butyldimethylsilyl)oxy)ethoxy)phenyl)amino)-5-fluoropyrimidin-4-yl)amino)phenyl)amino)-2-hydroxy-3-oxopropyl methanesulfonate (0.240 g) in THF was added NaH (0.018 g) and the reaction mixture was stirred at room temperature for 30 min. The reaction was monitored on TLC using $CHCl_3$:methanol (9:1) as mobile phase. After completion, the reaction mixture was poured into water and extracted with ethyl acetate. The organic layer was dried over sodium sulfate and the solvent was removed under reduced pressure. The crude material was purified by Combiflash, and the product eluted with 1.6% methanol in $CHCl_3$ to give 0.16 g of N-(3-((2-((4-(2-((tert-butyldimethylsilyl)oxy)ethoxy)phenyl)amino)-5-fluoropyrimidin-4-yl)amino)phenyl)oxirane-2-carboxamide.

Synthesis of N-(3-((5-fluoro-2-((4-(2-hydroxyethoxy)phenyl)amino)pyrimidin-4-yl)amino)phenyl)oxirane-2-carboxamide (I-22)

A solution of N-(3-((2-((4-(2-((tert-butyldimethylsilyl)oxy)ethoxy)phenyl)amino)-5-fluoropyrimidin-4-yl)amino)phenyl)oxirane-2-carboxamide (0.160 g) in THF was cooled to 0° C. and TBAF was added. The reaction mixture was stirred at 0° C. for 1 hr. The reaction was monitored on TLC using $CHCl_3$:methanol (9:1) as mobile phase. After completion, the reaction mixture was poured into water and extracted with ethyl acetate. The organic layer was dried over sodium sulfate and solvent was removed under reduced pressure. The crude material was purified by Combiflash eluted with 3.1% methanol in $CHCl_3$ to give 0.051 g of N-(3-((5-fluoro-2-((4-(2-hydroxyethoxy)phenyl)amino)pyrimidin-4-yl)amino)phenyl)oxirane-2-carboxamide. $^1H$ NMR: DMSO-$d_6$ (400 MHz): 2.676-2.901 (q, 1H), 2.974-3.00 (q, 1H), 3.575-3.674 (m, 2H), 3.901-3.926 (m, 2H), 4.830-4.858 (t, 1H, J=5.6), 6.764-6.786 (d, 1H, J=8.8), 7.256-7.296 (d, 1H, J=8), 7.345-7.366 (d, 1H, J=8.4), 7.514-7.537 (d, 3H, J=9.2), 7.933 (s, 1H), 8.065-8.074 (d, 1H, J=3.6), 8.896 (s, 1H), 9.391 (s, 1H), 10.119 (s, 1H).

Example 14

2-(4-((4-((3-acrylamidophenyl)amino)-5-fluoropyrimidin-2-yl)amino)phenoxy)acetic acid (I-2)

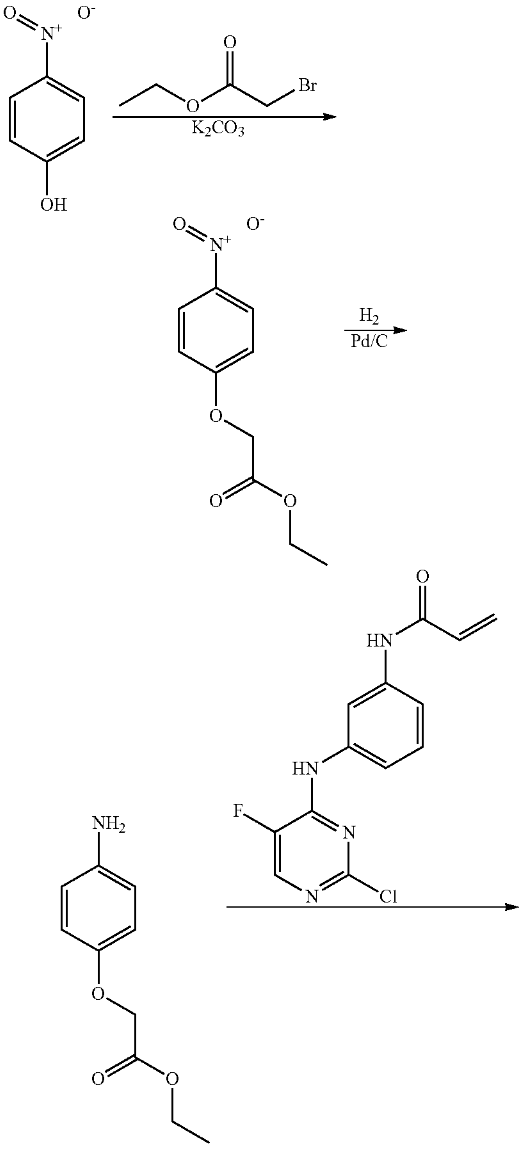

-continued

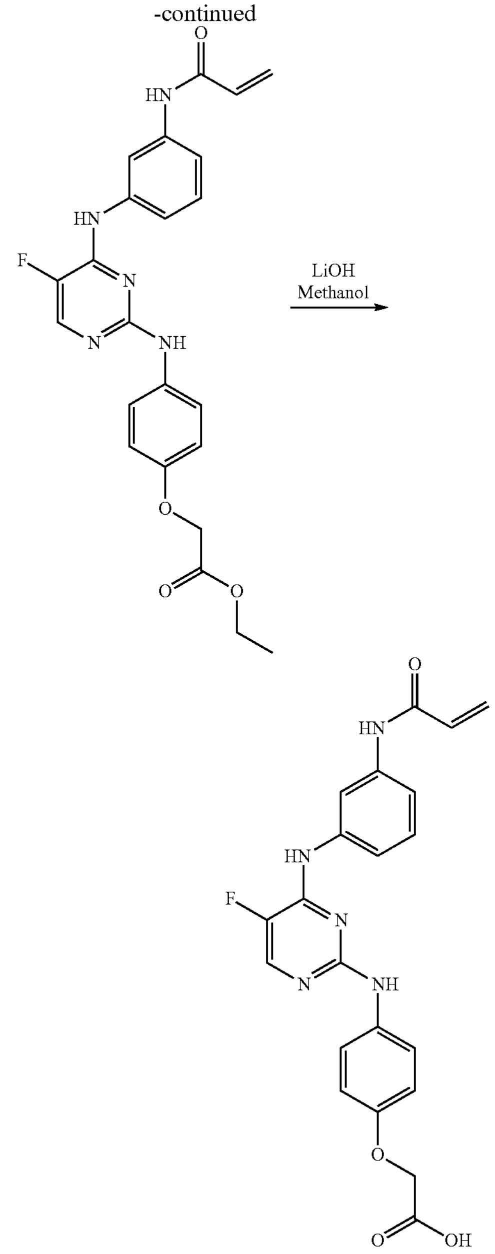

I-2

Synthesis of ethyl 2-(4-nitrophenoxy)acetate

Into a 50 mL 3-neck RBF equipped with a magnetic stirrer, reflux condenser, and thermo pocket were sequentially charged 4-nitro phenol (1.00 g), $K_2CO_3$ (1.98 g) and DMF (7 mL). The reaction mixture was heated to 70° C. for 15 minutes. Ethyl bromoacetate (1.44 g) was added at 70° C. and the reaction mixture was stirred at the same temperature for 30 minutes. The reaction was monitored on TLC using $CHCl_3$:methanol (9.5:0.5) as mobile phase. After completion of the reaction, the mixture was cooled to room temperature and poured into cold water. Solid precipitate was filtered and washed with water. The solid was dried under reduced pressure at 45° C. for 1 hr to give 1.50 g of ethyl 2-(4-nitrophenoxy)acetate. The obtained solid was taken for the next step without further purification.

Synthesis of ethyl 2-(4-aminophenoxy)acetate

To a suspension of Pd/C (0.5 g) in methanol (10 mL), ethyl 2-(4-nitrophenoxy)acetate (1.5 g) was added under nitrogen atmosphere into the 50 mL 3-neck RBF at room temperature. Hydrogen gas was bubbled through the reaction for 2 hr at room temperature. The reaction was monitored on TLC using $CHCl_3$:methanol (9.5:0.5) as mobile phase. After completion of the reaction, the mixture was filtered using Celite and the filter cake was washed with methanol. The filtrate was concentrated under reduced pressure at 40° C. to give 1.0 g of ethyl 2-(4-aminophenoxy)acetate as a brown solid.

Synthesis of ethyl 2-(4-((4-((3-acrylamidophenyl) amino)-5-fluoropyrimidin-2-yl)amino)phenoxy)acetate A solution of ethyl 2-(4-aminophenoxy)acetate (0.801 g) and N-(3-((2-chloro-5-fluoropyrimidin-4-yl)amino)phenyl) acrylamide (1.0 g) in 1-butanol (10 mL) was heated to 135° C. for 2 hr. The reaction was monitored on TLC using hexanes: ethyl acetate (3:7) as mobile phase. After completion of the reaction, butanol was removed under reduced pressure and water was added. The mixture was extracted with ethyl acetate and the organic layer was dried over sodium sulfate and solvent was removed under reduced pressure. Crude material was purified by Combiflash chromatography and eluted with 29% ethyl acetate in hexane to give 0.30 g of ethyl 2-(4-((4-((3-acrylamidophenyl)amino)-5-fluoropyrimidin-2-yl)amino)phenoxy)acetate.

Synthesis of 2-(4-((4-((3-acrylamidophenyl)amino)-5-fluoropyrimidin-2-yl)amino)phenoxy)acetic acid (I-2)

A solution of ethyl 2-(4-((4-((3-acrylamidophenyl) amino)-5-fluoropyrimidin-2-yl)amino)phenoxy)acetate (0.300 g) in methanol was cooled to 0° C. and a solution of $LiOH.H_2O$ (0.056 g) in water was added. The reaction mixture was stirred at room temperate for 2 hr. The reaction was monitored on TLC using $CHCl_3$:methanol (8:2) as mobile phase. After completion of the reaction, methanol was removed under reduced pressure and water was added. The aqueous layer was washed with ethyl acetate, acidified with acetic acid and the solid precipitate was filtered and washed with water. Solid material was dried under vacuumed at 45° C. to give 0.115 g of 2-(4-((4-((3-acrylamidophenyl)amino)-5-fluoropyrimidin-2-yl)amino)phenoxy)acetic acid. $^1H$ NMR: DMSO-$d_6$ (400 MHz): 4.492 (s, 2H), 5.740-5.767 (d, 1H, J=10.8), 6.238-6.280 (d, 1H, J=16.8), 6.446-6.513 (dd, 1H, J=6.8, 10), 6.717-6.739 (d, 2H, J=8.8), 7.252-7.292 (t, 1H, J=8), 7.377-7.396 (d, 1H, J=7.6), 7.502-7.523 (d, 3H, J=7.6), 7.961 (s, 1H), 8.060-8.068 (d, 1H, J=3.2), 8.988 (s, 1H), 9.386 (s, 1H), 10.191 (s, 1H).

Example 15

N-(3-((5-fluoro-2-((4-(2-methoxyethoxy)phenyl) amino)pyrimidin-4-yl)amino)phenyl)-N-hydroxy-acrylamide (I-9)

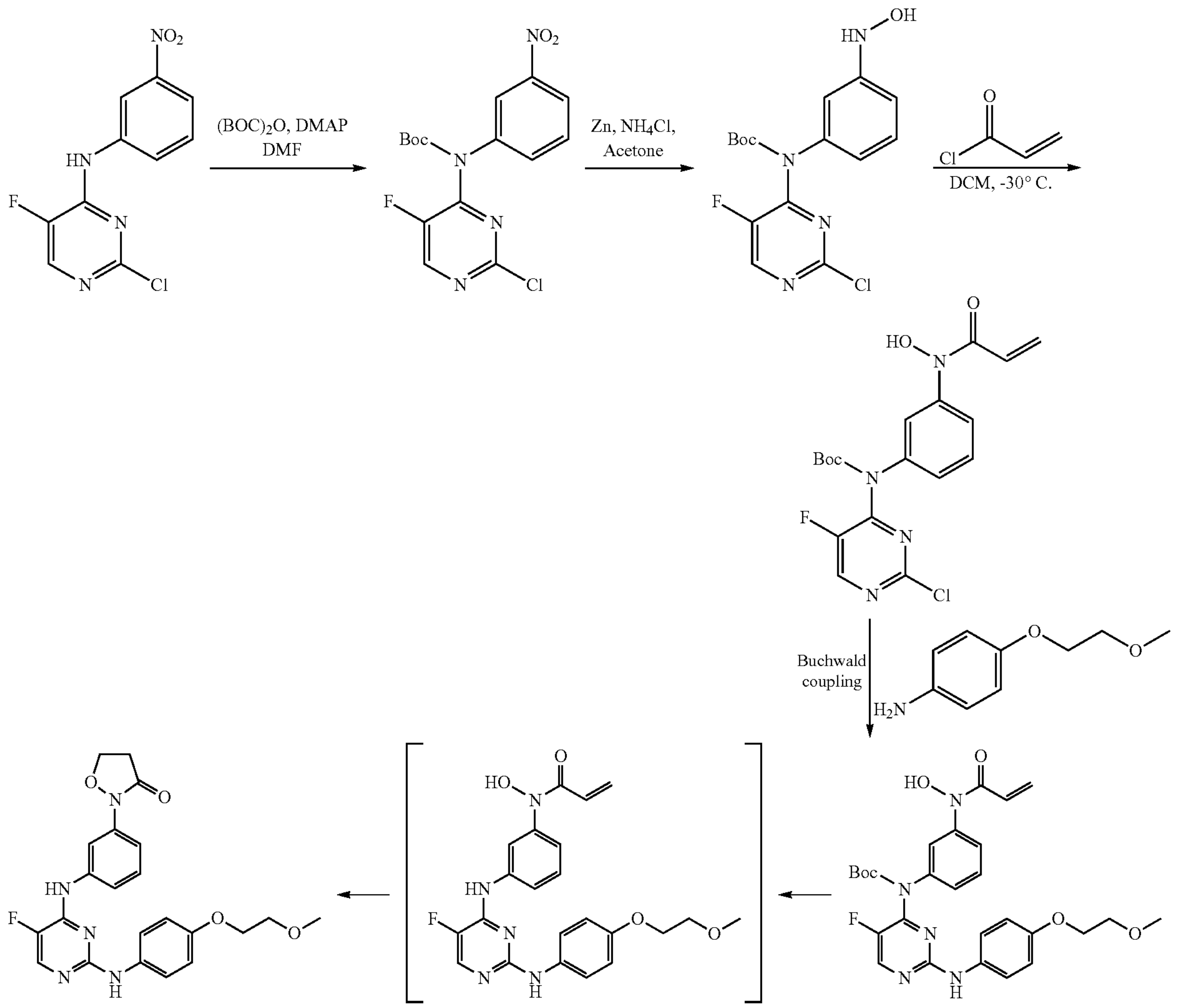

I-27

I-9

Synthesis of tert-butyl (2-chloro-5-fluoropyrimidin-4-yl)(3-nitrophenyl)carbamate In a 50 mL 3-neck RBF, to a solution of 2-chloro-5-fluoro-N-(3-nitrophenyl)pyrimidin-4-amine (1.0 g) in DMF (10 mL), were added Boc anhydride (1.22 g) and DMAP (0.670 g). The reaction mixture was stirred at room temperature for 1.5 h. The reaction was monitored by TLC using hexane:ethyl acetate (6:4) as mobile phase. After completion of the reaction, the reaction mixture was poured into water and extracted with ethyl acetate (3×50 ml). The ethyl acetate layer was washed with brine solution, dried over sodium sulfate and concentrated under reduced pressure at 40° C. Purification was purified by column chromatography. Product was eluted with 5% ethyl acetate in hexane to give, after concentration, 0.78 g of tert-butyl (2-chloro-5-fluoropyrimidin-4-yl)(3-nitrophenyl)carbamate. $^1H$ NMR: DMSO-$d_6$ (400 MHz): 1.451 (s, 9H), 7.710-7.750 (t, 1H, J=8), 7.823 (d, 1H, J=8.0), 8.212 (d, 1H, J=8), 8.259 (s, 1H), 9.00 (s, 1H).

Synthesis of tert-butyl (2-chloro-5-fluoropyrimidin-4-yl)(3-(hydroxyamino)phenyl)carbamate To a solution of tert-butyl (2-chloro-5-fluoropyrimidin-4-yl)(3-nitrophenyl)carbamate (0.78 g) in mixture of acetone (3 ml) and water (2 ml) was added $NH_4Cl$ (0.22 g) and the reaction mixture was heated to 60° C. Zn dust (289 mg) was added to the reaction mixture at 60° C. portion wise. The reaction mixture was stirred for 45 minute at 60° C. and monitored on TLC using hexane:ethyl acetate (3:7) as mobile phase. After completion of the reaction, the reaction mixture was poured in water. The product was extracted into ethyl acetate and the organic layer was washed with brine, dried over sodium sulfate and concentrated completely under reduce pressure to give crude product. Crude material was purified by using column chromatography. Desired product eluted with 5% ethyl acetate in hexane to give, after concentration, 0.409 g of tert-butyl (2-chloro-5-fluoropyrimidin-4-yl)(3-(hydroxyamino)phenyl)carbamate. M+1=354.8. $^1$H NMR: DMSO-$d_6$ (400 MHz): 1.400 (s, 9H), 6.612 (d, 1H, J=7.6), 6.688 (s, 1H), 6.774 (d, 1H, J=8.4), 7.170-7.210 (t, 1H, J=8), 8.434 (d, 2H, J=6.4), 8.95 (s, 1H).

Synthesis of tert-butyl (2-chloro-5-fluoropyrimidin-4-yl)(3-(N-hydroxyacrylamido)phenyl)carbamate In a 25 ml 3-neck RBF was equipped with a magnetic stirrer and $CaCl_2$ guard tube was added tert-butyl (2-chloro-5-fluoropyrimidin-4-yl)(3-(hydroxyamino)phenyl)carbamate (0.409 g in 5 ml DCM). The reaction was cooled to −40° C. and acryloyl chloride (0.114 g in 3 ml DCM) was slowly added. The reaction mixture was warmed to room temperature and stirred at room temperature for 30 min. The reaction was monitored on TLC using hexane:ethyl acetate (7:3) as mobile phase. The reaction was complete after 30 min and was poured in water (100 ml) and basified using sodium bicarbonate solution. The reaction mixture was extracted with DCM (2×25 ml) and the combined organic layer was washed with brine solution, dried over sodium sulfate and concentrated completely under reduced pressure at 40° C. Crude material was purified by using column chromatography. Product was eluted with 14% ethyl acetate in hexane to give, after concentration, 0.250 g of tert-butyl (2-chloro-5-fluoropyrimidin-4-yl)(3-(N-hydroxyacrylamido)phenyl)carbamate Synthesis of tert-butyl (5-fluoro-2-((4-(2-methoxyethoxy)phenyl)amino)pyrimidin-4-yl)(3-(N-hydroxyacrylamido)phenyl)carbamate In a 25 mL three neck RBF with thermometer pocket, a solution of tert-butyl (2-chloro-5-fluoropyrimidin-4-yl)(3-(N-hydroxyacrylamido)phenyl)carbamate (0.250 g) in 1,4-dioxane (8.0 mL) was added. 4-(2-Methoxyethoxy)aniline (0.122 g) was added and the reaction was degassed for 10 minutes under argon. After 10 minutes, Xantphose (0.0176 g) and $Cs_2CO_3$ (0.396 g) were added and again degassed the reaction for 10 minutes followed by addition of Pd $(OAc)_2$ (0.003 g) under argon. The reaction was heated to 80° C. and stirred for 3.5 hr under argon. The reaction was monitored on TLC using hexane:ethyl acetate (2:8) as mobile phase. After completion of the reaction, the reaction mixture was allowed to cool at room temperature. The reaction mixture was poured into water and product was extracted with ethyl acetate (3×25 ml). Ethyl acetate layer washed with brine solution, dried over sodium sulfate and concentrated under reduced pressure to give 0.250 g of tert-butyl (5-fluoro-2-((4-(2-methoxyethoxy)phenyl)amino)pyrimidin-4-yl)(3-(N-hydroxyacrylamido)phenyl)carbamate. This crude material was used in the next step without any further purification. M+1=539.9.

Synthesis of N-(3-((5-fluoro-2-((4-(2-methoxyethoxy)phenyl)amino)pyrimidin-4-yl)amino)phenyl)-N-hydroxyacrylamide In a 25 ml, 3-neck RBF equipped with a calcium chloride guard tube, to a solution of tert-butyl (5-fluoro-2-((4-(2-methoxyethoxy)phenyl)amino)pyrimidin-4-yl)(3-(N-hydroxyacrylamido)phenyl)carbamate (0.250 g) in DCM (10 ml) was added trifluoroacetic acid (5.0 ml) drop wise into the reaction mixture at 0° C. The reaction mixture was stirred at 0° C. for 15 minutes and then at room temperature for 30 minutes. The reaction was monitored by TLC using hexane: ethyl acetate (3:7) as mobile phase. After completion of the reaction, the reaction mixture was quenched in water and neutralized with sodium bicarbonate. Product was extracted into DCM and the organic layer was washed with brine, dried over sodium sulfate and concentrated completely under reduce pressure at 40° C. Crude material was purified by preparative-HPLC to give 8.3 mg of N-(3-((5-fluoro-2-((4-(2-methoxyethoxy)phenyl)amino)pyrimidin-4-yl)amino)phenyl)-N-hydroxyacrylamide. $^1$H NMR: DMSO-$d_6$ (400 MHz): 3.236-3.208 (t, 2H, J=8), 3.356 (s, 3H), 3.628-3.250 (t, 2H, J=4.4), 4.018-4.040 (t, 2H, J=4.4), 4.488-4.528 (t, 2H, J=8), 6.798 (d, 2H, J=8.8), 7.35 (d, 2H, J=6.4), 7.72 (d, 2H, J=6), 7.84 (s, 1H), 8.085 (d, 1H, J=3.6), 9.011 (s, 1H), 9.457 (s, 1H).

In the attempted synthesis of I-9 it was determined that the final de-protection conditions (TFA) lead to the formation of a pyrrolidinone product I-27 after formation of I-9. It is believed that conducting the de-protection before step 4 (prior to introduction of the acrylamide) or use of an alternate protecting group, such as a parmethoxybenzyl (which can be removed under mild oxidative conditions), would lead to the desired compound I-9.

Example 16

N-(3-((5-fluoro-2-((4-(2-hydroxyethoxy)phenyl)amino)pyrimidin-4-yl)amino)phenyl)-N-methylacrylamide (I-23)

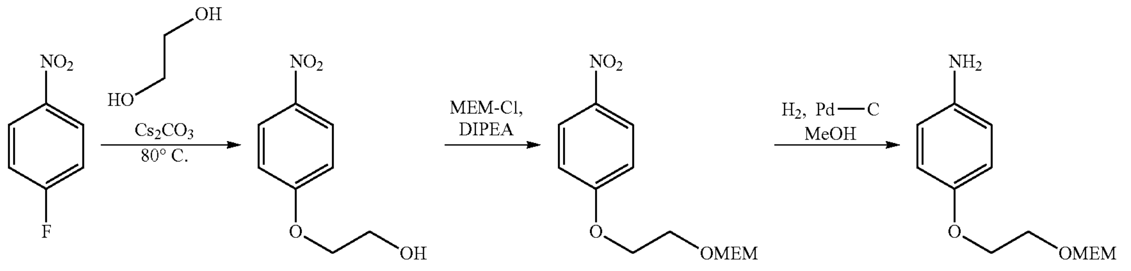

-continued

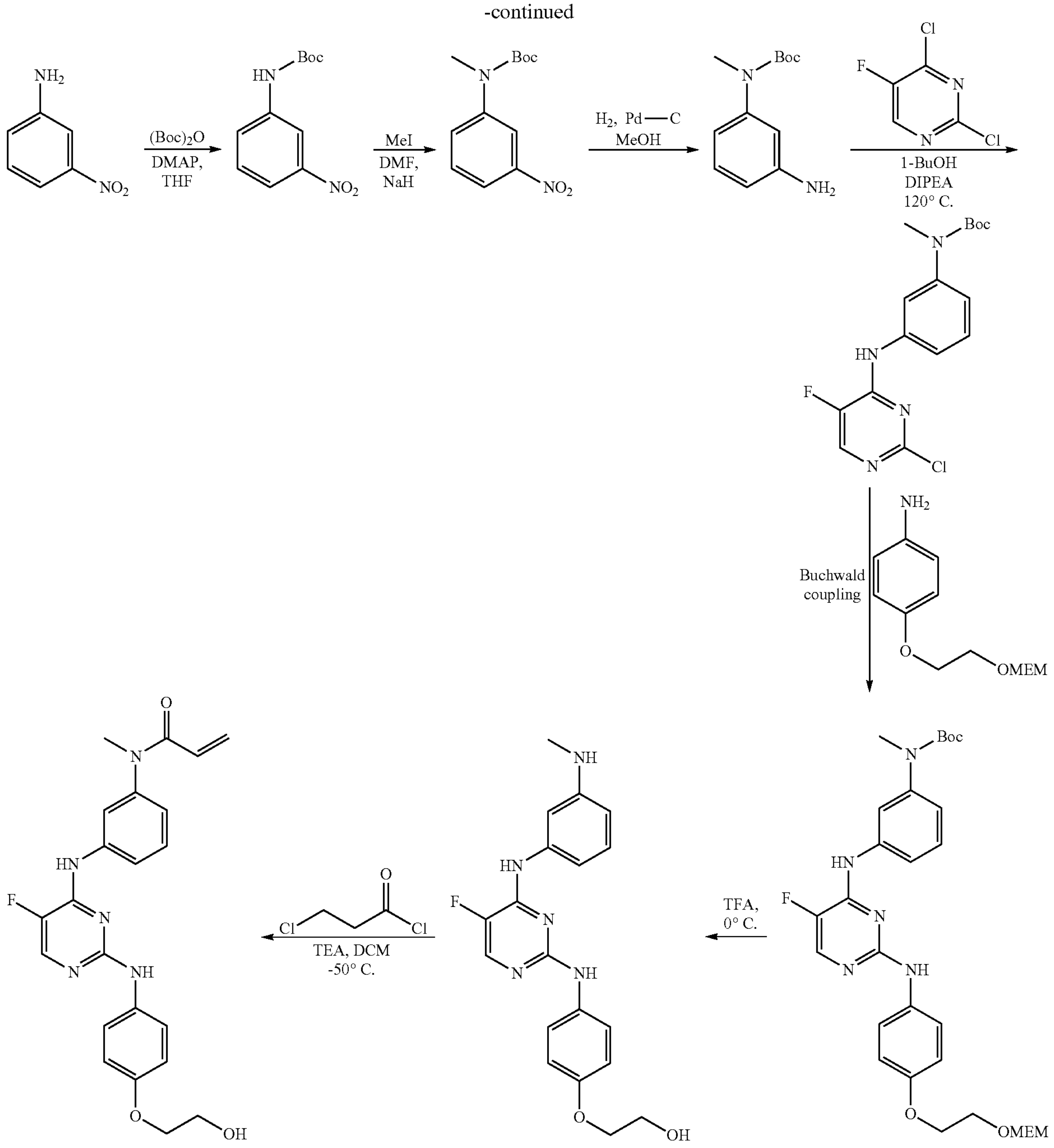

I-23

Synthesis of 2-(4-nitrophenoxy)ethanol

In a 250 ml, 3-neck RBF equipped with a magnetic stirrer, reflux condenser, calcium chloride guard tube, 1-fluoro-4-nitrobenzene (10.0 g), ethylene glycol (50 ml) and cesium carbonate (46.0 g) were added. The reaction mixture was heated to 80° C. for 30 minutes and the reaction was monitored on TLC using hexane:ethyl acetate (5:5) as mobile phase. After completion of the reaction, the reaction mixture was cooled to room temperature and poured into cold water. Solid precipitate was filtered out and washed with water. Solid material was dried under reduced pressure at 45° C. for 1 hr to give 10.7 g of 2-(4-nitrophenoxy)ethanol, which was used in the next step without further purification.

Synthesis of 1-(2-((2-methoxyethoxy)methoxy)ethoxy)-4-nitrobenzene

Into a 100 mL 3-neck RBF, equipped with $N_2$ Bubbler and thermo pocket 2-(4-nitrophenoxy)ethanol (10.8 g) in DCM (30 mL), and DIPEA (11.44 g) were added; the reaction mixture was cooled to 0° C. Methoxyethoxymethyl chloride (11.02 g in 20 mL DCM) was added drop wise during 10 min, and the reaction mixture was stirred at room temperature for 16 hr. The reaction was monitored on TLC using ethyl acetate:hexane (5:5) as mobile phase. After completion of the reaction, reaction mixture was poured into water and neutralized with saturated $NaHCO_3$ solution. Product was extracted into DCM. The organic layer was washed with brine, dried over sodium sulfate and concentrated completely under reduce pressure at 40° C. to give 10.54 g of 1-(2-((2-methoxyethoxy)methoxy)ethoxy)-4-nitrobenzene.

Synthesis of 4-(2-((2-methoxyethoxy)methoxy)ethoxy)aniline

In a 50 mL 3-neck RBF equipped with $N_2$ Bubbler and gas purger; to a suspension of Pd—C (1.0 g) in methanol (10 mL) was added 1-(2-((2-methoxyethoxy)methoxy)ethoxy)-4-nitrobenzene (5.0 g) in methanol (20 mL) under nitrogen atmosphere. Hydrogen gas was bubbled through the reaction mixture for 2 h at room temperature. The reaction was monitored on TLC using ethyl acetate:hexane (5:5) as mobile phase. After completion of the reaction, the reaction mixture was filtered using Celite and washed with methanol. The filtrate was concentrated under reduced pressure at 40° C. to give 4.28 g of 4-(2-((2-methoxyethoxy)methoxy)ethoxy)aniline as a brown liquid.

Synthesis of tert-butyl(3-nitrophenyl)carbamate

In a 50 mL 3-neck RBF, 3-nitroaniline 5 (5.0 g) in THF (40 mL) and $(BOC)_2O$ (7.89 g) was charged and cooled to 0° C. DMAP (6.09 g) was added portion-wise into the reaction mixture and reaction mixture was warmed to room temperature and stirred at room temperature for 5 hr. The reaction was monitored on TLC using hexane:ethyl acetate (5:5) as mobile phase. After completion of the reaction, the reaction mixture was poured into water and extracted with ethyl acetate. The organic layer was washed with 50 mL brine solution, dried over sodium sulfate and concentrated completely under reduced pressure at 40° C. Crude material was purified by using column chromatography. Product was eluted with 4% ethyl acetate in hexane and concentrated to give 7.1 g of tert-butyl(3-nitrophenyl)carbamate.

Synthesis of methyl(3-nitrophenyl)carbamate

To a solution of tert-butyl(3-nitrophenyl)carbamate (6.0 g) in DMF (35 mL) in a 100 mL 3-neck RBF equipped with $N_2$ Bubbler and thermo pocket was added NaH (1.21 g) portion wise and stirred 1.0 hr at room temperature. Methyl iodide (5.37 g in 15 mL DMF) was added dropwise to the reaction mixture at 0° C. The mixture was allowed to cool to room temperature and stirred for 2 hr. The reaction was monitored on TLC using hexane:ethyl acetate (9:1) as mobile phase. After completion of the reaction, the reaction mixture was poured into water and extracted with ethyl acetate. The organic layer was washed with brine solution, dried over sodium sulfate and concentrated completely under reduce pressure at 40° C. to give 6.0 g of tert-butyl methyl(3-nitrophenyl)carbamate 7. $^1H$ NMR: DMSO-$d_6$ (400 MHz): 1.43 (s, 9H), 3.26 (s, 3H), 7.62 (t, 1H, J=8.4), 7.77 (d, 1H, J=8), 8.00 (d, 1H, J=9.2), 8.18 (s, 1H).

Synthesis of tert-butyl(3-aminophenyl)(methyl)carbamate

A solution of methyl(3-nitrophenyl)carbamate (6.0 g) in methanol was charged in an autoclave. Pd/C (0.65 g) in methanol was added to reaction mixture. The vessel was pressurized to 5 kg/cm$^2$ $H_2$ pressure and stirred at room temperature for 3 h. After completion of the reaction, the reaction mixture was filtered using Celite and the filter cake was washed with methanol. The filtrate was concentrated under reduced pressure at 40° C. Crude material was purified by using column chromatography. Desired product was eluted with 8% ethyl acetate in hexane and was concentrated to give 4.1 g of tert-butyl(3-aminophenyl)(methyl)carbamate.

Synthesis of tert-butyl (3-((2-chloro-5-fluoropyrimidin-4-yl)amino)phenyl)(methyl)carbamate In a pressure tube tert-butyl(3-aminophenyl)(methyl)carbamate (2.0 g), 2,4-dichloro-5-fluoropyrimidine (2.25 g) and DIPEA (2.32 g) were added in 1-butanol (15 ml). The reaction mixture was heated at 120° C. for 3 hr. The reaction was monitored on TLC using hexane:ethyl acetate (7:3) as mobile phase. The reaction was complete after 3 hr. After completion of the reaction, the reaction mixture was allowed to cool at room temperature. The reaction mixture was poured into water and extracted with ethyl acetate (3×25 ml). Ethyl acetate layer washed with brine solution, dried over sodium sulfate and concentrated under reduced pressure at 40° C. Crude material was purified by using Combiflash chromatography. Product was eluted with 14.8% ethyl acetate in hexane to give 1.93 g of tert-butyl (3-((2-chloro-5-fluoropyrimidin-4-yl)amino)phenyl)(methyl)carbamate. M+1=466.8.

Synthesis of tert-butyl (3-((5-fluoro-2-((4-(2-((2-methoxyethoxy)methoxy)ethoxy)phenyl)amino)pyrimidin-4-yl)amino)phenyl)(methyl)carbamate In a 25 ml 3-Neck RBF, tert-butyl (3-((2-chloro-5-fluoropyrimidin-4-yl)amino)phenyl)(methyl)carbamate (0.88 g), 4-(2-((2-methoxyethoxy)methoxy)ethoxy)aniline (0.901 g), $Cs_2CO_3$ (1.21 g) and Xantphose (0.144 g) were added in degassed 1,4-dioxane (10 mL) and the reaction mixture was degassed under argon for 30 minutes. Palladium(II)acetate (0.055 g) was added to reaction mixture and again it was degassed for 30 minutes. The reaction mixture was heated to 80° C. and stirred for 3.5 h. The reaction was monitored on TLC using $CHCl_3$:methanol (9.5:0.5) as mobile phase. After completion of the reaction, reaction mixture was allowed to cool at room temperature. The reaction mixture was poured into water and product was extracted with ethyl acetate (3×25 ml). Ethyl acetate layer was washed with brine solution, dried over sodium sulfate and concentrated under reduced pressure. Crude material was purified by using Combiflash chromatography. Product was eluted with 2% methanol in $CHCl_3$ to give 0.8 g of tert-butyl (3-((5-fluoro-2-((4-(2-((2-methoxyethoxy)methoxy)ethoxy)phenyl)amino)pyrimidin-4-yl)amino)phenyl)(methyl)carbamate. M+1=557.9.

Synthesis of 2-(4-((5-fluoro-4-((3-(methylamino)phenyl)amino)pyrimidin-2-yl)amino)phenoxy)ethanol In a 25 mL, 3-neck RBF equipped with a calcium chloride guard tube, tert-butyl (3-((5-fluoro-2-((4-(2-((2-methoxyethoxy)methoxy)ethoxy)phenyl)amino)pyrimidin-4-yl)amino)phenyl)(methyl)carbamate (0.4 g) in was charged in trifluoroacetic acid (6.0 mL) at 0° C. The reaction mixture was stirred at 0° C. for 8 hr. The reaction was monitored by TLC using DCM:methanol (9.6:0.4) as mobile phase. After completion of the reaction, the reaction mixture was quenched in water and neutralized with sodium bicarbonate. Product was extracted in DCM and the organic layer was washed with brine, dried over sodium sulfate and concentrated completely under reduce pressure at 40° C. Crude material was purified by using Combiflash chromatography. Product was eluted with 1.7% methanol in DCM and concentrated to give 0.105 g of 2-(4-((5-fluoro-4-((3-(methylamino)

phenyl)amino)pyrimidin-2-yl)amino)phenoxy)ethanol. M+1=457.8. $^1H$ NMR: DMSO-$d_6$ (400 MHz): 2.65 (d, 3H, J=5.2), 3.69 (t, 2H, J=4.8), 3.92 (t, 2H, J=4.8), 4.85 (t, 1H, J=5.6), 5.54 (d, 1H, J=4.8), 6.29 (s, 1H), 6.79 (d, 2H, J=8.8), 6.86 (s, 1H), 7.03 (s, 2H), 7.55 (d, 2H, J=9.2), 8.02 (s, 1H), 8.93 (s, 1H), 9.04 (s, 1H).

Synthesis of N-(3-((5-fluoro-2-((4-(2-hydroxyethoxy)phenyl)amino)pyrimidin-4-yl)amino)phenyl)-N-methylacrylamide (I-23)

To a solution of 2-(4-((5-fluoro-4-((3-(methylamino)phenyl)amino)pyrimidin-2-yl)amino)phenoxy)ethanol (0.05 g) in DCM, in a 25 ml 3-neck RBF equipped with a calcium chloride guard tube was added and TEA (0.0150 g). The reaction mixture was cooled to −50° C. and 3-chloropropanoyl chloride (0.0172 g) was added drop wise. The reaction mixture was stirred at −50° C. for 15 min. The reaction was monitored by TLC using DCM:methanol (9.4:0.6) as mobile phase. After completion of the reaction, the reaction mixture was quenched in water and neutralized with sodium bicarbonate. Product was extracted in DCM. Organic layer was washed with brine, dried over sodium sulfate and concentrated completely under reduce pressure at 40° C. Crude material was purified by using Combiflash chromatography. Product was eluted with 2.6% methanol in DCM to give 0.007 g of N-(3-((5-fluoro-2-((4-(2-hydroxyethoxy)phenyl)amino)pyrimidin-4-yl)amino)phenyl)-N-methylacrylamide I-23. $^1H$ NMR: DMSO-$d_6$ (400 MHz): 3.22 (s, 3H), 3.70 (s, 2H), 3.94 (s, 2H), 4.85 (s, 1H), 5.59 (s, 1H), 6.16 (s, 2H), 6.81 (d, 2H, J=8.0), 6.94 (d, 1H, J=6.8), 7.39 (m, 3H), 7.74 (s, 1H), 7.87 (d, 1H, J=6), 8.10 (s, 1H), 9.04 (s, 1H), 9.43 (s, 1H).

Example 17

N-(3-((5-fluoro-2-((4-(2-((2-methoxyethoxy)methoxy)ethoxy)phenyl)amino)pyrimidin-4-yl)(methyl)amino)phenyl)acrylamide (I-24)

I-24

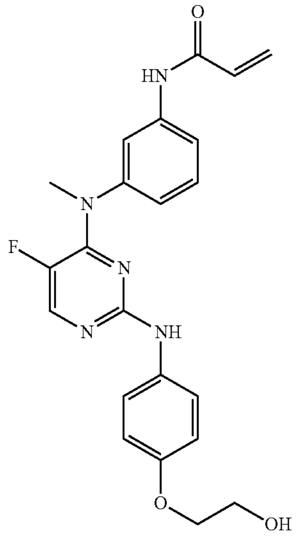

Synthesis of 2-chloro-5-fluoro-N-methyl-N-(3-nitrophenyl)pyrimidin-4-amine

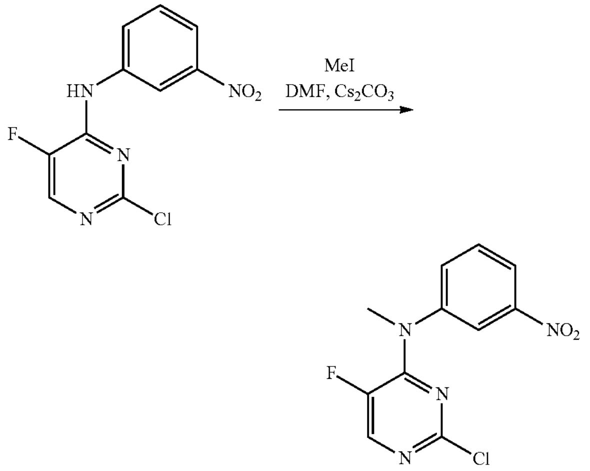

In a 100 ml 3-neck RBF equipped with a magnetic stirrer, calcium chloride guard tube were charged of 2-chloro-5-fluoro-N-(3-nitrophenyl)pyrimidin-4-amine (1.10 g) in DMF (10 ml), and cesium carbonate (23.0 g), $CH_3I$ (0.641 g) was added. The reaction mixture was stirred at room temperature for 1 h. The reaction was monitored on TLC using hexane: ethyl acetate (5:5) as mobile phase. After completion, the reaction was poured into cold water. Solid precipitate was filtered out and washed with water. Solid material was dried under reduced pressure at 45° C. for 1 hr to give 1.00 g of 2-chloro-5-fluoro-N-methyl-N-(3-nitrophenyl)pyrimidin-4-amine, which was used in the next step without further purification. M+1=282.8. $^1H$ NMR (DMSO-$d_6$, 400 MHz) 3.50 (s, 3H), 7.701-7.741 (t, 1H, J=8), 7.883-7.902 (d, 1H, J=7.6), 8.287-8.300 (d, 1H, J=5.2), 8.325 (s, 1H).

Synthesis of N-(3-((5-fluoro-2-((4-(2-((2-methoxyethoxy)methoxy)ethoxy)phenyl)amino)pyrimidin-4-yl)(methyl)amino)phenyl)acrylamide (I-24)

Synthesis of I-24 was performed as described for I-3 (Example 1) using 2-chloro-5-fluoro-N-methyl-N-(3-nitrophenyl)pyrimidin-4-amine in place of 2-chloro-5-fluoro-N-(3-nitrophenyl)pyrimidin-4-amine and 4-(2-((2-methoxyethoxy)methoxy)ethoxy)aniline in place of 4-[(2-methoxyethoxy)methoxy]aniline. M+1=423.9. $^1H$ NMR (DMSO-$d_6$, 400 MHz) 3.44 (s, 3H), 3.664-3.688 (t, 2H, J=4.8), 3.900-3.924 (t, 2H, J=4.8), 5.754-5.779 (d, 1H, J=10), 6.232-6.274 (d, 1H, J=16.8), 6.385-6.453 (m, 2H), 6.810-6.832 (d, 1H, J=8.8), 7.009-7.028 (d, 1H, J=7.6), 7.328-7.368 (t, 1H, J=8), 7.512-7.572 (m, 3H), 7.652 (s, 1H), 7.965-9.978 (d, 1H, J=5.2), 8.196 (s, 1H), 9.120 (s, 1H), 10.245 (s, 1H).

Example 18

N-(3-((5-fluoro-2-((4-(2-hydroxyethoxy)phenyl)(methyl)amino)pyrimidin-4-yl)amino)phenyl)acrylamide (I-25)

I-25

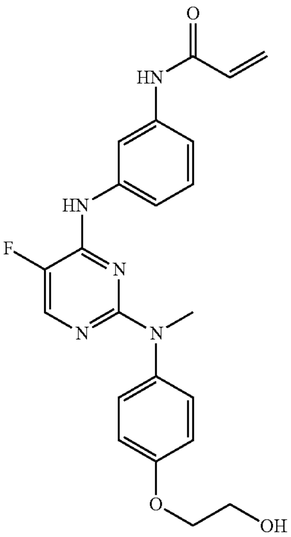

Synthesis of 4-(2-((2-methoxyethoxy)methoxy)ethoxy)-N-methylaniline

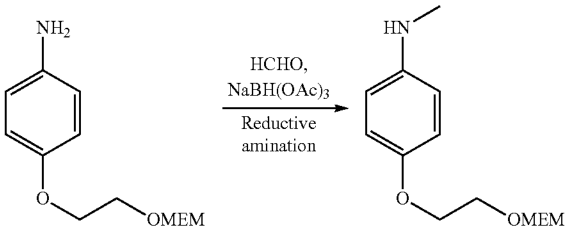

To a 25 mL, 3-neck RBF equipped with a magnetic stirrer and calcium chloride guard tube, 4-(2-((2-methoxyethoxy)methoxy)ethoxy)aniline (1.0 g in 10 mL DMF) and formaldehyde (0.062 g) were added portion wise to the reaction mixture at 0° C. and stirred for an additional 10 minutes. $NaBH(OAc)_3$ (0.88 g) was added and the mixture was stirred for 5 minutes. The reaction was monitored on TLC using hexane:ethyl acetate (5:5) as mobile phase. After completion of the reaction, the reaction mixture was poured in water and extracted with ethyl acetate. Organic layer was washed with brine, dried over sodium sulfate and concentrated completely under reduce pressure at 40° C. Crude material was purified by using column chromatography. Desired product was eluted with 7% ethyl acetate in hexane to give 0.200 g of 4-(2-((2-methoxyethoxy)methoxy)ethoxy)-N-methylaniline. M+1=256.0.

Synthesis of N-(3-((5-fluoro-2-((4-(2-hydroxyethoxy)phenyl)(methyl)amino)pyrimidin-4-yl)amino)phenyl)acrylamide (I-25)

Synthesis of N-(3-((5-fluoro-2-((4-(2-hydroxyethoxy)phenyl)(methyl)amino)pyrimidin-4-yl)amino)phenyl)acrylamide I-25 was performed as described for the synthesis of I-23 (Example 16) using 4-(2-((2-methoxyethoxy)methoxy)ethoxy)-N-methylaniline in place of 4-(2-((2-methoxyethoxy)methoxy)ethoxy)aniline and tert-butyl (3-((2-chloro-5-fluoropyrimidin-4-yl)amino)phenyl)carbamate in place of (3-((2-chloro-5-fluoropyrimidin-4-yl)amino)phenyl)(methyl)carbamate. M+1=423.9. $^1H$ NMR: DMSO-$d_6$ (400 MHz): 3.366 (s, 3H), 3.775 (s, 2H), 3.985 (s, 2H), 5.737-5.761 (d, 1H, J=9.6), 6.231-6.274 (d, 1H, J=17.2), 6.428-6.495 (m, 1H), 6.906-6.926 (d, 2H, J=8), 7.023-7.063 (t, 1H, J=8.8), 7.176-7.218 (t, 2H, J=8.4), 7.390-7.412 (d, 1H, J=8.8), 7.948-7.994 (d, 2H, J=18.4), 8.265 (s, 1H), 9.284 (s, 1H), 10.052 (s, 1H).

Example 19

N-(3-((5-fluoro-2-(hydroxy(4-(2-methoxyethoxy)phenyl)amino)pyrimidin-4-yl)amino)phenyl)acrylamide (I-7)

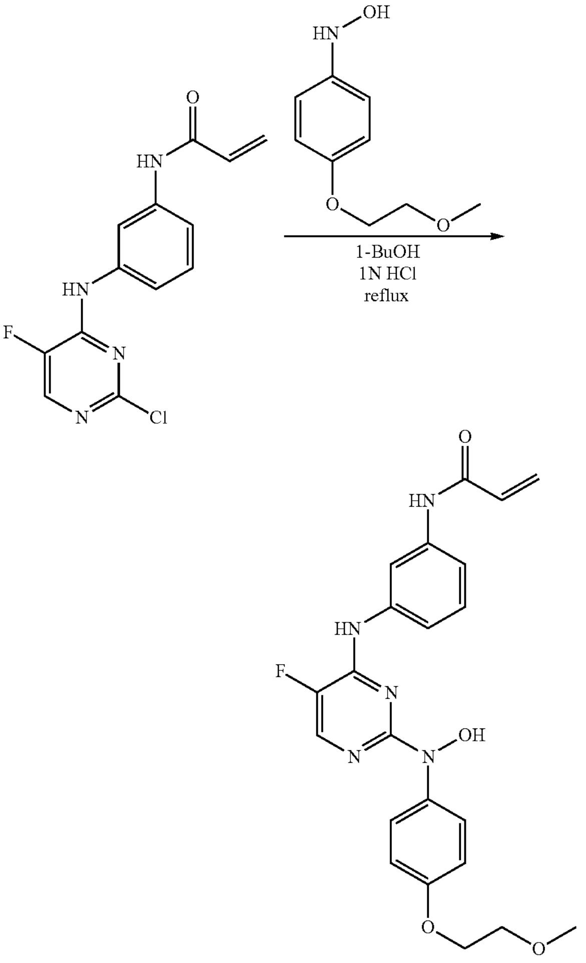

I-7

The synthesis of I-7 may be performed in an analogous manner to the synthesis of I-1 (Example 2) using N-(4-(2-methoxyethoxy)phenyl)hydroxylamine in place of 2-(4-aminophenoxy)ethanol.

I-12, I-8, I-11, I-10, I-16, I-20 and I-21 may be prepared according to the schemes depicted in Examples 20-26.

Example 20
N-(3-((5-fluoro-6-hydroxy-2-((4-(2-methoxyethoxy)phenyl)amino)pyrimidin-4-yl)amino)phenyl)acrylamide (I-12)
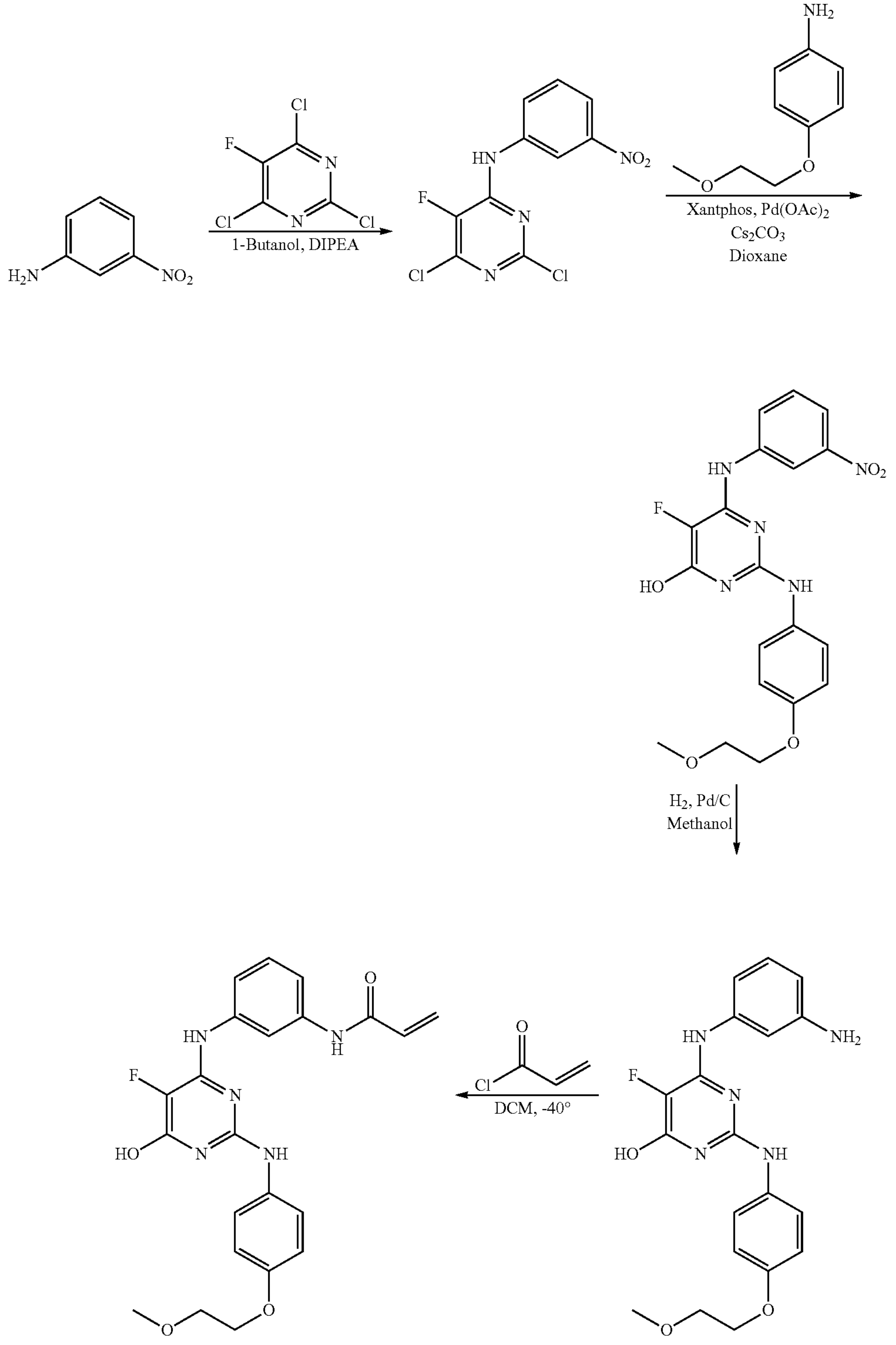
I-12

Example 21
N-(3-((5-fluoro-2-((4-(2-methoxyethoxy)phenyl)amino)pyrimidin-4-yl)(hydroxy)amino)phenyl)acrylamide (I-8)
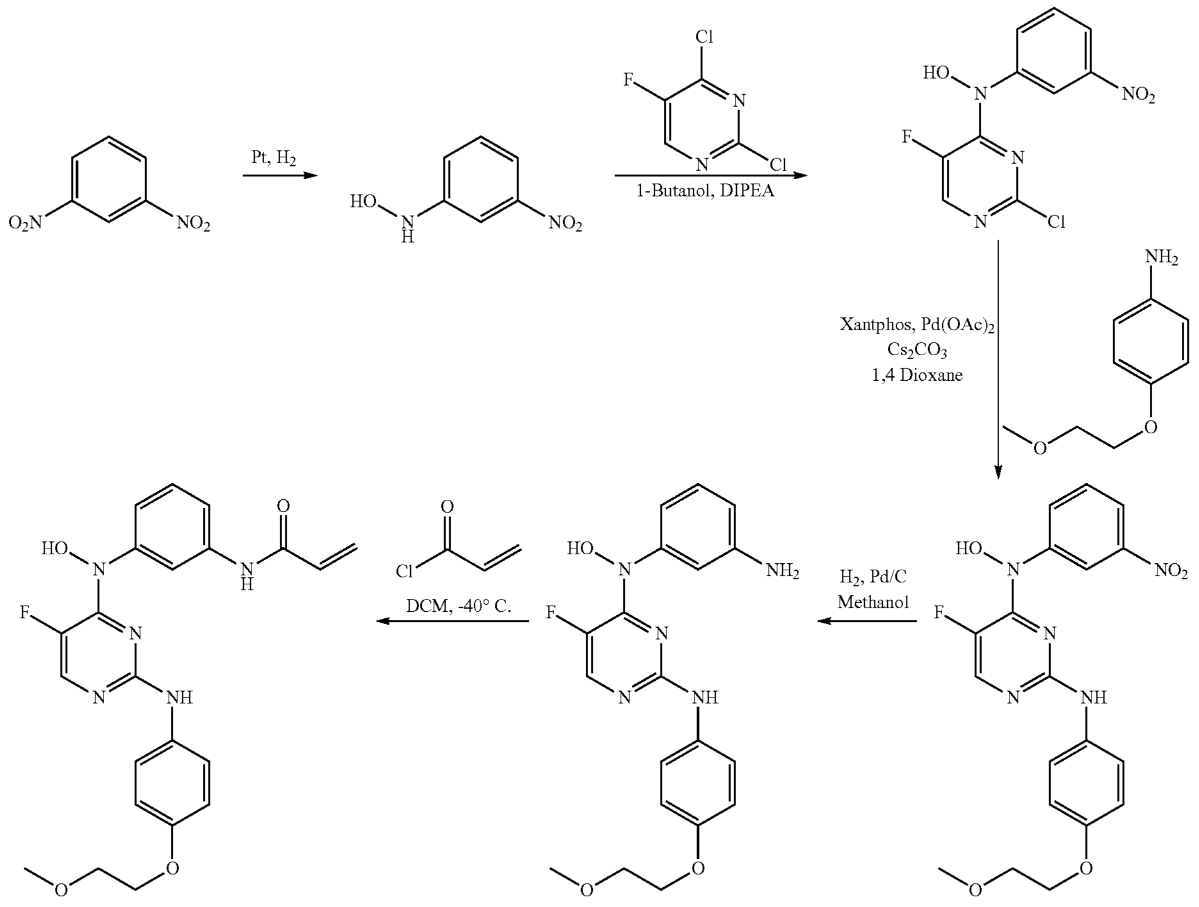
I-8
Example 22
4-((3-acrylamidophenyl)amino)-5-fluoro-2-((4-(2-methoxyethoxy)phenyl)amino)pyrimidine 1-oxide (I-11)
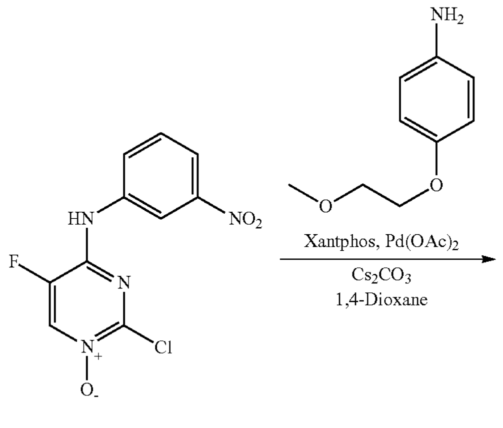
-continued
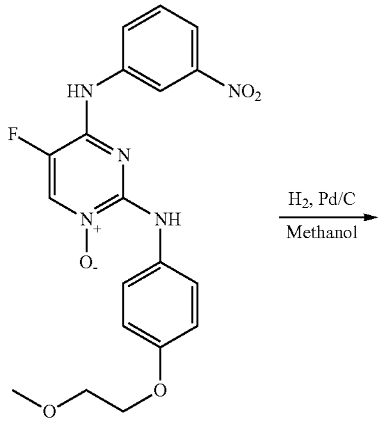

-continued
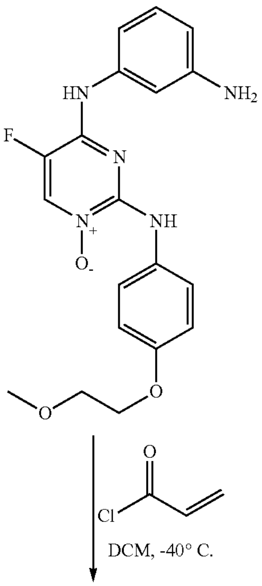
-continued
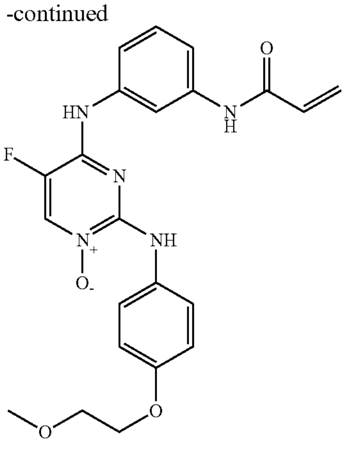
I-11
Example 23
6-((3-acrylamidophenyl)amino)-5-fluoro-2-((4-(2-methoxyethoxy)phenyl)amino)pyrimidine 1-oxide (I-10)
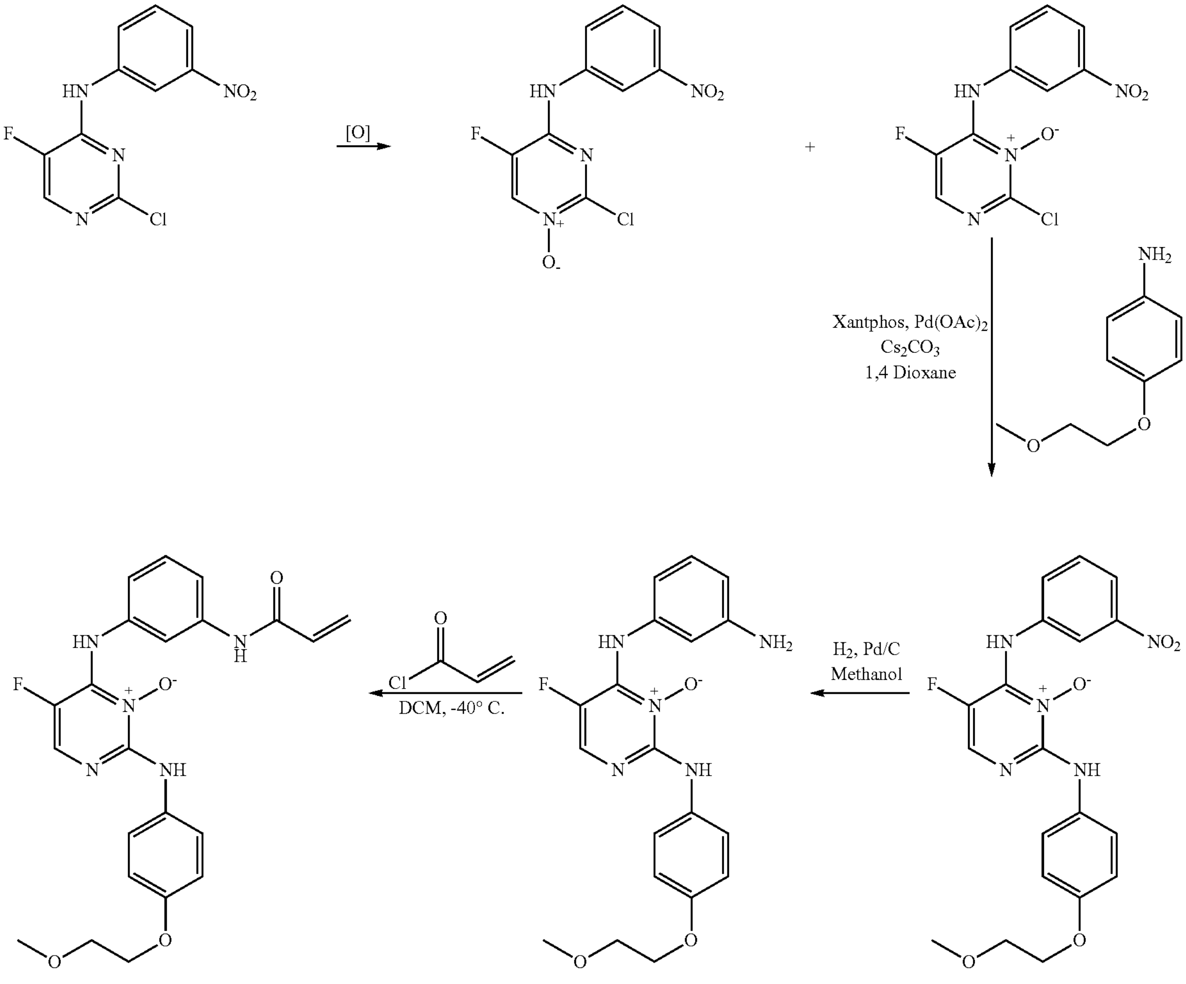
I-10

Example 24
N-(3-((5-fluoro-2-((4-(2-methoxyethoxy)phenyl) amino)pyrimidin-4-yl)amino)-5-hydroxyphenyl) acrylamide (I-16)
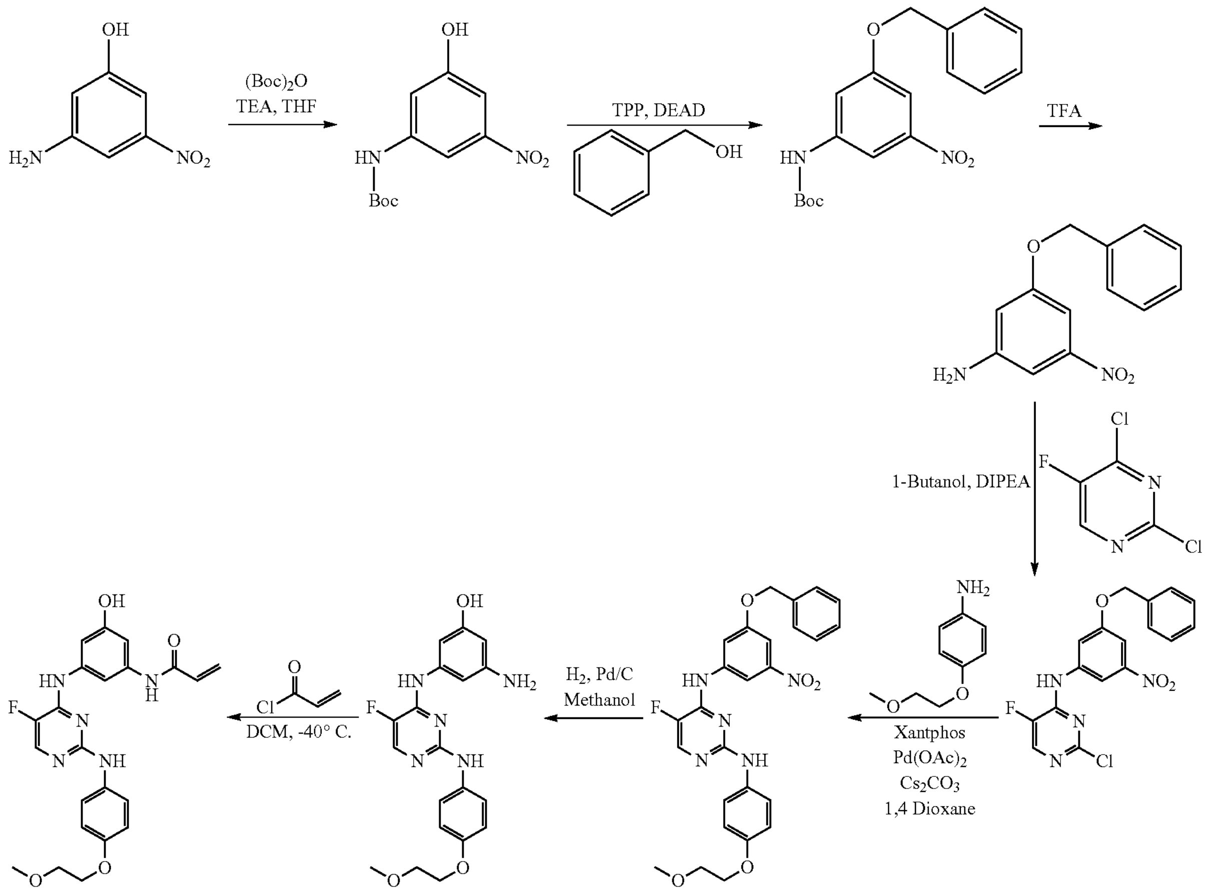
I-16
Example 25
4-((3-((5-fluoro-2-((4-(2-methoxyethoxy)phenyl) amino)pyrimidin-4-yl)amino)phenyl)amino)-4-oxobutanoic acid (I-20)
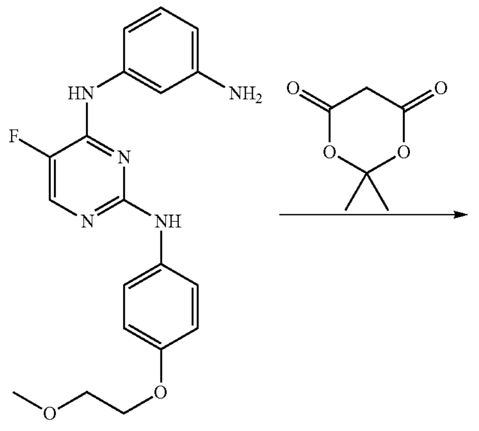
-continued
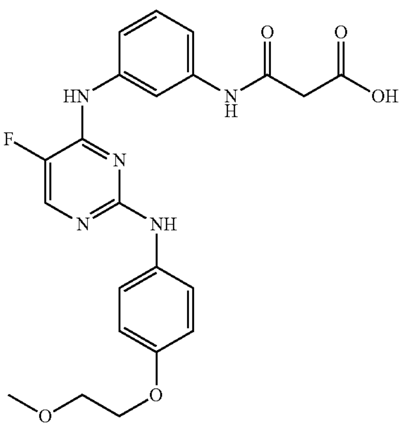
I-20

Example 26

N-(3-((5-fluoro-2-((4-(2-methoxyethoxy)phenyl) amino)pyrimidin-4-yl)amino)phenyl)-2-oxopropanamide (I-21)

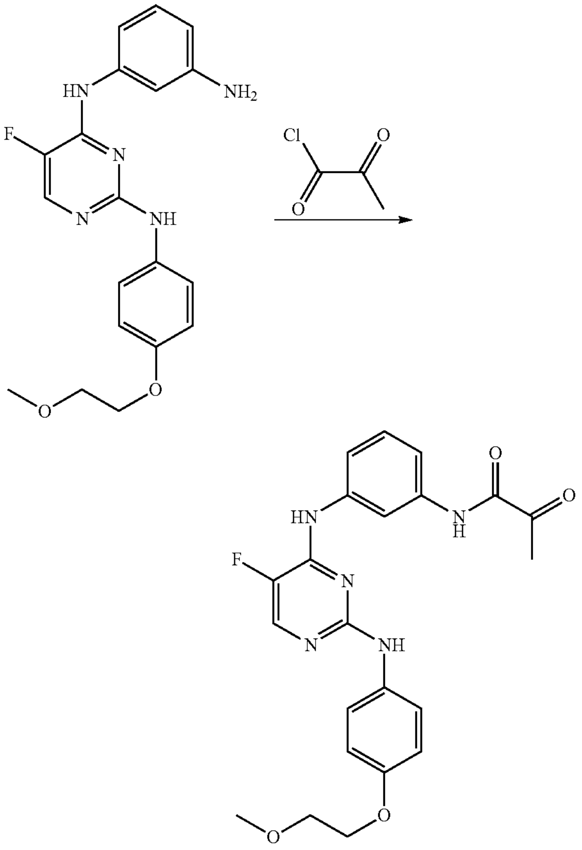

I-21

Example 27

N4-(3-aminophenyl)-5-fluoro-N2-(4-(2-methoxyethoxy)phenyl)pyrimidine-2,4-diamine (I-28)

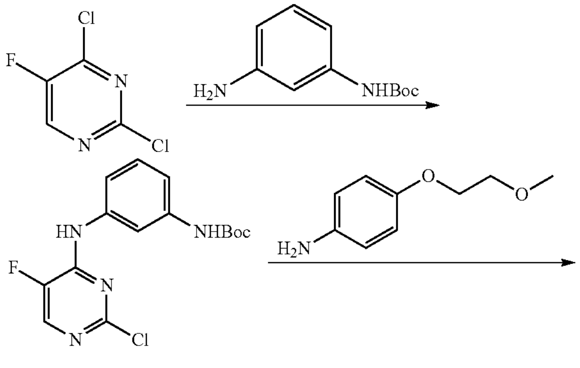

-continued

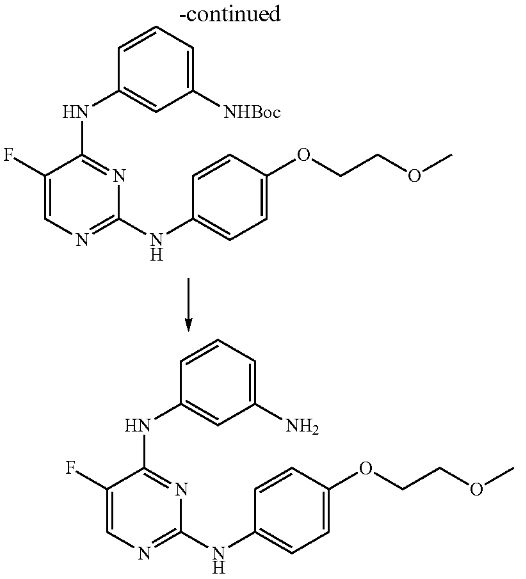

Synthesis of tert-butyl (3-((2-chloro-5-fluoropyrimidin-4-yl)amino)phenyl)carbamate 2,4-Dichloro-5-fluoropyrimidine (800 mg, 4.8 mmoL), tert-butyl (3-aminophenyl)carbamate (996 mg, 4.8 mmoL) and Hunig's base (948 uL, 5.75 mmoL) were dissolved in THF (20 mL). The reaction mixture was heated at reflux overnight. After cooling, partitioned between water/brine (10 mL), agitated and separated the layers. Dried organic phase over sodium sulfate, and the solvent was removed via rotary evaporation. Titration with EtOAc and Heptane gave after filtration a white solid, 1 g. LC/MS (RT=2.03/(M+1)) 339.1.

Synthesis of tert-butyl (3-((5-fluoro-2-((4-(2-methoxyethoxy)phenyl)amino)pyrimidin-4-yl)amino)phenyl)carbamate tert-Butyl (3-((2-chloro-5-fluoropyrimidin-4-yl)amino)phenyl)carbamate (800 mg, 2.37 mmoL) and 4-(2-methoxyethoxy)aniline (576 mg, 2.84 mmoL) were suspended in tert-amyl alcohol (14 mL) and acetic acid (5 drops). Heated to reflux for 4 h. After cooling, solvent was removed via rotary evaporation. The dark oil was partitioned between water/brine and THF (10 mL each), agitated, and separated layers and dried organic phase over sodium sulfate. The solvent was removed via rotary evaporation to afford a purple solid, 0.55 g. LC/MS (RT=2.997/(M+1)) 470.2. Additional 150 mg of product minus the (BOC) protecting group crystallized from the aqueous layer Synthesis of N4-(3-aminophenyl)-5-fluoro-N2-(4-(2-methoxyethoxy)phenyl)pyrimidine-2,4-diamine (I-28)

To a solution of tert-butyl (3-((5-fluoro-2-((4-(2-methoxyethoxy)phenyl)amino)pyrimidin-4-yl)amino)phenyl)carbamate (550 mg, 1.17 mmol) in DCM (20 mL) was added TFA (2 mL). Stirred for 30 min at rt for 4 h; removed solvent via rotary evaporation and partitioned oil with cold (0° C.) saturated sodium bicarbonate (10 mL) and EtOAc (10 mL), agitated and separated layers. Organic phase was dried over sodium sulfate and the solvent was removed via rotary evaporation to give a dark oil. Flash chromatography using 20%-100% Heptane/EtOAc gradient using combiflash system gave 309 mg of a light pink solid. LC/MS (RT=2.78/(M+1)) 370.2.

Example 28

Biochemical Kinase Assay

The following Example describes testing certain compounds according to the invention for inhibition of BTK activity. The Omnia® Continuous Read Kinase Assay uses an unnatural amino acid chelation enhanced fluorophore (Sox; 8-hydroxy-5-(N,N-dimethylsulfonamido)-2 methylquinoline) incorporated into a kinase-specific peptide substrate to characterize Btk enzyme kinetics and inhibition. Following Btk-mediated phosphorylation, a sensitive, highly quantifiable increase in real-time fluorescence is noted based upon the ability of chelated Mg2+ to form a bridge between Sox and the phosphate group on a tyrosine residue of the peptide substrate. The Omnia® continuous read assay was performed essentially as described by the vendor (Invitrogen; Carlsbad, Calif.). First, a 10× stock of human recombinant full-length Btk enzyme was prepared in Kinase Reaction Buffer. 5 μL of the 10× enzyme was pre-incubated with 0.5 μL of serially diluted compound prepared in 50% DMSO, in a 384-well microtiter plate for 30 minutes at 27° C. 1.13×ATP and the Tyr5-Sox conjugated peptide substrate were prepared in 1× Kinase Reaction Buffer. Kinase reactions were initiated by the addition of 45 μL of the 1.13×ATP-Sox peptide substrate master mix and monitored every 30 to 90 seconds for 60 minutes at λex360/λem485 in a Synergy plate reader. The IC50 values for each compound assayed were determined from test concentrations of 0.5 nM to 10 μM in half-log intervals performed in duplicate.

At the conclusion of each assay, progress curves from each well were examined for linear reaction kinetics and fit statistics (R2, 95% confidence interval, absolute sum of squares) using GraphPad software (GraphPad Prism version 5.01; San Diego, Calif.). Initial velocity (0 minutes to ~30+ minutes) from each reaction was determined from the slope of a plot of relative fluorescence units versus time (minutes). Using control normalized % inhibition data, plots were constructed against inhibitor concentration to estimate IC50 from log [inhibitor] versus response using a variable slope model in GraphPad. Table 3 sets forth the activity of selected compounds in the Btk inhibition assay. The compound numbers correspond to the compound numbers in Table 1. Compounds having an activity designated as “A” provided an $IC_{50}$≤10 nM; compounds having an activity designated as “B” provided an $IC_{50}$ 11-100 nM; compounds having an activity designated as “C” provided an $IC_{50}$ 101-500 nM; compounds having an activity designated as “D” provided an $IC_{50}$>501 nM.

TABLE 3

Btk Inhibition Data

| Compound | $IC_{50}$ (nM) |
|---|---|
| I-1 | A |
| I-2 | A |
| I-3 | A |
| I-4 | C |
| I-5 | C |
| I-6 | C |
| I-13 | A |
| I-14 | A |
| I-15 | B |
| I-16 | A |
| I-17 | A |
| I-18 | A |
| I-19 | A |
| I-22 | A |
| I-23 | A |
| I-24 | A |
| I-25 | C |
| I-26 | D |
| I-27 | C |

Example 29

Btk Ramos Cell Signaling Immunoblot Analysis

The following example describes testing certain compounds according to the invention for inhibition of BTK activity. Ramos cells were incubated in serum-free RPMI medium for 1-1.5 hours. Cells were then centrifuged for 5 minutes at 1100 RPM and resuspended in serum-free RPMI in 15 mL roundbottom Corning tubes (~2×$10^6$ cells/mL in 4 mL/tube). The compound was diluted in DMSO and was added to the cells to achieve a final concentration of 0.0003, 0.001, 0.003, 0.01, 0.03, 0.1, 0.3, and 1.0 μM. Cells were then incubated for 1 hour at 37° C. Following incubation, cells were spun at 1100 RPM for 5 minutes and then resuspended in 100 μL of serum-free RPMI. The content of each tube was then transferred to 1.5 mL chilled Eppendorf tubes and placed on ice. Goat anti-human IgM (1 μg) was added to each tube and incubated on ice for 10 minutes. Samples were then placed in a chilled centrifuge (4° C.) and spun at 1000 RPM for 5 minutes. The supernatant was aspirated off and the cells were washed again with chilled PBS. Following aspiration, 100 μL of cell lysis buffer was added to each pellet and incubated for 15 minutes. This was followed by centrifugation for 15 minutes at 14000 RPM. Supernatant was transferred to a fresh tube and analyzed for protein content. Immunoblot analysis was performed as outlined below.

Immunoblot Analysis:

10 μg of protein was denatured by adding 1:10 (v:v) of NuPage Reducing Agent plus 1:4 (v:v) of LDS Loading Buffer. This was then incubated in a heat block at 95° C. for 5-10 minutes and then loaded into a 4-12% gradient gel which was run at 150 V for approximately 1.5 hours. The gel was then cut and transferred to nitrocellulose membrane on a semi-dry apparatus at 0.55 A (2 gels) or 0.35 A (1 gel) for 50-55 minutes (set to 25 V maximum). Blockade of non-specific binding was accomplished through membrane incubation in a 1:2 (v:v) dilution of Odyssey® Blocking Buffer in PBS at pH 7.4 for 1 hour at room temperature. The primary antibody (Table 4) in phosphate-buffered saline containing 0.1% Tween 20 and 5% bovine serum albumin was then incubated with the membrane overnight at 4° C. on a rocking platform. The membrane was then washed three times for 10 minutes each in a solution of PBS containing 0.1% Tween 20. The secondary antibody (see Table 4) in PBS containing 0.1% Tween 20 and 5% bovine serum albumin was then incubated with membrane for 1 hour at room temperature. This was followed by three washes of 10 minutes each in a solution of PBS containing 0.1% Tween 20. The membrane was then scanned on a LiCor Odyssey Scanner using infrared fluorescence detection.

TABLE 4

| Primary and Secondary Antibodies Used for Immunoblots | | | |
|---|---|---|---|
| Antibody | Type | Dilution | Source/Catalog No. |
| Total PLCγ2 | 1° Rabbit Polyclonal | 1:1000 | CST #3872 |
| Phospho Y-1217 PLCγ2 | 1° Rabbit Polyclonal | 1:1000 | CST #3871 |
| Total Btk | 1° Mouse Monoclonal | 1:250 | BD Biosciences #611116 |
| Phospho Y223 Btk | 1° Rabbit Monoclonal | 1:1000 | Epitomics #2207 |
| Anti-mouse 680 red | 2° Mouse | 1:10000 | Invitrogen #A21057 |
| Anti-mouse 800 green | 2° Mouse | 1:10000 | Rockland #610-431-020 |
| Anti-rabbit 680 red | 2° Rabbit | 1:10000 | Invitrogen #A21076 |
| Anti-rabbit 800 green | 2° Rabbit | 1:10000 | Rockland #611-132-122 |

TABLE 5

| BTK Inhibition | | |
|---|---|---|
| Compound | pBtk $EC_{50}$ | pPLCγ2 $EC_{50}$ |
| I-1 | A | A |
| I-3 | B | B |

Example 30

Btk Target Site Occupancy

A covalent probe shown below was used in an ELISA assay to determine occupancy of the target BTK by certain compounds according to the invention.

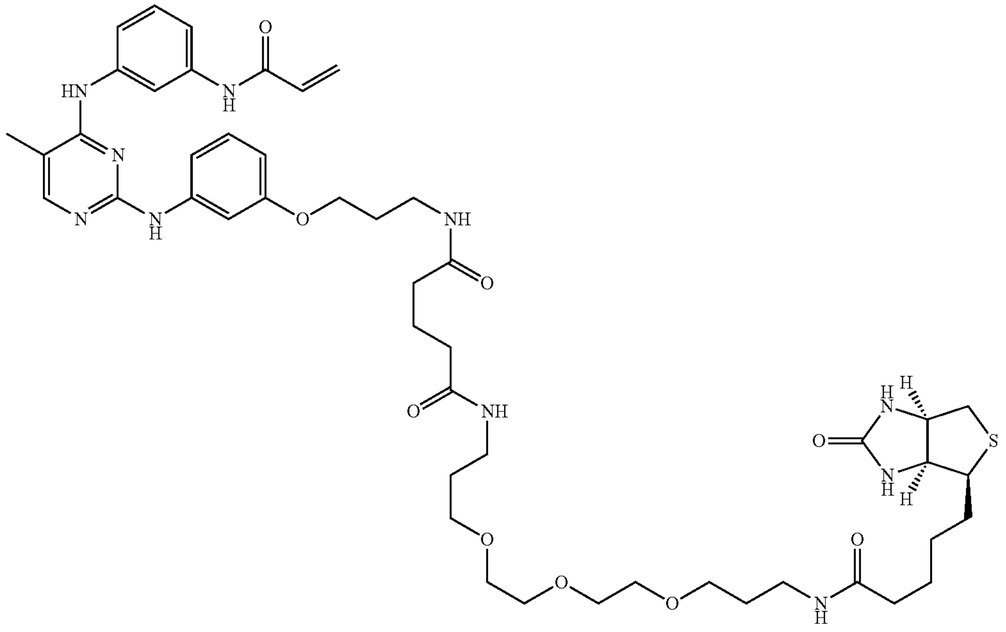

Covalent Probe

Data analysis was accomplished using the analysis package found in Odyssey Infrared Imaging System software in which intensities of total Btk and phospho-Btk were measured. Phospho-Btk was normalized to total Btk protein in each lane as a loading control and results are expressed as % activity compared to the DMSO control (100%) Inhibition of phospho-PLCγ2 was quantitated in a similar manner. EC50 values were generated using a 4 parameter curve fit analysis in GraphPad Prism version 5.0. Table 5 demonstrates that I-1 and I-3 inhibit BTK activity through a demonstration that these compounds inhibit BTK autophosphorylation and PLCγ2 phosphorylation. Compounds having an activity designated as "A" provided an $EC_{50}$<10 nM; compounds having an activity designated as "B" provided an $EC_{50}$ 10-50 nM; compounds having an activity designated as "C" provided an $EC_{50}$ 51-100 nM; compounds having an activity designated as "D" provided an $EC_{50}$>100 nM.

Ramos cells were incubated in serum-free RPMI medium for 1 hour (~2×106 cells/mL in 2 mL). Test compounds were diluted from a 10 mM DMSO stock solution, to achieve a final concentration of 0.09, 0.27, 0.82, 2.47, 7.42, 22.2, 66, and 200 nM. Cells were then incubated for 1 hour at 37° C. Following incubation, cells were spun at 1100 RPM for 5 minutes then washed in 200 μL of chilled PBS. Following the wash, cells were spun at 1100 RPM for 5 minutes. The supernatant was aspirated and then cells were resuspended in lysis buffer containing protease and phosphatase inhibitors. This was followed by centrifugation for 15 minutes at 14000 RPM at 4° C. Supernatant was transferred to a fresh tube. Lysates were stored at −80° C. until assayed.

Samples were thawed and mixed well by vortexing for 5 seconds. 60 μL of each sample was added into the 96-well mixing plate followed by addition of 60 μL of covalent probe solution (2 μM probe in PBS+0.05% Tween-20+1% BSA; 1:2 sample dilution) to each well containing sample. An adhesive cover was then placed on the plate followed by mixing of the plate on a shaker for 1 hour at room temperature. The streptavidin plate was pre-washed 3 times with PBS+0.05% Tween-20. 50 μL of the standards, QCs, and samples were then transferred from the mixing plate to the streptavidin plate. The plate was covered with an adhesive cover and mixed while shaking for 1 hour at room temperature. A 1:1000 dilution of the primary anti-Btk antibody (catalog #611116, Becton Dickinson; Franklin Lakes, N.J.) in PBS+0.05% Tween-20+0.5% BSA was prepared. The streptavidin plate was washed 3 times with PBS+0.05% Tween-20 and 50 μL/well of diluted anti-Btk antibody was then pipetted into the streptavidin plate. The plate was covered and incubated for 1 hour at room temperature. A 1:5000 dilution of secondary antibody (goat anti-mouse-HRP, catalog #62-6520, Zymed-Invitrogen; Carlsbad, Calif.) in PBS+0.05% Tween-20+0.5% BSA was prepared. The streptavidin plate was again washed 3 times with PBS+0.05% Tween-20 and 50 μL/well of diluted secondary antibody was pipetted into the streptavidin plate. The plate was covered and incubated for 1 hour at room temperature. The streptavidin plate was again washed 3 times with PBS+0.05% Tween-20 followed by the addition of 100 μL of TMB solution to each well. The plate was then read on a Synergy$^2$ plate reader at OD 650 nm until the OD maximum reached 1.0. This was followed by the addition of 100 μL of the Stop Solution. The plate was then read at OD 450 nm. A human recombinant Btk protein standard curve (11.7-3000 pg/μL) was plotted using a 4 parameter curve fit in GenS software (Version 1.05.11; Biotek; Winooski, Vt.;). The sample ODs were read against the standard curve to calculate free protein amounts.

Data were generated as ODs on an ELISA plate reader (Synergy$^2$, BioTek; Winooski, Vt.). Uninhibited Btk captured by the biotinylated covalent probe was quantitated and normalized to untreated control samples. Results were expressed as % Btk occupancy. EC50 values were generated using a 4 parameter curve fit analysis in GraphPad Prism version 5.0.

$EC_{50}$ values are set forth in Table 6. The compound numbers correspond to the compound numbers in Table 1. Compounds having an activity designated as "A" provided an $EC_{50}$<10 nM; compounds having an activity designated as "B" provided an $EC_{50}$<50 nM; compounds having an activity designated as "C" provided an $EC_{50}$<100 nM; compounds having an activity designated as "D" provided an $EC_{50}$ 101-200 nM; compounds having an activity designated as "E" provided an $EC_{50}$>200 nM.

TABLE 6

BTK Occupancy

| Compound | Ramos cell $EC_{50}$ (nM) |
|---|---|
| I-1 | B |
| I-2 | E |
| I-3 | B |
| I-13 | B |
| I-18 | B |
| I-19 | A |
| I-22 | B |
| I-23 | C |
| I-24 | A |

Example 31

Covalent Bonding Assay

The following example describes testing certain compounds to determine whether they covalently bind to BTK.

The full-length recombinant human Btk protein (Lot #619547Q; 0.35 mg/mL) was obtained from Invitrogen (Carlsbad, Calif.). Btk protein was diluted 2:3 in phosphate-buffered saline and stock concentration (10 mM) of compound was diluted 1:115 in 50% DMSO.

For all compounds, 1 μL of diluted compound was added to 5 μL of diluted protein. These mixtures were then incubated for 60 minutes at a 10-fold excess of compound to protein under room temperature (~24° C.) conditions.

At the end of the incubation, 5 μL aliquots of the samples were diluted with 15 μL of 0.2% TFA prior to micro C4 ZipTipping® directly onto the MALDI target plate using sinapinic acid as the desorption matrix (10 mg/mL in 0.2% TFA:Acetonitrile 50:50). Samples were immediately analyzed on an ABSciex 4800 MALDI TOF-TOF mass spectrometer.

For intact protein mass measurement, the mass spectrometer was set in linear mode using a pulsed extraction setting of 81,500. Bovine serum albumin (BSA; Sigma, St Louis, Mo.) was used as the standard to calibrate the instrument. Percent MS modification values are set forth in Table 7. These values correspond to the percentage of total protein covalently modified by the tested compound after one hour incubation. Compounds having a percent MS modification designated as "A" exhibited >70% modification; compounds having a percent MS modification designated as "B" exhibited 31-69% modification; compounds having a percent MS modification designated as "C" exhibited <30% modification.

TABLE 7

Mass Modification of Selected Compounds

| Compound | MS % modification |
|---|---|
| I-1 | B |
| I-3 | A |
| I-4 | C |
| I-5 | C |
| I-6 | C |
| I-19 | A |

We claim:

1. A combination comprising a compound of Formula I-a:

I-a

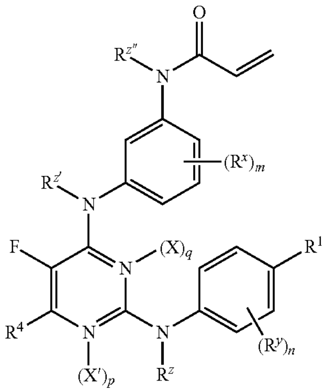

or a pharmaceutically acceptable salt thereof, wherein:

X and X' are each independently O;

p and q are each independently 0 or 1, wherein p and q are not both 1;

$R^1$ is —$OCH_2CO_2H$, —OH, —$OCH_3$, —$OSO_3H$, —OGlu, —$OCH_2CH_2OCH_3$, —$OCH_2CH_2OSO_3H$, or —$OCH_2CH_2OGlu$;

each Glu is a glucuronyl moiety;

$R^4$ is —H, —OH, —$OSO_3H$ or —OGlu;

$R^x$ and $R^y$ are each independently —OH, —$OSO_3H$, or —OGlu;

$R^z$, $R^{z'}$ and $R^{z''}$ are each independently —H, —$CH_3$, —OH, —$OSO_3H$, or —OGlu; and m and n are each independently 0, 1, 2, 3 or 4, provided that at least one of the following is true:

(a) $R^1$ is —OH, —$OSO_3H$, —OGlu, —$OCH_2CO_2H$, —$OCH_2CH_2OSO_3H$ or —$OCH_2CH_2OGlu$;

(b) at least one of $R^4$, $R^z$, $R^{z'}$ and $R^{z''}$ is —OH, —$OSO_3H$ or —OGlu;

(c) at least one of m and n is 1, 2, 3 or 4; or (d) one of p or q is 1;

and an additional therapeutic agent selected from:

(i) a compound of formula A:

A

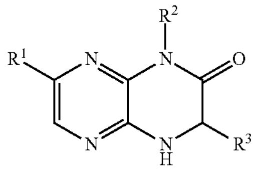

or a pharmaceutically acceptable salt thereof, wherein:

$R^1$ is an optionally substituted group selected from straight or branched $C_{1-8}$ aliphatic, aryl, cycloalkyl, heteroaryl, heterocyclyl, heteroaralkyl or heterocyclylalkyl;

$R^2$ is hydrogen or an optionally substituted group selected from straight or branched $C_{1-8}$ aliphatic, cycloalkyl, heteroaryl, heterocyclyl, heteroaralkyl, heterocyclylalkyl, aralkyl, or cycloalkylalkyl; and $R^3$ is hydrogen or an optionally substituted straight or branched $C_{1-8}$ aliphatic group;

wherein when an aliphatic group is substituted with one or more substituents, such substituents are independently selected from halogen; aliphatic; hydroxyl; alkoxy; alkoxyaliphatic; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; oxo (=O); $B(OH)_2$, or —O(aliphatic)aminocarbonyl; or (ii) a compound selected from a compound of formulae C, D, F or G or a compound selected from B and E:

B

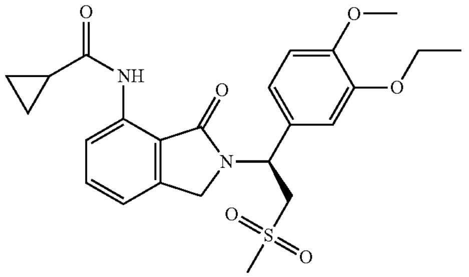

C

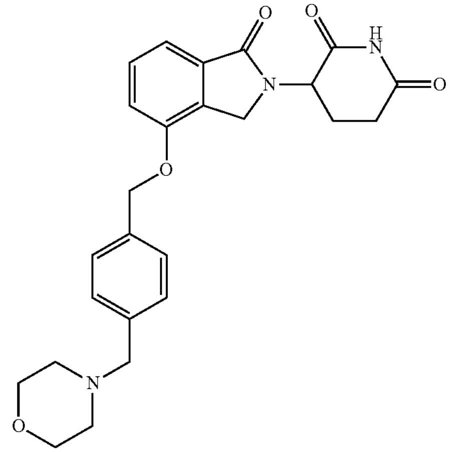

D

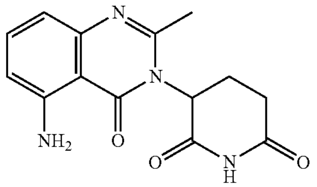

E

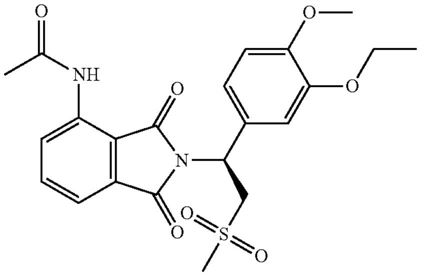

F

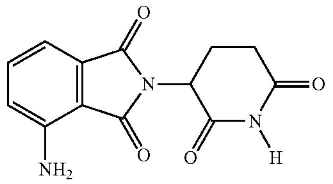

G

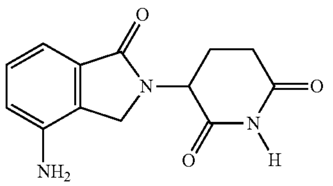

or a pharmaceutically acceptable salt thereof.

2. The combination according to claim 1, wherein in the compound of Formula I-a:

$R^4$ is —H or —OH;

$R^x$ and $R^y$ are each independently —OH; and $R^z$, $R^{z'}$ and $R^{z''}$ are each independently —H, —$CH_3$ or —OH;

provided that at least one of the following is true:

(a) $R^1$ is —OH or —$OCH_2CO_2H$;

(b) at least one of $R^4$, $R^z$, $R^{z'}$ and $R^{z''}$ is —OH;

(c) at least one of m and n is 1, 2, 3 or 4; or (d) one of p or q is 1.

3. The combination according to claim 1, wherein in the compound of Formula I-a $R^1$ is —$OCH_2CH_2OCH_3$.

4. The combination according to claim 1, wherein the compound of Formula I-a has the structure:

IV

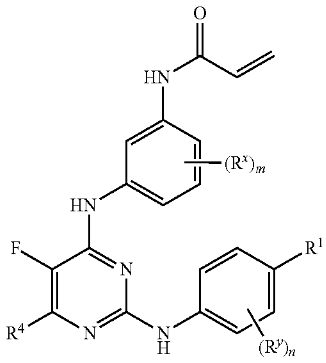

or a pharmaceutically acceptable salt thereof.

5. The combination according to claim 4, wherein in the compound of Formula IV $R^1$ is —$OCH_2CH_2OCH_3$.

6. The combination according to claim 4, wherein in the compound of Formula IV $R^1$ is —OH.

7. The combination according to claim 4, wherein in the compound of Formula IV $R^1$ is —$OCH_2CO_2H$.

8. The combination according to claim 4, wherein in the compound of Formula IV $R^4$ is —OH.

9. The combination according to claim 4, wherein in the compound of Formula IV m is 1 and $R^x$ is —OH.

10. The combination according to claim 4, wherein in the compound of Formula IV:

$R^4$ is —H or —OH; and $R^x$ and $R^y$ are each independently —OH;

provided that at least one of the following is true:

(a) $R^1$ is —OH or —$OCH_2CO_2H$; or (b) $R^4$ is —OH; or (c) at least one of m and n is 1, 2, 3 or 4.

11. A combination comprising a compound selected from the group consisting of:

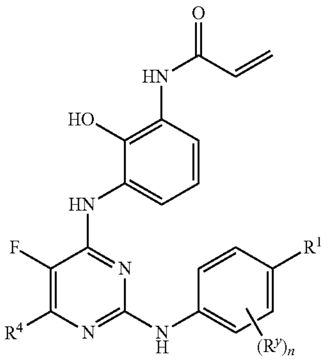

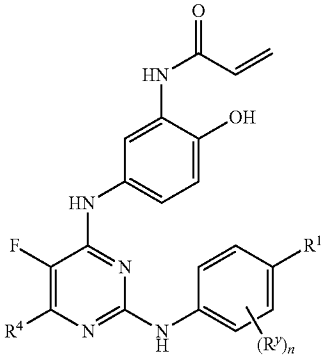

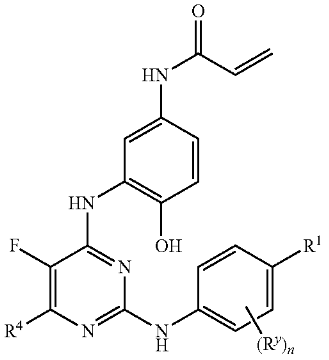

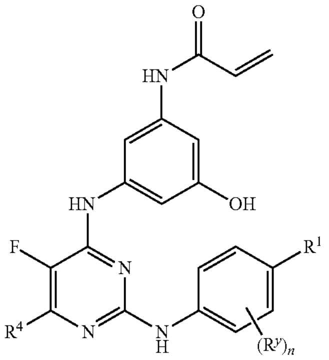

or a pharmaceutically acceptable salt thereof wherein:

$R^1$ is —OR', —$OCH_2CH_2OR'$ or —$OCH_2CO_2H$;

R' is —H, —$CH_3$, —$SO_3H$ or -Glu;

each Glu is a glucuronyl moiety;

$R^4$ is —H, —OH, —$OSO_3H$ or —OGlu;

$R^y$ is —OH, —$OSO_3H$, or —OGlu; and n is 0, 1, 2, 3 or 4;

and an additional therapeutic agent selected from:

(i) a compound of formula A:

A

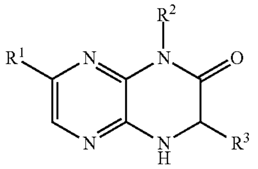

or a pharmaceutically acceptable salt thereof, wherein:

$R^1$ is an optionally substituted group selected from straight or branched $C_{1-8}$ aliphatic, aryl, cycloalkyl, heteroaryl, heterocyclyl, heteroaralkyl or heterocyclylalkyl;

$R^2$ is hydrogen or an optionally substituted group selected from straight or branched $C_{1-8}$ aliphatic, cycloalkyl, heteroaryl, heterocyclyl, heteroaralkyl, heterocyclylalkyl, aralkyl, or cycloalkylalkyl; and $R^3$ is hydrogen or an optionally substituted straight or branched $C_{1-8}$ aliphatic group;

wherein when an aliphatic group is substituted with one or more substituents, such substituents are independently selected from halogen; aliphatic; hydroxyl; alkoxy; alkoxyaliphatic; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; oxo (═O); $B(OH)_2$, or —O(aliphatic)aminocarbonyl; or (ii) a compound selected from a compound of formulae C, D, F or G or a compound selected from B and E:

B

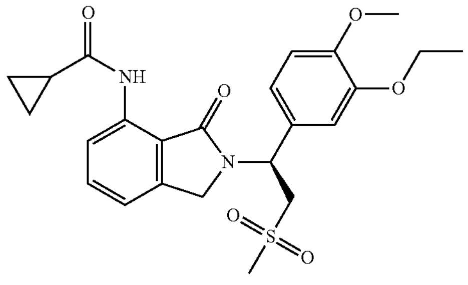

C

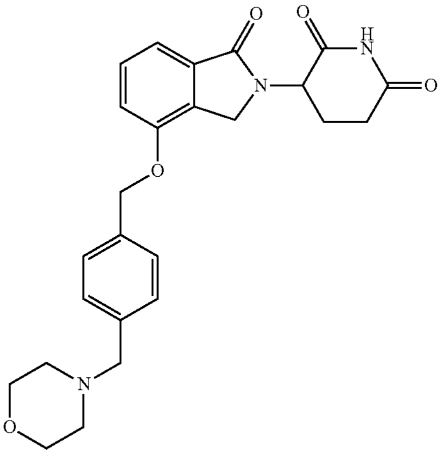

-continued

D

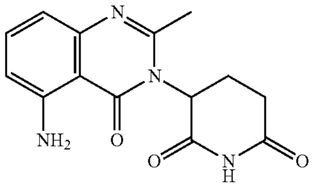

E

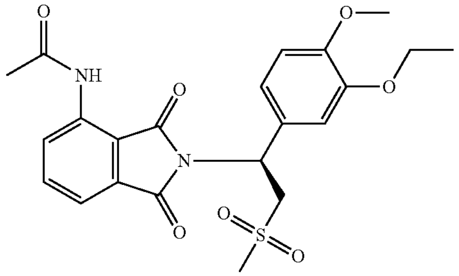

F

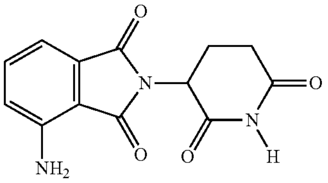

G

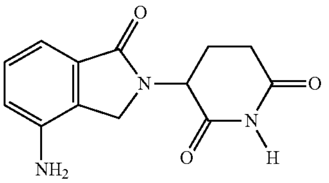

or a pharmaceutically acceptable salt thereof.

12. A combination comprising a compound of Formula I-a:

I-a

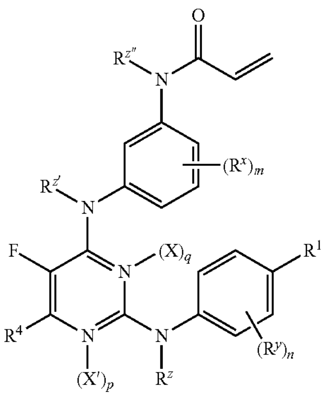

or a pharmaceutically acceptable salt thereof, wherein:

X and X' are each independently O;

p is 1 and q is 0;

$R^1$ is —OR', $—OCH_2CH_2OR'$ or $—OCH_2CO_2H$;

R' is —H, $—CH_3$, $—SO_3H$ or -Glu;

each Glu is a glucuronyl moiety;

$R^4$ is —H, —OH, $—OSO_3H$ or —OGlu;

$R^x$ and $R^y$ are each independently —OH, $—OSO_3H$, or —OGlu;

$R^z$, $R^{z'}$ and $R^{z''}$ are each independently —H, —$CH_3$, —OH, —$OSO_3H$, or —OGlu; and m and n are each independently 0, 1, 2, 3 or 4;

and an additional therapeutic agent selected from:

(i) a compound of formula A:

A

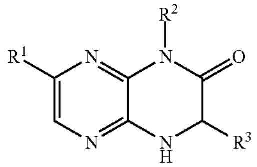

or a pharmaceutically acceptable salt thereof, wherein:

$R^1$ is an optionally substituted group selected from straight or branched $C_{1-8}$ aliphatic, aryl, cycloalkyl, heteroaryl, heterocyclyl, heteroaralkyl or heterocyclylalkyl;

$R^2$ is hydrogen or an optionally substituted group selected from straight or branched $C_{1-8}$ aliphatic, cycloalkyl, heteroaryl, heterocyclyl, heteroaralkyl, heterocyclylalkyl, aralkyl, or cycloalkylalkyl; and $R^3$ is hydrogen or an optionally substituted straight or branched $C_{1-8}$ aliphatic group;

wherein when an aliphatic group is substituted with one or more substituents, such substituents are independently selected from halogen; aliphatic; hydroxyl; alkoxy; alkoxyaliphatic; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; oxo (=O); $B(OH)_2$, or —O(aliphatic)aminocarbonyl; or (ii) a compound selected from a compound of formulae C, D, F or G or a compound selected from B and E:

B

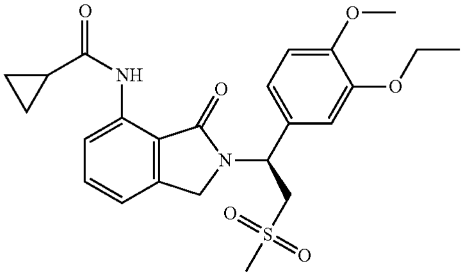

C

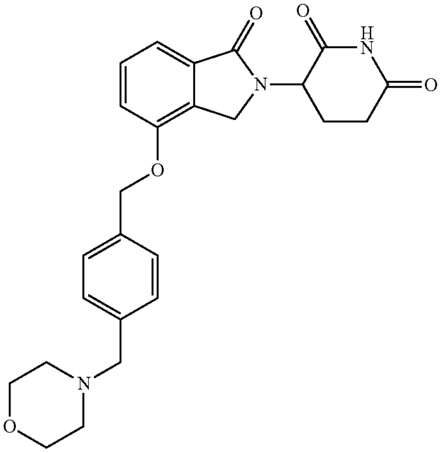

-continued

D

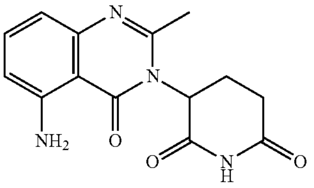

E

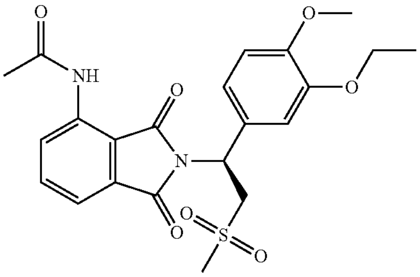

F

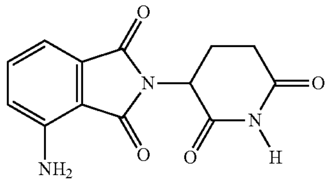

G

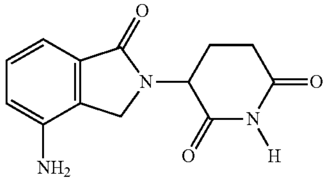

or a pharmaceutically acceptable salt thereof.

13. A combination comprising a compound of Formula I-a:

I-a

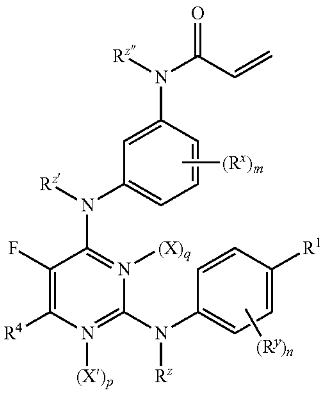

or a pharmaceutically acceptable salt thereof, wherein:

X and X' are each independently O;

p is 0 and q is 1;

$R^1$ is —OR', —$OCH_2CH_2OR'$ or —$OCH_2CO_2H$;

R' is —H, —$CH_3$, —$SO_3H$ or -Glu;

each Glu is a glucuronyl moiety;

$R^4$ is —H, —OH, —$OSO_3H$ or —OGlu;

$R^x$ and $R^y$ are each independently —OH, —$OSO_3H$, or —OGlu;

$R^z$, $R^{z'}$ and $R^{z''}$ are each independently —H, —$CH_3$, —OH, —$OSO_3H$, or —OGlu; and m and n are each independently 0, 1, 2, 3 or 4;

and an additional therapeutic agent selected from:

(i) a compound of formula A:

A

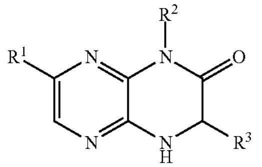

or a pharmaceutically acceptable salt thereof, wherein:

$R^1$ is an optionally substituted group selected from straight or branched $C_{1-8}$ aliphatic, aryl, cycloalkyl, heteroaryl, heterocyclyl, heteroaralkyl or heterocyclylalkyl;

$R^2$ is hydrogen or an optionally substituted group selected from straight or branched $C_{1-8}$ aliphatic, cycloalkyl, heteroaryl, heterocyclyl, heteroaralkyl, heterocyclylalkyl, aralkyl, or cycloalkylalkyl; and $R^3$ is hydrogen or an optionally substituted straight or branched $C_{1-8}$ aliphatic group;

wherein when an aliphatic group is substituted with one or more substituents, such substituents are independently selected from halogen; aliphatic; hydroxyl; alkoxy; alkoxyaliphatic; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; oxo (=O); $B(OH)_2$, or —O(aliphatic)aminocarbonyl; or (ii) a compound selected from a compound of formulae C, D, F or G or a compound selected from B and E:

B

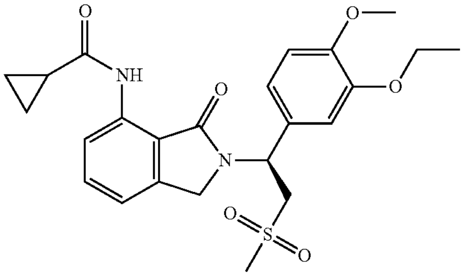

C

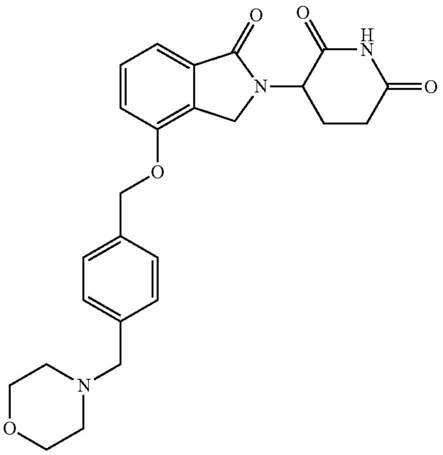

-continued

D

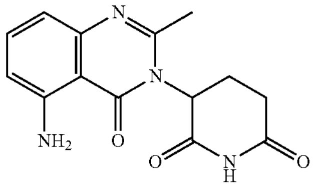

E

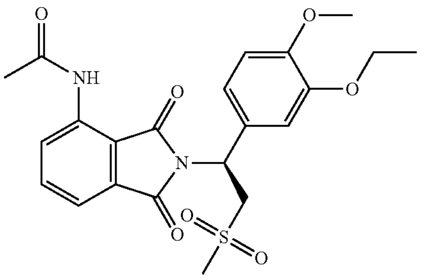

F

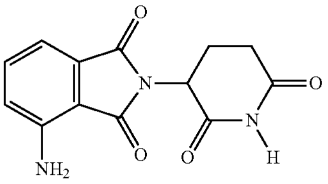

G

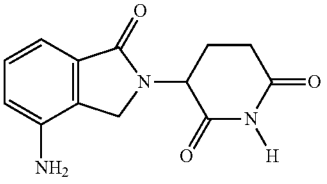

or a pharmaceutically acceptable salt thereof.

14. A combination comprising a compound of Formula I-a:

I-a

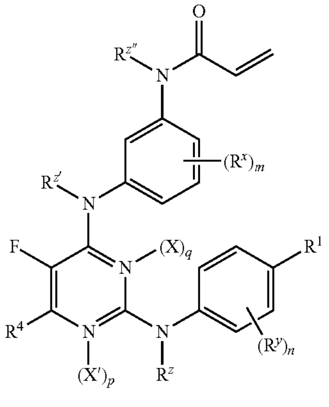

or a pharmaceutically acceptable salt thereof, wherein:

$R^z$ is selected from —$CH_3$, —OH, —$OSO_3H$, and —OGlu;

$R^{z'}$ and $R^{z''}$ are each independently —H, —$CH_3$, —OH, —$OSO_3H$, or —OGlu;

X and X' are each independently O;

p and q are each independently 0 or 1, wherein p and q are not both 1;

$R^1$ is —OR', —$OCH_2CH_2OR'$ or —$OCH_2CO_2H$;

R' is —H, —$CH_3$, —$SO_3H$ or -Glu;

each Glu is a glucuronyl moiety;

$R^4$ is —H, —OH, —$OSO_3H$ or —OGlu;

$R^x$ and $R^y$ are each independently —OH, —$OSO_3H$, or —OGlu; and m and n are each independently 0, 1, 2, 3 or 4; and an additional therapeutic agent selected from:

(i) a compound of formula A:

A

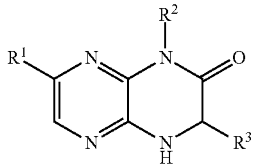

or a pharmaceutically acceptable salt thereof, wherein:

$R^1$ is an optionally substituted group selected from strai ht or branched $C_{1-8}$ aliphatic, aryl, cycloalkyl, heteroaryl, heterocyclyl, heteroaralkyl or heterocyclylalkyl;

$R^2$ is hydrogen or an optionally substituted group selected from straight or branched $C_{1-8}$ aliphatic, cycloalkyl, heteroaryl, heterocyclyl, heteroaralkyl, heterocyclylalkyl, aralkyl, or cycloalkylalkyl; and $R^3$ is hydrogen or an optionally substituted straight or branched $C_{1-8}$ aliphatic group;

wherein when an aliphatic group is substituted with one or more substituents, such substituents are independently selected from halogen; aliphatic; hydroxyl; alkoxy; alkoxyaliphatic; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; oxo (=O); $B(OH)_2$, or —O(aliphatic)aminocarbonyl; or (ii) a compound selected from a compound of formulae C, D, F or G or a compound selected from B and E:

B

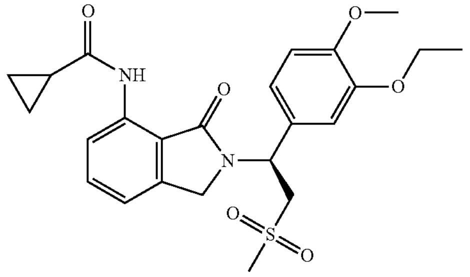

C

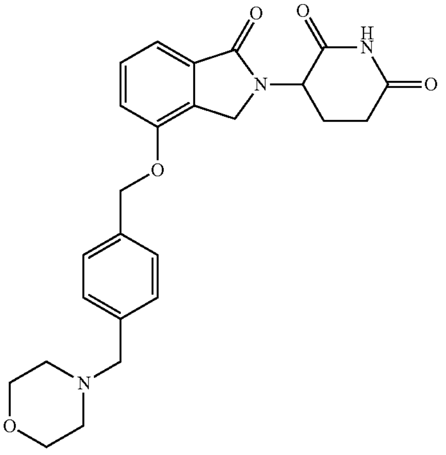

-continued

D

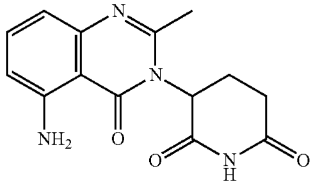

E

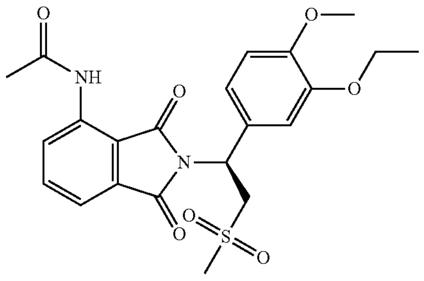

F

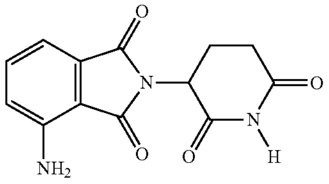

G

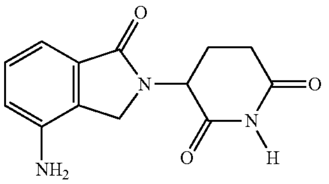

or a pharmaceutically acceptable salt thereof.

15. The combination according to claim 14, wherein in the compound of Formula I-a $R^z$ is —OH.

16. The combination according to claim 14, wherein in the compound of Formula I-a $R^z$ is —$CH_3$.

17. A combination comprising a compound of Formula I-a:

I-a

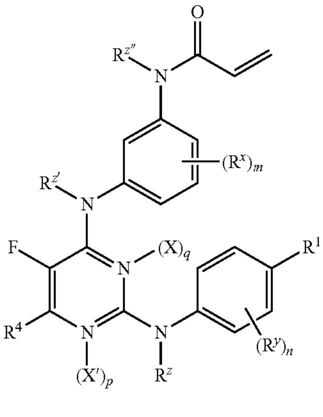

or a pharmaceutically acceptable salt thereof, wherein:

$R^{z'}$ is selected from —$CH_3$, —OH, —$OSO_3H$, and —OGlu;

$R^z$ and $R^{z''}$ are each independently —H, —$CH_3$, —OH, —$OSO_3H$, or —OGlu;

X and X' are each independently O;

p and q are each independently 0 or 1, wherein p and q are not both 1;

$R^1$ is —OR', —$OCH_2CH_2OR'$ or —$OCH_2CO_2H$;

R' is —H, —$CH_3$, —$SO_3H$ or -Glu;

each Glu is a glucuronyl moiety;

$R^4$ is —H, —OH, —$OSO_3H$ or —OGlu;

$R^x$ and $R^y$ are each independently —OH, —$OSO_3H$, or —OGlu; and m and n are each independently 0, 1, 2, 3 or 4;

and an additional therapeutic agent selected from:

(i) a compound of formula A:

A

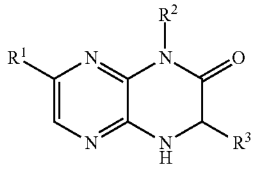

or a pharmaceutically acceptable salt thereof, wherein:

$R^1$ is an optionally substituted group selected from straight or branched $C_{1-8}$ aliphatic, aryl, cycloalkyl, heteroaryl, heterocyclyl, heteroaralkyl or heterocyclylalkyl;

$R^2$ is hydrogen or an optionally substituted group selected from straight or branched $C_{1-8}$ aliphatic, cycloalkyl, heteroaryl, heterocyclyl, heteroaralkyl, heterocyclylalkyl, aralkyl, or cycloalkylalkyl; and $R^3$ is hydrogen or an optionally substituted straight or branched $C_{1-8}$ aliphatic group;

wherein when an aliphatic group is substituted with one or more substituents, such substituents are independently selected from halogen; aliphatic; hydroxyl; alkoxy; alkoxyaliphatic; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; oxo (=O); $B(OH)_2$, or —O(aliphatic)aminocarbonyl; or (ii) a compound selected from a compound of formulae C, D, F or G or a compound selected from B and E:

B

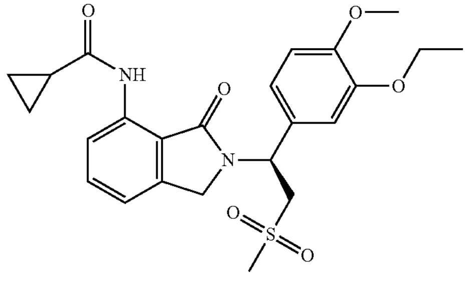

-continued

C

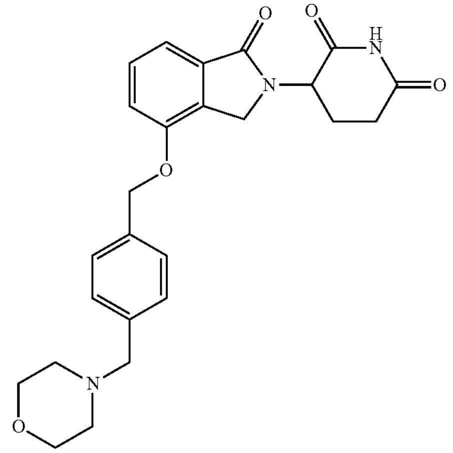

D

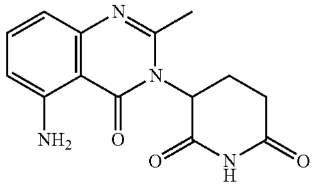

E

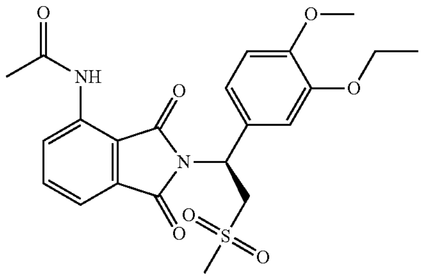

F

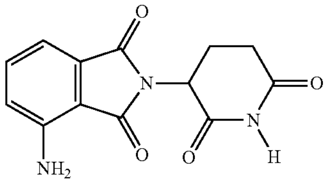

G

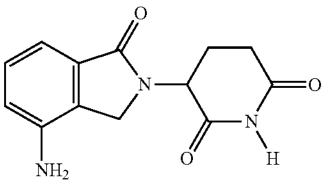

or a pharmaceutically acceptable salt thereof.

18. The combination according to claim 17, wherein in the compound of Formula I-a $R^{z'}$ is —OH.

19. The combination according to claim 17, wherein in the compound of Formula I-a $R^{z'}$ is —$CH_3$.

20. A combination comprising a compound of Formula I-a:

I-a

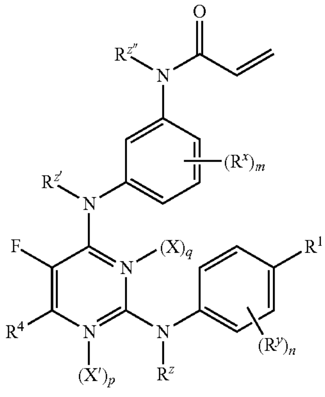

or a pharmaceutically acceptable salt thereof, wherein:

$R^{z''}$ is selected from —$CH_3$, —OH, —$OSO_3H$, and —OGlu;

$R^z$ and $R^{z'}$ are each independently —H, —$CH_3$, —OH, —$OSO_3H$, or —OGlu;

X and X' are each independently O;

p and q are each independently 0 or 1, wherein p and q are not both 1;

$R^1$ is —OR', —$OCH_2CH_2OR'$ or —$OCH_2CO_2H$;

R' is —H, —$CH_3$, —$SO_3H$ or -Glu;

each Glu is a glucuronyl moiety;

$R^4$ is —H, —OH, —$OSO_3H$ or —OGlu;

$R^x$ and $R^y$ are each independently —OH, —$OSO_3H$, or —OGlu; and m and n are each independently 0, 1, 2, 3 or 4;

and an additional therapeutic agent selected from:

(i) a compound of formula A:

A

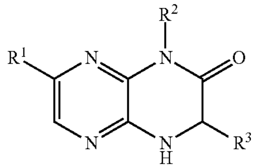

or a pharmaceutically acceptable salt thereof, wherein:

$R^1$ is an optionally substituted group selected from straight or branched $C_{1-8}$ aliphatic, aryl, cycloalkyl, heteroaryl, heterocyclyl, heteroaralkyl or heterocyclylalkyl;

$R^2$ is hydrogen or an optionally substituted group selected from straight or branched $C_{1-8}$ aliphatic, cycloalkyl, heteroaryl, heterocyclyl, heteroaralkyl, heterocyclylalkyl, aralkyl, or cycloalkylalkyl; and $R^3$ is hydrogen or an optionally substituted straight or branched $C_{1-8}$ aliphatic group;

wherein when an aliphatic group is substituted with one or more substituents, such substituents are independently selected from halogen; aliphatic; hydroxyl; alkoxy; alkoxyaliphatic; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; oxo (═O); $B(OH)_2$, or —O(aliphatic)aminocarbonyl; or (ii) a compound selected from a compound of formulae C, D, F or G or a compound selected from B and E:

B

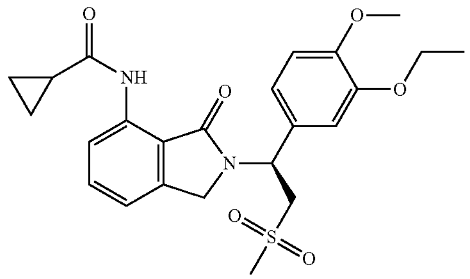

C

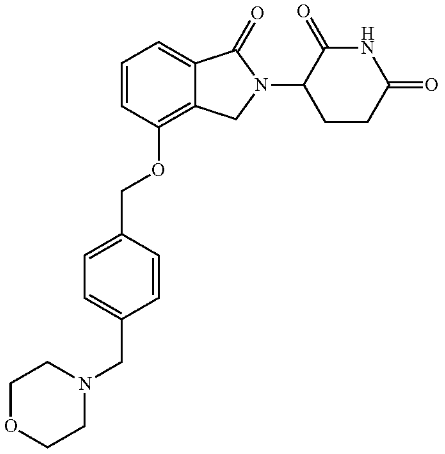

D

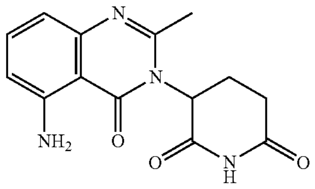

E

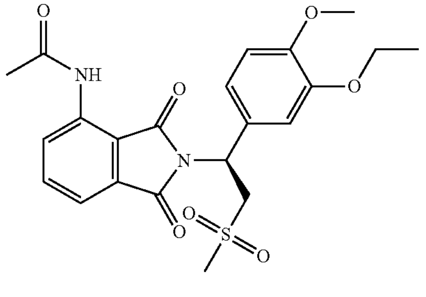

F

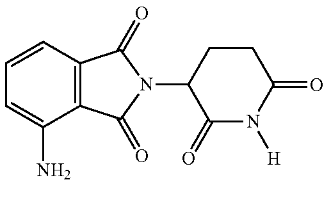

-continued

G

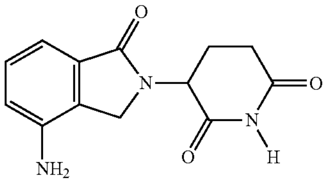

or a pharmaceutically acceptable salt thereof.

21. The combination according to claim 20, wherein in the compound of Formula I-a $R^{z''}$ is —OH.

22. The combination according to claim 20, wherein in the compound of Formula I-a $R^{z''}$ is —$CH_3$.

23. A combination comprising a compound of Formula IV:

IV

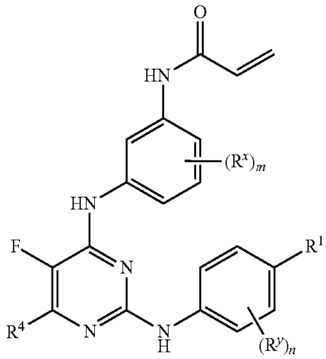

or a pharmaceutically acceptable salt thereof wherein:

$R^1$ is —OR', —$OCH_2CH_2OR'$ or —$OCH_2CO_2H$; or $R^1$ is —$OCH_2CH_2OR'$ wherein R' is —$CH_3$, —$SO_3H$ or -Glu;

R' is —H, —$CH_3$, —$SO_3H$ or -Glu;

each Glu is a glucuronyl moiety;

$R^4$ is —H, —OH, —$OSO_3H$ or —OGlu;

$R^x$ is —OH, —$OSO_3H$, or —OGlu;

$R^y$ is —OH;

m is 0, 1, 2, 3 or 4; and n is 1;

and an additional therapeutic agent selected from:

(i) a compound of formula A:

A

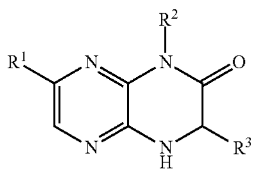

or a pharmaceutically acceptable salt thereof, wherein:

$R^1$ is an optionally substituted group selected from straight or branched $C_{1-8}$ aliphatic, aryl, cycloalkyl, heteroaryl, heterocyclyl, heteroaralkyl or heterocyclylalkyl;

$R^2$ is hydrogen or an optionally substituted group selected from straight or branched $C_{1-8}$ aliphatic, cycloalkyl, heteroaryl, heterocyclyl, heteroaralkyl, heterocyclylalkyl, aralkyl, or cycloalkylalkyl; and $R^3$ is hydrogen or an optionally substituted straight or branched $C_{1-8}$ aliphatic group;

wherein when an aliphatic group is substituted with one or more substituents, such substituents are independently selected from halogen; aliphatic; hydroxyl; alkoxy; alkoxyaliphatic; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; oxo (=O); $B(OH)_2$, or —O(aliphatic)aminocarbonyl; or (ii) a compound selected from a compound of formulae C, D, F or G or a compound selected from B and E:

B

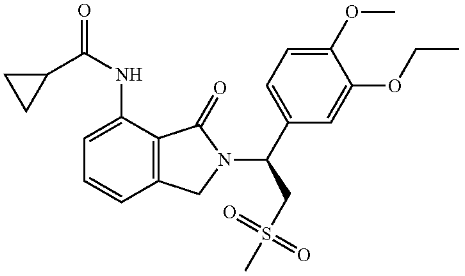

C

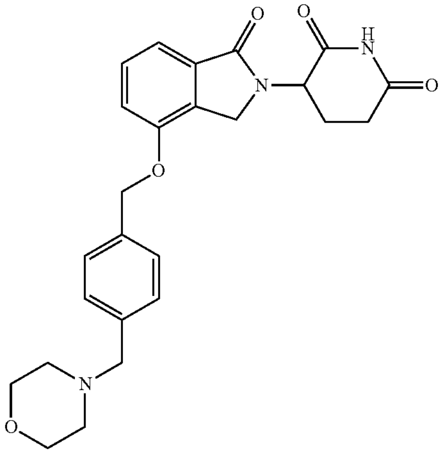

D

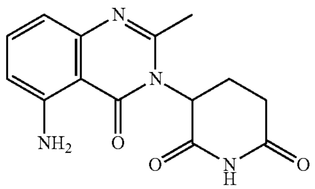

E

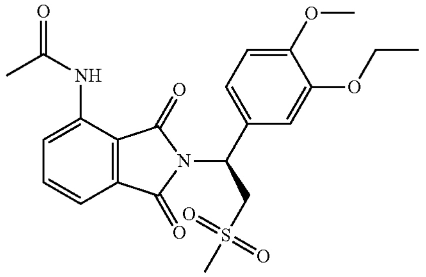

-continued

F

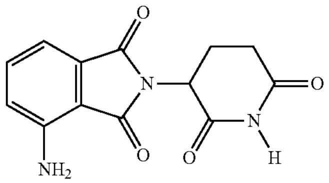

G

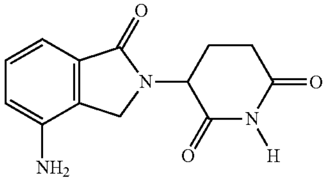

or a pharmaceutically acceptable salt thereof.

24. The combination according to claim 1, wherein the compound of formula A is selected from:

7-(5-fluoro-2-methyl-4-(1H-1,2,4-triazol-3-yl)phenyl)-1-((trans-4-methoxycyclohexyl)methyl)-3,4-dihydropyrazino[2,3-b]pyrazin-2(1H)-one 7-(6-(1H-1,2,4-triazol-3-yl)pyridin-3-yl)-1-(cis-4-methoxycyclohexyl)-3,4-dihydropyrazino[2,3-b]pyrazin-2(1H)-one 7-(1H-pyrrolo[2,3-b]pyridin-3-yl)-1-(2-(tetrahydro-2H-pyran-4-yl)ethyl)-3,4-dihydropyrazino[2,3-b]pyrazin-2(1H)-one 7-(5-fluoro-2-methyl-4-(1H-1,2,4-triazol-3-yl)phenyl)-1-((cis-4-methoxycyclohexyl)methyl)-3,4-dihydropyrazino[2,3-b]pyrazin-2(1H)-one 1-ethyl-7-(1H-pyrrolo[3,2-b]pyridin-5-yl)-3,4-dihydropyrazino[2,3-b]pyrazin-2(1H)-one 7-(6-(1H-1,2,4-triazol-3-yl)pyridin-3-yl)-1-((cis-4-methoxycyclohexyl)methyl)-3,4-dihydropyrazino[2,3-b]pyrazin-2(1H)-one 7-(1H-benzo[d]imidazol-4-yl)-1-(2-(tetrahydro-2H-pyran-4-yl)ethyl)-3,4-dihydropyrazino[2,3-b]pyrazin-2(1H)-one 7-(1H-pyrrolo[2,3-b]pyridin-4-yl)-1-(2-(tetrahydro-2H-pyran-4-yl)ethyl)-3,4-dihydropyrazino[2,3-b]pyrazin-2(1H)-one 7-(6-(1H-1,2,4-triazol-3-yl)pyridin-3-yl)-1-((trans-4-methoxycyclohexyl)methyl)-3,4-dihydropyrazino[2,3-b]pyrazin-2(1H)-one 7-(6-(1H-1,2,4-triazol-3-yl)pyridin-3-yl)-1-((trans-4-hydroxycyclohexyl)methyl)-3,4-dihydropyrazino[2,3-b]pyrazin-2(1H)-one 7-(6-(1H-1,2,4-triazol-3-yl)pyridin-3-yl)-1-(cis-4-hydroxycyclohexyl)-3,4-dihydropyrazino[2,3-b]pyrazin-2(1H)-one 7-(5-fluoro-2-methyl-4-(1H-1,2,4-triazol-3-yl)phenyl)-1-(cis-4-hydroxycyclohexyl)-3,4-dihydropyrazino[2,3-b]pyrazin-2(1H)-one 7-(6-(1H-1,2,4-triazol-3-yl)pyridin-3-yl)-1-(tetrahydro-2H-pyran-4-yl)-3,4-dihydropyrazino[2,3-b]pyrazin-2(1H)-one 7-(6-(1H-1,2,4-triazol-3-yl)pyridin-3-yl)-1-(2-methoxyethyl)-3,4-dihydropyrazino[2,3-b]pyrazin-2(1H)-one 7-(6-(1H-1,2,4-triazol-3-yl)pyridin-3-yl)-1-ethyl-3,4-dihydropyrazino[2,3-b]pyrazin-2(1H)-one 7-(5-fluoro-2-methyl-4-(1H-1,2,4-triazol-3-yl)phenyl)-1-((cis-4-hydroxycyclohexyl)methyl)-3,4-dihydropyrazino[2,3-b]pyrazin-2(1H)-one 7-(5-fluoro-2-methyl-4-(1H-1,2,4-triazol-3-yl)phenyl)-1-(tetrahydro-2H-pyran-4-yl)-3,4-dihydropyrazino[2,3-b]pyrazin-2(1H)-one 7-(1H-indol-4-yl)-1-(2-(tetrahydro-2H-pyran-4-yl)ethyl)-3,4-dihydropyrazino[2,3-b]pyrazin-2(1H)-one 7-(5-fluoro-2-methyl-4-(1H-1,2,4-triazol-3-yl)phenyl)-1-((trans-4-hydroxycyclohexyl)methyl)-3,4-dihydropyrazino[2,3-b]pyrazin-2(1H)-one 7-(6-(1H-1,2,4-triazol-3-yl)pyridin-3-yl)-1-((cis-4-hydroxycyclohexyl)methyl)-3,4-dihydropyrazino[2,3-b]pyrazin-2(1H)-one 7-(6-(1H-1,2,4-triazol-3-yl)pyridin-3-yl)-1-(trans-4-hydroxycyclohexyl)-3,4-dihydropyrazino[2,3-b]pyrazin-2(1H)-one 7-(6-(1H-1,2,4-triazol-3-yl)pyridin-3-yl)-1-(trans-4-methoxycyclohexyl)-3,4-dihydropyrazino[2,3-b]pyrazin-2(1H)-one 7-(6-(1H-1,2,4-triazol-3-yl)pyridin-3-yl)-1-isopropyl-3,4-dihydropyrazino[2,3-b]pyrazin-2(1H)-one 7-(5-fluoro-2-methyl-4-(1H-1,2,4-triazol-3-yl)phenyl)-1-(trans-4-methoxycyclohexyl)-3,4-dihydropyrazino[2,3-b]pyrazin-2(1H)-one 7-(5-fluoro-2-methyl-4-(1H-1,2,4-triazol-3-yl)phenyl)-1-(trans-4-hydroxycyclohexyl)-3,4-dihydropyrazino[2,3-b]pyrazin-2(1H)-one 7-(5-fluoro-2-methyl-4-(1H-1,2,4-triazol-3-yl)phenyl)-1-(2-methoxyethyl)-3,4-dihydropyrazino[2,3-b]pyrazin-2(1H)-one 7-(5-fluoro-2-methyl-4-(1H-1,2,4-triazol-3-yl)phenyl)-1-isopropyl-3,4-dihydropyrazino[2,3-b]pyrazin-2(1H)-one 1-ethyl-7-(5-fluoro-2-methyl-4-(1H-1,2,4-triazol-3-yl)phenyl)-3,4-dihydropyrazino[2,3-b]pyrazin-2(1H)-one 7-(2-hydroxypyridin-4-yl)-1-(2-(tetrahydro-2H-pyran-4-yl)ethyl)-3,4-dihydropyrazino[2,3-b]pyrazin-2(1H)-one 1-isopropyl-7-(4-methyl-6-(1H-1,2,4-triazol-3-yl)pyridin-3-yl)-3,4-dihydropyrazino[2,3-b]pyrazin-2(1H)-one 5-(8-isopropyl-7-oxo-5,6,7,8-tetrahydropyrazino[2,3-b]pyrazin-2-yl)-4-methylpicolinamide 7-(1H-indazol-4-yl)-1-(2-(tetrahydro-2H-pyran-4-yl)ethyl)-3,4-dihydropyrazino[2,3-b]pyrazin-2(1H)-one 7-(2-aminopyrimidin-5-yl)-1-(2-(tetrahydro-2H-pyran-4-yl)ethyl)-3,4-dihydropyrazino[2,3-b]pyrazin-2(1H)-one 7-(2-aminopyridin-4-yl)-1-(2-(tetrahydro-2H-pyran-4-yl)ethyl)-3,4-dihydropyrazino[2,3-b]pyrazin-2(1H)-one 7-(6-(methylamino)pyridin-3-yl)-1-(2-(tetrahydro-2H-pyran-4-yl)ethyl)-3,4-dihydropyrazino[2,3-b]pyrazin-2(1H)-one 7-(6-hydroxypyridin-3-yl)-1-(2-(tetrahydro-2H-pyran-4-yl)ethyl)-3,4-dihydropyrazino[2,3-b]pyrazin-2(1H)-one 7-(4-(1H-pyrazol-3-yl)phenyl)-1-(2-methoxyethyl)-3,4-dihydropyrazino[2,3-b]pyrazin-2(1H)-one 7-(pyridin-3-yl)-1-(2-(tetrahydro-2H-pyran-4-yl)ethyl)-3,4-dihydropyrazino[2,3-b]pyrazin-2(1H)-one 7-(1H-indazol-4-yl)-1-(2-methoxyethyl)-3,4-dihydropyrazino[2,3-b]pyrazin-2(1H)-one 7-(1H-indazol-6-yl)-1-(2-methoxyethyl)-3,4-dihydropyrazino[2,3-b]pyrazin-2(1H)-one 7-(pyrimidin-5-yl)-1-(2-(tetrahydro-2H-pyran-4-yl)ethyl)-3,4-dihydropyrazino[2,3-b]pyrazin-2(1H)-one 7-(6-methoxypyridin-3-yl)-1-(2-(tetrahydro-2H-pyran-4-yl)ethyl)-3,4-dihydropyrazino[2,3-b]pyrazin-2(1H)-one 1-(2-methoxyethyl)-7-(1H-pyrrolo[2,3-b]pyridin-5-yl)-3,4-dihydropyrazino[2,3-b]pyrazin-2(1H)-one
1-ethyl-7-(1H-pyrrolo[2,3-b]pyridin-5-yl)-3,4-dihydropyrazino[2,3-b]pyrazin-2(1H)-one
1-ethyl-7-(1H-indazol-4-yl)-3,4-dihydropyrazino[2,3-b]pyrazin-2(1H)-one 7-(pyridin-4-yl)-1-(2-(tetrahydro-2H-pyran-4-yl)ethyl)-3,4-dihydropyrazino[2,3-b]pyrazin-2(1H)-one
7-(6-aminopyridin-3-yl)-1-(2-(tetrahydro-2H-pyran-4-yl)ethyl)-3,4-dihydropyrazino[2,3-b]pyrazin-2(1H)-one
1-methyl-7-(2-methyl-6-(4H-1,2,4-triazol-3-yl)pyridin-3-yl)-3,4-dihydropyrazino[2,3-b]pyrazin-2(1H)-one
2-(2-hydroxypropan-2-yl)-5-(8-(trans-4-methoxycyclohexyl)-7-oxo-5,6,7,8-tetrahydropyrazino[2,3-b]pyrazin-2-yl)pyridine 1-oxide
4-methyl-5-(7-oxo-8-((tetrahydro-2H-pyran-4-yl)methyl)-5,6,7,8-tetrahydropyrazino[2,3-b]pyrazin-2-yl)picolinamide
5-(8-((cis-4-methoxycyclohexyl)methyl)-7-oxo-5,6,7,8-tetrahydropyrazino[2,3-b]pyrazin-2-yl)-4-methylpicolinamide
7-(1H-pyrazol-4-yl)-1-(2-(tetrahydro-2H-pyran-4-yl)ethyl)-3,4-dihydropyrazino[2,3-b]pyrazin-2(1H)-one
1-(trans-4-methoxycyclohexyl)-7-(4-methyl-6-(1H-1,2,4-triazol-3-yl)pyridin-3-yl)-3,4-dihydropyrazino[2,3-b]pyrazin-2(1H)-one
3-((7-(2-methyl-6-(4H-1,2,4-triazol-3-yl)pyridin-3-yl)-2-oxo-3,4-dihydropyrazino[2,3-b]pyrazin-1 (2H)-yl)methyl)benzonitrile
1-((trans-4-methoxycyclohexyl)methyl)-7-(4-methyl-6-(1H-1,2,4-triazol-3-yl)pyridin-3-yl)-3,4-dihydropyrazino[2,3-b]pyrazin-2(1H)-one
3-(7-oxo-8-(2-(tetrahydro-2H-pyran-4-yl)ethyl)-5,6,7,8-tetrahydropyrazino[2,3-b]pyrazin-2-yl)benzamide
5-(8-((trans-4-methoxycyclohexyl)methyl)-7-oxo-5,6,7,8-tetrahydropyrazino[2,3-b]pyrazin-2-yl)-4-methylpicolinamide
3-((7-(6-(2-hydroxypropan-2-yl)pyridin-3-yl)-2-oxo-3,4-dihydropyrazino[2,3-b]pyrazin-1 (2H)-yl)methyl)benzonitrile
7-(6-(2-hydroxypropan-2-yl)pyridin-3-yl)-1-((1R,3R)-3-methoxycyclopentyl)-3,4-dihydropyrazino[2,3-b]pyrazin-2(1H)-one
7-(6-(2-hydroxypropan-2-yl)pyridin-3-yl)-1-((1S,3R)-3-methoxycyclopentyl)-3,4-dihydropyrazino[2,3-b]pyrazin-2(1H)-one
7-(6-(2-hydroxypropan-2-yl)pyridin-3-yl)-1-((1S,3S)-3-methoxycyclopentyl)-3,4-dihydropyrazino[2,3-b]pyrazin-2(1H)-one
7-(6-(2-hydroxypropan-2-yl)pyridin-3-yl)-1-((1R,3S)-3-methoxycyclopentyl)-3,4-dihydropyrazino[2,3-b]pyrazin-2(1H)-one
7-(1H-indazol-6-yl)-1-(2-(tetrahydro-2H-pyran-4-yl)ethyl)-3,4-dihydropyrazino[2,3-b]pyrazin-2(1H)-one
7-(2-methyl-6-(4H-1,2,4-triazol-3-yl)pyridin-3-yl)-1-(2-morpholinoethyl)-3,4-dihydropyrazino[2,3-b]pyrazin-2(1H)-one
1-(trans-4-hydroxycyclohexyl)-7-(2-methyl-6-(4H-1,2,4-triazol-3-yl)pyridin-3-yl)-3,4-dihydropyrazino[2,3-b]pyrazin-2(1H)-one
1-(cis-4-hydroxycyclohexyl)-7-(2-methyl-6-(4H-1,2,4-triazol-3-yl)pyridin-3-yl)-3,4-dihydropyrazino[2,3-b]pyrazin-2(1H)-one
7-(6-(2-hydroxypropan-2-yl)pyridin-3-yl)-1-(2-morpholinoethyl)-3,4-dihydropyrazino[2,3-b]pyrazin-2(1H)-one
1-isopropyl-7-(2-methyl-6-(4H-1,2,4-triazol-3-yl)pyridin-3-yl)-3,4-dihydropyrazino[2,3-b]pyrazin-2(1H)-one
7-(1H-imidazo[4,5-b]pyridin-6-yl)-1-(2-(tetrahydro-2H-pyran-4-yl)ethyl)-3,4-dihydropyrazino[2,3-b]pyrazin-2(1H)-one
1-((cis-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one
1-(trans-4-hydroxycyclohexyl)-7-(6-(2-hydroxypropan-2-yl)pyridin-3-yl)-3,4-dihydropyrazino[2,3-b]pyrazin-2(1H)-one
1-(cis-4-hydroxycyclohexyl)-7-(6-(2-hydroxypropan-2-yl)pyridin-3-yl)-3,4-dihydropyrazino[2,3-b]pyrazin-2(1H)-one
4-(7-oxo-8-(2-(tetrahydro-2H-pyran-4-yl)ethyl)-5,6,7,8-tetrahydropyrazino[2,3-b]pyrazin-2-yl)benzamide
7-(1H-indazol-5-yl)-1-(2-(tetrahydro-2H-pyran-4-yl)ethyl)-3,4-dihydropyrazino[2,3-b]pyrazin-2(1H)-one
7-(1H-pyrrolo[2,3-b]pyridin-5-yl)-1-(2-(tetrahydro-2H-pyran-4-yl)ethyl)-3,4-dihydropyrazino[2,3-b]pyrazin-2(1H)-one
7-(2-methyl-6-(4H-1,2,4-triazol-3-yl)pyridin-3-yl)-1-(tetrahydro-2H-pyran-4-yl)-3,4-dihydropyrazino[2,3-b]pyrazin-2(1H)-one
1-((1S,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one
1-((1R,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one
1-((1R,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one
1-((1S,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one
7-(1H-indol-5-yl)-1-(2-(tetrahydro-2H-pyran-4-yl)ethyl)-3,4-dihydropyrazino[2,3-b]pyrazin-2(1H)-one
1-ethyl-7-(2-methyl-6-(1H-1,2,4-triazol-3-yl)pyridin-3-yl)-3,4-dihydropyrazino[2,3-b]pyrazin-2(1H)-one
7-(1H-indol-6-yl)-1-(2-(tetrahydro-2H-pyran-4-yl)ethyl)-3,4-dihydropyrazino[2,3-b]pyrazin-2(1H)-one
7-(4-(2-hydroxypropan-2-yl)phenyl)-1-(trans-4-methoxycyclohexyl)-3,4-dihydropyrazino[2,3-b]pyrazin-2(1H)-one
7-(6-(2-hydroxypropan-2-yl)pyridin-3-yl)-1-(tetrahydro-2H-pyran-4-yl)-3,4-dihydropyrazino[2,3-b]pyrazin-2(1H)-one
1-((trans-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one
7-(6-(2-hydroxypropan-2-yl)pyridin-3-yl)-1-((cis-4-methoxycyclohexyl)methyl)-3,4-dihydropyrazino[2,3-b]pyrazin-2(1H)-one
1-(2-methoxyethyl)-7-(4-methyl-2-(methylamino)-1H-benzo[d]imidazol-6-yl)-3,4-dihydropyrazino[2,3-b]pyrazin-2(1H)-one
7-(7-methyl-2-oxo-2,3-dihydro-1H-benzo[d]imidazol-5-yl)-1-((tetrahydro-2H-pyran-4-yl)methyl)-3,4-dihydropyrazino[2,3-b]pyrazin-2(1H)-one
7-(2-methyl-4-(4H-1,2,4-triazol-3-yl)phenyl)-3,4-dihydropyrazino[2,3-b]pyrazin-2(1H)-one
1-(2-methoxyethyl)-7-(4-methyl-6-(1H-1,2,4-triazol-3-yl)pyridin-3-yl)-3,4-dihydropyrazino[2,3-b]pyrazin-2(1H)-one 1-benzyl-7-(2-methyl-4-(4H-1,2,4-triazol-3-yl)phenyl)-3,4-dihydropyrazino[2,3-b]pyrazin-2(1H)-one
7-(3-fluoro-4-(4H-1,2,4-triazol-3-yl)phenyl)-1-(2-methoxyethyl)-3,4-dihydropyrazino[2,3-b]pyrazin-2(1H)-one
7-(3-fluoro-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one
7-(3-fluoro-2-methyl-4-(1H-1,2,4-triazol-3-yl)phenyl)-1-(2-methoxyethyl)-3,4-dihydropyrazino[2,3-b]pyrazin-2(1H)-one
1-(trans-4-methoxycyclohexyl)-7-(2-methyl-6-(4H-1,2,4-triazol-3-yl)pyridin-3-yl)-3,4-dihydropyrazino[2,3-b]pyrazin-2(1H)-one
7-(6-(2-hydroxypropan-2-yl)pyridin-3-yl)-1-(trans-4-methoxycyclohexyl)-3,4-dihydropyrazino[2,3-b]pyrazin-2(1H)-one
7-(5-fluoro-2-methyl-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one
7-(3-fluoro-2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one
1-(2-methoxyethyl)-7-(2-methyl-6-(4H-1,2,4-triazol-3-yl)pyridin-3-yl)-3,4-dihydropyrazino[2,3-b]pyrazin-2(1H)-one
7-(6-(2-hydroxypropan-2-yl)pyridin-3-yl)-1-((trans-4-methoxycyclohexyl)methyl)-3,4-dihydropyrazino[2,3-b]pyrazin-2(1H)-one
1-(cyclopentylmethyl)-7-(6-(2-hydroxypropan-2-yl)pyridin-3-yl)-3,4-dihydropyrazino[2,3-b]pyrazin-2(1H)-one
7-(4-(2-hydroxypropan-2-yl)phenyl)-1-(2-methoxyethyl)-3,4-dihydropyrazino[2,3-b]pyrazin-2(1H)-one
(S)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one
(R)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one
7-(2-methyl-6-(4H-1,2,4-triazol-3-yl)pyridin-3-yl)-1-((tetrahydro-2H-pyran-4-yl)methyl)-3,4-dihydropyrazino[2,3-b]pyrazin-2(1H)-one
7-(4-(2-hydroxypropan-2-yl)phenyl)-1-(2-(tetrahydro-2H-pyran-4-yl)ethyl)-3,4-dihydropyrazino[2,3-b]pyrazin-2(1H)-one
7-(6-(2-hydroxypropan-2-yl)pyridin-3-yl)-1-(4-(trifluoromethyl)benzyl)-3,4-dihydropyrazino[2,3-b]pyrazin-2(1H)-one
7-(6-(2-hydroxypropan-2-yl)pyridin-3-yl)-1-(3-(trifluoromethyl)benzyl)-3,4-dihydropyrazino[2,3-b]pyrazin-2(1H)-one
7-(6-(2-hydroxypropan-2-yl)pyridin-3-yl)-1-(3-methoxypropyl)-3,4-dihydropyrazino[2,3-b]pyrazin-2(1H)-one
7-(4-methyl-6-(1H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one
7-(6-(2-hydroxypropan-2-yl)pyridin-3-yl)-1-(2-methoxyethyl)-3,4-dihydropyrazino[2,3-b]pyrazin-2(1H)-one
7-(6-(2-hydroxypropan-2-yl)pyridin-3-yl)-1-((tetrahydro-2H-pyran-4-yl)methyl)-3,4-dihydropyrazino[2,3-b]pyrazin-2(1H)-one
7-(4-methyl-2-(methylamino)-1H-benzo[d]imidazol-6-yl)-1-((tetrahydro-2H-pyran-4-yl)methyl)-3,4-dihydropyrazino[2,3-b]pyrazin-2(1H)-one
7-(2-amino-4-methyl-1H-benzo[d]imidazol-6-yl)-1-((tetrahydro-2H-pyran-4-yl)methyl)-3,4-dihydropyrazino[2,3-b]pyrazin-2(1H)-one
7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one
(R)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one
(S)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one
7-(6-(2-hydroxypropan-2-yl)pyridin-3-yl)-3,3-dimethyl-1-(2-(tetrahydro-2H-pyran-4-yl)ethyl)-3,4-dihydropyrazino[2,3-b]pyrazin-2(1H)-one
7-(2-amino-4-methyl-1H-benzo[d]imidazol-6-yl)-1-(2-(tetrahydro-2H-pyran-4-yl)ethyl)-3,4-dihydropyrazino[2,3-b]pyrazin-2(1H)-one
7-(6-(2-hydroxypropan-2-yl)pyridin-3-yl)-1-(2-(tetrahydro-2H-pyran-4-yl)ethyl)-3,4-dihydropyrazino[2,3-b]pyrazin-2(1H)-one
7-(2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one
7-(4-(1H-1,2,4-triazol-5-yl)phenyl)-1-(2-(tetrahydro-2H-pyran-4-yl)ethyl)-3,4-dihydropyrazino[2,3-b]pyrazin-2(1H)-one
1-(1-hydroxypropan-2-yl)-7-(2-methyl-6-(1H-1,2,4-triazol-3-yl)pyridin-3-yl)-3,4-dihydropyrazino[2,3-b]pyrazin-2(1H)-one
1-(2-hydroxyethyl)-7-(2-methyl-6-(1H-1,2,4-triazol-3-yl)pyridin-3-yl)-3,4-dihydropyrazino[2,3-b]pyrazin-2(1H)-one.

25. The combination according to claim 1, wherein the compound of formula C is selected from:

C-i

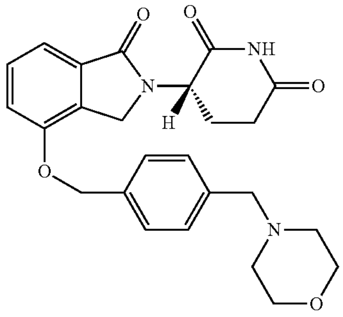

C-ii

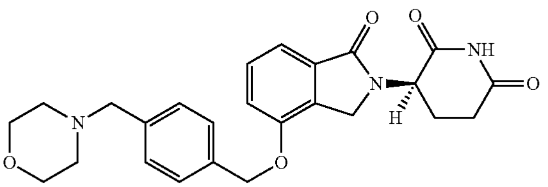

or a pharmaceutically acceptable salt thereof.

26. The combination according to claim 1, wherein the compound of formula F is selected from:

F-i
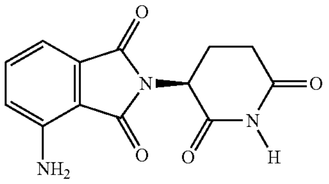
F-ii
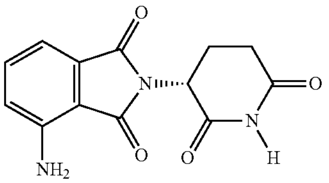
or a pharmaceutically acceptable salt thereof.
27. The combination according to claim 1, wherein the compound of formula G is selected from:
G-i
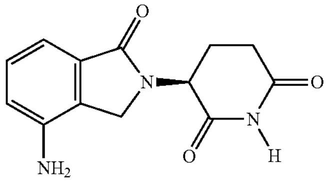
G-ii
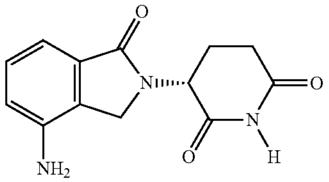
or a pharmaceutically acceptable salt thereof.
* * * * *